(12) United States Patent
Kakuuchi et al.

(10) Patent No.: US 12,269,817 B2
(45) Date of Patent: *Apr. 8, 2025

(54) COMPOUND HAVING KDM5 INHIBITORY ACTIVITY AND PHARMACEUTICAL USE THEREOF

(71) Applicant: ONO PHARMACEUTICAL CO., LTD., Osaka (JP)

(72) Inventors: Akito Kakuuchi, Osaka (JP); Shuhei Umemura, Osaka (JP); Masaki Asada, Osaka (JP); Anatoly Ruvinsky, Lexington, MA (US); Yan Zhang, New York, NY (US); Hidenori Takahashi, Lagrangeville, NY (US); Goran Krilov, Long Island City, NY (US); Daigo Inoyama, Ridgewood, NJ (US); Kyle Konze, Brooklyn, NY (US); Mats Svensson, New York, NY (US)

(73) Assignee: ONO PHARMACEUTICAL CO., LTD., Osaka (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/144,030

(22) Filed: May 5, 2023

(65) Prior Publication Data

US 2023/0271952 A1 Aug. 31, 2023

Related U.S. Application Data

(63) Continuation of application No. 17/971,844, filed on Oct. 24, 2022, now Pat. No. 11,691,968, which is a continuation of application No. PCT/CN2021/091843, filed on May 6, 2021.

(30) Foreign Application Priority Data

May 7, 2020 (WO) ................ PCT/CN2020/088925

(51) Int. Cl.
*C07D 413/14* (2006.01)
(52) U.S. Cl.
CPC ................. *C07D 413/14* (2013.01)
(58) Field of Classification Search
CPC .................................................. C07D 413/14
USPC ....................................................... 548/240
See application file for complete search history.

(56) References Cited

U.S. PATENT DOCUMENTS

| 6,313,312 B1 | 11/2001 | Banks et al. |
| 11,691,968 B2 * | 7/2023 | Kakuuchi ............ C07D 413/14 548/240 |
| 2002/0072616 A1 | 6/2002 | Banks et al. |
| 2003/0013875 A1 | 1/2003 | Banks et al. |
| 2004/0235844 A1 | 11/2004 | Goodacre |
| 2006/0135767 A1 | 6/2006 | Feng et al. |

FOREIGN PATENT DOCUMENTS

| CN | 108341819 A | 7/2018 |
| EP | 1 140 828 | 7/2000 |
| WO | 2016/057924 A1 | 4/2016 |
| WO | 2021/223699 A1 | 11/2021 |

OTHER PUBLICATIONS

Communication issued Jun. 30, 2023 by the European Patent Office for EP Patent Application No. 20841280.9.
International Search Report (PCT/ISA/210) dated Jul. 15, 2021, issued by the International Searching Authority in counterpart International Application No. PCT/CN2021/091843.
Written Opinion (PCT/ISA/237) dated Jul. 15, 2021, issued by the International Searching Authority in counterpart International Application No. PCT/CN2021/091843.
International Search Report (PCT/ISA/210) dated Oct. 27, 2020, issued by the International Searching Authority in counterpart International Application No. PCT/JP2020/028771.
Written Opinion (PCT/ISA/237) dated Oct. 27, 2020, issued by the International Searching Authority in counterpart International Application No. PCT/JP2020/028771.

* cited by examiner

*Primary Examiner* — Kahsay Habte
(74) *Attorney, Agent, or Firm* — Sughrue Mion, PLLC

(57) ABSTRACT

Disclosed are compounds of following formula (I):

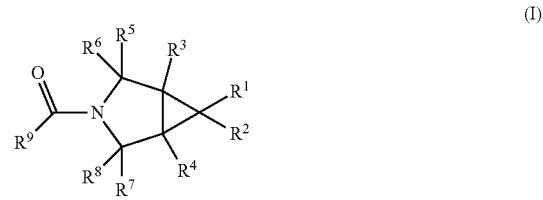

in which all symbols have the same meanings as the definitions described in the specification; or a salt thereof. The compounds or a salt thereof are useful as a prophylactic and/or therapeutic agent for cancer, Huntington's disease, Alzheimer's disease and the like.

3 Claims, No Drawings

COMPOUND HAVING KDM5 INHIBITORY ACTIVITY AND PHARMACEUTICAL USE THEREOF

CROSS-REFERENCE TO RELATED APPLICATION

This application is a continuation of U.S. patent application Ser. No. 17/971,844 filed Oct. 24, 2022, which is a bypass continuation of and claims the benefits of PCT/CN21/091843 filed May 6, 2021, which claims the benefit of Chinese Patent Application No. PCT/CN2020/088925, filed on May 7, 2020 in the Chinese Intellectual Property Office, the disclosures of which are incorporated herein by reference in their entireties.

TECHNICAL FIELD

The present invention relates to a compound represented by the general formula (I) described hereinbelow having KDM5 inhibitory activity, or a salt thereof, and pharmaceutical use thereof.

BACKGROUND ART

Eukaryotic DNA exists in the nucleus as a chromatin structure that is a complex with histone proteins. Histone proteins are subject to modifications such as methylation, acetylation and phosphorylation through various enzymes, and changes in such modifications are known to induce chromatin remodeling and transcriptional alterations. Epigenetic modifications including histone methylation reversely regulate gene expression without altering the nucleotide sequence and play an important role in physiological processes.

KDM5 proteins are members of JARID histone demethylase protein family, which demethylates tri-methylation of the fourth lysine residue of histone H3 protein (H3K4me3). In mammalian species including humans, there are four subfamilies: KDM5A, KDM5B, KDM5C, and KDM5D, which have five conserved domains, namely JmjN, ARID, JmjC, PHDs, and C5HC2 zinc finger. The KDM5 family is widely distributed in blood cells and various organs, in vivo, and particularly, is known to be highly expressed in cancer tissues. Epigenetic aberrations in cancer cells are known to be involved in the cell proliferation and metastasis, and KDM5 inhibitors have been reported to have efficacy against cancer cells. The involvement of epigenetic abnormalities, including histone modifications, has also been reported in other pathologies, such as neuropsychiatric disorders and metabolic diseases.

Therefore, compounds with KDM5 inhibitory activity may improve the epigenetic abnormalities and be useful for the prevention and treatment of these diseases.

In related art of the present invention, WO2016057924 reports that compounds of formula (A) are useful as inhibitors of one or more histone demethylases such as KDM5.

Formula (A):

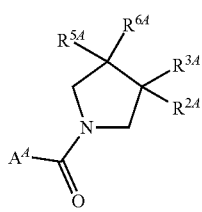

(A)

or a salt thereof, wherein:
$A^A$ is selected from the group consisting of:

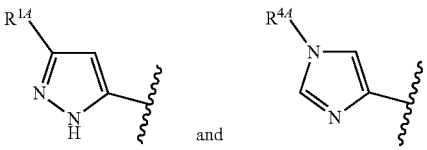

$R^{1A}$ is alkyl, cyclic group, or the like;
$R^{2A}$ is optionally substituted cyclic group, —$OR^{aA}$, —$C(O)N(R^{aA})_2$, or $NR^{aA}R^{bA}$;
$R^{aA}$ and $R^{bA}$ are each independently selected from H, optionally substituted alkyl group, optionally substituted cyclic group, etc.;
$R^{3A}$ is H or alkyl;
$R^{4A}$ is H, alkyl, or cyclic group; and
$R^{5A}$ is H, halo, or alkyl, and
$R^{6A}$ is H, alkyl, or cyclic group;
or $R^{5A}$ and $R^{6A}$ taken together to form cyclic group (where the definitions of the groups are excerpted).

In addition, WO2000039089 reports that compounds represented by the following formula (B) are useful as opiate receptors ligands.

Formula (B):

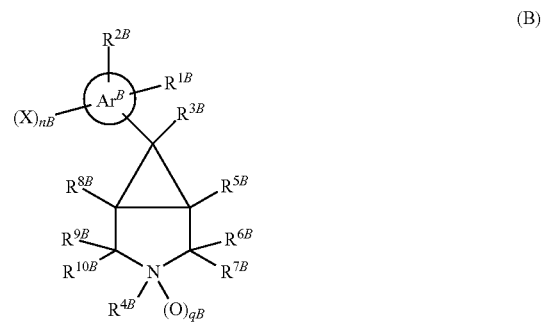

(B)

wherein the $Ar^B$ ring represents an optionally benzo-fused phenyl or 5- or 6-membered heteroaryl ring;
$R^{1B}$ is selected from various substituents;
$R^{2B}$ is H or halogen;
$R^{3B}$ is H, halogen, alkyl group, cyclic group, or the like,
$R^{4B}$ is optionally substituted alkyl, alkenyl or alkynyl, $R^{5B}$ and $R^{8B}$ are each independently H or $C_{1-6}$ alkyl,
$R^{6B}$, $R^{7B}$, $R^{9B}$ and $R^{10B}$ when taken separately are H,
X is halogen, alkyl, alkoxy, or the like (where the definitions of the groups are excerpted) or a pharmaceutically or veterinary acceptable derivative or prodrug thereof.

In addition, WO2021010492 reports that compounds of formula (C) are useful as KDM5 inhibitor.

Formula (C):

(C)

wherein ring$^C$ is 3- to 10-membered mono or bicyclic hetero ring containing 1 to 4 nitrogen atoms, one oxygen atom and/or one sulfur atom, which may be substituted with 1 to 3 substituents;
A$^C$ is R$^{1-1C}$-L$^{1C}$-, or the like;
B$^C$ is R$^{2-1C}$-L$^{2C}$-, or the like;
R$^{1-1C}$ is a C3-8 cycloalkyl which may be substituted with 1 to 4 substituents, or the like;
L$^{1C}$ is a bond, or carbonyl(—C(=O)—);
L$^{2C}$ is a bond, carbonyl(—C(=O)—), or the like;
R$^{2-1C}$ is 5- or 6-membered monocyclic heterocycle which may be substituted with 1 to 4 substituents, or the like;
R$^{3C}$ is a hydrogen atom, or the like;
r$^C$ represents an integer of 0 to 1;
or a salt thereof.

CITATION LIST

Patent Literature

[PTL 1] WO 2016/057924
[PTL 2] WO 2000/039089
[PTL 3] WO 2021/010492

SUMMARY OF INVENTION

Technical Problem

For example, a compound having KDM5 inhibitory activity for the treatment or prevention of diseases such as cancer, Huntington's disease, Alzheimer's disease and the like has been desired.

Solution to Problem

The inventors of the present invention have carried out extensive studies in order to achieve the above problem, and as a result, found that the compound represented by the general formula (I) described hereinafter, or a salt thereof can achieve the above object. The inventors have carried out further researches and completed the present invention.

Thus the present invention relates to:
[1] A compound represented by the general formula (I):

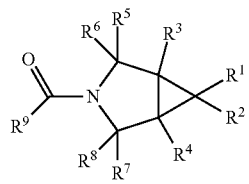

(I)

wherein R$^1$ represents Cyc1, —CO-Cyc2 or —CONR$^{10}$R$^{11}$;
Cyc1 represents a 5 to 9 membered aromatic hetero ring or 5 membered non-aromatic hetero ring, each of which may be substituted with 1 to 5 R$^{12}$;
R$^{12}$ represents (1) C1-4 alkyl, (2) C3-7 cycloalkyl, (3) C1-4 haloalkyl, (4) C1-4 alkoxy, (5) phenyl which may be substituted with 1 to 3 R$^{17}$, (6) C1-4 alkyl which is substituted with phenyl, (7) dimethylamino, (8) pyridyl or (9) 1-(cyclopropylmethyl)pyrazol-3-yl; a plurality of R$^{12}$ may be the same or different;
two R$^{12}$ together with an atom to which these R$^{12}$ are attached may form a C3-5 cycloalkane, wherein the carbon atom of C3-5 cycloalkane may be replaced with hetero atom selected from 1 to 2N, O and S;
R$^{17}$ represents C1-4 alkyl, C1-4 alkoxy or halogen;
a plurality of R$^{17}$ may be the same or different;
Cyc2 represents a C3-12 mono or bicyclic carbocycle or a 5- to 9-membered mono or bicyclic heterocycle, each of which may be substituted with 1 to 5 R$^{13}$;
R$^{13}$ represents C1-4 alkyl, C1-4 alkoxy or halogen;
a plurality of R$^{13}$ may be the same or different;
R$^{10}$ represents

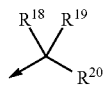

wherein R$^{18}$ and R$^{19}$ independently represents C1-4 alkyl;
R$^{18}$ and R$^{19}$ together with a carbon atom to which R$^{18}$ and R$^{19}$ are attached may form a C3-5 cycloalkane;
R$^{20}$ represents a hydrogen atom, C1-4 alkyl, C1-4 haloalkyl or nitrile; (in the group, the arrow indicates the binding to the nitrogen atom of —CON<);
R$^{11}$ represents a hydrogen atom, C1-4 alkyl or 1 to 9 deuterated C1-4 alkyl;
R$^2$, R$^3$, R$^4$, R$^5$, R$^6$, R$^7$ and R$^8$ independently represent a hydrogen atom, C1-4 alkyl, halogen or C1-4 alkoxy;
R$^9$ represents imidazole which may be substituted with 1 to 3 R$^{14}$ or pyrazole which may be substituted with 1 to 3 R$^{15}$;
R$^{14}$ represents (1) C1-8 alkyl, (2) C3-7 cycloalkyl which may be substituted with C1-4 alkyl, (3) C1-8 haloalkyl, (4) C1-8 alkyl which is substituted with Cyc3 which may be substituted with 1 to 3 R$^{16}$ or (5) C1-8 alkyl which is substituted with phenoxy;
Cyc3 represents phenyl, C3-7 cycloalkyl, pyridyl, thiazolyl or tetrahydropyranyl;
R$^{16}$ represents C1-4 alkyl, halogen, C1-4 alkoxy or cyano;
a plurality of R$^{14}$ may be the same or different;
a plurality of R$^{16}$ may be the same or different;
R$^{15}$ represents (1) C1-8 alkyl, (2) C3-7 cycloalkyl which may be substituted with C1-4 alkyl, (3) C1-8 haloalkyl, (4) C1-8 alkyl which is substituted with Cyc4 which may be substituted with 1 to 3 R$^{21}$ or (5) C1-8 alkyl which is substituted with phenoxy; Cyc4 represents phenyl, C3-7 cycloalkyl, pyridyl, thiazolyl or tetrahydropyranyl;
R$^{21}$ represents C1-4 alkyl, halogen, C1-4 alkoxy or cyano;
a plurality of R$^{15}$ may be the same or different;
a plurality of R$^{21}$ may be the same or different;
each hydrogen atom may be a deuterium atom or a tritium atom;
with the proviso that ((1R,5S,6r)-6-(Cyclopropanecarbonyl)-3-azabicyclo[3.1.0]hexan-3-yl)(5-isopropyl-1H-pyrazol-3-yl)methanone, (5-Isopropyl-1H-pyrazol-3-yl)-[(1R,5S)-6-[(2R)-2-methylpyrrolidine-1-carbonyl]-3-azabicyclo[3.1.0]hexan-3-yl]methanone, (5-Isopropyl-1H-pyrazol-3-yl)-[(1S,5R)-6-[(2S)-2-methylpyrrolidine-1-carbonyl]-3-azabicyclo[3.1.0] hexan-3-yl]methanone, [(1S,5R)-6-(2,2-Dimethylpyrrolidine-1-carbonyl)-3-azabicyclo[3.1.0]hexan-3-yl]-(5-isopropyl-1H-pyrazol-3-yl)methanone and (5-Isopropyl-1H-pyrazol-3-yl)-[(1S,5R)-6-(5-methyl-4-phenyl-isoxazol-3-yl)-3-azabicyclo[3.1.0]hexan-3-yl]methanone are excluded; or a salt thereof;
[2] The compound according to the preceding item [1], wherein R$^1$ represents Cyc1, and the Cyc1 represents 5 membered non-aromatic hetero ring which may be substituted with 1 to 5 $R^{12}$, or a salt thereof;

[3] The compound according to the preceding item [2], wherein 5 membered non-aromatic hetero ring represents 4,5-dihydroisoxazole or 4,5-dihydro-1,2,4-oxadiazole, or a salt thereof, [3-1] The compound according to the preceding item [3], wherein the compound represented by the general formula (I) is represented by the general formula (I-01)

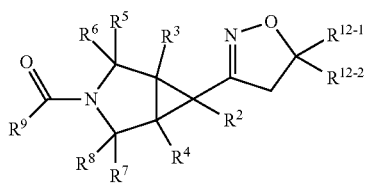

(I-01)

wherein $R^{12-1}$ and $R^{12-2}$ independently represent C1-4 alkyl;

$R^{12-1}$ and $R^{12-2}$ together with an atom to which the $R^{12-1}$ and $R^{12-2}$ are bound may form C3-5 cycloalkane;

other symbols represent the same meaning as described in the preceding item [1]; or a salt thereof;

[4] The compound according to any one of the preceding item [1] to [3] and [3-1], wherein $R^9$ represents imidazole which may be substituted with 1 to 3 $R^{14}$, or a salt thereof,

[5] The compound according to any one of the preceding item [1] to [4] and [3-1], wherein the compound represented by the general formula (I) is represented by the general formula (I-1)

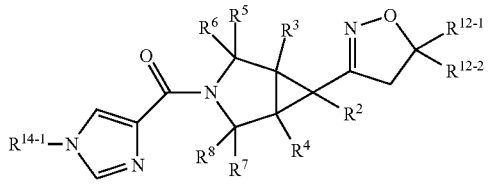

(I-1)

wherein $R^{12-1}$ and $R^{12-2}$ independently represent C1-4 alkyl;

$R^{12-1}$ and $R^{12-2}$ together with an atom to which the $R^{12-1}$ and $R^{12-2}$ are bound may form C3-5 cycloalkane;

$R^{14-1}$ represents C1-4 alkyl or C3-5 cycloalkyl which may be substituted with C1-4 alkyl; other symbols represent the same meaning as described in [1];

or a salt thereof;

[6] The compound according to any one of the preceding item [1] to [5] and [3-1], wherein the compound is:
(1) [(1R,5S,6r)-6-(5,5-dimethyl-4,5-dihydro-1,2-oxazol-3-yl)-3-azabicyclo[3.1.0]hex-3-yl](1-isopropyl-1H-imidazol-4-yl)methanone;
(2) [(1R,5S,6r)-6-(5,5-dimethyl-4,5-dihydro-1,2-oxazol-3-yl)-3-azabicyclo[3.1.0]hex-3-yl][1-(1-methylcyclopropyl)-1H-imidazol-4-yl]methanone;
(3) (1-cyclopropyl-1H-imidazol-4-yl)[(1R,5S,6r)-6-(5,5-dimethyl-4,5-dihydro-1,2-oxazol-3-yl)-6-methyl-3-azabicyclo[3.1.0]hex-3-yl]methanone;
(4) (1-cyclopropyl-1H-imidazol-4-yl)[(1R,5S,6r)-6-methyl-6-(4-oxa-5-azaspiro[2.4]hept-5-en-6-yl)-3-azabicyclo[3.1.0]hex-3-yl]methanone;
(5) {1-[(2S)-butan-2-yl]-1H-imidazol-4-yl}[(1R,5S,6S)-6-(5,5-dimethyl-4,5-dihydro-1,2-oxazol-3-yl)-3-azabicyclo[3.1.0]hex-3-yl]methanone;
(6) [(1R,5S,6r)-6-(5,5-dimethyl-4,5-dihydro-1,2-oxazol-3-yl)-6-methyl-3-azabicyclo[3.1.0]hex-3-yl](1-isopropyl-1H-imidazol-4-yl)methanone;
(7) (1-isopropyl-1H-imidazol-4-yl)[(1R,5S,6r)-6-methyl-6-(4-oxa-5-azaspiro[2.4]hept-5-en-6-yl)-3-azabicyclo[3.1.0]hex-3-yl]methanone;
(8) (1-cyclopropyl-1H-imidazol-4-yl)[(1R,5S,6r)-6-(4-oxa-5-azaspiro[2.4]hept-5-en-6-yl)-3-azabicyclo[3.1.0]hex-3-yl]methanone or
(9) [1-(1-methylcyclopropyl)-1H-imidazol-4-yl][(1R,5S,6r)-6-(4-oxa-5-azaspiro[2.4]hept-5-en-6-yl)-3-azabicyclo[3.1.0]hex-3-yl]methanone;
or a salt thereof;

[7] The compound according to any one of the preceding item [1] to [3] and [3-1], wherein $R^9$ represents pyrazole which may be substituted with 1 to 3 $R^{15}$ or a salt thereof;

[8] The compound according to any one of the preceding item [1] to [3], [3-1] and [7], wherein the compound represented by the general formula (I) is represented by the general formula (I-2)

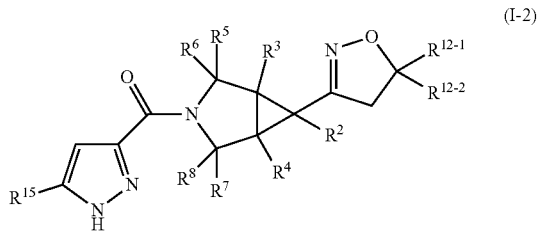

(I-2)

wherein all symbols represent the same meaning as described in the preceding item [1] or [5]; or a salt thereof;

[9] The compound according to any one of the preceding item [1] to [3], [3-1], [7] and [8] wherein the compound is:
(1) [(1R,5S,6r)-6-(5,5-dimethyl-4,5-dihydro-1,2-oxazol-3-yl)-3-azabicyclo[3.1.0]hex-3-yl](5-isopropyl-1H-pyrazol-3-yl)methanone;
(2) (5-isopropyl-1H-pyrazol-3-yl)[(1R,5S,6r)-6-(2-oxa-3-azabicyclo[3.1.0]hex-3-en-4-yl)-3-azabicyclo[3.1.0]hex-3-yl]methanone;
(3) [5-(1-cyclopropylethyl)-1H-pyrazol-3-yl][(1R,5S,6r)-6-(5,5-dimethyl-4,5-dihydro-1,2-oxazol-3-yl)-3-azabicyclo[3.1.0]hex-3-yl]methanone;
(4) [(1R,5S,6r)-6-(5,5-dimethyl-4,5-dihydro-1,2-oxazol-3-yl)-6-methyl-3-azabicyclo[3.1.0]hex-3-yl](5-isopropyl-1H-pyrazol-3-yl)methanone or
(5) (5-cyclopropyl-1H-pyrazol-3-yl)[(1R,5S,6r)-6-methyl-6-(4-oxa-5-azaspiro[2.4]hept-5-en-6-yl)-3-azabicyclo[3.1.0]hex-3-yl]methanone or a salt thereof;

[10] The compound according to the preceding item [1], wherein $R^1$ represents —$CONR^{10}R^{11}$, or a salt thereof;

[11] The compound according to the preceding item [1] or [10], wherein $R^{10}$ represents isopropyl, tert-butyl, 1,1,1-trifluoro-2-methylpropan-2-yl, 1-methylcyclopropyl, 1-(trifluoromethyl)cyclopropyl or 1-cyanocyclopropyl, or a salt thereof;

[11-1] The compound according to the preceding item [11], wherein the compound represented by the general formula (I) is represented by the general formula (I-02)

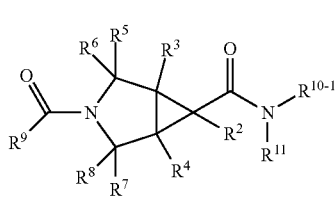
(I-02)

wherein $R^{10-1}$ represents isopropyl, tert-butyl, 1,1,1-trifluoro-2-methylpropan-2-yl, 1-methylcyclopropyl, 1-(trifluoromethyl)cyclopropyl or 1-cyanocyclopropyl;

other symbols represent the same meaning as described in the preceding item [1]; or a salt thereof;

[12] The compound according to the preceding item [10], [11] or [11-1], wherein $R^9$ represents imidazole which may be substituted with 1 to 3 $R^{14}$, or a salt thereof;

[13] The compound according to any one of the preceding item [1], [10] to [12] and [11-1], wherein the compound represented by the general formula (I) is represented by the general formula (I-3)

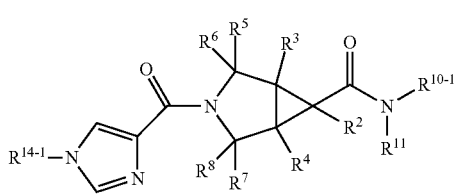
(I-3)

wherein $R^{10-1}$ represents isopropyl, tert-butyl, 1,1,1-trifluoro-2-methylpropan-2-yl, 1-methylcyclopropyl, 1-(trifluoromethyl)cyclopropyl or 1-cyanocyclopropyl;

other symbols represent the same meaning as described in the preceding item [1] or [5]; or a salt thereof;

[14] The compound according to any one of the preceding item [1], [10] to [13] and [11-1], wherein the compound is:
(1) (1R,5S,6r)-N-tert-butyl-6-methyl-3-[1-(propan-2-yl)-1H-imidazole-4-carbonyl]-3-azabicyclo[3.1.0]hexane-6-carboxamide;
(2) (1R,5S,6r)-N-tert-butyl-3-[1-(propan-2-yl)-1H-imidazole-4-carbonyl]-3-azabicyclo[3.1.0]hexane-6-carboxamide;
(3) (1R,5S,6r)-N-(propan-2-yl)-3-[1-(propan-2-yl)-1H-imidazole-4-carbonyl]-3-azabicyclo[3.1.0]hexane-6-carboxamide or
(4) (1R,5S,6r)-N-(1-cyanocyclopropyl)-3-[1-(propan-2-yl)-1H-imidazole-4-carbonyl]-3-azabicyclo[3.1.0]hexane-6-carboxamide or a salt thereof;

[15] The compound according to the preceding item [10], [11] and [11-1], wherein $R^9$ represents pyrazole which may be substituted with 1 to 3 $R^{15}$ or a salt thereof;

[16] The compound according to any one of the preceding item [1], [10], [11], [11-1] and [15], wherein the compound represented by the general formula (I) is represented by the general formula (I-4)

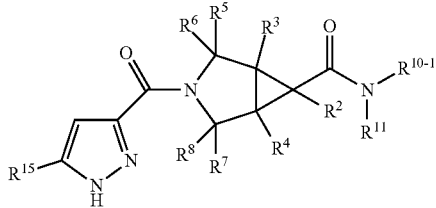
(I-4)

wherein all symbols represent the same meaning as described in the preceding item [1] or [13];
or a salt thereof;

[17] The compound according to any one of the preceding item [1], [10], [11], [11-1], [15] and [16], wherein the compound is:
(1) (1R,5S,6r)-N-(propan-2-yl)-3-[5-(propan-2-yl)-1H-pyrazole-3-carbonyl]-3-azabicyclo[3.1.0]hexane-6-carboxamide;
(2) (1R,5S,6r)-N-tert-butyl-6-methyl-3-[5-(propan-2-yl)-1H-pyrazole-3-carbonyl]-3-azabicyclo[3.1.0]hexane-6-carboxamide;
(3) (1R,5S,6r)-N-tert-butyl-N-methyl-3-[5-(propan-2-yl)-1H-pyrazole-3-carbonyl]-3-azabicyclo[3.1.0]hexane-6-carboxamide or
(4) (1R,5S,6r)-N-methyl-N-(1-methylcyclopropyl)-3-[5-(propan-2-yl)-1H-pyrazole-3-carbonyl]-3-azabicyclo [3.1.0]hexane-6-carboxamide, or a salt thereof;

[18] A pharmaceutical composition comprising the compound represented by the general formula (I) according to the preceding item [1] or a salt thereof, and a pharmaceutically acceptable carrier;

[19] The pharmaceutical composition according to the preceding item [18], which is KDM5 inhibitor;

[20] The pharmaceutical composition according to the preceding item [18] or [19], which is a prophylactic and/or therapeutic agent for KDM5-related disease;

[21-1] The pharmaceutical composition according to the preceding item [20], wherein the KDM5-related disease is hyperproliferative disease, cancer, stroke, diabetes, hepatomegaly, cardiovascular disease, multiple sclerosis, Huntington's disease, Alzheimer's disease, cystic fibrosis, viral disease, autoimmune diseases, atherosclerosis, restenosis, psoriasis, rheumatoid arthritis, inflammatory bowel disease, asthma, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, liver disease, pathologic immune conditions involving T cell activation, CNS disorders, myeloproliferative disorder, Parkinson's disease, Lewy body disease, frontotemporal lobar degeneration, mild cognitive impairment, cognitive impairment, cerebrovascular disease, schizophrenia, depression, anxiety disorder, bipolar disorder, autism spectrum disorder, attention deficit/hyperactivity disorder, learning disabilities, movement disorders, obsessive-compulsive disorder, personality disorder, sleeping disorder, delirium, amyotrophic lateral sclerosis, developmental disorders, intellectual disability, post-traumatic stress disorder, or hepatitis;

[21-2] The pharmaceutical composition according to the preceding item [20], wherein the KDM5-related disease is cancer, or Alzheimer Disease;

[22] A prophylactic and/or therapeutic agent for KDM5-related disease, comprising the compound represented by the general formula (I) according to the preceding item [1] or a salt thereof as an active component, wherein the prophylactic and/or therapeutic agent is administered together with at least one drug selected from the group consisting of donepezil hydrochloride, galantamine hydrobromide, huperzine A, idebenone, levacecarnine hydrochloride, memantine hydrochloride, memantine hydrochloride/donepezil hydrochloride, proteolytic peptide fraction from porcine brain protein, rivastigmine tartrate, tacrine hydrochloride and aducanumab;

[23] A method for prophylaxis and/or therapy of KDM5-related disease, comprising administering to a mammal (preferably, a patient in need thereof) an effective amount of the compound represented by the general formula (I) according to the preceding item [1] or a salt thereof;

[24] The compound represented by the general formula (I) according to the preceding item [1] or a salt thereof for use in prophylaxis and/or therapy of KDM5-related disease; and

[25] Use of the compound represented by the general formula (I) according to the preceding item [1] or a salt thereof in the manufacture of a prophylactic and/or therapeutic agent for KDM5-related disease.

Advantageous Effects of Invention

The compound represented by the general formula (I) or a salt thereof (hereinafter collectively referred to as the present compound) as disclosed herein has KDM5 inhibitory activity. Therefore, the present compound can be used as a therapeutic and/or prophylactic agent for diseases such as hyperproliferative disease, cancer, stroke, diabetes, hepatomegaly, cardiovascular disease, multiple sclerosis, Huntington's disease, Alzheimer's disease, cystic fibrosis, viral disease, autoimmune diseases, atherosclerosis, restenosis, psoriasis, rheumatoid arthritis, inflammatory bowel disease, asthma, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, liver disease, pathologic immune conditions involving T cell activation, CNS disorders, myeloproliferative disorder, Parkinson's disease, Lewy body disease, frontotemporal lobar degeneration, mild cognitive impairment, cognitive impairment, cerebrovascular disease, schizophrenia, depression, anxiety disorder, bipolar disorder, autism spectrum disorder, attention deficit/hyperactivity disorder, learning disabilities, movement disorders, obsessive-compulsive disorder, personality disorder, sleeping disorder, delirium, amyotrophic lateral sclerosis, developmental disorders, intellectual disability, post-traumatic stress disorder, or hepatitis.

DESCRIPTION OF EMBODIMENTS

Examples of "halogen" as used herein include fluorine, chlorine, bromine and iodine atoms.

The "C1-4 alkyl" as used herein includes methyl, ethyl, propyl, isopropyl, butyl, sec-butyl, tert-butyl and isobutyl groups.

The "1 to 9 deuterated C1-4 alkyl" as used herein includes $CH_2D$-, $CHD_2$-, $CD_3$-, $CD_3CD_2$-, $CD_3CD_2CD_2$-, $(CD_3)_2CD$-, $CD_3CD_2CD_2CD_2$-, $CD_3CD_2CD(CD_3)$-, $(CD_3)_3C$—, and $(CD_3)_2CDCD_2$- and the like (D means deuterium).

The "C1-8 alkyl" as used herein includes methyl, ethyl, propyl, isopropyl, butyl, sec-butyl, tert-butyl, isobutyl, pentyl, 1,2-dimethylpropyl, 1-ethylpropyl, hexyl, 1,3-dimethylbutyl, heptyl and octyl groups.

The "C1-4 alkoxy" as used herein includes methoxy, ethoxy, propoxy, isopropoxy, butoxy, sec-butoxy, tert-butoxy and isobutoxy groups.

The "C1-4 haloalkyl" as used herein includes fluoromethyl, difluoromethyl, trifluoromethyl, chloromethyl, dichloromethyl, trichloromethyl, 2,2,2-trifluoroethyl, perfluoroethyl, perfluoropropyl, perfluoro(isopropyl), perfluorobutyl, perfluoro(sec-butyl), perfluoro(tert-butyl) and perfluoro (isobutyl) groups and the like.

The "C1-8 haloalkyl" as used herein includes fluoromethyl, difluoromethyl, trifluoromethyl, chloromethyl, dichloromethyl, trichloromethyl, 2,2,2-trifluoroethyl, perfluoroethyl, perfluoropropyl, perfluoro(isopropyl), perfluorobutyl, perfluoro(sec-butyl), perfluoro(tert-butyl), perfluoro (isobutyl), perfluoropentyl, perfluorohexyl, perfluoroheptyl and perfluorooctyl groups and the like.

Examples of "C3-5 cycloalkyl" as used herein include cyclopropyl, cyclobutyl, and cyclopentyl groups.

Examples of "C3-5 cycloalkane" as used herein include cyclopropane, cyclobutane, and cyclopentane rings.

Examples of "C3-5 cycloalkane, wherein the carbon atom of C3-5 cycloalkane may be replaced with hetero atom selected from 1 to 2 N, O and S" as used herein include cyclopropane, cyclobutane, cyclopentane, aziridine, oxirane, thiirane, azetidine, oxetane, thietane, pyrrolidine, tetrahydrofuran, tetrahydrothiophene, pyrazolidine, isoxazolidine, isothiazolidine, imidazolidine, oxazolidine, thiazolidine, and 1,3-dioxolane rings and the like.

Examples of "C3-7 cycloalkyl" as used herein include cyclopropyl, cyclobutyl, cyclopentyl, cyclohexyl, cycloheptyl, bicyclo[1.1.0]butyl, bicyclo[2.1.0]pentyl, bicyclo[1,1,1] pentyl, bicyclo[3.1.0]hexyl, bicyclo[2.2.0]hexyl, bicyclo [2.1.1]hexyl, bicyclo[4.1.0]heptyl, bicyclo[3.2.0]heptyl, bicyclo[2.2.1]heptyl and bicyclo[3.1.1]heptyl groups and the like.

Examples of "5 to 9 membered aromatic hetero ring" as used herein include "5 to 9 membered aromatic hetero ring containing 1 to 4 nitrogen atoms, 1 oxygen atoms and/or 1 sulfur atom" and the like. Examples of the "5 to 9 membered aromatic hetero ring containing 1 to 4 nitrogen atoms, 1 oxygen atom and/or 1 sulfur atom" include 1,2,5-oxadiazole, 1,2,5-thiadiazole, 1,2,4-oxadiazole, 1,2,4-thiadiazole, isothiazole, 1,3,4-thiadiazole, benzo[d]isothiazole, isoxazole, 1,3,4-oxadiazole, 1,2,4-triazole, tetrazole, benzo[d]isoxazole, [1,2,3]triazolo[1,5-a]pyridine or [1,2,4]triazolo[4,3-a]pyridine rings and the like.

Examples of "5 membered non-aromatic hetero ring" as used herein include "5 membered non-aromatic hetero ring containing 1 to 4 nitrogen atoms, 1 oxygen atom and/or 1 sulfur atom" and the like. Examples of the "5 membered non-aromatic hetero ring containing 1 to 4 nitrogen atoms, 1 oxygen atoms and/or 1 sulfur atom" include 2,3-dihydro-1,2,3-oxadiazole, 2,3-dihydro-1,2,3-thiadiazole, 2,3-dihydro-1,2,4-oxadiazole, 2,3-dihydro-1,2,4-thiadiazole, 2,3-dihydro-1,2,5-oxadiazole, 2,3-dihydro-1,2,5-thiadiazole, 2,3-dihydro-1,3,4-oxadiazole, 2,3-dihydro-1,3,4-thiadiazole, 2,3-dihydro-1H-1,2,3-triazole, 2,3-dihydro-1H-1,2,4-triazole, 2,3-dihydro-1H-imidazole, 2,3-dihydro-1H-pyrazole, 2,3-dihydro-1H-pyrrole, 2,3-dihydro-1H-tetrazole, 2,3-dihydrofuran, 2,3-dihydroisothiazole, 2,3-dihydroisoxazole, 2,3-dihydrooxazole, 2,3-dihydrothiazole, 2,3-dihydrothiophene, 4,5-dihydro-1,2,3-oxadiazole, 4,5-dihydro-1,2,3-thiadiazole, 4,5-dihydro-1,2,4-oxadiazole, 4,5-dihydro-1,2, 4-thiadiazole, 4,5-dihydro-1H-1,2,3-triazole, 4,5-dihydro-1H-1,2,4-triazole, 4,5-dihydro-1H-imidazole, 4,5-dihydro-1H-pyrazole, 4,5-dihydro-1H-tetrazole, 4,5-dihydroisothiazole, 4,5-dihydroisoxazole, 4,5-dihydrooxazole and 4,5-dihydrothiazole rings and the like.

Examples of "C3-12 mono or bicyclic carbocycle" as used herein include cyclopropane, cyclobutane, cyclopentane, cyclohexane, cyclopentene, cyclohexene, cyclopentadiene, cyclohexadiene, benzene, indene, dihydroindene, naphthalene, dihydronaphthalene, and tetrahydronaphthalene rings and the like.

Examples of "5- to 9-membered mono or bicyclic heterocycle" as used herein include "5- to 9-membered mono or bicyclic heterocycles containing 1 to 4 nitrogen atoms, 1 to 2 oxygen atoms and/or 1 sulfur atom" and the like. Examples of the "5- to 9-membered mono or bicyclic heterocycles containing 1 to 4 nitrogen atoms, 1 to 2 oxygen atoms and/or 1 sulfur atom" include pyrrole, imidazole, triazole, tetrazole, pyrazole, pyridine, pyrazine, pyrimidine, pyridazine, furan, pyran, thiophene, thiopyran, oxazole, isoxazole, thiazole, isothiazole, furazan, oxadiazole, oxazine, oxadiazine, thiadiazole, thiazine, thiadiazine, pyrroline, pyrrolidine, imidazoline, imidazolidine, triazoline, triazolidine, tetrazoline, tetrazolidine, pyrazoline, pyrazolidine, dihydropyridine, tetrahydropyridine, piperidine, dihydropyrazine, tetrahydropyrazine, piperazine, dihydropyrimidine, tetrahydropyrimidine, perhydropyrimidine, dihydropyridazine, tetrahydropyridazine, perhydropyridazine, dihydrofuran, tetrahydrofuran, dihydropyran, tetrahydropyran, dihydrothiophene, tetrahydrothiophene, dihydrothiopyran, tetrahydrothiopyran, dihydrooxazole, tetrahydrooxazole (oxazolidine), dihydroisoxazole, tetrahydroisoxazole (isoxazolidine), dihydrothiazole, tetrahydrothiazole (thiazolidine), dihydroisothiazole, tetrahydroisothiazole (isothiazolidine), dihydrofurazan, tetrahydrofurazan, dihydrooxadiazole, tetrahydrooxadiazole (oxadiazolidine), dihydrooxazine, tetrahydrooxazine, dihydrooxadiazine, tetrahydrooxadiazine, dihydrothiadiazole, tetrahydrothiadiazole (thiadiazolidine), dihydrothiazine, tetrahydrothiazine, dihydrothiadiazine, tetrahydrothiadiazine, morpholine, thiomorpholine, oxathiane, dioxolane, dioxane, dioxole, indole, benzimidazole, benztriazole, indazole, benzofuran, benzothiophene, benzoxazole, indoline, dihydrobenzimidazole, dihydrobenztriazole, dihydroindazole, dihydrobenzofuran, dihydrobenzothiophene, and dihydrobenzoxazole, rings and the like.

In the present invention, unless particularly stated, the symbol: 
indicates that the bond projects above the plane of the paper (i.e., β-configuration), and the symbol: 
indicates that the bond projects below the plane of the paper (i.e., α-configuration), and the symbol: 
indicates that the bond is the α-configuration, β-configuration or the mixture of these configurations at arbitrary proportions, as apparent to a person skilled in the art.

In the present invention, $R^1$ is preferably, for example, Cyc1 or —$CONR^{10}R^{11}$, more preferably, for example, Cyc1, and particularly preferably, for example, 5 membered non-aromatic hetero ring.

In the present invention, Cyc1 is preferably, for example, 5 membered non-aromatic hetero ring which may be substituted with 1 to 5 $R^{12}$, more preferably, for example, 2,3-dihydro-1,2,5-oxadiazole, 2,3-dihydro-1,2,5-thiadiazole, 4,5-dihydro-1,2,3-oxadiazole, 4,5-dihydro-1,2,3-thiadiazole, 4,5-dihydro-1,2,4-oxadiazole, 4,5-dihydro-1,2,4-thiadiazole, 4,5-dihydro-1H-1,2,3-triazole, 4,5-dihydroisothiazole, or 4,5-dihydroisoxazole, each of which may be substituted with 1 to 5 $R^{12}$, particularly preferably, for example, 4,5-dihydro-1,2,4-oxadiazole or 4,5-dihydroisoxazole, each of which may be substituted with 1 to 5 $R^{12}$, and especially preferably, for example, 4,5-dihydroisoxazole which may be substituted with 1 to 5 $R^{12}$.

In the present invention, Cyc1 is also preferably, for example, 5 to 9 membered aromatic hetero ring which may be substituted with 1 to 5 $R^{12}$, more preferably, for example, 1,2,5-oxadiazole, 1,2,5-thiadiazole, 1,2,4-oxadiazole, 1,2,4-thiadiazole, isothiazole, 1,3,4-thiadiazole, benzo[d]isothiazole, isoxazole, 1,3,4-oxadiazole, 1,2,4-triazole, tetrazole, benzo[d]isoxazole, [1,2,3]triazolo[1,5-a]pyridine or [1,2,4]triazolo[4,3-a]pyridine, each of which may be substituted with 1 to 5 $R^{12}$, and particularly preferably, for example, isoxazole, 1,3,4-oxadiazole, 1,2,4-triazole, tetrazole, benzo[d]isoxazole, [1,2,3]triazolo[1,5-a]pyridine or [1,2,4]triazolo[4,3-a]pyridine, each of which may be substituted with 1 to 5 $R^{12}$.

In the present invention, $R^{12}$ is preferably, for example, (1) C1-4 alkyl, (2) C3-7 cycloalkyl, (3) C1-4 haloalkyl, (4) C1-4 alkoxy, (5) phenyl which may be substituted with 1 to 3 $R^{17}$, (6) C1-4 alkyl which is substituted with phenyl, (7) dimethylamino, (8) pyridyl or (9) 1-(cyclopropylmethyl)pyrazol-3-yl, or (10) two $R^{12}$ together with an atom to which these $R^{12}$ are attached may form a C3-5 cycloalkane, more preferably, for example, (1) C1-4 alkyl, (2) C3-7 cycloalkyl, (3) phenyl which may be substituted with 1 to 3 $R^{17}$, or (4) two $R^{12}$ together with an atom to which these $R^{12}$ are attached may form a C3-5 cycloalkane, and particularly preferably, for example, C1-4 alkyl, or two $R^{12}$ together with an atom to which these $R^{12}$ are attached may form a C3-5 cycloalkane.

In the present invention, $R^{17}$ is preferably, for example, C1-4 alkyl or C1-4 alkoxy.

In the present invention, Cyc2 is preferably, for example, cyclopropane, cyclobutane, cyclopentane, cyclohexane, cyclopentene, cyclohexene, cyclopentadiene, cyclohexadiene, benzene, pyrrole, imidazole, triazole, tetrazole, pyrazole, pyridine, pyrazine, pyrimidine, pyridazine, furan, pyran, thiophene, thiopyran, oxazole, isoxazole, thiazole, isothiazole, furazan, oxadiazole, oxazine, oxadiazine, thiadiazole, thiazine, thiadiazine, indole, benzimidazole, benztriazole, indazole, benzofuran, benzothiophene, benzoxazole, indoline, dihydrobenzimidazole, dihydrobenztriazole, dihydroindazole, dihydrobenzofuran, dihydrobenzothiophene, or dihydrobenzoxazole, each of which may be substituted with 1 to 5 $R^{13}$, and more preferably, for example, cyclopropane, benzene, pyridine, thiophene, thiazole, or indoline, each of which may be substituted with 1 to 5 $R^{13}$.

In the present invention, $R^{10}$ is preferably, for example, isopropyl, tert-butyl, 1,1,1-trifluoro-2-methylpropan-2-yl, 1-methylcyclopropyl, 1-(trifluoromethyl)cyclopropyl or 1-cyanocyclopropyl.

In the present invention, $R^{13}$ is preferably, for example, C1-4 alkyl or C1-4 alkoxy.

In the present invention, $R^{11}$ is preferably, for example, a hydrogen atom or C1-4 alkyl.

In the present invention, $R^2$ is preferably, for example, a hydrogen atom or C1-4 alkyl.

In the present invention, $R^3$ is preferably, for example, a hydrogen atom or C1-4 alkyl.

In the present invention, $R^4$ is preferably, for example, a hydrogen atom or C1-4 alkyl.

In the present invention, $R^5$ is preferably, for example, a hydrogen atom or C1-4 alkyl.

In the present invention, $R^6$ is preferably, for example, a hydrogen atom or C1-4 alkyl.

In the present invention, $R^7$ is preferably, for example, a hydrogen atom or C1-4 alkyl.

In the present invention, $R^8$ is preferably, for example, a hydrogen atom or C1-4 alkyl.

In the present invention, $R^9$ is preferably, for example, imidazole which may be substituted with 1 to 3 $R^{14}$.

In the present invention, $R^9$ is also preferably, for example, pyrazole which may be substituted with 1 to 3 $R^{15}$.

In the present invention, $R^{14}$ is preferably, for example, (1) C1-8 alkyl, (2) C3-7 cycloalkyl which may be substituted with C1-4 alkyl, (3) C1-8 alkyl which is substituted with Cyc3 which may be substituted with 1 to 3 $R^{16}$ or (4) C1-8 alkyl which is substituted with phenoxy, and more preferably, for example, (1) C1-8 alkyl or (2) C3-7 cycloalkyl which may be substituted with C1-4 alkyl.

In the present invention, Cyc3 is preferably, for example, phenyl or C3-7 cycloalkyl.

In the present invention, $R^{16}$ is preferably, for example, C1-4 alkyl or cyano.

In the present invention, $R^{15}$ is preferably, for example, (1) C1-8 alkyl, (2) C3-7 cycloalkyl which may be substituted with C1-4 alkyl, (3) C1-8 alkyl which is substituted with Cyc3 which may be substituted with 1 to 3 $R^{21}$, and more preferably, for example, (1) C1-8 alkyl or (2) C3-7 cycloalkyl which may be substituted with C1-4 alkyl.

In the present invention, Cyc4 is preferably, for example, phenyl or C3-7 cycloalkyl.

In the present invention, $R^{21}$ is preferably, for example, C1-4 alkyl or cyano.

In the present invention, examples of the general formula (I) preferably include the general formula (I-1A):

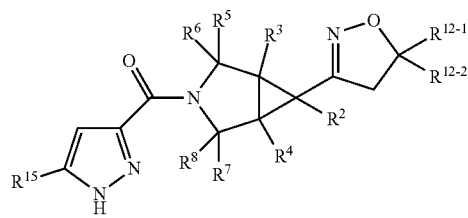

(I-1A)

wherein all symbols have the same meanings as above,

In the present invention, examples of the general formula (I) preferably include the general formula (I-1):

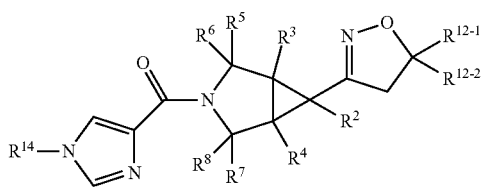

(I-1)

wherein a symbols have the same meanings as above, the general formula (I-1A-1):

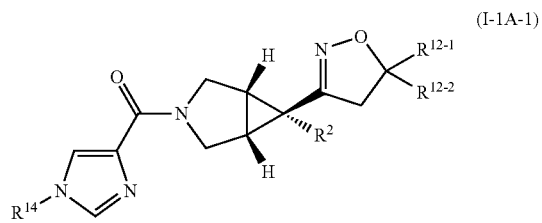

(I-1A-1)

wherein $R^2$ represents a hydrogen atom, or C1-4 alkyl;
$R^{14}$ represents (1) C1-8 alkyl, (2) C3-7 cycloalkyl which may be substituted with C1-4 alkyl, or (5) C1-8 alkyl which is substituted with phenoxy;
wherein $R^{12-1}$ and $R^{12-2}$ independently represent C1-4 alkyl; and
$R^{12-1}$ and $R^{12-2}$ together with an atom to which the $R^{12-1}$ and $R^{12-2}$ are bound may form C3-5 cycloalkane;
the general formula (I-2):

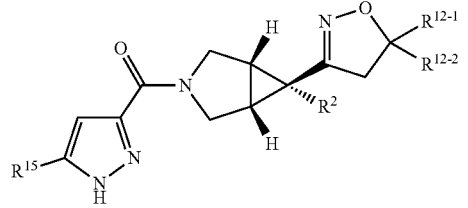

(I-2)

wherein all symbols have the same meanings as above,
the general formula (I-2-1):

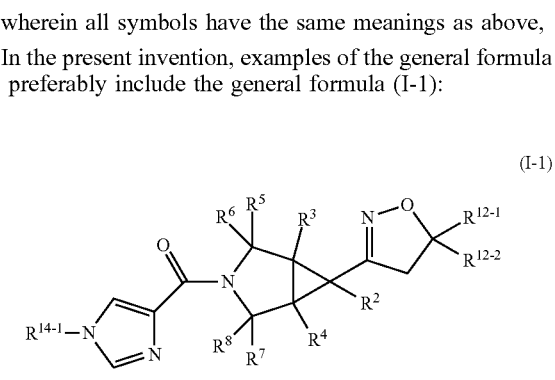

(I-2-1)

wherein $R^2$ represents a hydrogen atom, C1-4 alkyl, halogen or C1-4 alkoxy;
$R^{15}$ represents (1) C1-8 alkyl, or (3) C1-8 haloalkyl;
wherein $R^{12-1}$ and $R^{12-2}$ independently represent C1-4 alkyl; and
$R^{12-1}$ and $R^{12-2}$ together with an atom to which the $R^{12-1}$ and $R^{12-2}$ are bound may form C3-5 cycloalkane;
the general formula (I-3A):

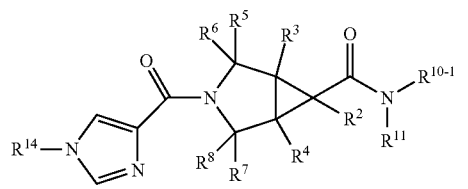

(I-3A)

wherein all symbols have the same meanings as above, the general formula (I-3):

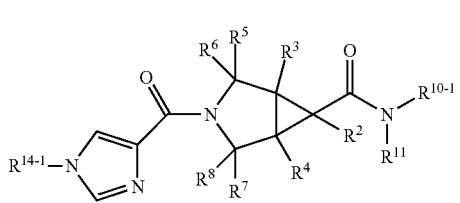
(I-3)

wherein all symbols have the same meanings as above,
the general formula (I-4):

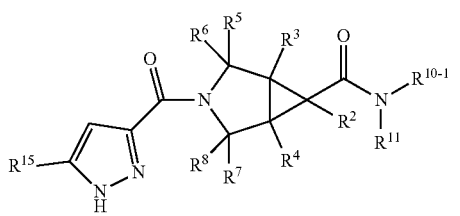
(I-4)

wherein all symbols have the same meanings as above,
the general formula (I-5):

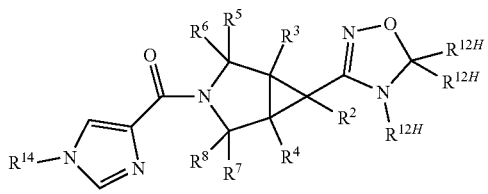
(I-5)

wherein $R^{12H}$ represents (1) a hydrogen atom, (2) C1-4 alkyl, (3) C3-7 cycloalkyl, (4) C1-4 haloalkyl, (5) C1-4 alkoxy, (6) phenyl which may be substituted with 1 to 3 $R^{17}$, (7) C1-4 alkyl which is substituted with phenyl, (8) dimethylamino, (9) pyridyl or (10) 1-(cyclopropylmethyl)pyrazol-3-yl, and other symbols have the same meanings as above,
the general formula (I-6):

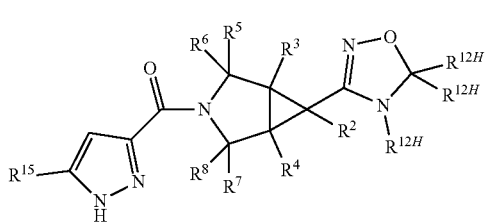
(I-6)

wherein all symbols have the same meanings as above, the general formula (I-7):

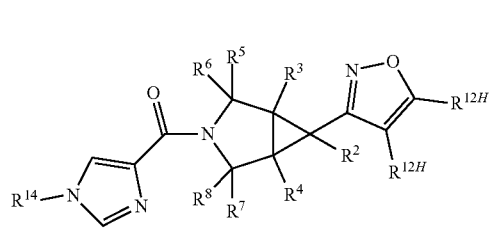
(I-7)

wherein all symbols have the same meanings as above,
the general formula (I-7-1):

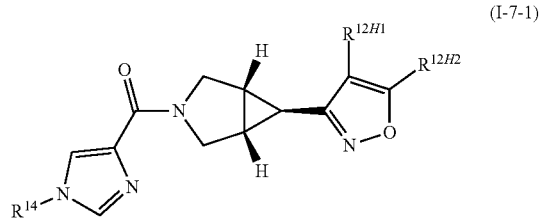
(I-7-1)

wherein $R^{14}$ represents (1) C1-8 alkyl, or (3) C1-8 haloalkyl;

$R^{12H1}$ represents (2) C1-4 alkyl, (3) C3-7 cycloalkyl, (4) C1-4 haloalkyl, (5) C1-4 alkoxy, (6) phenyl which may be substituted with 1 to 3 $R^{17}$, (7) C1-4 alkyl which is substituted with phenyl, (8) dimethylamino, (9) pyridyl or (10) 1-(cyclopropylmethyl)pyrazol-3-yl; preferably, $R^{12H1}$ represents (2) C1-4 alkyl, (3) C3-7 cycloalkyl, (4) C1-4 haloalkyl, (6) phenyl which may be substituted with 1 to 3 $R^{17}$, (7) C1-4 alkyl which is substituted with phenyl, (9) pyridyl or (10) 1-(cyclopropylmethyl)pyrazol-3-yl;

$R^{12H2}$ represents (1) a hydrogen atom, (2) C1-4 alkyl, (3) C3-7 cycloalkyl, (4) C1-4 haloalkyl, (5) C1-4 alkoxy, (6) phenyl which may be substituted with 1 to 3 $R^{17}$, (7) C1-4 alkyl which is substituted with phenyl, (8) dimethylamino, (9) pyridyl or (10) 1-(cyclopropylmethyl)pyrazol-3-yl; preferably, $R^{12H2}$ represents (1) a hydrogen atom, (2) C1-4 alkyl, (4) C1-4 haloalkyl, (7) C1-4 alkyl which is substituted with phenyl, (8) dimethylamino;

and $R^{17}$ represents C1-4 alkyl, C1-4 alkoxy or halogen.
the general formula (I-8):

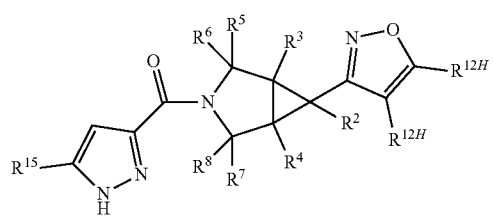
(I-8)

wherein all symbols have the same meanings as above, the general formula (I-8-1):

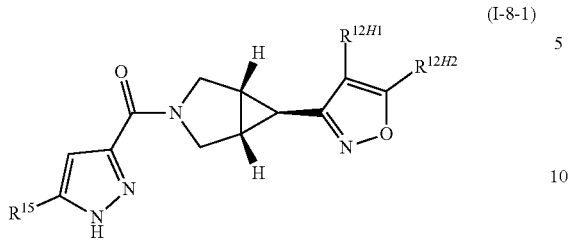

wherein R$^{15}$ represents (1) C1-8 alkyl, or (3) C1-8 haloalkyl;

R$^{12H1}$ represents (2) C1-4 alkyl, (3) C3-7 cycloalkyl, (4) C1-4 haloalkyl, (5) C1-4 alkoxy, (6) phenyl which may be substituted with 1 to 3 R$^{17}$, (7) C1-4 alkyl which is substituted with phenyl, (8) dimethylamino, (9) pyridyl or (10) 1-(cyclopropylmethyl)pyrazol-3-yl; preferably, R$^{12H1}$ represents (2) C1-4 alkyl, (3) C3-7 cycloalkyl, (4) C1-4 haloalkyl, (6) phenyl which may be substituted with 1 to 3 R$^{17}$, (7) C1-4 alkyl which is substituted with phenyl, (9) pyridyl or (10) 1-(cyclopropylmethyl)pyrazol-3-yl;

R$^{12H2}$ represents (1) a hydrogen atom, (2) C1-4 alkyl, (3) C3-7 cycloalkyl, (4) C1-4 haloalkyl, (5) C1-4 alkoxy, (6) phenyl which may be substituted with 1 to 3 R$^{17}$, (7) C1-4 alkyl which is substituted with phenyl, (8) dimethylamino, (9) pyridyl or (10) 1-(cyclopropylmethyl)pyrazol-3-yl; preferably, R$^{12H2}$ represents (1) a hydrogen atom, (2) C1-4 alkyl, (4) C1-4 haloalkyl, (7) C1-4 alkyl which is substituted with phenyl, (8) dimethylamino;

and R$^{17}$ represents C1-4 alkyl, C1-4 alkoxy or halogen.

the general formula (I-9):

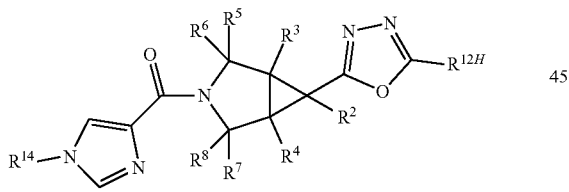

wherein all symbols have the same meanings as above, the general formula (I-10):

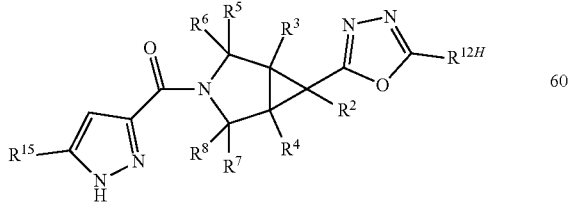

wherein all symbols have the same meanings as above, the general formula I-11):

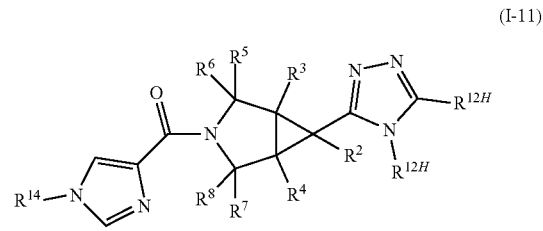

wherein all symbols have the same meanings as above, the general formula (I-11-1):

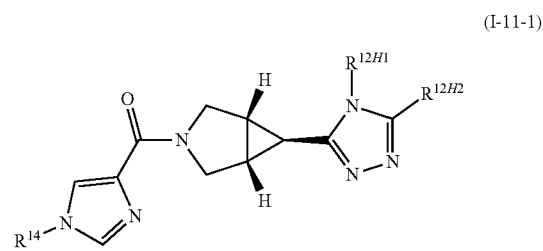

wherein R$^{14}$ represents (1) C1-8 alkyl, or (3) C1-8 haloalkyl;

R$^{12H1}$ represents (2) C1-4 alkyl, (3) C3-7 cycloalkyl, (4) C1-4 haloalkyl, (5) C1-4 alkoxy, (6) phenyl which may be substituted with 1 to 3 R$^{17}$, (7) C1-4 alkyl which is substituted with phenyl, (8) dimethylamino, (9) pyridyl or (10) 1-(cyclopropylmethyl)pyrazol-3-yl; preferably, R$^{12H1}$ represents (2) C1-4 alkyl, (3) C3-7 cycloalkyl, (4) C1-4 haloalkyl, (6) phenyl which may be substituted with 1 to 3 R$^{17}$, (7) C1-4 alkyl which is substituted with phenyl, (9) pyridyl or (10) 1-(cyclopropylmethyl)pyrazol-3-yl;

R$^{12H2}$ represents (1) a hydrogen atom, (2) C1-4 alkyl, (3) C3-7 cycloalkyl, (4) C1-4 haloalkyl, (5) C1-4 alkoxy, (6) phenyl which may be substituted with 1 to 3 R$^{17}$, (7) C1-4 alkyl which is substituted with phenyl, (8) dimethylamino, (9) pyridyl or (10) 1-(cyclopropylmethyl)pyrazol-3-yl; preferably, R$^{12H2}$ represents (1) a hydrogen atom, (2) C1-4 alkyl, (4) C1-4 haloalkyl, (7) C1-4 alkyl which is substituted with phenyl, (8) dimethylamino; and R$^{17}$ represents C1-4 alkyl, C1-4 alkoxy or halogen.

the general formula (I-12):

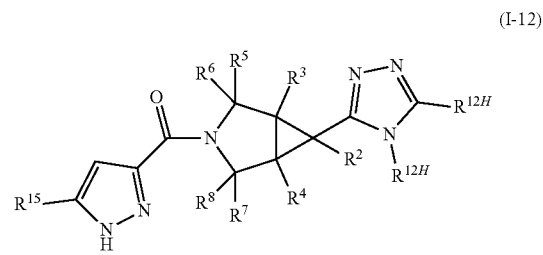

wherein all symbols have the same meanings as above, the general formula (I-12-1):

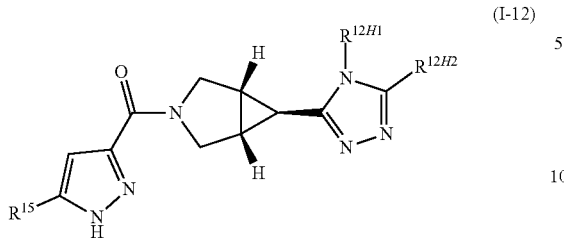
(I-12)

wherein R$^{15}$ represents (1) C1-8 alkyl, or (3) C1-8 haloalkyl;
R$^{12H1}$ represents (2) C1-4 alkyl, (3) C3-7 cycloalkyl, (4) C1-4 haloalkyl, (5) C1-4 alkoxy, (6) phenyl which may be substituted with 1 to 3 R$^{17}$, (7) C1-4 alkyl which is substituted with phenyl, (8) dimethylamino, (9) pyridyl or (10) 1-(cyclopropylmethyl)pyrazol-3-yl; preferably, R$^{12H1}$ represents (2) C1-4 alkyl, (3) C3-7 cycloalkyl, (4) C1-4 haloalkyl, (6) phenyl which may be substituted with 1 to 3 R$^{17}$, (7) C1-4 alkyl which is substituted with phenyl, (9) pyridyl or (10) 1-(cyclopropylmethyl)pyrazol-3-yl;
R$^{12H2}$ represents (1) a hydrogen atom, (2) C1-4 alkyl, (3) C3-7 cycloalkyl, (4) C1-4 haloalkyl, (5) C1-4 alkoxy, (6) phenyl which may be substituted with 1 to 3 R$^{17}$, (7) C1-4 alkyl which is substituted with phenyl, (8) dimethylamino, (9) pyridyl or (10) 1-(cyclopropylmethyl)pyrazol-3-yl; preferably, R$^{12H2}$ represents (1) a hydrogen atom, (2) C1-4 alkyl, (4) C1-4 haloalkyl, (7) C1-4 alkyl which is substituted with phenyl, (8) dimethylamino;
and R$^{17}$ represents C1-4 alkyl, C1-4 alkoxy or halogen.

the general formula (I-13):

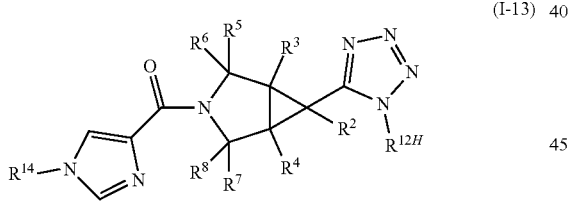
(I-13)

wherein all symbols have the same meanings as above,
the general formula (I-13-1):

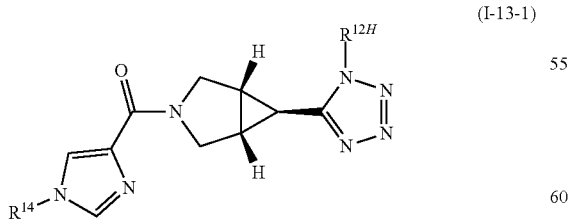
(I-13-1)

wherein R$^{14}$ represents (1) C1-8 alkyl, or (3) C1-8 haloalkyl;
R$^{12H}$ represents (1) a hydrogen atom, (2) C1-4 alkyl, (3) C3-7 cycloalkyl, (4) C1-4 haloalkyl, (5) C1-4 alkoxy, (6) phenyl which may be substituted with 1 to 3 R$^{17}$, (7) C1-4 alkyl which is substituted with phenyl, (8) dimethylamino, (9) pyridyl or (10) 1-(cyclopropylmethyl)pyrazol-3-yl; preferably, R$^{12H}$ represents (1) a hydrogen atom, (2) C1-4 alkyl, (4) C1-4 haloalkyl;
and R$^{17}$ represents C1-4 alkyl, C1-4 alkoxy or halogen.

the general formula (I-14):

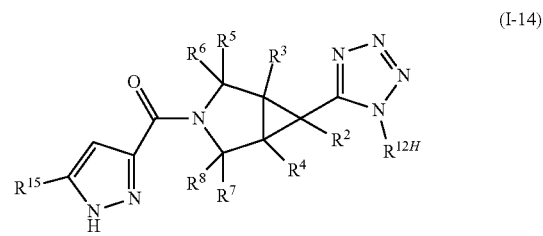
(I-14)

wherein all symbols have the same meanings as above,
the general formula (I-14-1):

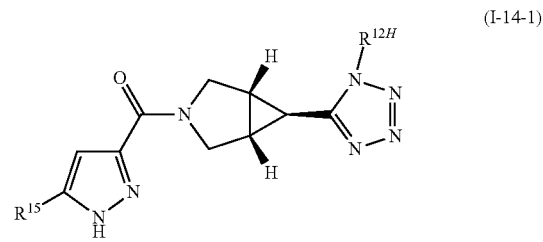
(I-14-1)

wherein R$^{15}$ represents (1) C1-8 alkyl, or (3) C1-8 haloalkyl;
R$^{12H}$ represents (1) a hydrogen atom, (2) C1-4 alkyl, (3) C3-7 cycloalkyl, (4) C1-4 haloalkyl, (5) C1-4 alkoxy, (6) phenyl which may be substituted with 1 to 3 R$^{17}$, (7) C1-4 alkyl which is substituted with phenyl, (8) dimethylamino, (9) pyridyl or (10) 1-(cyclopropylmethyl)pyrazol-3-yl; preferably, R$^{12H}$ represents (1) a hydrogen atom, (2) C1-4 alkyl, (4) C1-4 haloalkyl;
and R$^{17}$ represents C1-4 alkyl, C1-4 alkoxy or halogen.

the general formula (I-15):

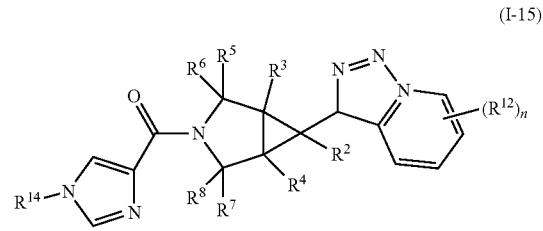
(I-15)

wherein n represents an integer of 0 to 4, and other symbols have the same meanings as above, the general formula (I-15-1):

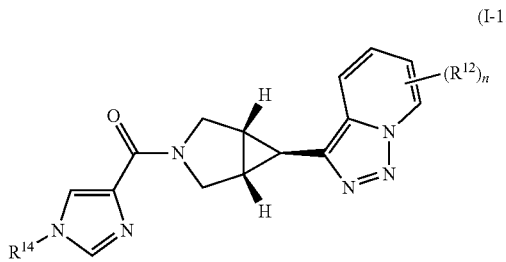

(I-15-1)

wherein R$^{14}$ represents (1) C1-8 alkyl, or (3) C1-8 haloalkyl;
R$^{12}$ represents (1) C1-4 alkyl, (2) C3-7 cycloalkyl, (3) C1-4 haloalkyl, (4) C1-4 alkoxy, (5) phenyl which may be substituted with 1 to 3 R$^{17}$, (6) C1-4 alkyl which is substituted with phenyl, (7) dimethylamino, (8) pyridyl or (9) 1-(cyclopropylmethyl)pyrazol-3-yl;
n represents an integer of 0 to 4, preferably, n is 0;
and R$^{17}$ represents C1-4 alkyl, C1-4 alkoxy or halogen.

the general formula (I-16):

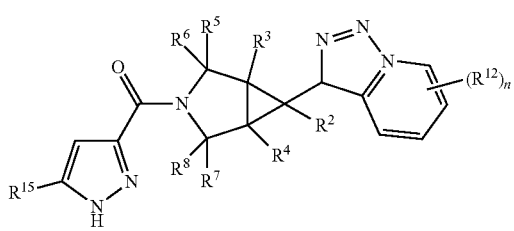

(I-16)

wherein all symbols have the same meanings as above,
the general formula (I-16-1):

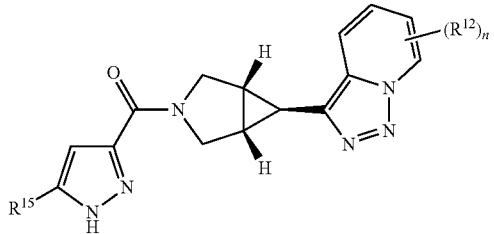

(I-16-1)

wherein R$^{15}$ represents (1) C1-8 alkyl, or (3) C1-8 haloalkyl;
R$^{12}$ represents (1) C1-4 alkyl, (2) C3-7 cycloalkyl, (3) C1-4 haloalkyl, (4) C1-4 alkoxy, (5) phenyl which may be substituted with 1 to 3 R$^{17}$, (6) C1-4 alkyl which is substituted with phenyl, (7) dimethylamino, (8) pyridyl or (9) 1-(cyclopropylmethyl)pyrazol-3-yl;
n represents an integer of 0 to 4, preferably, n is 0;
and R$^{17}$ represents C1-4 alkyl, C1-4 alkoxy or halogen.

the general formula (I-17):

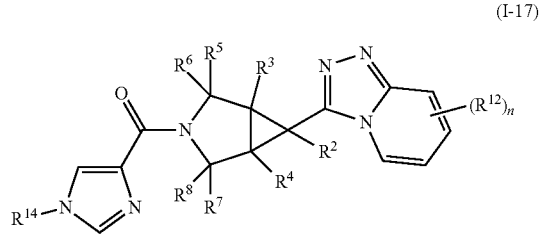

(I-17)

wherein all symbols have the same meanings as above,
the general formula (I-17-1):

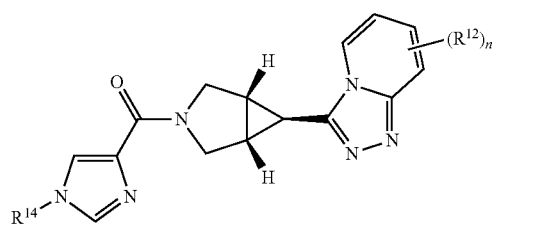

(I-17-1)

wherein R$^{14}$ represents (1) C1-8 alkyl, or (3) C1-8 haloalkyl;
R$^{12}$ represents (1) C1-4 alkyl, (2) C3-7 cycloalkyl, (3) C1-4 haloalkyl, (4) C1-4 alkoxy, (5) phenyl which may be substituted with 1 to 3 R$^{17}$, (6) C1-4 alkyl which is substituted with phenyl, (7) dimethylamino, (8) pyridyl or (9) 1-(cyclopropylmethyl)pyrazol-3-yl;
n represents an integer of 0 to 4, preferably, n is 0;
and R$^{17}$ represents C1-4 alkyl, C1-4 alkoxy or halogen;
the general formula (I-18):

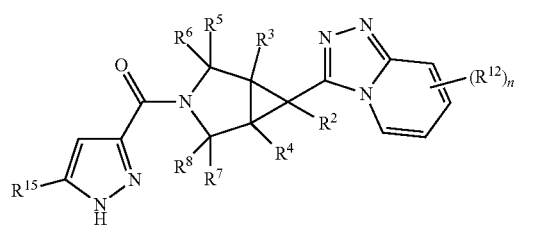

(I-18)

wherein all symbols have the same meanings as above,
the general formula (I-18-1):

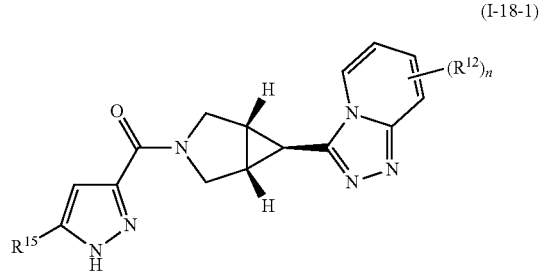

(I-18-1)

wherein R$^{15}$ represents (1) C1-8 alkyl, or (3) C1-8 haloalkyl;

$R^{12}$ represents (1) C1-4 alkyl, (2) C3-7 cycloalkyl, (3) C1-4 haloalkyl, (4) C1-4 alkoxy, (5) phenyl which may be substituted with 1 to 3 $R^{17}$, (6) C1-4 alkyl which is substituted with phenyl, (7) dimethylamino, (8) pyridyl or (9) 1-(cyclopropylmethyl)pyrazol-3-yl; preferably, $R^{12}$ represents (1) C1-4 alkyl, (2) C3-7 cycloalkyl, (3) C1-4 haloalkyl, (4) C1-4 alkoxy, n represents an integer of 0 to 4, preferably, n is 1;

and $R^{17}$ represents C1-4 alkyl, C1-4 alkoxy or halogen.

the general formula (I-19):

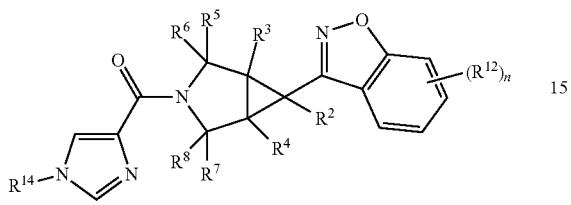

(I-19)

wherein all symbols have the same meanings as above, the general formula (I-20):

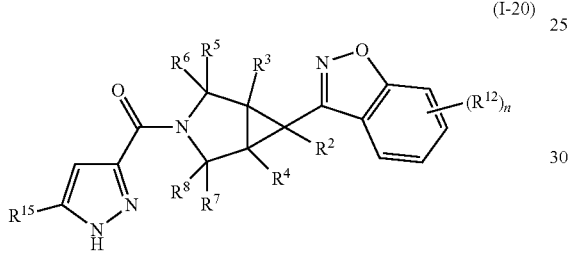

(I-20)

wherein all symbols have the same meanings as above, the general formula (I-21):

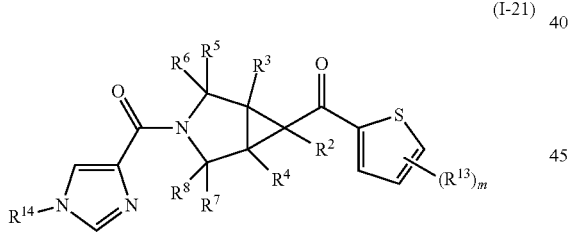

(I-21)

wherein m represents an integer of 0 to 2, and other symbols have the same meanings as above, the general formula (I-21-1):

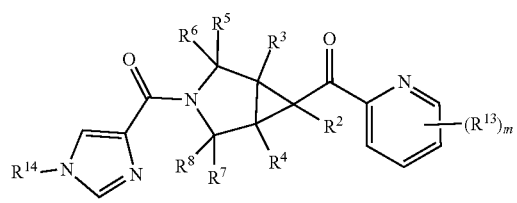

(I-21-1)

wherein $R^{14}$ represents (1) C1-8 alkyl, or (3) C1-8 haloalkyl;

$R^{13}$ represents C1-4 alkyl, C1-4 alkoxy or halogen; and m represents an integer of 0 to 2.

the general formula (I-22):

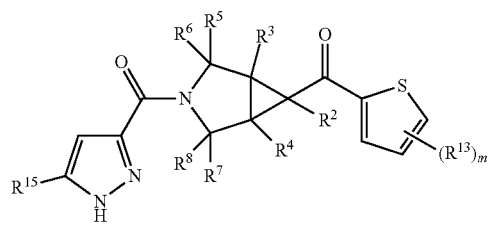

(I-22)

wherein a symbols have the same meanings as above, the general formula (I-23):

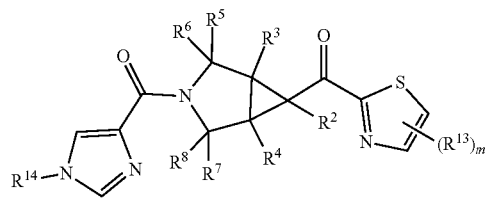

(I-23)

wherein all symbols have the same meanings as above, the general formula (I-24):

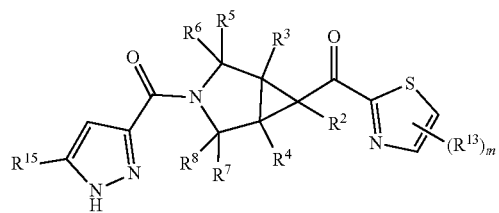

(I-24)

wherein all symbols have the same meanings as above, the general formula (I-25):

(I-25)

wherein all symbols have the same meanings as above, the general formula (I-26):

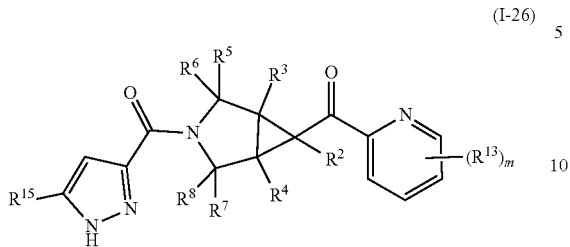

(I-26)

wherein all symbols have the same meanings as above,
the general formula (I-27):

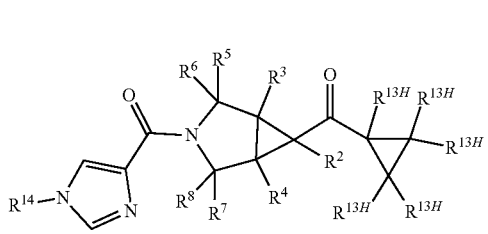

(I-27)

wherein $R^{13H}$ represents a hydrogen atom, C1-4 alkyl, C1-4 alkoxy or halogen, and other symbols have the same meanings as above, the general formula (I-28):

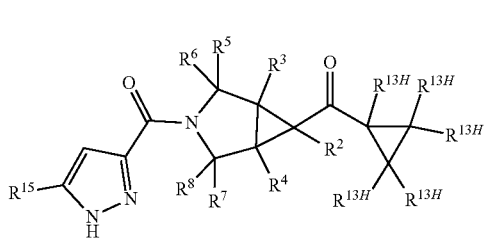

(I-28)

wherein all symbols have the same meanings as above,
the general formula (I-29):

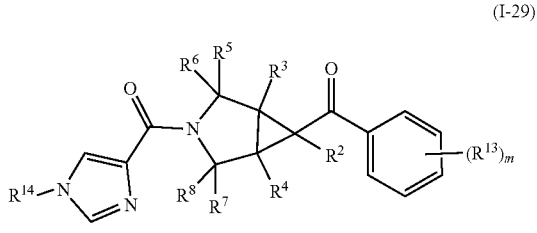

(I-29)

wherein all symbols have the same meanings as above, the general formula (I-30):

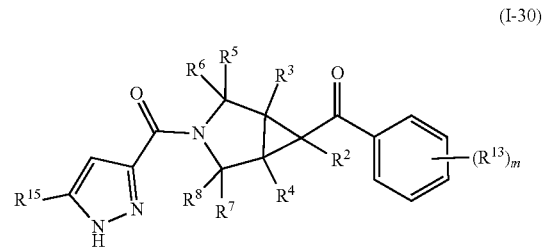

(I-30)

wherein all symbols have the same meanings as above,
the general formula (I-31):

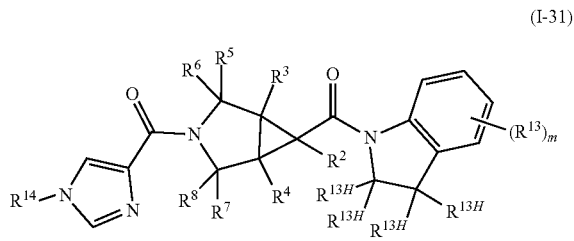

(I-31)

wherein all symbols have the same meanings as above,
the general formula (I-32):

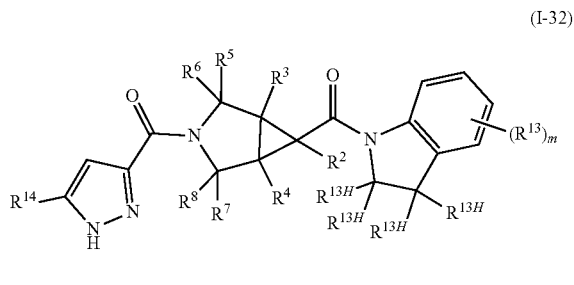

(I-32)

wherein all symbols have the same meanings as above,
the general formula (I-33):

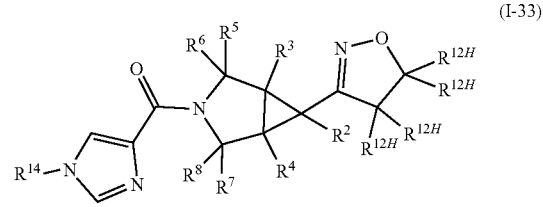

(I-33)

wherein all symbols have the same meanings as above, the general formula (I-33-1):

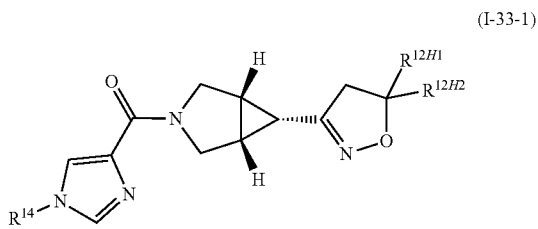

wherein R$^{14}$ represents (1) C1-8 alkyl, or (3) C1-8 haloalkyl;

R$^{12H1}$ represents (2) C1-4 alkyl, (3) C3-7 cycloalkyl, (4) C1-4 haloalkyl, (5) C1-4 alkoxy, (6) phenyl which may be substituted with 1 to 3 R$^{17}$, (7) C1-4 alkyl which is substituted with phenyl, (8) dimethylamino, (9) pyridyl or (10) 1-(cyclopropylmethyl)pyrazol-3-yl; preferably, R$^{12H1}$ represents (2) C1-4 alkyl, (3) C3-7 cycloalkyl, (4) C1-4 haloalkyl, (6) phenyl which may be substituted with 1 to 3 R$^{17}$, (7) C1-4 alkyl which is substituted with phenyl, (9) pyridyl or (10) 1-(cyclopropylmethyl)pyrazol-3-yl;

R$^{12H2}$ represents (1) a hydrogen atom, (2) C1-4 alkyl, (3) C3-7 cycloalkyl, (4) C1-4 haloalkyl, (5) C1-4 alkoxy, (6) phenyl which may be substituted with 1 to 3 R$^{17}$, (7) C1-4 alkyl which is substituted with phenyl, (8) dimethylamino, (9) pyridyl or (10) 1-(cyclopropylmethyl) pyrazol-3-yl; preferably, R$^{12H2}$ represents (1) a hydrogen atom, (2) C1-4 alkyl, (4) C1-4 haloalkyl, (7) C1-4 alkyl which is substituted with phenyl, (8) dimethylamino;

and R$^{17}$ represents C1-4 alkyl, C1-4 alkoxy or halogen;

the general formula (I-34):

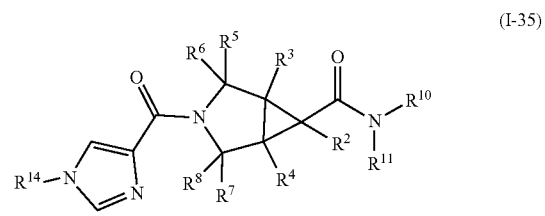

wherein all symbols have the same meanings as above, the general formula (I-34-1)

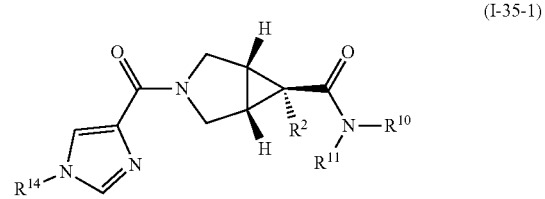

wherein R$^{15}$ represents (1) C1-8 alkyl, or (3) C1-8 haloalkyl;

R$^{12H1}$ represents (2) C1-_4 alkyl, (3) C3-7 cycloalkyl, (4) C1-4 haloalkyl, (5) C1-4 alkoxy, (6) phenyl which may be substituted with 1 to 3 R$^{17}$, (7) C1-4 alkyl which is substituted with phenyl, (8) dimethylamino, (9) pyridyl or (10) 1-(cyclopropylmethyl)pyrazol-3-yl; preferably, R$^{12H1}$ represents (2) C1-_4 alkyl, (3) C3-7 cycloalkyl, (4) C1-4 haloalkyl, (6) phenyl which may be substituted with 1 to 3 R$^{17}$, (7) C1-4 alkyl which is substituted with phenyl, (9) pyridyl or (10) 1-(cyclopropylmethyl)pyrazol-3-yl;

R$^{12H2}$ represents (1) a hydrogen atom, (2) C1-4 alkyl, (3) C3-7 cycloalkyl, (4) C1-4 haloalkyl, (5) C1-4 alkoxy, (6) phenyl which may be substituted with 1 to 3 R$^{17}$, (7) C1-4 alkyl which is substituted with phenyl, (8) dimethylamino, (9) pyridyl or (10) 1-(cyclopropylmethyl) pyrazol-3-yl; preferably, R$^{12H2}$ represents (1) a hydrogen atom, (2) C1-4 alkyl, (4) C1-4 haloalkyl, (7) C1-4 alkyl which is substituted with phenyl, (8) dimethylamino; and R$^{17}$ represents C1-4 alkyl, C1-4 alkoxy or halogen;

the general formula (I-35):

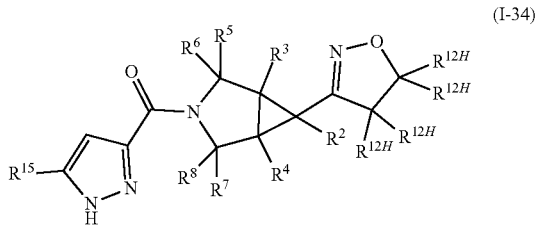

wherein all symbols have the same meanings as above, the general formula (I-35-1):

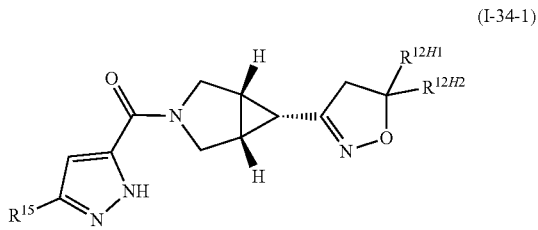

wherein R$^2$ represents a hydrogen atom, C1-4 alkyl, halogen or C1-4 alkoxy;

R$^{14}$ represents (1) C1-8 alkyl, or (3) C1-8 haloalkyl;

R$^{10}$ represents C1-8 alkyl, or C1-8 haloalkyl, preferably, R$^{10}$ represents isopropyl, tert-butyl, 1,1,1-trifluoro-2-methylpropan-2-yl; and R$^{11}$ represents a hydrogen atom or C1-4 alkyl;

the general formula (I-36):

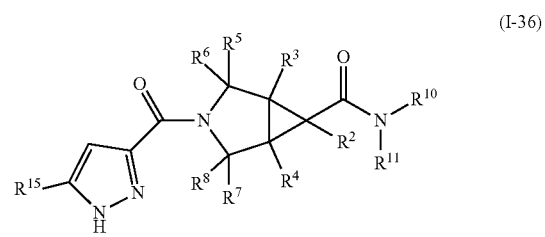

wherein all symbols have the same meanings as above;

and the general formula (I-36-1-1):

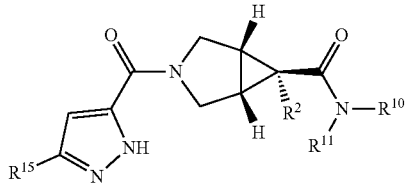
(I-36-1-1)

wherein R² represents a hydrogen atom, C1-4 alkyl, halogen or C1-4 alkoxy;
R¹⁵ represents (1) C1-8 alkyl, or (3) C1-8 haloalkyl;
R¹⁰ represents C1-8 alkyl, or C1-8 haloalkyl, preferably, R¹⁰ represents isopropyl, tert-butyl, 1,1,1-trifluoro-2-methylpropan-2-yl; and
R¹¹ represents a hydrogen atom or C1-4 alkyl.

In the present invention, examples of the general formula (I) preferably include the general formula (I-37):

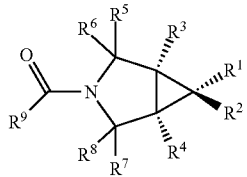
(I-37)

wherein all symbols have the same meanings as above.

In the present invention, examples of the general formula (I) preferably include the general formula (I-01):

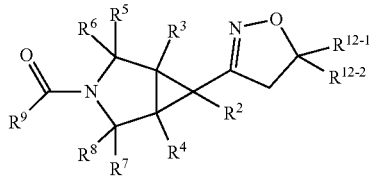
(I-01)

wherein all symbols have the same meanings as above.

In the present invention, examples of the general formula (I) preferably include the general formula (I-02):

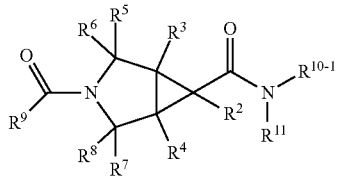
(I-02)

wherein all symbols have the same meanings as above.

In the present invention, the stereo configuration of substituents corresponding to the substituents represented by R¹, R³ and R⁴ on 3-azabicyclo[3.1.0]hexane ring of the general formulae (I-1) to (1-36) is preferably in the same direction, like the general formula (I-37).

In the present invention, or in the general formula (I) or (I-1), the compound is preferably, for example:

(1) [(1R,5S,6r)-6-(5,5-dimethyl-4,5-dihydro-1,2-oxazol-3-yl)-3-azabicyclo[3.1.0]hex-3-yl](1-isopropyl-1H-imidazol-4-yl)methanone;
(2) [(1R,5S,6r)-6-(5,5-dimethyl-4,5-dihydro-1,2-oxazol-3-yl)-3-azabicyclo[3.1.0]hex-3-yl][1-(1-methylcyclopropyl)-1H-imidazol-4-yl]methanone;
(3) (1-cyclopropyl-1H-imidazol-4-yl)[(1R,5S,6r)-6-(5,5-dimethyl-4,5-dihydro-1,2-oxazol-3-yl)-6-methyl-3-azabicyclo[3.1.0]hex-3-yl]methanone;
(4) (1-cyclopropyl-1H-imidazol-4-yl)[(1R,5S,6r)-6-methyl-6-(4-oxa-5-azaspiro[2.4]hept-5-en-6-yl)-3-azabicyclo[3.1.0]hex-3-yl]methanone;
(5) {1-[(2S)-butan-2-yl]-1H-imidazol-4-yl}[(1R,5S,6S)-6-(5,5-dimethyl-4,5-dihydro-1,2-oxazol-3-yl)-3-azabicyclo[3.1.0]hex-3-yl]methanone;
(6) [(1R,5S,6r)-6-(5,5-dimethyl-4,5-dihydro-1,2-oxazol-3-yl)-6-methyl-3-azabicyclo[3.1.0]hex-3-yl](1-isopropyl-1H-imidazol-4-yl)methanone;
(7) (1-isopropyl-1H-imidazol-4-yl)[(1R,5S,6r)-6-methyl-6-(4-oxa-5-azaspiro[2.4]hept-5-en-6-yl)-3-azabicyclo[3.1.0]hex-3-yl]methanone;
(8) (1-cyclopropyl-1H-imidazol-4-yl)[(1R,5S,6r)-6-(4-oxa-5-azaspiro[2.4]hept-5-en-6-yl)-3-azabicyclo[3.1.0]hex-3-yl]methanone or
(9) [1-(1-methylcyclopropyl)-1H-imidazol-4-yl][(1R,5S,6r)-6-(4-oxa-5-azaspiro[2.4]hept-5-en-6-yl)-3-azabicyclo[3.1.0]hex-3-yl]methanone;
or a salt thereof.

In the present invention, or in the general formula (I) or (I-2), the compound is also preferably, for example:

(1) [(1R,5S,6r)-6-(5,5-dimethyl-4,5-dihydro-1,2-oxazol-3-yl)-3-azabicyclo[3.1.0]hex-3-yl](5-isopropyl-1H-pyrazol-3-yl)methanone;
(2) (5-isopropyl-1H-pyrazol-3-yl)[(1R,5S,6r)-6-(2-oxa-3-azabicyclo[3.1.0]hex-3-en-4-yl)-3-azabicyclo[3.1.0]hex-3-yl]methanone;
(3) [5-(1-cyclopropylethyl)-1H-pyrazol-3-yl][(1R,5S,6r)-6-(5,5-dimethyl-4,5-dihydro-1,2-oxazol-3-yl)-3-azabicyclo[3.1.0]hex-3-yl]methanone;
(4) [(1R,5S,6r)-6-(5,5-dimethyl-4,5-dihydro-1,2-oxazol-3-yl)-6-methyl-3-azabicyclo[3.1.0]hex-3-yl](5-isopropyl-1H-pyrazol-3-yl)methanone or
(5) (5-cyclopropyl-1H-pyrazol-3-yl)[(1R,5S,6r)-6-methyl-6-(4-oxa-5-azaspiro[2.4]hept-5-en-6-yl)-3-azabicyclo[3.1.0]hex-3-yl]methanone or a salt thereof.

In the present invention, or in the general formula (I) or (1-3), the compound is also preferably, for example:

(1) (1R,5S,6r)-N-tert-butyl-6-methyl-3-[1-(propan-2-yl)-1H-imidazole-4-carbonyl]-3-azabicyclo[3.1.0]hexane-6-carboxamide;
(2) (1R,5S,6r)-N-tert-butyl-3-[1-(propan-2-yl)-1H-imidazole-4-carbonyl]-3-azabicyclo[3.1.0]hexane-6-carboxamide;
(3) (1R,5S,6r)-N-(propan-2-yl)-3-[1-(propan-2-yl)-1H-imidazole-4-carbonyl]-3-azabicyclo[3.1.0]hexane-6-carboxamide or
(4) (1R,5S,6r)-N-(1-cyanocyclopropyl)-3-[1-(propan-2-yl)-1H-imidazole-4-carbonyl]-3-azabicyclo[3.1.0]hexane-6-carboxamide or a salt thereof.

In the present invention, or in the general formula (I) or (I-4), the compound is also preferably, for example:

(1) (1R,5S,6r)-N-(propan-2-yl)-3-[5-(propan-2-yl)-1H-pyrazole-3-carbonyl]-3-azabicyclo[3.1.0]hexane-6-carboxamide;
(2) (1R,5S,6r)-N-tert-butyl-6-methyl-3-[5-(propan-2-yl)-1H-pyrazole-3-carbonyl]-3-azabicyclo[3.1.0]hexane-6-carboxamide;

(3) (1R,5S,6r)-N-tert-butyl-N-methyl-3-[5-(propan-2-yl)-1H-pyrazole-3-carbonyl]-3-azabicyclo[3.1.0]hexane-6-carboxamide or
(4) (1R,5S,6r)-N-methyl-N-(1-methylcyclopropyl)-3-[5-(propan-2-yl)-1H-pyrazole-3-carbonyl]-3-azabicyclo[3.1.0]hexane-6-carboxamide, or a salt thereof.

[Isomers]

The present invention encompasses all isomers unless otherwise particularly stated. For example, alkyl groups, alkoxy groups and the like include linear and branched groups. Moreover, the present invention encompasses isomers for double bonds, rings and condensed rings (E-forms, Z-forms, cis forms and trans forms), isomers due to asymmetrical carbon atoms (R and S forms, a and 3 configurations, enantiomers and diastereomers), optically active substances having optical rotating activity (D, L, d and l forms), polar substances which can be separated by chromatography (high polarity substances and low polarity substances), equilibrium compounds, rotamers, mixtures thereof at arbitrary proportions and racemic mixtures. The present invention also encompasses tautomers.

[Salt and Solvate]

A salt of the compound represented by the general formula (I) disclosed herein encompasses all pharmacologically acceptable salts. The pharmacologically acceptable salt is preferably a water-soluble salt with low toxicity. Examples of appropriate salts include acid addition salts (such as inorganic acid salt [examples: hydrochloride, hydrobromide, hydroiodide, sulphate, phosphate, nitrate and the like], organic acid salts [examples: acetate, trifluoroacetate, lactate, tartrate, oxalate, fumarate, maleate, benzoate, citrate, methanesulphonate, ethanesulphonate, benzenesulphonate, toluenesulphonate, isethionate, glucuronate, gluconate and the like], salts with acidic natural amino acids [examples: aspartate, glutamate and the like] and the like) and the like.

A salt also encompasses quaternary ammonium salts. The quaternary ammonium salt represents a compound represented by the general formula (I) in which a nitrogen atom thereof is quaternised with an $R^0$ group. The $R^0$ group as used herein represents, for example, a C1-8 alkyl group which may be substituted with a phenyl group.

The compound represented by the general formula (I) can be converted to the salt, N-oxide and solvate according to well-known methods.

The N-oxide of the compound represented by the general formula (I) represents the compound represented by the general formula (I) in which a nitrogen atom is oxidized. The N-oxide may form salts such as acid addition salts as described above.

The compound represented by the general formula (I), a salt thereof or an N-oxide thereof may form a solvate with, for example, water or an alcoholic solvent (such as ethanol). The solvate preferably has low toxicity and is water soluble.

The compound represented by the general formula (I) and a salt thereof may be in the form of without forming a solvate or may be in the form of a solvate with a pharmaceutically acceptable solvent such as water and ethanol. The solvate is preferably a hydrate. The compound represented by the general formula (I) or a salt thereof can be converted to the solvate according to well-known methods.

The compound represented by the general formula (I) and a salt thereof may form a co-crystal with an appropriate co-crystal former. The co-crystal is preferably pharmaceutically acceptable as formed with a pharmaceutically acceptable co-crystal former. A co-crystal is defined to be a crystal typically formed of 2 or more molecules by intermolecular interaction that is not ionic bonding. The co-crystal may be a complex of a neutral molecule and a salt. Co-crystals may be prepared according to well-known methods such as melt crystallization, recrystallization from a solvent or physical grinding of components together. Appropriate co-crystal formers include those disclosed in WO 2006/007448.

In the present invention, all the recitations on the present compound encompass the compound represented by the general formula (I), a salt thereof, a solvate (such as hydrate) thereof, an N-oxide thereof or a co-crystal thereof, or a solvate (such as hydrate), N-oxide or co-crystal of a salt of the compound represented by the general formula (I).

Namely, in the present invention, the compound represented by the general formula (I) or a salt thereof encompasses a solvate (such as hydrate), N-oxide or co-crystal of the compound represented by the general formula (I) or a solvate (such as hydrate), N-oxide or co-crystal of a salt of the compound represented by the general formula (I).

[Prodrug]

The prodrug of the compound represented by the general formula (I) refers to a compound which is converted in vivo to the compound represented by the general formula (I) by the reaction with enzymes, gastric acid and the like. Examples of the prodrug of the compound represented by the general formula (I) include, when the compound represented by the general formula (I) has an amino group, compounds in which the amino group is acylated, alkylated or phosphorylated (e.g. compounds represented by the general formula (I) in which the amino group thereof is converted to eicosanoyl, alanyl, pentylaminocarbonyl, (5-methyl-2-oxo-1,3-dioxolen-4-yl)methoxycarbonyl, tetrahydrofuranyl, pyrrolidylmethyl, pivaloyloxymethyl, acetoxymethyl, tert-butyl or the like); when the compound represented by the general formula (I) has a hydroxy group, compounds in which the hydroxy group is acylated, alkylated, phosphorylated or converted to borate (e.g. compounds represented by the general formula (I) in which the hydroxy group thereof is converted to acetyl, palmitoyl, propanoyl, pivaloyl, succinyl, fumaryl, alanyl, dimethylaminomethylcarbonyl or the like) and the like. The prodrug of the compound represented by the general formula (I) may be the one which is converted to the compound represented by the general formula (I) under the physiological condition such as those disclosed in "Iyakuhin no Kaihatsu", vol. 7 "Bunshi Sekkei", p. 163-198, 1990, Hirokawa Shoten Co. The prodrug of the compound represented by the general formula (I) can be produced by the methods well known per se. The prodrug of the compound represented by the general formula (I) may form, similarly to the compound represented by the general formula (I), for example, salts such as acid addition salts, or may form solvates with water or an alcoholic solvent (such as ethanol).

[Labelled Compound]

In the present invention, the compound represented by the general formula (I), or a salt thereof encompasses a so-called labelled compound in which some or all atoms constituting the compound is substituted with an isotope thereof. The labelled compound may be produced according to the methods well known per se. Examples of isotopes which may be used for labelling suitably include, but are not limited to, $^2H$, $^3H$, $^{13}C$, $^{14}C$, $^{15}N$, $^{16}N$, $^{17}O$, $^{18}O$, $^{35}S$, $^{36}Cl$, $^{77}Br$, $^{125}I$ and the like.

[Production Method]

[Method for Producing Compound of the Present Invention]

The compound represented by the general formula (I) or a salt thereof may be produced by well-known methods, for example, methods described in the following methods represented in Scheme I to XII, methods equivalent to these methods, methods described in Examples, methods equivalent to those described in Examples, or methods described in Comprehensive Organic Transformations: A Guide to Functional Group Preparations, 2nd Edition (Richard C. Larock, John Wiley & Sons Inc., 1999), methods adapted from the foregoing or methods combining the foregoing without limitation. In the production methods described hereinbelow, raw material compounds may be those forming salts. Examples of the salts include those mentioned above as salts of the compound represented by the general formula (I).

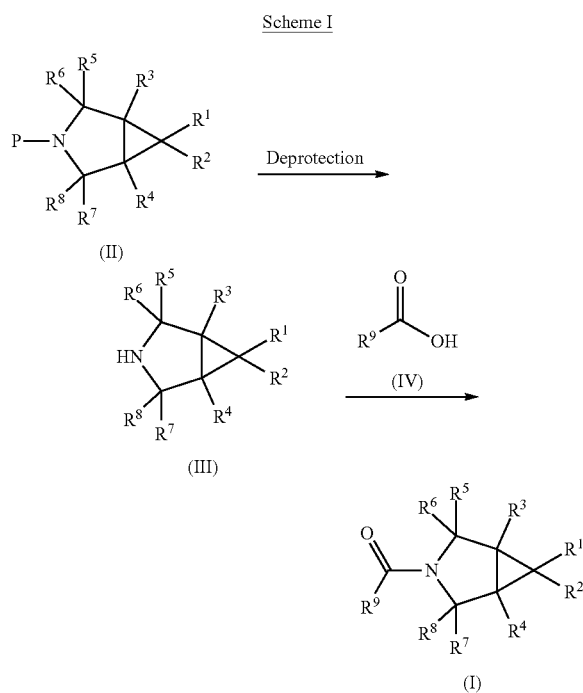

Scheme I

Wherein the compound represented by the general formula (I) can be produced by subjecting the compound represented by the general formula (III) and the compound represented by the general formula (IV) to an amidation reaction.

The amidation is known. For example, it includes the method
(1) via an acyl halide,
(2) via a mixed acid anhydride,
(3) using a condensing agent.

These methods are explained as follows.

(1) The method via an acyl halide may be carried out, for example, by reacting a carboxylic acid with an acyl halide (e.g., oxalyl chloride or thionyl chloride) in an organic solvent (e.g., chloroform, dichloromethane, diethyl ether or tetrahydrofuran) or without a solvent at about −20° C. to reflux temperature. And then, the obtained acyl halide derivative may be reacted with an amine in an organic solvent (e.g., chloroform, dichloromethane, diethyl ether or tetrahydrofuran) in the presence of a base (e.g., pyridine, triethylamine, dimethylaniline, dimethylaminopyridine or diisopropylethylamine etc.) at about 0 to 40° C. As an alternative, the obtained acyl halide derivative may be reacted with an amine in an organic solvent (e.g., dioxane, tetrahydrofuran) using an alkaline aqueous solution (e.g., sodium hydrogen carbonate, sodium hydroxide) at about −78 to 40° C.

(2) The method via a mixed acid anhydride may be carried out, for example, by reacting a carboxylic acid with an acyl halide (e.g., pivaloyl chloride, p-toluenesulfonyl chloride or methanesulfonyl chloride) or an acid derivative (e.g., ethyl chloroformate or isobutyl chloroformate) in an organic solvent (e.g., chloroform, dichloromethane, diethyl ether, tetrahydrofuran) or without a solvent, in the presence of a base (e.g., pyridine, triethylamine, dimethylaniline, dimethylaminopyridine or diisopropylethylamine) at about 0 to 40° C. And then the obtained mixed acid anhydride derivative may be reacted with an amine in an organic solvent (e.g., chloroform, methylene chloride, diethyl ether or tetrahydrofuran), at about 0 to 40° C.

(3) The method using a condensing agent may be carried out, for example, by reacting a carboxylic acid with amine in an organic solvent (e.g., chloroform, dichloromethane, dimethylformamide, diethyl ether or tetrahydrofuran) or without a solvent, in the presence or absence of a base (e.g., pyridine, triethylamine, dimethylaniline or dimethylaminopyridine), using a condensing agent (e.g., 1,3-dicyclohexyl carbodiimide (DCC), 1-ethyl-3-[3-(dimethylamino)propyl] carbodiimide (EDC), 1,1'-carbodiimidazole (CDI), 2-chloro-1-methylpyridinium iodide, or 1-propanephosphonic acid cyclic anhydride (PPA)), in the presence or absence of 1-hydroxybenzotriazole (HOBt), at about 0 to 40° C.

The reaction described in (1), (2) and (3) may be carried out under an inert gas (e.g., argon, nitrogen) to avoid water in order to obtain a preferable result.

The compound represented by the general formula(III) can be produced by subjecting the compound represented by the general formula (II) to a deprotection reaction of protecting group of amino group.

P in the general formula (II) is represented a protecting group of amino group.

P includes such as benzyloxycarbonyl (Z), tert-butoxycarbonyl (Boc), allyloxycarbonyl (Alloc), 1-methyl-1-(4-biphenyl)ethoxycarbonyl (Bpoc), trifluoroacetyl, 9-fluorenylmethoxycarbonyl (Fmoc), benzyl (Bn), p-methoxybenzyl, benzyloxymethyl (BOM) or 2-(trimethylsilyl)ethoxymethyl (SEM) etc.

Deprotection reaction of protecting group of amino group can be conducted by suitable condition of each protective group.

For example, a deprotection of tert-butoxycarbonyl (Boc) group can be conducted with acidic reagent (e.g., HCl/dioxane, TFA or MsOH) in solvent (e.g., dioxane or dichloromethane) at 0° C. to 40° C.

For example, a deprotection of benzyloxycarbonyl (Z) group can be conducted by hydrogenation condition such as hydrogen and catalytic Pd—C in solvent (e.g., MeOH or EtOH etc.) at 20° C. to 60° C.

Deprotection reaction of protecting group of amino group is well known and well described in T. W. Greene, *Protective Groups in Organic Synthesis*, Wiley, New York, 1999.

Scheme II

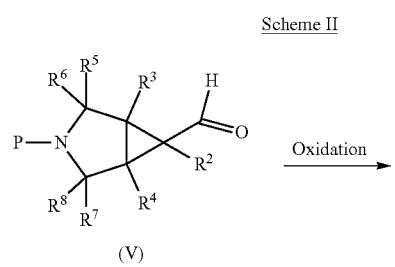

Oxidation

-continued

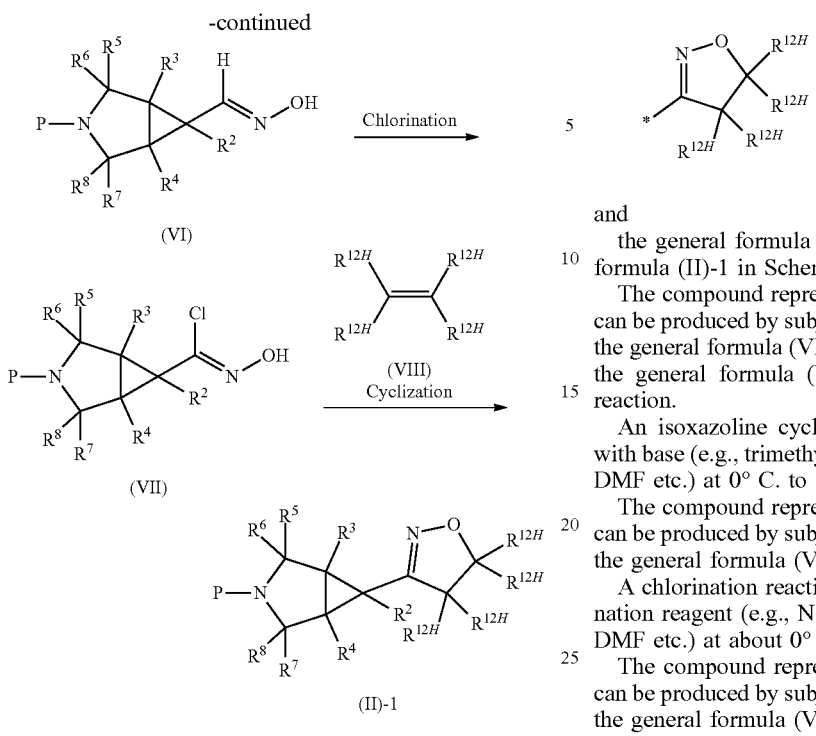

Wherein R¹ in the general formula (II) in Scheme I represents.

and
the general formula (II) can be described as the general formula (II)-1 in Scheme II.

The compound represented by the general formula (II)-1 can be produced by subjecting the compound represented by the general formula (VII) and the compound represented by the general formula (VIII) to an isoxazoline cyclization reaction.

An isoxazoline cyclization reaction can be carried out with base (e.g., trimethylamine or DIPEA) and solvent (e.g., DMF etc.) at 0° C. to 80° C.

The compound represented by the general formula (VII) can be produced by subjecting the compound represented by the general formula (VI) to a chlorination reaction.

A chlorination reaction can be carried out with a chlorination reagent (e.g., N-chlorosuccinimide) in solvent (e.g., DMF etc.) at about 0° C. to 40° C.

The compound represented by the general formula (VI) can be produced by subjecting the compound represented by the general formula (V) to an oxime forming reaction.

An oxime forming reaction can be carried out with hydroxylamine hydrochloride, potassium acetate and acetic acid in solvent (e.g., EtOH etc.) at about 20° C. to 40° C.

Scheme III

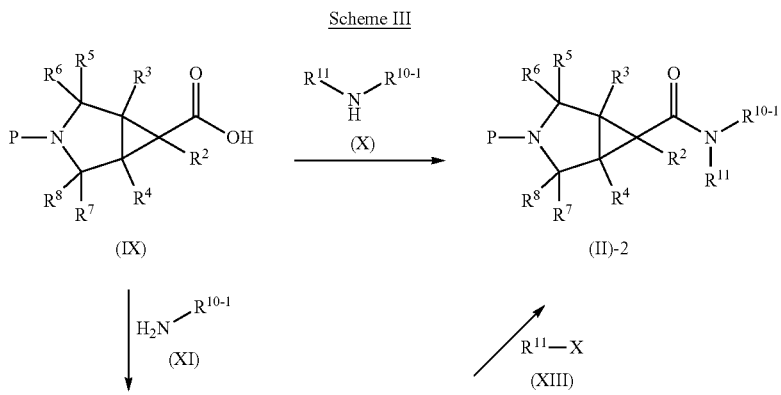

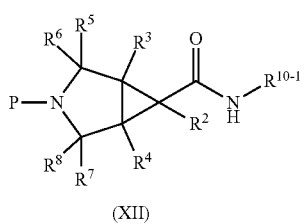

Wherein R¹ in the general formula (II) in Scheme I represents

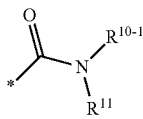

and the general formula (II) can be described as the general formula (II)-2 in Scheme III.

The compound represented by the general formula (II)-2 can be produced by subjecting the compound represented by the general formula (IX) and the compound represented by the general formula (X) to an amidation reaction.

An amidation can be carried out by the same method described above for the preparation of the general formula (I) in Scheme I.

The compound represented by the general formula (II)-2 can be produced by subjecting the compound represented by the general formula (XII) and the compound represented by the general formula (XIII) to an alkylation reaction.

An alkylation reaction can be carried out with base (e.g., sodium hydride, potassium hydride, lithium hydride, sodium methoxide, sodium ethoxide, potassium tert-butoxide, butyl lithium, LDA, LHMDS, NaHMDS, KHMDS etc.) in solvent (e.g., THF, DMF, DMA, diethyl ether etc) at −78° C. to 40° C.

The compound represented by the general formula (XII) can be produced by subjecting the compound represented by the general formula (IX) and the compound represented by the general formula (XI) to an amidation reaction.

An amidation can be carried out by the same method described above for the preparation of the general formula (I) in Scheme I.

Wherein R¹ in the general formula (II) in Scheme I represents

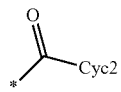

and the general formula (II) can be described as the general formula (II)-3 in Scheme IV.

The compound represented by the general formula (II)-3 can be produced by subjecting the compound represented by the general formula (XV) to an oxidation reaction of hydroxyl group.

The oxidation of hydroxyl group is known. For example, it includes the method
(1) Dess-Martin oxidation
(2) DMSO oxidation
(3) Chromium reagent oxidation.

These methods are explained as follows.
(1) The method of Dess-Martin oxidation can be carried out with Dess-Martin Periodinane in solvent (for example methylene chloride) at 0° C. to 40° C.
(2) The method of DMSO oxidation can be carried out with DMSO and its activator (e.g., oxalyl chloride, thionyl chloride or sulfur trioxide pyridinium complex etc.) and base (for example trimethylamine or DIPEA etc) at −78° C. to 40° C.
(3) The method of chromium reagent oxidation is carried out with chromium oxidant (for example PCC or PDC) in solvent (for example dichloromethane) at −20° C. to 40° C.

The compound represented by the general formula (XV) can be produced by subjecting the compound represented by the general formula (V) and the compound represented by the general formula (XIV) to an addition reaction.

Wherein M in the general formula (XIV) represents metal (e.g., Li, Na or K) or metal halide (MgCl, MgBr, MgI, ZnCl, ZnBr or ZnI).

An addition reaction can be carried out in solvent (e.g., THF) at −78° C. to 0° C. under inert atmosphere (e.g., dry nitrogen or argon).

Scheme IV

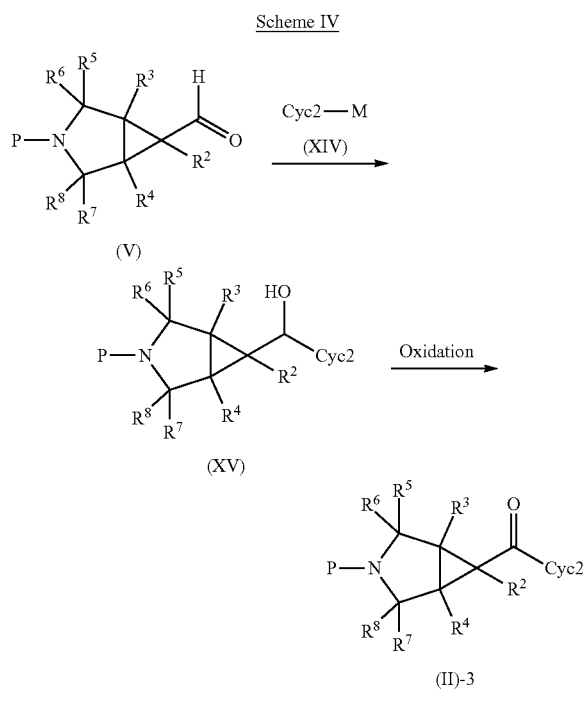

Scheme V

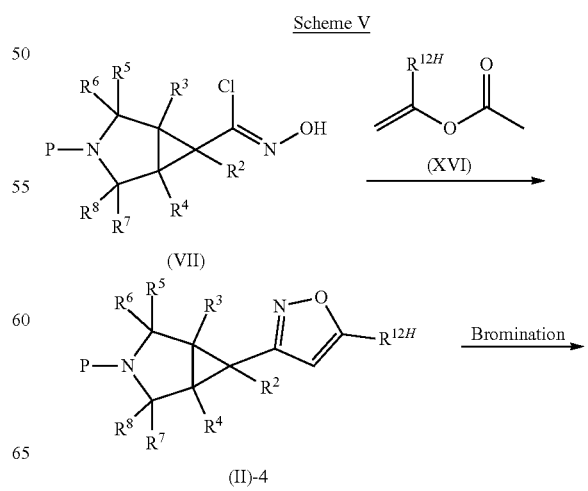

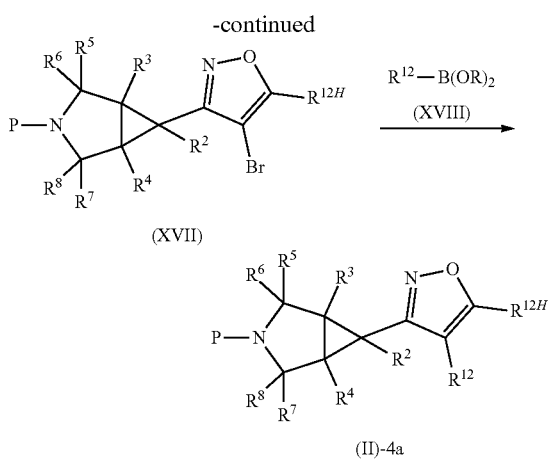

(XVII)

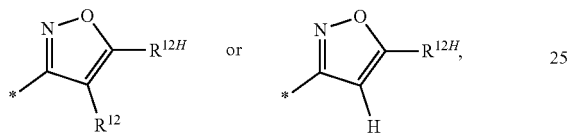

(II)-4a

Wherein R¹ in the general formula (II) in Scheme I represents

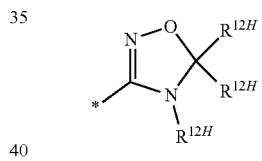

and
the general formula (II) can be described as the general formula (II)-4 and (II)-4a in Scheme V.

The compound represented by the general formula (II)-4 can be produced by subjecting the compound represented by the general formula (VII) and the compound represented by the general formula (XVI) to an isoxazole cyclization reaction.

An isoxazole cyclization reaction can be carried out with base (for example trimethylamine etc.) in solvent (for example dichloromethane etc.) at −20° C. to 40° C.

The compound represented by the general formula (II)-4a can be produced by subjecting the compound represented by the general formula (XVII) and the compound represented by the general formula (XVIII) to a coupling reaction.

The coupling reaction is well known and can be carried out by, for example, reacting in an organic solvent (examples: benzene, toluene, dimethylformamide, 1,4-dioxane, tetrahydrofuran, methanol, acetonitrile, dimethoxyethane, acetone or mixed solvents thereof), with a base (examples: sodium ethylate, sodium hydroxide, potassium hydroxide, triethylamine, sodium carbonate, sodium hydrogen carbonate, potassium carbonate, caesium carbonate, thallium carbonate, tripotassium phosphate, caesium fluoride, barium hydroxide, tetrabutylammonium fluoride and the like) or aqueous solutions thereof or mixtures thereof in the presence of a catalyst (examples: bis(di-tert-butyl(4-dimethylaminophenyl)phosphine)dichloropalladium(II) ((A-taPhos)$_2$PdCl$_2$), tetrakis(triphenylphosphine)palladium (Pd(PPh$_3$)$_4$), bis(triphenylphosphine)palladium dichloride (PdCl$_2$(PPh$_3$)$_2$), palladium acetate (Pd(OAc)$_2$), palladium black, 1,1'-bis(diphenylphosphinoferrocene)dichloropalladium (PdCl$_2$(dppf)$_2$), diallylpalladium dichloride (PdCl$_2$(allyl)$_2$), iodophenyl bis(triphenylphosphine)palladium (PhPdI(PPh$_3$)$_2$) and the like) at room temperature to 150° C.

The compound represented by the general formula (XVII) can be produced by subjecting the compound represented by the general formula (II)-4 to a bromination reaction.

A bromination reaction can be carried out with bromination reagent (e.g., NBS or bromine etc.) in solvent (for example DMF etc.) at −20° C. to 40° C.

Scheme VI

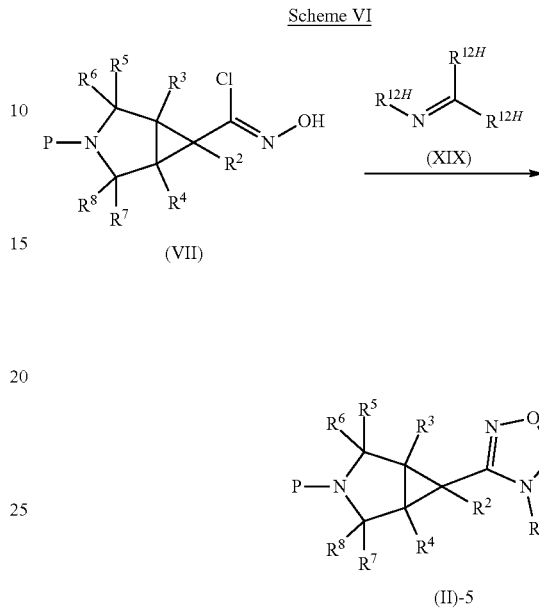

(II)-5

Wherein R¹ in the general formula (II) in Scheme I represents and
the general formula (II) can be described as the general formula (II)-5 in Scheme VI.

The compound represented by the general formula (II)-5 can be produced by subjecting the compound represented by the general formula (VII) and the compound represented by the general formula (XIX) to a 1,2,4-oxadiazoline cyclization reaction.

A 1,2,4-oxadiazoline cyclization reaction can be carried out with base (for example trimethylamine etc.) in solvent (for example THF, toluene or DMF etc.) at 0° C. to 40° C.

Scheme VII

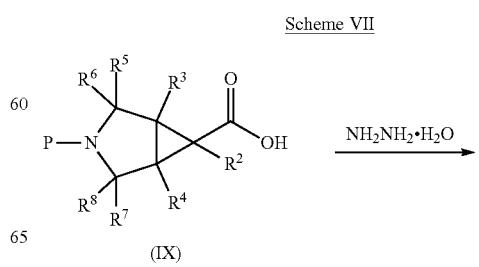

(IX)

-continued

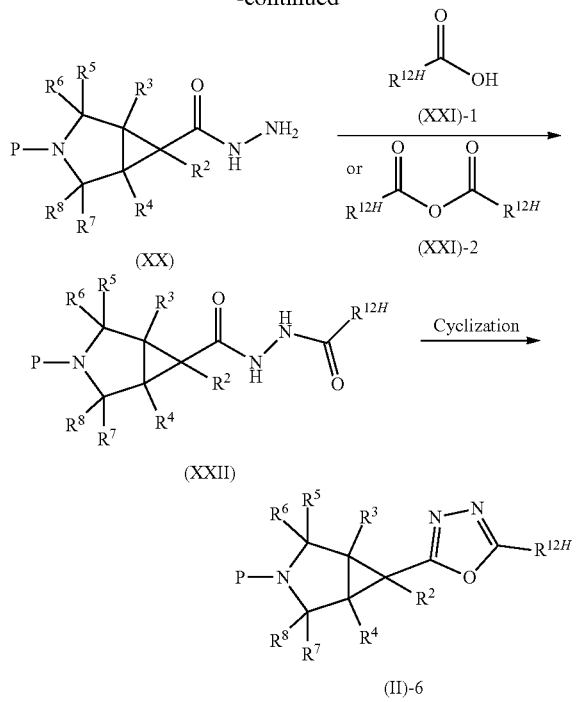

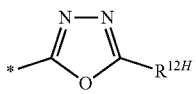

and the general formula (II) can be described as the general formula (II)-6 in Scheme VII.

The compound represented by the general formula (II)-6 can be produced by subjecting the compound represented by the general formula (XXII) to a 1,3,4-oxadiazole cyclization reaction.

A 1,3,4-oxadiazole cyclization reaction can be carried out with dehydrating agent (e.g., POCl$_3$ etc.) at 80° C. to 120° C.

The compound represented by the general formula (XXII) can be produced by subjecting the compound represented by the general formula (XX) and the compound represented by the general formula (XXI)-1 or (XXI)-2 to an amidation reaction.

An amidation can be carried out by the same method described above for the preparation of the general formula (I) in Scheme I.

The compound represented by the general formula (XX) can be produced by subjecting the compound represented by the general formula (IX) to an amidation reaction.

An amidation can be carried out by the same method described above for the preparation of the general formula (I) in Scheme I.

Wherein R$^1$ in the general formula (II) in Scheme I represents

Scheme VIII

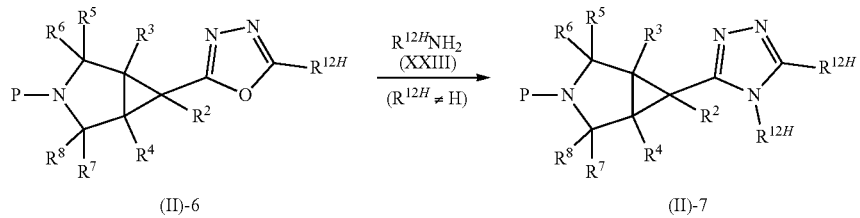

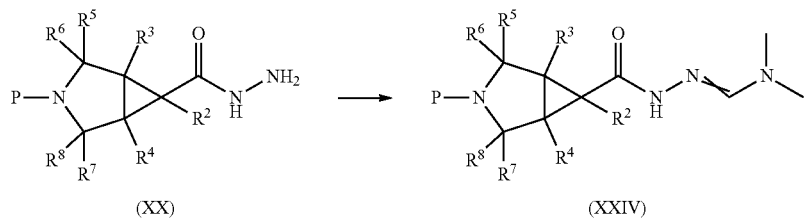

Wherein $R^1$ in the general formula (II) in Scheme I represents

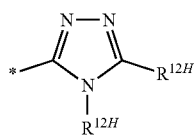

and the general formula (II) can be described as the general formula (II)-7 in Scheme VIII.

The compound represented by the general formula (II)-7 can be produced by subjecting the compound represented by the general formula (II)-6 and the compound represented by the general formula (XXIII) to a replacement reaction.

A replacement reaction can be carried out with acidic catalyst (e.g., TsOH etc.) in solvent (e.g., xylene etc.) at 120° C. to 150° C.

The compound represented by the general formula (II)-7 can be produced by subjecting the compound represented by the general formula (XXIV) and the compound represented by the general formula (XXIII) to a 1,3,4-triazole cyclization reaction.

A 1,3,4-triazole cyclization reaction can be carried out with acetic acid at 0° C. to 100° C.

The compound represented by the general formula (XXIV) can be produced by subjecting the compound represented by the general formula (XX) to a hydrazonoformamide formation reaction.

A hydrazonoformamide formation reaction can be carried out with 1,1-dimethoxy-N,N-dimethylmethanamine in solvent (e.g., acetonitrile or DMF etc.) at 100° C. to 120° C.

Scheme IX

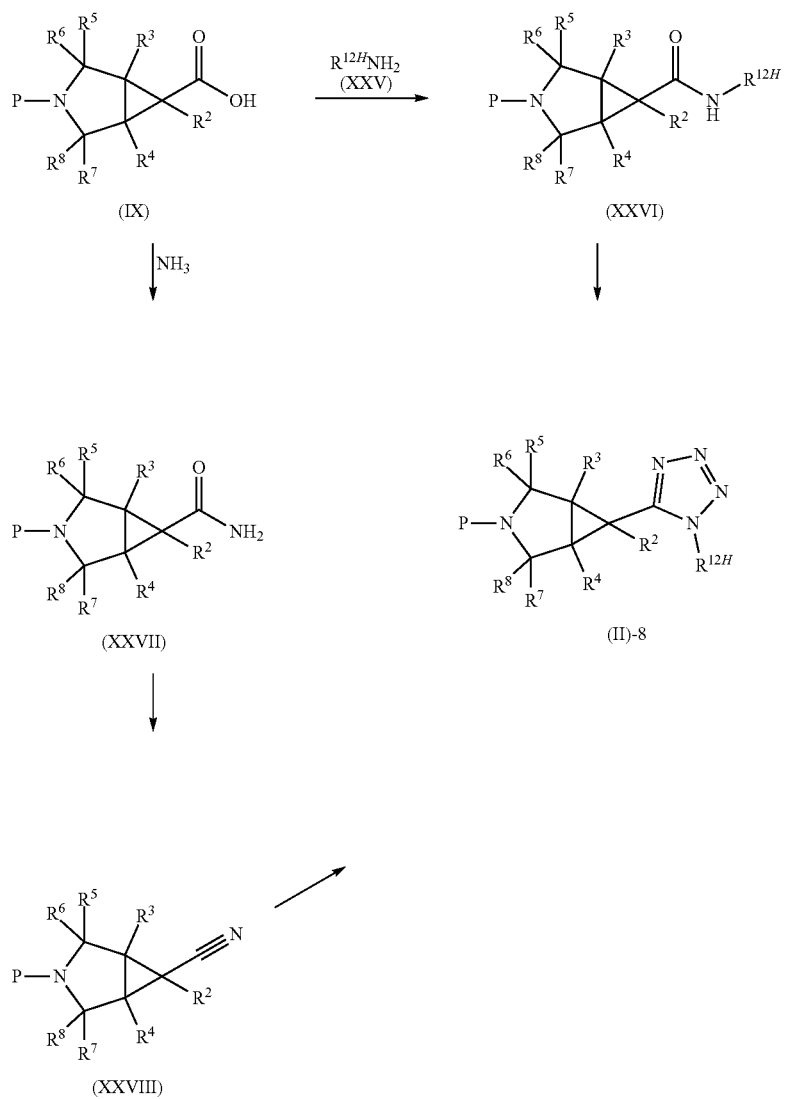

Wherein R¹ in the general formula (II) in Scheme I represents

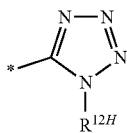

and the general formula (II) can be described as the general formula (II)-8 in Scheme IX.

The compound represented by the general formula (II)-8 can be produced by subjecting the compound represented by the general formula (XXVI) to a dehydrative tetrazole cyclization reaction.

A dehydrative tetrazole cyclization reaction can be carried out with Tf$_2$O and TMSN$_3$ in solvent (e.g., dichloromethane etc.) at 0° C. to 30° C.

The compound represented by the general formula (XXVI) can be produced by subjecting the compound represented by the general formula (IX) and the compound represented by the general formula (XXV) to an amidation reaction.

An amidation can be carried out by the same method described above for the preparation of the general formula (I) in Scheme I.

Wherein R$^{12}$ represents H, the compound represented by the general formula (II)-8 can be produced by subjecting the compound represented by the general formula (XXVIII) to a tetrazole cyclization reaction.

A tetrazole cyclization reaction can be carried out with NaN$_3$ and NH$_4$Cl in solvent (e.g., DMF etc.) at 100° C. to 140° C.

The compound represented by the general formula (XXVIII) can be produced by subjecting the compound represented by the general formula (XXVII) to a nitrile formation reaction.

A nitrile formation reaction can be carried out with dehydration agent (e.g., cyanuric chloride, thionyl chloride or P$_2$O$_5$ etc.) in solvent (e.g., DMF, benzene, toluene or xylene etc.) at 100° C. to 140° C.

The compound represented by the general formula (XXVII) can be produced by subjecting the compound represented by the general formula (IX) and ammonia to an amidation reaction.

An amidation can be carried out by the same method described above for the preparation of the general formula (I) in Scheme I.

Scheme X

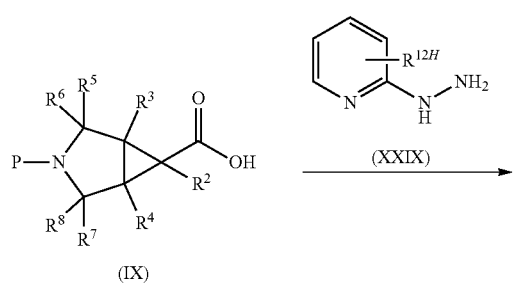

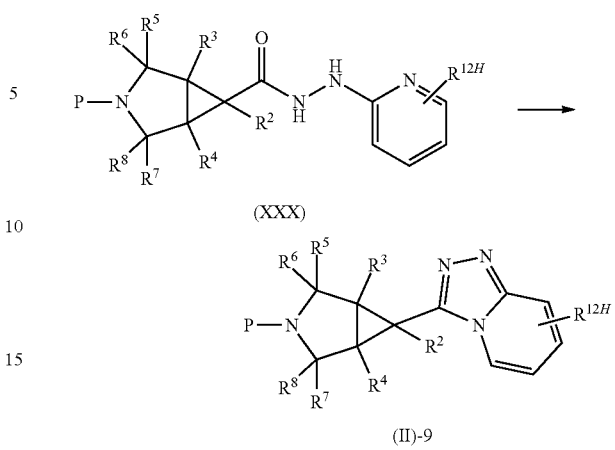

Wherein R¹ in the general formula (II) in Scheme I represents

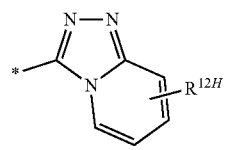

and the general formula (II) can be described as the general formula (II)-9 in Scheme X.

The compound represented by the general formula (II)-9 can be produced by subjecting the compound represented by the general formula (XXX) to a [1,2,4]triazolo[4,3-a]pyridine cyclization reaction.

A [1,2,4]triazolo[4,3-a]pyridine cyclization reaction can be carried out with Burgess reagent in solvent (e.g., acetonitrile etc.) at 100° C. to 140° C.

The compound represented by the general formula (XXX) can be produced by subjecting the compound represented by the general formula (IX) and the compound represented by the general formula (XXIX) to an amidation reaction.

An amidation can be carried out by the same method described above for the preparation of the general formula (I) in Scheme I.

Scheme XI

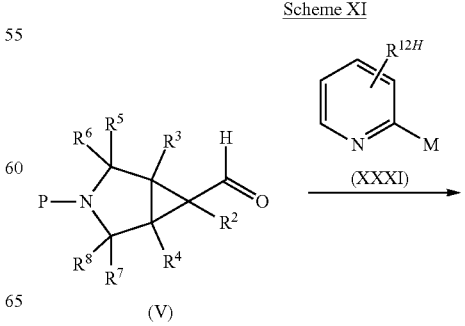

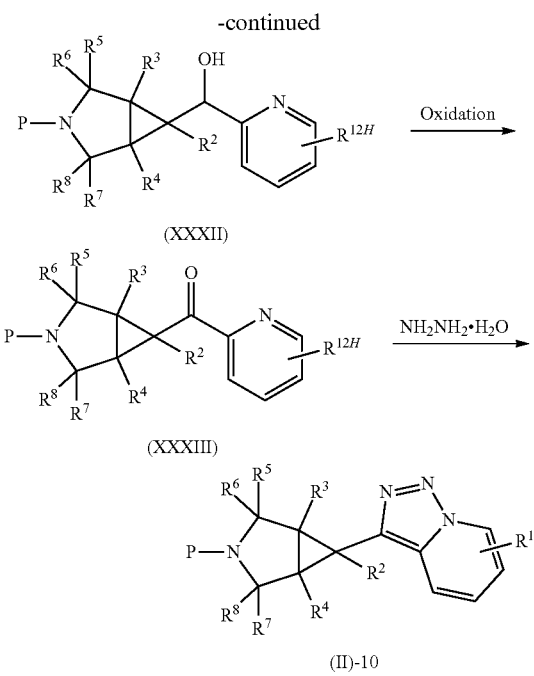

Wherein $R^1$ in the general formula (II) in Scheme I represents PGP

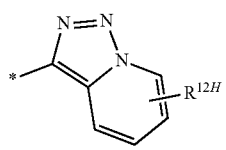

and
the general formula (II) can be described as the general formula (II)-10 in Scheme XI.

The compound represented by the general formula (II)-10 can be produced by subjecting the compound represented by the general formula (XXXIII) to a [1,2,3]triazolo[1,5-a]pyridine cyclization reaction.

A [1,2,4]triazolo[4,3-a]pyridine cyclization reaction can be carried out with hydrazine hydrate at 50° C. to 70° C., followed by the treatment of cupper acetate in solvent (e.g., ethylacetate etc.) at 20° C. to 40° C.

The compound represented by the general formula (XXXIII) can be produced by subjecting the compound represented by the general formula (XXXII) to an oxidation reaction of hydroxyl group.

An oxidation reaction of hydroxyl group can be carried out by the same method described above for the preparation of the general formula (II)-3 in Scheme IV.

The compound represented by the general formula (XXXII) can be produced by subjecting the compound represented by the general formula (V) and the compound represented by the general formula (XXXI) to an addition reaction.

An addition reaction can be carried out by the same method described above for the preparation of the general formula (XV) in Scheme IV.

Wherein the compounds represented by the general formula (IV), (VIII), (X), (XI), (XIII), (XIV), (XVI), (XVIII), (XIX), (XXI)-1, (XXI)-2, (XXIII), (XXV), (XXVII), (XXIX) and (XXXI) can be available commercially, or easily prepared from commercial chemicals by well-known method described in, for example, Comprehensive Organic Transformations: A Guide to Functional Group Preparations, 2nd Edition (Richard C. Larock, John Wiley & Sons Inc., 1999) and the like.

Wherein the compound represented by the general formula (V) can be available commercially or prepared by the method described in Scheme XII.

Scheme XII

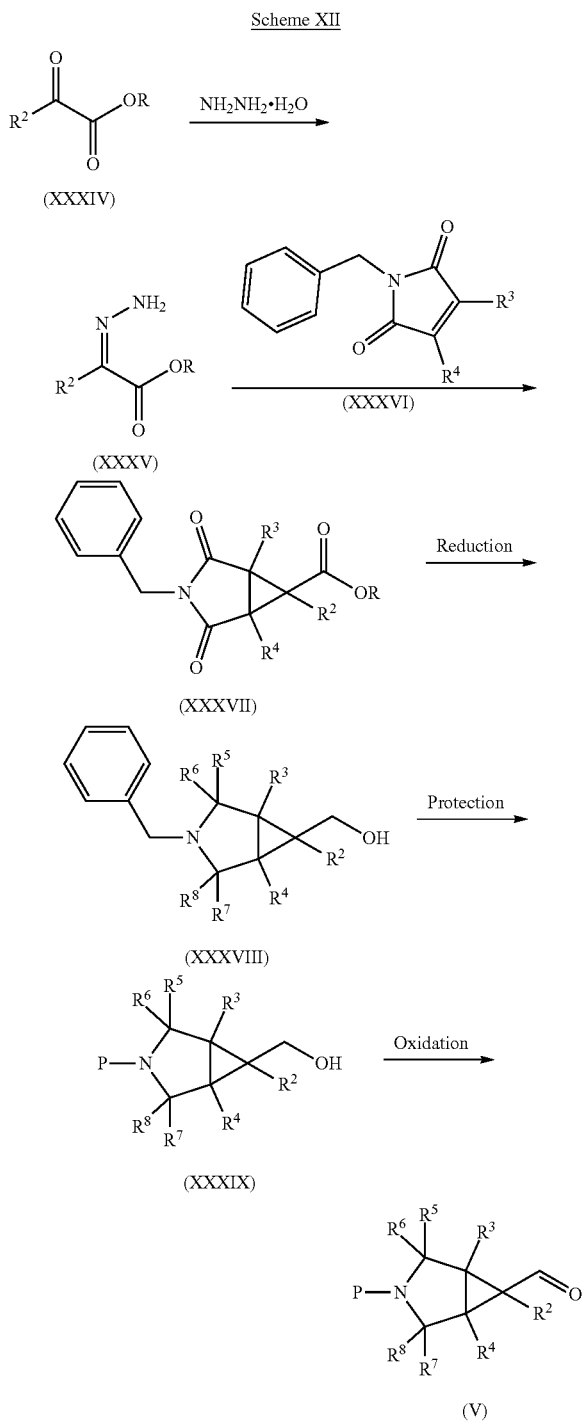

Wherein the compound represented by the general formula (V) can be produced by subjecting the compound represented by the general formula (XXXIX) to an oxidation reaction of hydroxyl group.

An oxidation reaction of hydroxyl group can be carried out by the same method described above for the preparation of the general formula (II)-3 in Scheme IV.

The compound represented by the general formula (XXXIX) can be produced by subjecting the compound represented by the general formula (XXXVIII) to a protection exchange reaction.

A protection exchange reaction can be carried out with hydrogen gas, Pd catalyst (e.g., Pd—C or Pd(OH)$_2$—C etc.) and (Boc)$_2$O in solvent (e.g., MeOH, EtOH or THF etc.) at 20° C. to 40° C.

The compound represented by the general formula (XXXVIII) can be produced by subjecting the compound represented by the general formula (XXXVII) to an ester reduction reaction.

An ester reduction reaction can be carried out with reductant (e.g., LiAlH$_4$, DIBAL-H, Red-Al etc.) in solvent (e.g., THF, diethylether or DME etc.) at −20° C. to 20° C.

The compound represented by the general formula (XXXVII) can be produced by subjecting the compound represented by the general formula (XXXVIII) and to an imide reduction reaction.

An imide reduction reaction can be carried out with borane reductant (e.g., BH$_3$ THF, BH$_3$ Me$_2$S or B$_2$H$_6$ etc.) in solvent (e.g., THF, diethylether or DME etc.) at 20° C. to 80° C.

The compound represented by the general formula (XXXVII) can be produced by subjecting the compound represented by the general formula (XXXV) and the compound represented by the general formula (XXXVI) to a cyclopropanation reaction.

A cyclopropanation reaction can be carried out with MnO$_2$ in solvent (e.g., dioxane etc) at 20° C. to 100° C.

The compound represented by the general formula (XXXV) can be produced by subjecting the compound represented by the general formula (XXXIV) to a hydrazone formation reaction.

A hydrazone formation reaction can be carried out with hydrazine hydrate and acetic acid in water at 0° C. to 40° C.

Wherein the compound represented by the general formula (XXXIV) and (XXXVI) can be available commercially, or easily prepared from commercial chemicals by well-known method described in, for example, Comprehensive Organic Transformations: A Guide to Functional Group Preparations, 2nd Edition (Richard C. Larock, John Wiley & Sons Inc., 1999) and the like.

In the reactions exemplified herein, any heating means such as water bath, oil bath, sand bath and microwave may be used.

In the reactions exemplified herein, a solid phase-supported reagent supported on a polymer (such as polystyrene, polyacrylamide, polypropylene and polyethylene glycol) may be used, if appropriate.

The products from the reactions exemplified herein may be purified by a conventional purification means, for example, distillation under normal or reduced pressure, chromatography (such as high performance liquid chromatography, thin layer chromatography or column chromatography) using silica gel, an ion exchange resin, scavenger resin or magnesium silicate, or by washing or recrystallization. Purification may be carried out after each reaction step or after a series of reactions.

[Toxicity]

The present compound has low toxicity and thus can be safely used as a medicament.

[Application to Medicaments]

The present compound has KDM5 inhibitory activity, and thus can be used as an agent for prophylaxis and/or therapy of KDM5-related diseases in mammals, particularly in humans.

Examples of such diseases include hyperproliferative disease, cancer, stroke, diabetes, hepatomegaly, cardiovascular disease, multiple sclerosis, Huntington's disease, Alzheimer's disease, cystic fibrosis, viral disease, autoimmune diseases, atherosclerosis, restenosis, psoriasis, rheumatoid arthritis, inflammatory bowel disease, asthma, allergic disorders, inflammation, neurological disorders, a hormone-related disease, conditions associated with organ transplantation, immunodeficiency disorders, destructive bone disorders, proliferative disorders, infectious diseases, conditions associated with cell death, thrombin-induced platelet aggregation, liver disease, pathologic immune conditions involving T cell activation, CNS disorders, myeloproliferative disorder, Parkinson's disease, Lewy body disease, frontotemporal lobar degeneration, mild cognitive impairment, cognitive impairment, cerebrovascular disease, schizophrenia, depression, anxiety disorder, bipolar disorder, autism spectrum disorder, attention deficit/hyperactivity disorder, learning disabilities, movement disorders, obsessive-compulsive disorder, personality disorder, sleeping disorder, delirium, amyotrophic lateral sclerosis, developmental disorders, intellectual disability, post-traumatic stress disorder, and hepatitis and the like.

Among others, the present compound is useful for prophylaxis and/or therapy of cancer, Huntington's disease, Alzheimer's disease, Parkinson's disease, Lewy body disease, frontotemporal lobar degeneration, mild cognitive impairment, cognitive impairment, cerebrovascular disease, schizophrenia, depression, anxiety disorder, bipolar disorder, autism spectrum disorder, attention deficit/hyperactivity disorder, learning disabilities, movement disorders, obsessive-compulsive disorder, personality disorder, sleeping disorder, delirium, amyotrophic lateral sclerosis, developmental disorders, intellectual disability, post-traumatic stress disorder, or hepatitis. The present compound is particularly suitable for prophylaxis and/or therapy of cancer and Alzheimer's disease.

In addition to having a strong KDM5 inhibitory activity, the present compound is excellent in metabolic stability and can be present in the brain at a high concentration.

Examples of test methods for evaluating the pharmacological activity of the present compounds include an evaluation system of improvement of cognitive impairment in mice.

For example, improvement of cognitive impairment by the present compounds may be evaluated by using the following method.

Mice (16 to 23-month old male C57BL/6 mice (Charles River Laboratories Japan, Inc.)) are used. A test compound and its vehicle are orally administered once daily for 2 weeks. After that, the cognitive function will be assessed by the novel object recognition (NOR) test using a plastic cage (ECON cage, CL-0107, 345 mm*403 mm*177 mm, CLEA Japan, Inc.) with a video camera as the experimental apparatus. The evaluation is performed in a dark room and the light intensity is adjusted to approximately 20 lux near the experimental apparatus. To acclimatize animals to the evaluation environment, the mice are moved to the evaluation room at least 1 hour prior to the start of the trial. The study will be conducted over 3 days. For acclimation to the experimental apparatus on Day 1, the mice are placed in a cage and allowed to move freely for 10 minutes. In the acquisition trial on Day 2, two identical objects (familiar objects) are placed on the cage and performed in the same way for 10 minutes. The two objects are placed apart on a line parallel to the long side of one cage. The distance between the object and the inner wall of the two adjacent surfaces is 10 cm. In the test trial on Day 3, one of the objects used in the acquisition trial is replaced by a novel object with a different color and shape, and the animals behave in the same manner for 10 minutes. The test trials start 24 hours (Acceptable range: 23 to 25 hours) after the acquisition trials. From the video images recorded in the test trials, the exploration time for each object is measured. From the exploration time of familiar and novel objects, the total exploration time and the novel object recognition rate are calculated by the following equation.

Total exploration time (seconds)=Exploration Time for familiar object+Exploration time for novel object Recognition index (%)=100*(Exploration time for novel object/Total exploration time)

Examples of test methods for evaluating the pharmacological activity of the present compounds include the clonogenic assay and the cytotoxicity assay in cancer cells. For example, efficacy of the present compounds in cancer cells may be evaluated by using the following methods.

MCF-7, T47D and MBA-MB231 human breast cancer cells are purchased from ATCC with certification. Cells are cultured for at most 10-12 passages, then replaced by cells from early passages, kept in liquid nitrogen since collection. Cells are grown in adherence in high glucose Dulbecco's Modified Eagle Medium (DMEM) with 1% penicillin/streptomycin, 2 mM L-glutamine, 10% previously inactivated fetal bovine serum. Cells are maintained at 37° C. and 5% $CO_2$ in an incubator and routinely passaged removing DMEM, washing with PBS and detaching them using a suitable amount of Trypsin/EDTA.

For the clonogenic assay, one hour after treatment with the compound, cells are exposed to X-ray using a MLG 300/6-D apparatus (Gilardoni) set to 200 V and 6 mA, in order to produce an equivalent absorbed dose of 1 cGy/s. Afterwards, cells are harvested, counted and then diluted in the growth medium containing the compound. Appropriate cell numbers are seeded in quadruplicate according to the doubling time of the cell line and to radiation dose. Twenty-four hours after this seeding, the medium with the compound is replaced with fresh DMEM and cells are then incubated for 14 days (enough time to allow at least six cell divisions). After this period of growth, cells are washed twice with PBS and then fixed and stained with a suitable volume of a solution made of 0.3% Methylene Blue and 80% Ethanol for 30 min at room temperature. After washing cells twice with ddH2O, plates are pictured with ChemiDoc XRS+ Imaging System (Bio-Rad) in colorimetric mode. Radiation-dose response curves to X-ray for DMSO and the compound samples are calculated using surviving fraction. Plating efficiency and surviving fraction are calculated as follows:

Plating efficiency=number of colonies counted/number of cells plated

Surviving fraction=Plating efficiency/plating efficiency of sham sample

For the cytotoxicity assay, Cell Counting Kit-8 (#CK04, DOJINDO) is used according to the manufacturer's instructions. MCF-7 T47D or MDA-MB231 cell suspension (5000 cells/100 μL/well) is dispensed in a 96-well plate. After 24 hours, the compound or DMSO is added in growth medium and then cells are irradiated. Forty-eight hours post irradiation, 10 μL of CCK-8 solution is added to each well of the plate and incubated again for 1 hour. The absorbance at 450 nm is read using a VICTOR2 1420 reader (Perkin Elmer).

Examples of test methods for evaluating the pharmacological activity of the present compounds include the primary human hepatocytes (PHH) assay for inhibition of hepatitis B virus antigen (HbsAg). For example, efficacy of the present compounds in the PHH assay may be evaluated by using the following methods.

Primary human hepatocytes (PHH) (Bioreclamation IVT) are plated on collagen-coated flasks using Plating Media (Life Technologies) containing William's Medium E supplemented with 1% penicillin/streptomycin, 4 pg/mL human recombinant insulin, 2 mM GlutaMAX, 15 mM HEPES, 1 μM dexamethasone, 5% fetal bovine serum, and 0.2% Antibiotic Mix. After a 4-hour incubation at 37° C., cells are switched to Maintenance Media (Life Technologies) containing William's Medium E supplemented with 0.5% penicillin/streptomycin, 6.25 pg/mL human recombinant insulin, 6.25 pg/mL human transferrin, 6.25 ng/mL selenious acid, 1.25 mg/mL bovine serum albumin, 5.35 pg/mL linoleic acid, 2 mM GlutaMAX, 15 mM HEPES, 0.1 μM dexamethasone, 2% fetal bovine serum, 2% DMSO, and 0.2% Antibiotic Mix. On the next day, PHH are infected with 500 genome equivalent per cell of genotype D (AD38-derived) HBV in Maintenance Media supplemented with 4% PEG 8000 (Promega). After 24 hour incubation, cells are washed three times with William's Medium E and fed with fresh Maintenance Media. At 3 days after infection, infected PHH cells are seeded on 96-well plates pre-coated with collagen at a density of 65000 cells per well containing serially diluted solutions of compounds or DMSO (1% final concentration) in a final volume of 125 pf of Maintenance Media (Life Technologies). Media with compounds is replenished every 2-3 days. After an incubation time of 12 days, secreted HBsAg in the supernatant are measured using a multiplex chemiluminescent (Mesoscale discovery, MSD) assay using capture and detection antibody pairs specific for HBsAg. EC50 values are calculated from the fit of the dose-response curves to a four-parameter equation.

Examples of test methods for evaluating the pharmacological activity of the present compounds include an evaluation system of improvement of the depressive symptoms in the social defeat stress model. For example, efficacy of the present compounds in the social defeat model may be evaluated by using the following methods.

Eight-week-old male DBA/2 mice are used for the study. The social defeat stress is given to the mice. The test mice are placed in a highly aggressive CD-1 mouse cage for 5 minutes. At this time, CD-1 mice will attack the test mice unilaterally (Physical Stress). After 5 minutes, CD-1 mice and test mice are separated by a transparent acrylic plate and maintained for 24 hours (psychological stress burden). This process is done for 5 consecutive days. The compound or vehicle is orally administered 2 hours before the social defeat stress in each day. After that, the social interaction test and the sucrose preference test are conducted.

For the social interaction test, CD-1 mice as a novel mouse are placed in a box of 42 cm square (Target Area). Test mice (DBA/2 mouse) are placed in the boxes and the time spent in the target area for 3 minutes is measured by a video tracking system (Any-Maze Software). Time contacting with a novel mouse is reduced in depressed animals.

For the sucrose preference test, bottles containing 1% sucrose solution and normal water are given simultaneously. The amount of sucrose solution and normal water consumed over 4 h is measured, and the percentage of sucrose water consumed (sucrose preference) is used as an indicator of anhedonia. Animals usually prefer sweet sucrose, but animals in the anhedonia state, a condition of depression, have reduced preference for sucrose.

Upon using the present compound for pharmaceutical purposes, the present compound may be used not only as a single drug but also as a combined drug with an additional active component, for example those listed hereinbelow, for the purposes of, for example, (1) supplementing and/or enhancement of the effect thereof for prophylaxis, therapy and/or amelioration of symptoms, (2) improvement of the kinetics and absorption, reduction of the dosage thereof and/or (3) alleviation of side-effects thereof.

When the present compound is used for prophylaxis and/or therapy of Alzheimer's disease, examples of the drugs which may be used in combination with the present compound include symptomatic agents, for example those known to modify cholinergic transmission such as M1 and M3 muscarinic receptor agonists or allosteric modulators, M2 muscarinic antagonists, M4 agonists or positive allosteric modulators (PAMs), acetylcholinesterase inhibitors (such as tetrahydroaminoacridine, donepezil hydrochloride and rivastigmine), nicotinic receptor agonists or allosteric modulators (such as α7 agonists or allosteric modulators or α4β2 agonists or allosteric modulators), PPAR agonists (such as PPARγ agonists), 5-$HT_4$ receptor agonists or partial agonists, histamine H3 antagonists, 5-$HT_6$ receptor antagonists or 5$HT_{1A}$ receptor ligands and NMDA receptor antagonists or modulators, 5-$HT_{2A}$ antagonists, 5-$HT_7$ antagonists, D1 agonists or PAMs, D4 agonists or PAMs, D5 agonists or PAMs, GABA-A a5 inverse agonists or negative allosteric modulators (NAMs), GABA-A a2/3 agonists or PAMs, mGluR2 modulators (PAMs or NAMs), mGluR3 PAMs, mGluR5 PAMs, PDE 1 inhibitors, PDE 2 inhibitors, PDE 4 inhibitors, PDE 5 inhibitors, PDE 9 inhibitors, PDE 10 inhibitors, GlyT1 inhibitors, DAAO inhibitors, ASCI inhibitors, AMPA modulators, SIRT1 activators or inhibitors, AT4 antagonists, GalR1 antagonists, GalR3 ligands, adenosine A1 antagonists, adenosine A2a antagonists, a2A antagonists or agonists, selective and unselective norepinephrine reuptake inhibitors (SNRIs), or potential disease modifying agents such as gamma secretase inhibitors or modulators, alpha secretase activators or modulators, amyloid aggregation inhibitors, amyloid antibodies, tau aggregation inhibitors or tau phosphorylation/kinase inhibitors, tau dephosphorylation/phosphatase activators, mitogen-activated protein kinase kinase 4 (MKK4/MEK4/MAP2K4) inhibitors, c-Jun N-terminal kinase (JNK) inhibitors, casein kinase inhibitors, MK2 (mitogen activated protein kinase-activated protein kinase 2) inhibitors, MARK (microtubule affinity regulating kinase) inhibitors, CDK5 (cyclin dependent kinase 5) inhibitors, GSK-3 (glycogen synthase kinase-3) inhibitors and tau-tubulin kinase-1 (TTBK1) inhibitors. Further examples of such other therapeutic agents may be calcium channel blockers, HMG-CoA (3-hydroxy-3-methylglutaryl-CoA) reductase inhibitors (statins) and lipid lowering agents, NGF (nerve growth factor) mimics, antioxidants, GPR3 ligands, plasmin activators, neprilysin (NEP) activators, IDE (insulin degrading enzyme) activators, melatonin MT1 and/or MT2 agonists, TLX/NR2E1 (tailless X receptor) ligands, GluR1 ligands, RAGE (receptor for advanced glycation end-products) antagonists, EGFR (epidermal growth factor receptor) inhibitors, FPRL-1 (formyl peptide-like receptor-1) ligands, GABA antagonists, and MICAL (molecule interacting with casL) inhibitors, e.g. oxidoreductase inhibitors, CB1 antagonists/inverse agonists, non-steroidal anti-inflammatory drugs (NSAIDs), anti-inflammatory agents (for example agents that could be used to treat neuroinflammation either by enhancing or reducing neuroinflammation), amyloid precursor protein (APP) ligands, anti-amyloid vaccines and/or antibodies, agents that promote or enhance amyloid efflux and/or clearance, histone deacetylase (HDAC) inhibitors, EP2 antagonists, 11-beta HSD1 (hydroxy steroid dehydrogenase) inhibitors, liver X receptor (LXR) agonists or PAMs, lipoprotein receptor-related protein (LRP) mimics and/or ligands and/or enhancers and/or inhibitors, butyryl cholinesterase inhibitors, kynurenic acid antagonists and/or inhibitors of kynurenine aminotransferase (KAT), orphanin FQ/nociceptin (NOP)/opioid-like receptor 1 (ORL1) antagonists, excitatory amino acid transporter (EAAT) ligands (activators or inhibitors), and plasminogen activator inhibitor-1 (PAI-1) inhibitors, niacin and/or GPR109 agonists or PAMs in combination with cholesterol lowering agents and/or HMGCoA reductase inhibitors (statins), dimebolin or similar agents, antihistamines, metal binding/chelating agents, antibiotics, growth hormone secretagogues, cholesterol lowering agents, vitamin E, cholesterol absorption inhibitors, cholesterol efflux promoters and/or activators, and insulin upregulating agents, and the like.

The present compound may alternatively be used in combination with, for example, donepezil hydrochloride, galantamine hydrobromide, huperzine A, idebenone, levacecamine hydrochloride, memantine hydrochloride, memantine hydrochloride/donepezil hydrochloride, proteolytic peptide fraction from porcine brain protein, rivastigmine tartrate, tacrine hydrochloride, aducanumab (genetical recombination) or the like.

The combined drug of the present compound and an additional drug may be administered in the form of a concomitant drug containing both components in one formulation, or separate formulations may be administered by the same or different routes of administration. It is not necessary that separate formulations are administered simultaneously and separate formulations may be administered sequentially with a time difference. When the formulations are sequentially administered, the order or administration is not particularly limited and may be appropriately adjusted so that desired efficacy of drugs can be obtained.

The dosage of the additional drug which is used in combination with the present compound may be appropriately increased or decreased according to the clinical dosage thereof or a similar drug. The ratio between the present compound and the additional drug may be appropriately adjusted by considering the age and weight of the subject, the administration method, the time of administration, the target disease and condition and the like. Generally, 1 part by weight of the present compound may be combined with the additional drug in an amount ranging from 0.01 to 100 parts by weight. A plurality of the additional drug may be used. The additional drug may be, in addition to those mentioned above, a drug having the same mechanism as those mentioned above. Such an additional drug includes not only the one which has been discovered by now but also the one which will be discovered in future.

The dosage of the present compound may vary according to the age, weight, condition, therapeutic effect, administration method, treatment period and the like. The present compound may be orally administered to an adult once to several times daily at the amount of 0.1 mg to 300 mg per administration, parenterally administered to an adult once to several times daily at the amount of 0.1 mg to 150 mg per administration or intravenously and continuously administered over 1 hour to 24 hours daily.

As described above, the dosage may vary according to various conditions, and thus the amount less than the dosage described above may be sufficient in some cases and the amount exceeding the above dosage may be required in other cases.

When the present compound is used for prophylaxis and/or therapy of the above diseases as a single drug or a combined drug with the additional drug, the present substance which is an active component is generally formulated with a pharmaceutically acceptable carrier such as various additives or solvents and the obtained formulation is administered systemically or locally and orally or parenterally. The pharmaceutically acceptable carrier as used herein means a substance other than an active component that is generally used for medicinal formulations. The pharmaceutically acceptable carrier preferably does not exhibit pharmacological activity, is harmless and does not prevent the therapeutic effect of the active component at the dosage of the formulation. The pharmaceutically acceptable carrier may also be used in order to increase the usefulness of the active component and the formulation, to facilitate production of the formulation, to stabilize the quality or to improve the usability. Specifically, the substances described in "Iyakuhin Tenkabutsu Jiten", 2000, Yakuji Nippo Ltd. (Ed. IPEC Japan) may be appropriately selected according to the need.

Examples of the dosage form include oral administration formulations (examples: tablets, capsules, granules, powders, oral liquids, syrups, oral jelly formulations and the like), oral cavity formulations (examples: tablets for the oral cavity, spray formulations for the oral cavity, semi-solid formulations for the oral cavity, oral rinse and the like), formulations for injection (examples: injections and the like), formulations for dialysis (examples: agents for dialysis and the like), formulations for inhalation (examples: agents for inhalation and the like), ophthalmic formulations (examples: ophthalmic solutions, ophthalmic ointments and the like), otological formulations (examples: ear drops and the like), nasologic formulations (examples: nasal drops and the like), rectal formulations (examples: suppositories, semi-solid formulations for rectal administration, enema formulations and the like), vaginal formulations (examples: vaginal tablets, vaginal suppositories and the like), skin formulations (examples: topical solid formulations, topical liquids, spray formulations, ointments, creams, gels, plasters and pressure sensitive adhesives and the like) and the like.

[Oral Administration Formulations]

Examples of an oral administration formulation include tablets, capsules, granules, powders, oral liquids, syrups, oral jelly formulations and the like. The oral administration formulation may be classified into rapidly disintegrating formulations for which the release of an active component from the formulations is not particularly controlled and release-controlled formulations for which the release is controlled according to the purposes by adjusting the dosage design and production method, such as enteric formulations and sustained release formulations. The enteric formulations refer to a formulation which is designed to release an active component mainly in the small intestine rather than in the stomach with the purpose of prevention of decomposition of the active component in the stomach or reduction of stimulation of the stomach by the active component. The enteric formulation may be generally produced by providing a coating of an acid-insoluble enteric base. The sustained release formulations refer to a formulation for which the release rate, release time and release site of an active component from the formulation is controlled with the purpose of reduction in the frequency of administration or reduction of side effects. The sustained release formulation may be generally produced by using an appropriate agent for sustained release. Among the oral administration formulations, capsules, granules, tablets may be provided with an appropriate coating film of a saccharide, sugar alcohol, polymer compound and the like with the purpose of easy ingestion or prevention of decomposition of an active component.

(1) Tablets

Tablets are an orally administered solid formulation having a certain shape. Examples thereof include those generally referred to as tablets such as plain tablets, film-coated tablets, sugar-coated tablets, multilayered tablets and dry-coated tablets as well as orally disintegrating tablets, chewable tablets, effervescent tablets, dispersible tablets, soluble tablets and the like. Plain tablets may be generally produced according to the following procedure (a), (b) or (c):

(a) An active component is mixed with an additive such as a vehicle, a binding agent and a disintegrating agent to obtain a homogeneous mixture which is granulated by an appropriate method using water or a solution containing a binding agent, mixed with a lubricant and the like, compressed and moulded;

(b) An active component is mixed with an additive such as a vehicle, a binding agent and a disintegrating agent to obtain a homogeneous mixture which is then directly compressed and moulded, or granules prepared with an additive are mixed with an active component, a lubricant and the like to obtain a homogeneous mixture which is then compressed and moulded;

(c) An active component is mixed with an additive such as a vehicle and a binding agent to obtain a homogeneous mixture which is then wetted and kneaded with a solvent, moulded in a certain mould and dried by an appropriate method. Film-coated tablets may be generally produced by providing appropriate thin coating films of a polymer and the like to plain tablets. Sugar-coated tablets may be generally produced by providing coating films containing a saccharide or sugar alcohol to plain tablets. Multilayerd tablets may be produced by stacking layers of powder granules having different compositions and compressing and moulding the product according to an appropriate method. Dry-coated tablets may be produced by coating inner core tablets with outer layers having different compositions. Tablets may be formed as enteric tablets or sustained release tablets according to appropriate well-known methods. Orally disintegrating tablets, chewable tablets, effervescent tablets, dispersible tablets and soluble tablets are the tablets to which unique functions are imparted by appropriately selecting additives, and may be produced according to the production procedures described above for the tablets. Orally disintegrating tablets refer to a tablet ingested by rapid dissolution or disintegration in the oral cavity; chewable tablets refer to a tablet ingested by chewing; effervescent tablets refer to a tablet which is dissolved or dispersed in water with rapid effervescence; dispersible tablets refer to a tablet which is ingested after dispersion in water; and the soluble tablets refer to a tablet which is ingested after dissolution in water. The effervescent tablets may be produced by using an additive which is an appropriate acidic substance, carbonate salt, hydrogen carbonate salt and the like.

(2) Capsules

Capsules are a formulation containing a capsule shell filled with an active component or an active component coated with a capsule base. Examples thereof include hard capsules, soft capsules and the like. Hard capsules may be produced by mixing an active component with an additive such as a vehicle to obtain a homogeneous mixture, or obtaining granules or moulded substance by an appropriate method, which is then directly, or after appropriately being moulded, added to a capsule shell. Soft capsules may be produced by capsulating and moulding a mixture of an active component and an additive into a certain shape with an appropriate capsule base such as gelatine having an increased plasticity by addition of glycerol, D-sorbitol or the like. Capsules may be formed as enteric capsules or sustained release capsules according to appropriate well-known methods. A capsule base may be added with a colorant, a preservative or the like.

(3) Granules

Granules are a granulated formulation. Examples thereof include those generally referred to as granules as well as effervescent granules. Granules may be generally produced according to the following procedure (a), (b) or (c):

(a) A powder active component is mixed with an additive such as a vehicle, a binding agent or a disintegrating agent to obtain a homogeneous mixture which is then granulated by an appropriate method;

(b) A granulated active component is mixed with an additive such as a vehicle to obtain a homogeneous mixture;

(c) A granulated active component is mixed with an additive such as a vehicle to obtain a homogeneous mixture which is then granulated by an appropriate method. Granules may be optionally provided with a film or may be formed as enteric granules or sustained release granules using appropriate well-known methods. Effervescent granules may be produced by using an additive which is an appropriate acidic substance, carbonate salt, hydrogen carbonate salt and the like. The effervescent granules refer to a granule which is dissolved or dispersed in water with rapid effervescence. The granules may also be formed as fine granules by controlling the particle size.

(4) Powders

Powders are powdery formulations and may be generally produced by mixing an active component with an additive such as a vehicle to obtain a homogeneous mixture.

(5) Oral Liquids

Oral liquids are a formulation in the form of solution or flowable and viscous gel. Examples thereof include those generally referred to as oral liquids as well as elixirs, suspensions, emulsions, lemonades and the like. Oral liquids may be generally produced by mixing an active component with an additive and purified water to homogeneously dissolve, emulsify or suspend the active component and optionally filtering the product. Elixirs refer to a clear oral liquid containing ethanol having sweet taste and aroma. Elixirs may be generally produced by dissolving a solid active component or an infusion thereof in ethanol, purified water, a flavouring agent and sucrose, an additional saccharide or a sweetening agent and obtaining a clear liquid by filtration or other methods. Suspensions refer to an oral liquid in which an active component is finely and homogeneously suspended. Suspensions may be generally produced by suspending a solid active component in a suspending agent or an additional additive and purified water or oil and homogenising the whole product according to an appropriate method. Emulsions refer to an oral liquid in which an active component is finely and homogeneously emulsified. Emulsions may be generally produced by adding an emulsifying agent and purified water to a liquid active component and emulsifying and homogenising the whole product according to an appropriate method.

Lemonades refer to a clear oral liquid having sweet taste and sour taste.

(6) Syrups

Syrups are a viscous liquid or solid formulation containing a saccharide or a sweetening agent. Examples thereof include agents for syrups. Syrups may be generally produced by dissolving, mixing, suspending or emulsifying an active component in a solution of sucrose, other saccharides or a sweetening agent or solely a syrup and optionally boiling the product followed by filtering while heating. Formulations for syrups refer to a granular or powdery formulation to which water is added to provide syrups and may be sometimes referred to as dry syrups. Formulations for syrups may be generally produced according to the production procedures described above for the granules or powders by using a saccharide or a sweetening agent as an additive.

(7) Oral Jelly Formulations

Oral jelly formulations are a shaped gel formulation without flowability. Oral jelly formulations may be generally produced by mixing an active component with an additive and a polymer gel base, allowing formation of gel and shaping into a certain shape according to appropriate methods.

[Oral Cavity Formulations]

(1) Tablets for the Oral Cavity

Tablets for the oral cavity are a formulation having a certain shape which is administered to the oral cavity. Examples thereof include troches, sublingual tablets, buccal tablets, adhering tablets, chewing gum tablets and the like. Tablets for the oral cavity may be generally produced according to the production procedures described for the tablets. Troches refer to a tablet for the oral cavity which is gradually dissolved or disintegrated in the oral cavity and is applied locally to the oral cavity or pharynx; sublingual tablets refer to a tablet for the oral cavity to be rapidly dissolved under the tongue to allow absorption of an active component through oral mucosa; buccal tablets refer to a tablet for the oral cavity to be gradually dissolved between the molars and cheeks to allow absorption of an active component through oral mucosa; adhering tablets refer to a tablet for the oral cavity which is adhered to oral mucosa; and chewing gum tablets refer to a tablet for the oral cavity to be chewed to release an active component.

(2) Spray Formulations for the Oral Cavity

Spray formulations for the oral cavity are a formulation to spray an active component in the form of mist, powder, foam or paste. Spray formulations for the oral cavity may be generally produced by dissolving or suspending an active component and an additive in a solvent or the like, optionally filtering thereof and packing the product into a container together with liquefied gas or compressed gas, or by preparing a solution or suspension with an active component and an additive and packing the product into a container to which a spraying pump is attached.

(3) Semi-Solid Formulations for the Oral Cavity

Semi-solid formulations for the oral cavity are a formulation to be applied to the oral mucosa. Examples thereof include creams, gels, ointments and the like. Semi-solid formulations for the oral cavity may be generally produced by emulsifying an active component together with an additive in purified water and an oil component such as petrolatum, or by mixing an active component and an additive with a base such as a polymer gel or an oil or fat and obtaining a homogeneous mixture. Creams refer to a semi-solid formulation in the form of an oil-in-water or water-in-oil emulsion and lipophilic formulations in the form of a water-in-oil emulsion may also be referred to as oil-based creams. Creams may be generally produced by preparing an oil phase from petrolatum or a higher alcohol or a mixture thereof with an additive such as an emulsifying agent, separately preparing a water phase from purified water or a mixture thereof with an additive such as an emulsifying agent, adding an active component either to the oil phase or the water phase, heating both phases and mixing the oil phase and the water phase until homogeneity to obtain an emulsion. Gels refer to a gel formulation and examples thereof include water-based gels, oil-based gels and the like. Water-based gels may be produced by dissolving or suspending an active component in an additive such as a polymer compound and purified water and allowing cross-linking by heating and cooling or addition of a gel-forming agent. Oil-based gels may be produced by mixing an active component with a liquid oil base such as a glycol or a higher alcohol and an additive. Ointments refer to a semi-solid formulation containing an active component dissolved or dispersed in a base. Examples thereof include oil- or fat-based ointments, water-soluble ointments and the like. Oil- or fat-based ointments may be generally produced by melting an oil- or fat-based base such as an oil or fat, a wax and a hydrocarbon including paraffin by heating, dissolving or dispersing an active component therein and mixing and kneading to obtain a homogeneous mixture. Water-soluble ointments may be generally produced by melting a water-soluble base such as macrogol by heating and mixing and kneading an active component therein to obtain a homogeneous mixture.

(4) Oral Rinses

Oral rinses are a liquid formulation to be applied locally to the oral cavity or pharynx and may include solid formulations which are dissolved upon use. Oral rinses may be generally produced by homogeneously dissolving an active component in a solvent and an additive and optionally filtering the solution. Solid formulations which are dissolved upon use may be generally produced according to the production procedures described for the tablets and granules.

[Formulations for Injection]
(1) Injections

Injections are an aseptic formulation in the form of solution, suspension or emulsion or solid to be dissolved or suspended upon use, which are directly administered to body tissues and organs such as under the skin, in the muscle or to a vessel. Examples thereof include those generally referred to as injections as well as lyophilised injections, powder injections, pre-filled syringes, cartridges, transfusions, implantable injections, sustained release injections and the like. Injections may be generally produced according to the following procedure (a) or (b):

(a) An active component or a mixture of an active component with an additive is dissolved, suspended or emulsified in water for injection or another aqueous solvent or a non-aqueous solvent and the product is packed into a container for injection which is then sterilised;

(b) An active component or a mixture of an active component with an additive is dissolved, suspended or emulsified in water for injection or another aqueous solvent or a non-aqueous solvent and the product is subjected to aseptic filtration or the product is homogeneously prepared in an aseptic manner and is charged into a container for injection which is then sealed. Lyophilised injections may be generally produced by dissolving an active component or an active component together with an additive such as a vehicle in water for injection, subjecting the solution to aseptic filtration, charging the solution in a container for injection followed by lyophilisation or lyophilising the solution in a container dedicated for lyophilisation followed by packing the product in a container for injection. Powder injections may be generally produced by aseptic filtration and crystallization to obtain powder which is directly or a mixture thereof with a sterilized additive is charged into a container for injection. Pre-filled syringes may be generally produced by charging an active component or a solution, suspension or emulsion of an active component and an additive into a syringe. Cartridges refer to an injection in the form of a cartridge containing a drug solution to be placed in a dedicated syringe. Cartridges containing a drug solution may be generally produced by charging an active component or a solution, suspension or emulsion of an active component and an additive into a cartridge. Transfusions refer to an injection generally of 100 mL or more which is intravenously administered. Implantable injections refer to an injection in the form of a solid or gel, which is to be applied using an implantable tool or by surgery under the skin or in the muscle in order to release an active component over a long period of time. Implantable injections may be generally produced by forming a pellet, microsphere or gel with a biodegradable polymer compound. Sustained release injections refer to an injection applied in the muscle in order to release an active component over a long period of time and may be generally produced by dissolving or suspending an active component in a vegetable oil or obtaining a microsphere suspension with a biodegradable polymer compound.

[Formulations for Dialysis]
(1) Agents for Dialysis

Agents for dialysis are a liquid formulation or a solid formulation dissolved upon use to be used for peritoneal dialysis or haemodialysis. Examples thereof include agents for peritoneal dialysis, agents for haemodialysis and the like. Agents for peritoneal dialysis refer to an aseptic agent for dialysis used for peritoneal dialysis and may be generally produced by charging a solution of an active component and an additive in a solvent at a certain volume or a mixture of an active component and an additive into a container, sealing the same and optionally sterilizing the same. Solid formulations to be dissolved upon use may be generally produced according to the production procedures described above for the tablets and granules. Agents for haemodialysis refer to an agent for dialysis used for haemodialysis and may be generally produced by charging a solution of an active component and an additive in a solvent at a certain volume or a mixture of an active component and an additive into a container. Solid formulations to be dissolved upon use may be generally produced according to the production procedures described above for the tablets and granules.

[Formulations for Inhalation]
(1) Agents for Inhalation

Agents for inhalation are a formulation applied to the bronchus or lung by inhaling aerosols of an active component. Examples thereof include powder agents for inhalation, liquid agents for inhalation, aerosols for inhalation and the like. Powder agents for inhalation refer to a formulation to be inhaled as aerosols of solid particles at a predetermined amount, and may be generally produced by preparing fine particles of an active component and optionally mixing thereof with an additive such as lactose to obtain a homogeneous mixture. Liquid agents for inhalation refer to a liquid agent for inhalation to be applied by a nebuliser and the like and may be generally produced by homogeneously dissolving or suspending an active component in a solvent, an appropriate tonicity agent, a pH-controlling agent and the like and optionally filtering the product. Aerosols for inhalation refer to a metered-dose agent for inhalation to spray a predetermined amount of active component packed in a container together with a propellant. Aerosols for inhalation may be generally produced by preparing a solution or suspension from an active component, a solvent, an appropriate dispersant, a stabilising agent and the like and charging the product in a pressure resistant container attached with a flow regulating valve together with a liquid propellant.

[Ophthalmic Formulations]
(1) Ophthalmic Solutions

Ophthalmic solutions are a liquid aseptic formulation or a solid aseptic formulation to be dissolved or suspended upon use, which is applied to ophthalmic tissue such as conjunctival sac. Ophthalmic solutions may be generally produced by charging a solution or suspension of an active component and an additive in a solvent or the like at a certain volume or a mixture of an active component and an additive in a container.

(2) Ophthalmic Ointments

Ophthalmic ointments are a semi-solid aseptic formulation to be applied to ophthalmic tissue such as conjunctival sac, and may be generally produced by charging a homogeneous mixture of a base such as petrolatum and a solution or fine powder of an active component in a container.

[Otological Formulations]
(1) Ear Drops

Ear drops are a liquid or semi-solid formulation or a solid formulation to be dissolved or suspended upon use, which is administered to the external ear or middle ear. Ear drops are generally produced by charging a solution or suspension of an active component and an additive in a solvent or like at a certain volume or a mixture of an active component and an additive in a container.

[Nasologic Formulations]
(1) Nasal Drops

Nasal drops are a formulation to be administered to the nasal cavity or nasal mucosa and examples thereof include nasal powders, nasal liquids and the like. Nasal powders refer to a fine powder nasal drop to be administered to the nasal cavity and may be generally produced by making appropriately fine powder of an active component and optionally mixing the active component with an additive to obtain a homogeneous mixture. Nasal liquids refer to a nasal drop which is liquid or solid to be dissolved or suspended upon use and is administered to the nasal cavity. Nasal liquids may be generally produced by dissolving or suspending an active component in a solvent and an additive and optionally filtering the product. An additive for nasal liquids which may be used includes a tonicity agent, a pH controlling agent and the like.

[Rectal Formulations]
(1) Suppositories

Suppositories are a semi-solid formulation having a certain shape, which is applied in the rectum and releases an active component by melting at body temperature or gradually dissolving or dispersing in water. Suppositories may be generally produced by dissolving or homogeneously dispersing a homogeneous mixture of an active component with an additive such as a dispersant and an emulsifying agent in a base liquefied by heating and the like, charging a predetermined amount of the product in a container and solidifying/moulding the same. Abase for suppositories which may be generally used includes oil- or fat-based bases and hydrophilic bases.

(2) Semi-Solid Formulations for Rectal Administration

Semi-solid formulations for rectal administration are a formulation applied around or in the anus and examples thereof include rectal creams, rectal gels, rectal ointments and the like. Semi-solid formulations for rectal administration may be generally produced by emulsifying an active component together with an additive in purified water and an oil component such as petrolatum, or by homogeneously mixing an active component and an additive with a base which is a polymer gel or an oil or fat. Rectal creams may be generally produced by preparing an oil phase from petrolatum or a higher alcohol or a mixture thereof with an additive such as an emulsifying agent, separately preparing a water phase from purified water or a mixture thereof with an additive such as an emulsifying agent, adding an active component either to the oil phase or the water phase, heating both phases and mixing the oil phase and the water phase until homogeneity to obtain an emulsion. Rectal gels refer to a gel formulation and examples thereof include water-based gels, oil-based gels and the like. Water-based gels may be produced by dissolving or suspending an active component in an additive such as a polymer compound and purified water and allowing crosslinking by heating and cooling or addition of a gel-forming agent. Oil-based gels may be produced by mixing an active component with a liquid oil base such as a glycol or a higher alcohol and an additive. Rectal ointments refer to a semi-solid formulation containing an active component dissolved or suspended in a base and examples thereof include oil- or fat-based ointments, water-soluble ointments and the like. Oil- or fat-based ointments may be generally produced by melting an oil- or fat-based base such as an oil or fat, a wax and a hydrocarbon including paraffin by heating, dissolving or suspending an active component therein and mixing and kneading to obtain a homogeneous mixture. Water-soluble ointments may be generally produced by melting a water-soluble base such as macrogol by heating and mixing and kneading an active component therein to obtain a homogeneous mixture.

(3) Enema Formulations

Enema formulations are a liquid or viscous gel formulation to be applied through the anus. Enema formulations are generally produced by dissolving or suspending an active component in a solvent or the like at a certain volume using purified water or an appropriate aqueous solvent and charging the product in a container. An additive which may be used for enema formulations includes a dispersant, a stabilising agent, a pH controlling agent and the like.

[Vaginal Formulations]
(1) Vaginal Tablets

Vaginal tablets are a solid formulation having a certain shape, which is applied in the vagina and releases an active component by gradually dissolving or dispersing in water. Vaginal tablets may be generally produced according to the production procedures described above for the tablets.

(2) Vaginal Suppositories

Vaginal suppositories are a semi-solid formulation having a certain shape, which is applied in the vagina and releases an active component by melting at body temperature or gradually dissolving or dispersing in water. Vaginal suppositories may be generally produced according to the production procedures described above for the rectal suppositories and the like.

[Skin Formulations]

(1) Topical Solid Formulations

Topical solid formulations are a solid formulation to be applied or spread on skin including the scalp or nails and examples thereof include topical powders. Topical powders refer to a topical solid powder formulation and may be generally produced by mixing an active component with an additive such as a vehicle to obtain a homogeneous mixture which is then formed into powders.

(2) Topical Liquids

Topical liquids are a liquid formulation to be applied on skin including the scalp or nails and examples thereof include liniments, lotions and the like. Topical liquids may be generally produced by dissolving, emulsifying or suspending an active component in a solvent, an additive and the like and optionally filtering the product. Liniments refer to a liquid or muddy topical liquid to be rubbed into the skin. Lotions refer to a topical liquid containing an active component dissolved, emulsified or finely dispersed in an aqueous liquid. Lotions may be generally produced by preparing a solution, suspension or emulsion of an active component, an additive and purified water to obtain a homogeneous product.

(3) Spray Formulations

Spray formulations are a formulation to spray an active component in the form of mist, powder, foam or paste on the skin and examples thereof include topical aerosols, pump spray formulations and the like. Spray formulations may be generally produced by preparing a solution or suspension of an active component, optionally filtering the product and charging the product in a container. Topical aerosols refer to a spray formulation which sprays an active component together with liquefied gas or compressed gas packed in a container. Topical aerosols may be generally produced by preparing a solution or suspension of an active component and packing the product into a pressure resistant container attached with a continuous injection valve together with a liquid propellant. An additive such as a dispersant and a stabilising agent may be optionally added to topical aerosols. Pump spray formulations refer to a spray formulation which sprays an active component in a container by means of a pump. Pump spray formulations may be generally produced by dissolving or suspending an active component and an additive and charging the product in a container to which a pump is attached.

(4) Ointments

Ointments are a semi-solid formulation to be applied on the skin containing an active component dissolved or dispersed in a base. Examples thereof include oil- or fat-based ointments, water soluble ointments and the like. Oil- or fat-based ointments may be generally produced by melting an oil- or fat-based base such as an oil or fat, a wax and a hydrocarbon including paraffin by heating, dissolving or suspending an active component therein and mixing and kneading to obtain a homogeneous mixture. Water soluble ointments may be generally produced by melting a water-soluble base such as macrogol by heating and mixing and kneading an active component therein to obtain a homogeneous mixture.

(5) Creams

Creams are a semi-solid formulation in the form of an oil-in-water or water-in-oil emulsion to be applied on the skin and lipophilic formulations in the form of a water-in-oil emulsion may also be referred to as oil-based creams. Creams may be generally produced by preparing an oil phase from petrolatum or a higher alcohol or a mixture thereof with an additive such as an emulsifying agent, separately preparing a water phase from purified water or a mixture thereof with an additive such as an emulsifying agent, adding an active component either to the oil phase or the water phase, heating both phases and mixing the oil phase and the water phase until homogeneity to obtain an emulsion.

(6) Gels

Gels are a gel formulation to be applied on the skin and examples thereof include water-based gels and oil-based gels. Water-based gels may be generally produced by dissolving or suspending an active component in an additive such as a polymer compound and purified water and allowing crosslinking by heating and cooling or addition of a gel-forming agent. Oil-based gels may be produced by mixing an active component with a liquid oil base such as a glycol or a higher alcohol and an additive.

(7) Plasters and Pressure Sensitive Adhesives

Plasters and pressure sensitive adhesives are a formulation to be adhered on the skin and examples thereof include tapes and cataplasms. Plasters and pressure sensitive adhesives may be generally produced by homogeneously mixing an active component with a base which is a polymer compound or a mixture thereof, spreading the mixture on a support or a liner (release material) and shaping the same. Plasters and pressure sensitive adhesives may be formed as transdermal absorption formulations by using a release-controlled film. An additive such as an adhesive or an absorption-promoting agent may be optionally used for plasters and pressure sensitive adhesives. Tapes refer to a plaster and pressure sensitive adhesive containing a base that contains little water and examples thereof include plasters and the like. Tapes may be generally produced with a base which is a water insoluble natural or synthetic polymer compound such as a resin, a plastic, a rubber or the like by spreading on a fabric or spreading on or incorporating into a plastic film an active component or a homogeneous mixture of an active component and an additive and shaping the product. Tapes may also be produced by incorporating a mixture of an active component and a base or another additive into a release material made of a release-controlled film, a support and a liner (release material) and shaping the same. Cataplasms refer to a plaster and pressure sensitive adhesive containing a base which contains water and may be generally produced by homogeneously mixing an active component with a liquid substance such as purified water or glycerol or homogeneously mixing and kneading a natural or synthetic polymer compound such as a water soluble polymer or a water-absorbable polymer and purified water together with an active component, spreading the mixture on a fabric or the like and shaping the same.

Unless otherwise defined, all technical and scientific terms and abbreviations used herein have the same meanings as those commonly understood by a person skilled in the art to which the present invention belongs.

Contents of all patent literatures and non patent literatures or references explicitly cited herein may be incorporated herein as a part of the present specification.

EXAMPLES

The present invention is hereinafter specifically described by way of Examples and Biological Examples which do not limit the present invention. The present compounds and compounds described in Examples are denominated according to the IUPAC nomenclature. Naming according to the IUPAC nomenclature can be done using, for example, ACD/Name (version 2019.2.0, available from Advanced Chemistry Development Inc.), ACD/Name Batch (version 12.02.45356, available from Advanced Chemistry Development Inc.) or ChemDraw Professional (version 17.1.0.105 or 18.0.0.231, available from PerkinElmer Inc.) In each of the following Examples, the name of the objective compound of the Example is described subsequently to the number of the Example, and the compound is sometimes referred to as the "title compound".

Analytical Methods $^1$H NMR spectra were recorded on Bruker DRX –400 instruments and are calibrated using residual undeuterated solvent ($CHCl_3$, DMSO, MeOH at 7.26, 2.50 and 3.31 ppm for $^1$H NMR, respectively). Chemical shifts (δ) are quoted in parts per million (ppm) and referenced to the appropriate NMR solvent peak(s) and are assigned in accordance with numbered diagrams; with resonances described as s (singlets), d (doublets), t (triplets), q (quartets), combinations thereof (i.e. td indicates a triplet of doublets) or m (multiplets) and br s (broad singlet).

The Liquid Chromatography Mass Spectroscopy (LCMS) systems used are:
General LCMS Procedures
Method 1
Simadzu LC20-MS2010, Agilent Pursit 5 $C_{18}$ 20×2.0 mm at 50° C. Elution with A: 1.5 mL of TFA in 4 L water; B: 0.75 mL of TFA in acetonitrile. Gradient:

| Gradient - Time | flow mL/min | % A | % B |
|---|---|---|---|
| 0.00 | 1.5 | 95 | 5 |
| 0.70 | 1.5 | 5 | 95 |
| 1.10 | 1.5 | 5 | 95 |
| 1.11 | 1.5 | 95 | 5 |
| 1.50 | 1.5 | 95 | 5 |

Detection—MS, UV 220, 254 nm. MS ionization method—Electrospray (positive ion).
Method 2:
Simadzu LC20-MS2010, Xbridge Shield RP-18.5 um, 2.1×50 mm at 50° C. Elution with A: 0.8 mL of $NH_3$—$H_2O$ in 4 L water; B: acetonitrile. Gradient:

| Gradient - Time | flow mL/min | % A | % B |
|---|---|---|---|
| 0.00 | 1.0 | 50 | 50 |
| 2.00 | 1.0 | 0 | 100 |
| 2.48 | 1.0 | 0 | 100 |
| 2.49 | 1.0 | 5 | 50 |
| 3.00 | 1.0 | 50 | 50 |

Detection—MS, UV 220, 254 nm. MS ionization method—Electrospray (positive ion).
Column: XBridge $C_{18}$ 3.5 um 2.1×50 mm;
The High Performance Liquid Chromatography (HPLC) systems used are:
General HPLC Procedures
Method 1
SHIMADZU 20A, Ultimate $C_{18}$ 3.0×50 mm, 3 um at 40° C. Elution with A: 2.75 mL of TFA in 4 L water; B: 2.5 mL of TFA in acetonitrile. Gradient:

| Gradient - Time | flow mL/min | % A | % B |
|---|---|---|---|
| 0.00 | 1.2 | 70 | 30 |
| 6.00 | 1.2 | 10 | 90 |
| 8.00 | 1.2 | 10 | 90 |
| 8.01 | 1.2 | 70 | 30 |
| 10.00 | 1.2 | 70 | 30 |

Detection—MS, UV 220, 254 nm. MS ionization method—Electrospray (positive ion).
Method 2
SHIMADZU 20A, Ultimate $C_{18}$ 3.0×50 mm, 3 um at 40° C. Elution with A: 2.75 mL of TFA in 4 L water; B: 2.5 mL of TFA in acetonitrile. Gradient:

| Gradient - Time | flow mL/min | % A | % B |
|---|---|---|---|
| 0.00 | 1.2 | 90 | 10 |
| 6.00 | 1.2 | 20 | 80 |
| 8.00 | 1.2 | 20 | 80 |
| 8.01 | 1.2 | 90 | 10 |
| 10.00 | 1.2 | 90 | 10 |

Detection—MS, UV 220, 254 nm. MS ionization method—Electrospray (positive ion).
Method 3:
SHIMADZU LC20-MS2020, Xbridge Shield RP-18, 5 um, 2.1×50 mm at 50° C. Elution with A: 0.8 mL of $NH_3H_2O$ in 4 L water; B: acetonitrile. Gradient:

| Gradient - Time | flow mL/min | % A | % B |
|---|---|---|---|
| 0.00 | 0.8 | 90 | 10 |
| 6.00 | 0.8 | 20 | 80 |
| 6.50 | 0.8 | 20 | 80 |
| 6.51 | 0.8 | 90 | 10 |
| 7.00 | 0.8 | 90 | 10 |

Detection—MS, UV 220, 254 nm. MS ionization method—Electrospray (positive ion).
The chiral Supercritical Fluid Chromatography (SFC) systems used are:
Chiral SFC Procedures
Method 1:
 Column: ChiralPak AD-3 150×4.6 mm I.D., 3 um
 Mobile phase: A: $CO_2$ B:IPA (0.05% DEA)
 Isocratic: 40% B
 Flow rate: 2.5 mL/min Column temp.: 40° C.
 Back pressure: 100 bar
Method 2:
 Column: Chiralcel OJ-3 150×4.6 mm I.D., 3 um
 Mobile phase: A: $CO_2$ B: EtOH (0.05% DEA)
 Gradient: from 5% to 40% of B in 5 min and from 40% to 5% of B in 0.5 min, hold 5% of B for 1.5 min
 Flow rate: 2.5 mL/min
 Column temp.: 35° C.
 ABPR: 1500 psi Method 3:
 Column: Chiralcel OD-3 150×4.6 mm I.D., 3 um
 Mobile phase: A: $CO_2$ B: EtOH (0.05% DEA)
 Gradient: from 5% to 40% of B in 5 min and from 40% to 5% of B in 0.5 min. hold 5% of B for 1.5 min
 Flow rate: 2.5 mL/min
 Column temp.: 35° C.
 ABPR: 1500 psi Abbreviations
 2-MeTHF=2-methyl tetrahydrofuran;
 4A MS=molecular sieves, 4A;
 DAST=N,N-diethylaminosulfur trifluoride;
 DCM=dichloromethane;
 DE=diethyl ether;
 DEA=diethylamine;
 DIPEA=diisopropyl ethylamine;
 DMF=N,N-dimethylformamide;
 DMP=Dess-Martin periodinane;
 DMSO=dimethyl sulfoxide;
 dppf=1,1'-Ferrocenebis(diphenylphosphine);
 EA=ethyl acetate;
 EDCI=1-Ethyl-3-(3-dimethylaminopropyl)carbodiimide;
 HATU=1-[Bis(dimethylamino)methylene]-1H-1,2,3-triazolo[4,5-b]pyridinium 3-oxide hexafluorophosphate;
 MTBE=methyl tert-butyl ether;
 NBS=N-bromosuccinimide;
 NCS=N-chlorosuccinimide;
 PE=petroleum ether;
 TBHP=tert-butyl hydroperoxide;
 TEA=triethylamine;
 TFA=trifluoroacetic acid;
 THF=tetrahydrofuran;
 TLC=thin layer chromatography; and
 X-Phos=2-Dicyclohexylphosphino-2',4',6'-triisopropylbiphenyl.

Example 1 [(1R,5S,6r)-6-(5,5-dimethyl-4,5-dihydro-1,2-oxazol-3-yl)-3-azabicyclo[3.1.0]hex-3-yl](1-isopropyl-1H-imidazol-4-yl)methanone

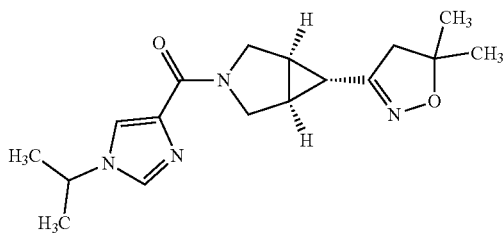 [SMILES: CC(C)n1cnc(C(=O)N2C[C@@H]3[C@H](C2)[C@H]3C2=NOC(C)(C)C2)c1]

tert-butyl (1R,5S,6r)-6-[(E)-(hydroxyimino)methyl]-3-azabicyclo[3.1.0]hexane-3-carboxylate To a solution of tert-butyl (1R,5S,6r)-6-formyl-3-azabicyclo[3.1.0]hexane-3-carboxylate (Pharmablock Inc., catalog No. PBG0012)(2 g, 9.47 mmol) in EtOH (20 mL) were added AcOH (0.54 mL, 9.47 mmol, 1.0 eq.), KOAc (0.93 g, 9.47 mmol, 1.0 eq.). Then $NH_2OH$ HCl (0.47 mL, 11.36 mmol) was added to the mixture. The mixture was stirred at 25° C. for 2 h to give white suspension. The reaction mixture was poured into $H_2O$ (40 mL) and extracted with EtOAc (40 mL×3). The combined organic layers were washed with brine (60 mL), dried over $Na_2SO_4$, filtered and concentrated under reduced pressure to give the title compound as white solid.
TLC: Rf=0.4, PE:EtOAc=3:1;
LC-MS Method1 0.694 min, MS (m/z) 170.8 (M–tBu, +$H^+$);
$^1$H NMR (400 MHz, CHLOROFORM-d) δ=7.16 (d, J=7.6 Hz, 0.5H), 6.13 (d, J=8.8 Hz, 0.5H), 3.75-3.55 (m, 2H), 3.50-3.35 (m, 2H), 2.23-2.15 (m, 0.5H), 2.10 (s, 1.5H), 1.80 (brs, 1H), 1.44 (s, 9H).

tert-butyl (1R,5S,6r)-6-[(Z)-chloro(hydroxyimino)methyl]-3-azabicyclo[3.1.0]hexane-3-carboxylate To a solution of tert-butyl (1R,5S,6r)-6-[(E)-(hydroxyimino)methyl]-3-azabicyclo[3.1.0]hexane-3-carboxylate (2.2 g, 9.72 mmol) in DMF (18.4 mL) were added N-chlorosuccinimide (1363 mg, 10.21 mmol), the mixture was stirred at 20° C. for 2 h. The mixture was poured into $H_2O$ (90 mL), extracted by EtOAc (50 mL×3). The organic phase was washed with brine (50 mL×3), dried over anhydrous $Na_2SO_4$, concentrated to give the title compound as a white solid.
LC-MS Method1 0.780 min, MS (m/z) 245.9 (M+$H^+$).
$^1$H NMR (400 MHz, CHLOROFORM-d) δ ppm 8.42 (s, 1H), 3.75 (d, J=11.2 Hz, 1H), 3.64 (d, J=10.8 Hz, 1H), 3.38 (d, J=10.8 Hz, 2H), 2.06 (s, 2H), 1.76 (t, J=3.2 Hz, 1H), 1.45 (s, 9H).

tert-butyl (1R,5S,6r)-6-(5,5-dimethyl-4,5-dihydro-1,2-oxazol-3-yl)-3-azabicyclo[3.1.0]hexane-3-carboxylate To a solution of tert-butyl (1R,5S,6r)-6-[(Z)-chloro(hydroxyimino)methyl]-3-azabicyclo[3.1.0]hexane-3-carboxylate (100 mg, 0.38 mmol) and $Et_3N$ (0.19 mL, 1.15 mmol) in DMF (1.0 mL) was added 2-methylprop-1-ene (0.72 mL, 1.15 mmol) (15% in isopropyl ether), and the mixture was stirred at 20° C. for 16 h. The reaction mixture was poured into $H_2O$ (20 mL), extracted with EtOAc (20 mL×3). The organic phase was washed with brine (20 mL×3), dried over anhydrous $Na_2SO_4$, concentrated to give the title compound (100 mg, 0.356 mmol, 92.9% yield) as a yellow oil.
LC-MS Method1 0.852 min, MS (m/z): 281 (M+$H^+$).
$^1$H NMR (400 MHz, DIMETHYL SUlFOXIDE-d6) δ ppm 3.50 (d, J=11.1 Hz, 2H), 3.30 (d, J=10.8 Hz, 2H), 2.61 (s, 2H), 1.91 (t, J=2.7 Hz, 2H), 1.40-1.38 (m, 1H), 1.37 (s, 9H), 1.23 (s, 6H).

(1R,5S,6r)-6-(5,5-dimethyl-4,5-dihydro-1,2-oxazol-3-yl)-3-azabicyclo[3.1.0]hexane hydrochloride The mixture of tert-butyl (1R,5S,6r)-6-(5,5-dimethyl-4,5-dihydro-1,2-oxazol-3-yl)-3-azabicyclo[3.1.0]hexane-3-carboxylate (100 mg, 0.36 mmol) in HCl/Dioxane (2.0 mL, 8.0 mmol, 4.0 M) was stirred at 20° C. for 0.5 h. The mixture was concentrated to afford the title compound (100 mg, 0.46 mmol, 129% yield, crude) as a yellow oil.
LC-MS Method1 0.232 min, MS (m/z): 181 (M–HCl+$H^+$).
$^1$H NMR (400 MHz, DIMETHYL SUlFOXIDE-d6) δ ppm 9.53 (brs, 1H), 9.06 (brs, 1H), 3.40-3.26 (m, 4H), 2.60 (s, 2H), 2.12 (brs, 2H), 1.99 (m, 1H), 1.23 (s, 6H).

[(1R,5S,6r)-6-(5,5-dimethyl-4,5-dihydro-1,2-oxazol-3-yl)-3-azabicyclo[3.1.0]hex-3-yl](1-isopropyl-1H-imidazol-4-yl)methanone To a solution of (1R,5S,6r)-6-(5,5-dimethyl-4,5-dihydro-1,2-oxazol-3-yl)-3-azabicyclo[3.1.0]hexane hydrochloride (100 mg, 0.46 mmol), 1-isopropylimidazole-4-carboxylic acid (92 mg, 0.6 mmol) and DIPEA (0.38 mL, 2.31 mmol) in DMF (3.0 mL) was added HATU (194 mg, 0.51 mmol), and the mixture was stirred at 20° C. for 16 h. The mixture was poured into H$_2$O (30 mL), extracted by EtOAc. The organic phase was washed with brine, dried over anhydrous Na$_2$SO$_4$, concentrated to give a residue. The residue was purified by Prep-HPLC (NH$_3$) to afford the title compound (4 mg, 0.012 mmol, 2.7% yield) as a white solid.

$^1$H NMR (400 MHz, CDCl$_3$-d): δ ppm 1.38 (s, 6H) 1.46 (t, J=3.5 Hz, 1H) 1.51 (d, J=6.8 Hz, 6H) 1.98 (br d, J=3.5 Hz, 1H) 2.08 (br d, J=3.0 Hz, 1H) 2.64 (s, 2H) 3.62 (dd, J=12.5, 4.5 Hz, 1H) 3.95 (dd, J=11.9, 3.6 Hz, 1H) 4.20 (d, J=12.5 Hz, 1H) 4.36 (dt, J=13.5, 6.7 Hz, 1H) 4.75 (d, J=12.0 Hz, 1H) 7.47 (d, J=1.3 Hz, 1H) 7.67 (d, J=1.5 Hz, 1H)

LCMS Method 1 0.65 mins MS (m/z) 317.0 [M+H$^+$]

Example 2 [(1R,5S,6r)-6-(5,5-dimethyl-4,5-dihydro-1,2-oxazol-3-yl)-3-azabicyclo[3.1.0]hex-3-yl](1-methyl-1H-imidazol-4-yl)methanone

[(1R,5S,6r)-6-(5,5-dimethyl-4,5-dihydro-1,2-oxazol-3-yl)-3-azabicyclo[3.1.0]hex-3-yl](1-methyl-1H-imidazol-4-yl)methanone To a mixture of 1-methyl-1H-imidazole-4-carboxylic acid (52.47 mg, 0.42 mmol), EDCI (79.76 mg, 0.42 mmol) in Pyridine (1.0 mL) was added (1R,5S,6r)-6-(5,5-dimethyl-4,5-dihydro-1,2-oxazol-3-yl)-3-azabicyclo[3.1.0]hexane hydrochloride (91 mg, 0.42 mmol). The suspension was stirred at 20° C. for 8 hr. The reaction mixture was concentrated in vacuum. The residue was purified by prep-HPLC (NH$_3$) and lyophilized to afford the title compound (17.45 mg, 21.8% yield) as yellow solid.

LC-MS Method1: 0.691 min, MS (m/z): 289.2 (M+H$^+$).

$^1$H NMR (400 MHz, CHLOROFORM-d) δ ppm 7.56 (d, J=1.25 Hz, 1H), 7.38 (s, 1H), 4.70 (d, J=12.05 Hz, 1H), 4.19 (d, J=12.30 Hz, 1H), 3.94 (dd, J=12.05, 4.02 Hz, 1H), 3.72 (s, 3H), 3.61 (dd, J=12.55, 4.27 Hz, 1H), 2.64 (s, 2H), 2.05-2.11 (m, 1H), 1.95-2.01 (m, 1H), 1.46 (t, J=3.39 Hz, 1H), 1.38 (s, 6H)

Example 3 [(1R,5S,6r)-6-(5,5-dimethyl-4,5-dihydro-1,2-oxazol-3-yl)-3-azabicyclo[3.1.0]hex-3-yl](1-ethyl-1H-imidazol-4-yl)methanone ethyl 1-ethyl-1H-imidazole-4-carboxylate A mixture of ethyl (2Z)-3-(dimethylamino)-2-isocyanoacrylate and ethylamine (1608.2 mg, 35.67 mmol, 1.60 mL, 20 eq) was stirred at 40° C. for 16 hr. The solution was then concentrated in vacuum. The residue was purified by prep-TLC (PE:EtOAc=0:1, Rf=0.2) to afford the title compound (126 mg, crude) as yellow oil.

LC-MS Method1: 0.259 min, MS (m/z): 168.8 (M+H$^+$).

$^1$H NMR (400 MHz, CHLOROFORM-d) δ ppm 7.64 (s, 1H), 7.51 (s, 1H), 4.37 (q, J=7.2 Hz, 2H), 4.04 (q, J=7.2 Hz, 2H), 1.39 (t, J=7.2 Hz, 3H), 1.26 (t, J=7.2 Hz, 3H).

1-ethyl-1H-imidazole-4-carboxylic acid

To a mixture of ethyl 1-ethyl-1H-imidazole-4-carboxylate in H$_2$O (0.5 mL) and THF (1.5 mL) was added LiOH·H$_2$O (47.16 mg, 1.12 mmol, 1.5 eq). The suspension was stirred at 40° C. for 6 hr. The residue was diluted with H$_2$O (1 mL), extracted with EtOAc (5 mL×4). The afforded H$_2$O layer was acidified with 1 N HCl aq. to pH=5, The combined organic layers were concentrated and then lyophilized to afford the title compound (70 mg, crude) as yellow solid.

$^1$H NMR (400 MHz, CHLOROFORM-d) δ ppm 7.69 (s, 1H), 7.45 (s, 1H), 3.98 (q, J=7.2 Hz, 2H), 1.33 (t, J=7.2 Hz, 3H).

[(1R,5S,6r)-6-(5,5-dimethyl-4,5-dihydro-1,2-oxazol-3-yl)-3-azabicyclo[3.1.0]hex-3-yl](1-ethyl-1H-imidazol-4-yl)methanone To a mixture of 1-ethyl-1H-imidazole-4-carboxylic acid in Pyridine (1 mL) were added EDCI (95.54 mg, 0.50 mmol) and (1R,5S,6r)-6-(5,5-dimethyl-4,5-dihydro-1,2-oxazol-3-yl)-3-azabicyclo[3.1.0]hexane hydrochloride (72 mg, 0.33 mmol). The suspension was stirred at 20° C. for 16 hr. The solution was purified by Prep-HPLC (NH$_3$) and lyophilized to afford the title compound (23.69 mg, 23.58% yield) as yellow solid.

LC-MS Method1: 2.045 min, MS (m/z): 303.2 (M+H$^+$).

$^1$H NMR (400 MHz, CHLOROFORM-d) δ ppm 7.54 (d, J=1.25 Hz, 1H) 7.35 (d, J=1.25 Hz, 1H) 4.65 (d, J=12.05 Hz, 1H) 4.12 (d, J=12.30 Hz, 1H) 3.94 (q, J=7.28 Hz, 2H) 3.87 (dd, J=12.05, 4.02 Hz, 1H) 3.54 (dd, J=12.55, 4.27 Hz, 1H) 2.57 (s, 2H) 2.00 (dt, J=7.47, 3.92 Hz, 1H) 1.91 (br d, J=3.76 Hz, 1H) 1.37-1.44 (m, 4H) 1.30 (s, 7H)

Example 4 (1-cyclopropyl-1H-imidazol-4-yl)[(1R,5S,6r)-6-(5,5-dimethyl-4,5-dihydro-1,2-oxazol-3-yl)-3-azabicyclo[3.1.0]hex-3-yl]methanone methyl 1-cyclopropyl-1H-imidazole-4-carboxylate To a suspension of 2,2'-bipyridine (618.79 mg, 3.96 mmol), Cu(OAc)$_2$ (720.01 mg, 3.96 mmol), Na$_2$CO$_3$ (840.54 mg, 7.93 mmol) in DCE (30 mL) were added methyl 1H-imidazole-4-carboxylate (500 mg, 3.96 mmol) and cyclopropylboronic acid (681.15 mg, 7.93 mmol). The mixture was stirred at 70° C. for 16 h under O$_2$. TLC (PE: EtOAc=1:4) showed the reaction was completed. The reaction mixture was cooled to 23° C. The solid was removed by filtration and the filtrate was concentrated under vacuum. The residue was purified by flash column (PE to 20% EtOAc in PE). The combined organic layers were concentrated under reduced pressure to afford the title compound (140 mg, 0.8425 mmol, 21.249% yield) as a brown oil.

$^1$H NMR (400 MHz, CHLOROFORM-d) δ ppm 7.66 (s, 1H), 7.60 (s, 1H), 3.87 (s, 3H), 3.42-3.36 (m, 1H), 1.10-0.90 (m, 4H).

1-cyclopropyl-1H-imidazole-4-carboxylic acid

To a solution of methyl 1-cyclopropyl-1H-imidazole-4-carboxylate (140 mg, 0.84 mmol) in THF (3 mL) and H$_2$O (1 mL) was added LiOH·H$_2$O (0.06 mL, 1.1 mmol). The resulting mixture was stirred at 20-25° C. for 2 h to give white suspension. TLC (PE:EtOAc=1:4) showed the reaction was completed (Rf=0). The reaction mixture was concentrated directly. The residue was acidified with 1 M HCl aq. to pH=6, then the combined organic layers were lyophilized to afford the title compound (120 mg, 0.7887 mmol, 93.618% yield) as a white solid.

(1-cyclopropyl-1H-imidazol-4-yl)[(1R,5S,6r)-6-(5,5-dimethyl-4,5-dihydro-1,2-oxazol-3-yl)-3-azabicyclo[3.1.0]hex-3-yl]methanone To a solution of 1-cyclopropyl-1H-imidazole-4-carboxylic acid (120 mg, 0.79 mmol) in DMF (3 mL) were added at HATU (361.82 mg, 0.95 mmol), Et$_3$N (0.51 mL, 3.94 mmol), (1R,5S,6r)-6-(5,5-dimethyl-4,5-dihydro-1,2-oxazol-3-yl)-3-azabicyclo[3.1.0]hexane hydrochloride (142.16 mg, 0.79 mmol). The resulting mixture was stirred at 20-25° C. for 14 hours. The residue was purified by prep-HPLC (HCl). The combined organic layers were concentrated and then lyophilized to afford the title compound (4.8 mg, 0.0137 mmol, 1.7347% yield) as a light yellow gum.

LC-MS Method1: 315.0 [M+H$^+$]

$^1$H NMR (400 MHz, METHANOL-d$_4$) δ=8.68-8.33 (m, 1H), 7.91 (br s, 1H), 4.10-3.84 (m, 3H), 3.60 (br d, J=4.8 Hz, 2H), 2.63 (s, 2H), 2.16-1.99 (m, 2H), 1.44 (br s, 1H), 1.24 (s, 7H), 1.07 (d, J=6.5 Hz, 4H).

Example 5 (1-cyclobutyl-1H-imidazol-4-yl)[(1R,5S,6r)-6-(5,5-dimethyl-4,5-dihydro-1,2-oxazol-3-yl)-3-azabicyclo[3.1.0]hex-3-yl]methanone ethyl 1-cyclobutyl-1H-imidazole-4-carboxylate A mixture of ethyl (2Z)-3-(dimethylamino)-2-isocyanoacrylate (400 mg, 2.38 mmol) and cyclobutanamine (1.02 mL, 11.89 mmol) was heated at 50° C. for 16 hr. The mixture was concentrated in vacuum, then the residue was purified by flash column (0-100% EA in PE, 0.5% NH$_3$—H$_2$O) to give the title compound (420 mg, 2.1624 mmol, 90.923% yield) as yellow oil.

LC-MS Method1 0.568 min, MS (M/Z) 194.9 (M+H$^+$).

1-cyclobutyl-1H-imidazole-4-carboxylic acid

To a mixture of ethyl 1-cyclobutyl-1H-imidazole-4-carboxylate (100 mg, 0.5100 mmol) in THF (0.8578 mL) and H$_2$O (1.0722 mL) was added LiOH·H$_2$O (0.09 mL, 1.54 mmol). The resulting suspension was then stirred at 20° C. for 3.5 hr. TLC (100% EA) showed new spot (Rf=0) and the reactant was consumed completely. The aqueous phase was washed with DCM (3 mL×2) and acidified with 1N HCl to pH=2. The residual aqueous solution was lyophilized to give the title compound (160 mg, 0.9628 mmol, 187.01% yield) as pale yellow solid.

$^1$H NMR (400 MHz, D$_2$O) δ ppm 8.77 (s, 1H), 8.03 (s, 1H), 4.85-4.75 (m, 1H), 2.50-2.40 (m, 2H), 2.40-2.30 (m, 2H), 1.90-1.75 (m, 2H).

(1-cyclobutyl-1H-imidazol-4-yl)[(1R,5S,6r)-6-(5,5-dimethyl-4,5-dihydro-1,2-oxazol-3-yl)-3-azabicyclo[3.1.0]hex-3-yl]methanone To a mixture of 1-cyclobutyl-1H-imidazole-4-carboxylic acid (110 mg, 0.5400 mmol) in DMF (0.9736 mL) were added HATU (247.8 mg, 0.6500 mmol), DIPEA (0.45 mL, 2.7 mmol) and (1R,5S,6r)-6-(5,5-dimethyl-4,5-dihydro-1,2-oxazol-3-yl)-3-azabicyclo[3.1.0]hexane hydrochloride (97.36 mg, 0.5400 mmol). The resulting mixture was stirred at 20° C. for 4 hr. The reaction mixture was diluted with H$_2$O (5 mL), extracted with EtOAc (5 mL×2). The combined organic layers were separated, then dried over Na$_2$SO$_4$ and concentrated in vacuum to give crude oil. The crude oil was purified by prep-TLC (EA/MeOH=10/1), then Prep-HPLC (NH$_3$) and lyophilized to give the title compound (12.15 mg, 0.0370 mmol, 6.8494% yield) as pale yellow solid.

LC-MS Method1: 328.9[M+H$^+$]

$^1$H NMR (400 MHz, DMSO-d$_6$) δ=8.03 (d, J=1.3 Hz, 1H), 7.99 (s, 1H), 4.96-4.89 (m, 1H), 4.75 (br d, J=12.0 Hz, 1H), 4.12 (br d, J=12.3 Hz, 1H), 3.99 (br d, J=9.0 Hz, 1H), 3.66 (br s, 1H), 2.83 (s, 2H), 2.57 (t, J=8.7 Hz, 4H), 2.25 (br d, J=11.3 Hz, 1H), 2.17 (br s, 1H), 2.00-1.90 (m, 2H), 1.60-1.57 (m, 1H), 1.44 (s, 6H)

Example 6 [1-(bicyclo[1,1,1]pent-1-yl)-1H-imidazol-4-yl][(1R,5S,6r)-6-(5,5-dimethyl-4,5-dihydro-1,2-oxazol-3-yl)-3-azabicyclo[3.1.0]hex-3-yl]methanone ethyl 1-(bicyclo[1,1,1]pent-1-yl)-1H-imidazole-4-carboxylate To a mixture of ethyl (2Z)-3-(dimethylamino)-2-isocyanoacrylate (100 mg, 0.5900 mmol) in 1-Butanol (0.40 mL) were added bicyclo[1,1,1]pentan-1-amine (284.42 mg, 2.38 mmol) and Et$_3$N (0.58 mL, 4.46 mmol). The resulting mixture was heated at 76° C. for 16 hr. The reaction mixture was diluted with H$_2$O (5 mL) and extracted with EtOAc (5 mL×3). The combined organic layers were dried over Na$_2$SO$_4$ and concentrated in vacuum to give the title compound (100 mg, crude product) as yellow oil.

1-(bicyclo[1,1,1]pent-1-yl)-1H-imidazole-4-carboxylic acid

To a mixture of ethyl 1-(bicyclo[1,1,1]pent-1-yl)-1H-imidazole-4-carboxylate (100 mg, 0.4800 mmol) in H$_2$O (1 mL) and MeOH (0.80 mL) was added LiOH·H$_2$O (0.06 mL, 0.9700 mmol). The reaction was stirred at 25° C. for 16 hr. The aqueous phase was washed with DCM (3 mL×2) and acidified with 1N HCl to pH=2. The aqueous solution was lyophilized to give the title compound (50 mg, 0.2806 mmol, crude product) as pale yellow solid.

[1-(bicyclo[1.1.1]pent-1-yl)-1H-imidazol-4-yl][(1R,5S,6r)-6-(5,5-dimethyl-4,5-dihydro-1,2-oxazol-3-yl)-3-azabicyclo[3.1.0]hex-3-yl]methanone To a mixture of 1-(bicyclo[1,1,1]pent-1-yl)-1H-imidazole-4-carboxylic acid (59.54 mg, 0.2800 mmol) in DMF (0.50 mL) were added HATU (137.86 mg, 0.3600 mmol), DIPEA (0.18 mL, 1.11 mmol) and (1R,5S,6r)-6-(5,5-dimethyl-4,5-dihydro-1,2-oxazol-3-yl)-3-azabicyclo[3.1.0]hexane hydrochloride (50 mg, 0.2800 mmol). The resulting mixture was stirred at 20° C. for 4 hr. The reaction mixture was diluted with H$_2$O (5 mL) and extracted with EtOAc (5 mL×2), The combined organic layers were separated, washed with brine (8 mL), dried over Na$_2$SO$_4$ and concentrated in vacuum to give crude oil. The crude oil was purified by prep-HPLC (NH$_3$) to give the title compound (2.4 mg, 0.0071 mmol, 2.5416% yield) as yellow solid.

$^1$H NMR (400 MHz, DMSO-d$_6$) δ=7.76 (d, J=1.0 Hz, 1H), 7.71 (d, J=1.3 Hz, 1H), 4.53 (br d, J=11.8 Hz, 1H), 3.93 (br d, J=12.0 Hz, 1H), 3.81 (br dd, J=3.6, 11.9 Hz, 1H), 3.47 (br dd, J=3.6, 11.9 Hz, 1H), 2.65 (s, 2H), 2.24 (s, 6H), 2.08-1.93 (m, 3H), 1.40 (t, J=3.4 Hz, 1H), 1.26-1.25 (m, 1H), 1.25 (s, 5H).

Example 7 (1-cyclopentyl-1H-imidazol-4-yl)[(1R,5S,6r)-6-(5,5-dimethyl-4,5-dihydro-1,2-oxazol-3-yl)-3-azabicyclo[3.1.0]hex-3-yl]methanone ethyl 1-cyclopentyl-1H-imidazole-4-carboxylate A mixture of ethyl (2Z)-3-(dimethylamino)-2-isocyanoacrylate (200 mg, 1.19 mmol) and cyclopentyl amine (0.58 mL, 5.95 mmol) was heated at 50° C. for 16 hr. The mixture was concentrated in vacuum. The residue was purified by flash column (0-100% EA in PE, 0.5% NH₃H₂O) to give the title compound (240 mg, 1.1524 mmol, 96.912% yield) as yellow oil.

LC-MS Method1 0.668 min, MS (M/Z) 209.1 (M+H⁺).

1-cyclopentyl-1H-imidazole-4-carboxylic acid

To a mixture of ethyl 1-cyclopentyl-1H-imidazole-4-carboxylate (100 mg, 0.4800 mmol) in THF (0.80 mL) and H₂O (1 mL) was added LiOH·H₂O (0.08 mL, 1.44 mmol). The reaction mixture was stirred at 25° C. for 3.5 hr. The aqueous phase was washed with DCM (3 mL×2) and acidified with 1N HCl to pH=2. The residual aqueous solution was lyophilized to give the title compound (150 mg, crude product) as pale yellow solid.

¹H NMR (400 MHz, D₂O) δ ppm 8.73 (s, 1H), 7.90 (s, 1H), 4.75-4.70 (m, 1H), 2.25-2.10 (m, 2H), 1.90-1.60 (m, 6H).

(1-cyclopentyl-1H-imidazol-4-yl)[(1R,5S,6r)-6-(5,5-dimethyl-4,5-dihydro-1,2-oxazol-3-yl)-3-azabicyclo [3.1.0]hex-3-yl]methanone To a mixture of 1-cyclopentyl-1H-imidazole-4-carboxylic acid (60.38 mg, 0.2800 mmol) in DMF (0.50 mL) were added HATU (137.86 mg, 0.3600 mmol), DIPEA (0.18 mL, 1.11 mmol) and (1R,5S,6r)-6-(5,5-dimethyl-4,5-dihydro-1, 2-oxazol-3-yl)-3-azabicyclo[3.1.0]hexane hydrochloride (50 mg, 0.2800 mmol). The resulting mixture was stirred at 20° C. for 4 hr. The reaction mixture was diluted with H₂O (5 mL) and extracted with EtOAc (5 mL×2). The combined organic layers were separated, washed with brine (8 mL), dried over Na₂SO₄ and concentrated in vacuum to give crude oil. The crude oil was purified by prep-TLC (EA/ MeOH=10/1), then prep-HPLC (NH₃) and lyophilized to give the title compound (11 mg, 0.0321 mmol, 4.6614% yield) as white solid.

¹H NMR (400 MHz, DMSO-d₆) δ=7.78 (d, J=1.3 Hz, 1H), 7.73 (d, J=1.3 Hz, 1H), 4.66-4.51 (m, 2H), 3.93 (br d, J=12.3 Hz, 1H), 3.81 (br d, J=6.5 Hz, 1H), 3.47 (br d, J=11.8 Hz, 1H), 2.65 (s, 2H), 2.19-2.03 (m, 3H), 1.99 (br d, J=6.0 Hz, 1H), 1.79 (br s, 4H), 1.64 (br s, 2H), 1.25 (s, 7H)

Example 8 (1-cyclohexyl-1H-imidazol-4-yl)[(1R,5S, 6r)-6-(5,5-dimethyl-4,5-dihydro-1,2-oxazol-3-yl)-3-azabicyclo[3.1.0]hex-3-yl]methanone ethyl 1-cyclohexyl-1H-imidazole-4-carboxylate A mixture of ethyl (2Z)-3-(dimethylamino)-2-isocyanoacrylate (200 mg, 1.19 mmol) and cyclohexyl amine (0.68 mL, 5.95 mmol) was heated at 50° C. for 16 hr. The mixture was concentrated in vacuum. The residue was purified by flash column (0-100% EA in PE, 0.5% NH₃H₂O) to give the title compound (280 mg, 1.2597 mmol, 105.93% yield) as yellow oil.

LC-MS Method1 0.719 min, MS (m/z) 223.1 (M+H⁺).

1-cyclohexyl-1H-imidazole-4-carboxylic acid

To a mixture of ethyl 1-cyclohexyl-1H-imidazole-4-carboxylate (110 mg, 0.4900 mmol) in THF (0.80 mL) and H₂O (1 mL) was added LiOH·H₂O (0.09 mL, 1.48 mmol), then stirred at 25° C. for 5 hr. TLC (100% EA) showed new spot (Rf=0) and the reactant was consumed completely, the aqueous phase was washed with DCM (3 mL×2) and acidified with 1N HCl to pH=2. The residual aqueous solution was lyophilized to give the title compound (190 mg, crude product) as pale yellow solid.

¹H NMR (400 MHz, Methanol-d₄) δ ppm 9.05 (s, 1H), 8.30 (s, 1H), 4.36-4.30 (m, 1H), 2.20-2.17 (m, 2H), 1.92-1.82 (m, 2H), 1.80-1.73 (m, 3H), 1.60-1.40 (m, 2H), 1.40-1.25 (m, 1H).

(1-cyclohexyl-1H-imidazol-4-yl)[(1R,5S,6r)-6-(5,5-dimethyl-4,5-dihydro-1,2-oxazol-3-yl)-3-azabicyclo [3.1.0]hex-3-yl]methanone To a mixture of 1-cyclohexyl-1H-imidazole-4-carboxylic acid (64.27 mg, 0.2800 mmol) in DMF (0.50 mL) were added HATU (106.05 mg, 0.2800 mmol), DIPEA (0.18 mL, 1.11 mmol) and (1R,5S,6r)-6-(5,5-dimethyl-4,5-dihydro-1, 2-oxazol-3-yl)-3-azabicyclo[3.1.0]hexane hydrochloride (50 mg, 0.2800 mmol). The resulting mixture was stirred at 20° C. for 4 hr. The reaction mixture was diluted with H₂O (5 mL) and extracted with EtOAc (5 mL×2). The combined organic layers were separated, dried over Na₂SO₄ and concentrated in vacuum to give crude oil. The crude oil was purified by prep-TLC (EA/MeOH=10/1) then lyophilized to give the title compound (9.5 mg, 0.0267 mmol, 9.6077% yield) as white powder.

¹H NMR (400 MHz, DMSO-d₆) δ=7.77 (d, J=5.5 Hz, 2H), 4.58 (br d, J=12.0 Hz, 1H), 4.14-4.02 (m, 1H), 3.93 (br d, J=12.0 Hz, 1H), 3.80 (br d, J=8.5 Hz, 1H), 3.51-3.43 (m, 1H), 2.64 (s, 2H), 2.05 (br s, 1H), 1.95 (br d, J=12.3 Hz, 3H), 1.80 (br d, J=13.3 Hz, 2H), 1.72-1.61 (m, 3H), 1.41-1.29 (m, 3H), 1.25 (s, 7H)

Example 9 [(1R,5S,6r)-6-(5,5-dimethyl-4,5-dihydro-1,2-oxazol-3-yl)-3-azabicyclo[3.1.0]hex-3-yl][1-(1, 1,1-trifluoropropan-2-yl)-1H-imidazol-4-yl]methanone ethyl 1-(1,1,1-trifluoropropan-2-yl)-1H-imidazole-4-carboxylate To a solution of 1,1,1-trifluoro-2-propanamine (403.4 mg, 3.57 mmol) in 2-MeTHF (3 mL, 1.19 mmol) was added n-BuLi (1.43 mL, 3.57 mmol) at −78° C. The reaction mixture was stirred at −78° C. for 15 min. Then ethyl (2Z)-3-(dimethylamino)-2-isocyanoacrylate (200 mg, 1.19 mmol) was added. The reaction mixture was allowed to warm to 25° C. for 0.5 hr to give black solution. The reaction mixture was poured into EtOH (5 mL) and concentrated. The crude product was purified by flash column (PE to 100% EtOAc in PE). The afforded residue was purified by prep-TLC (EtOAc) to give the title compound (50 mg, 0.2117 mmol, 17.802% yield) as brown oil.

1-(1,1,1-trifluoropropan-2-yl)-1H-imidazole-4-carboxylic acid

To a solution of ethyl 1-(1,1,1-trifluoropropan-2-yl)-1H-imidazole-4-carboxylate (50 mg, 0.2100 mmol) in THF (1.5 mL) and H₂O (0.3 mL, 16.67 mmol) was added hydroxylithium hydrate (26.65 mg, 0.6400 mmol). The mixture was stirred at 20° C. for 3 h to give black solution. LCMS showed the starting material (50 mg, 0.2100 mmol) was remained. The mixture was stirred at 40° C. for 12 h to give black solution. The reaction mixture was concentrated directly. The afforded H₂O layer was acidified with 1 N HCl aq. to pH=5-6 and lyophilized to give the title compound (30 mg, 0.1441 mmol, 68.086% yield) as brown solid.

[(1R,5S,6r)-6-(5,5-dimethyl-4,5-dihydro-1,2-oxazol-3-yl)-3-azabicyclo[3.1.0]hex-3-yl][1-(1,1,1-trifluoropropan-2-yl)-1H-imidazol-4-yl]methanone To a solution of 1-(1,1,1-trifluoropropan-2-yl)-1H-imidazole-4-carboxylic acid (30 mg, 0.1400 mmol) in DMF (1.5 mL) were added HATU (66.12 mg, 0.1700 mmol), DIPEA (0.12 mL, 0.7200 mmol). The mixture was stirred for 30 min. Then (1R,5S,6r)-6-(5,5-dimethyl-4,5-dihydro-1,2-oxazol-3-yl)-3-azabicyclo[3.1.0]hexane hydrochloride (36.48 mg, 0.1400 mmol) was added to the mixture. The mixture was stirred at 25° C. for 3 h to give brown solution. The reaction mixture was concentrated directly. The residue was purified by prep-HPLC (NH$_3$) to give the title compound (16.87 mg, 0.0455 mmol, 17.802% yield) as white powder.

LC-MS Method1: 371.1 [M+H$^+$]

$^1$H NMR (400 MHz, CHLOROFORM-d) δ ppm 7.72 (1H, s) 7.53 (1H, s) 4.59-4.78 (2H, m) 4.19 (1H, dd, J=12.80, 5.77 Hz) 3.95 (1H, dd, J=12.05, 7.91, 4.14 Hz) 3.63 (1H, br d, J=12.30 Hz) 2.65 (2H, s) 2.09 (1H, m d, J=3.76 Hz) 2.01 (1H, m d, J=6.53 Hz) 1.76 (3H, d, J=7.28 Hz) 1.44-1.50 (1H, m) 1.38 (6H, s)

Example 10 [(1R,5S,6S)-6-(5,5-dimethyl-4,5-dihydro-1,2-oxazol-3-yl)-3-azabicyclo[3.1.0]hex-3-yl]{1-[(2S)-3-methylbutan-2-yl]-1H-imidazol-4-yl}methanone (R)-2-methyl-N-[(1E)-2-methylpropylidene]-2-propanesulfinamide To a solution of (R)-t-BuS(O)NH$_2$ (8403.83 mg, 69.34 mmol) in THF (36.369 mL) were added 2-methylpropanal (6.3 mL, 69.34 mmol) and Ti(OEt)$_4$ (21.57 mL, 104.01 mmol) at 20° C. The resulting mixture was stirred at 60° C. for 0.5 hours to give yellow solution. H$_2$O (3 mL) was added dropwise and it was stirred at 20° C. for 5 mins, then it was filtered through a pad of celite and concentrated in vacuum to give the title compound (8330 mg, 47.521 mmol, 68.535% yield) as white solid. It was used directly for the next step.

LC-MS Method1 0.825 min, MS (m/z) 176.2 (M+H$^+$).

(R)-2-methyl-N-[(2S)-3-methyl-2-butanyl]-2-propanesulfinamide

To a stirred solution of (R)-2-methyl-N-[(1E)-2-methylpropylidene]-2-propanesulfinamide (2500 mg, 14.26 mmol) in THF (30 mL) cooled to −40° C. was added MeMgBr (5.7 mL, 17.11 mmol) dropwise. The reaction was stirred at −40° C. for 3 hr and warmed up to 20° C. slowly over 13 hr. TLC (DCM/EA=6/1, RF=0.3) showed two new spot. H$_2$O (30 mL) was added and it was extracted with EtOAc (30 mL×2). The combined organic layer dried over Na$_2$SO$_4$ and concentrated in vacuum to give a yellow oil. The crude was purified by silica gel chromatography (PE/EA=10/1 to 3/1) to give the title compound (2200 mg, 11.498 mmol, 80.623% yield) as colorless oil.

$^1$H NMR (400 MHz, CHLOROFORM-d) δ ppm 3.35-3.10 (m, 1H), 2.90-2.75 (m, 1H), 1.80-1.60 (m, 1H), 1.21 (d, J=6.8 Hz, 3H), 1.20 (s, 9H), 0.886 (d, J=6.8 Hz, 3H), 0.871 (d, J=6.8 Hz, H).

(2S)-3-methyl-2-butanamine

A solution of (R)-2-methyl-N-[(2S)-3-methyl-2-butanyl]-2-propanesulfinamide (2200 mg, 11.5 mmol) in HCl/MeOH (10 mL, 40 mmol) was stirred at 20° C. for 4 hr to give a colorless solution. The reaction mixture was evaporated in vacuum to give a white solid. It was triturated with toluene/PE=1/6 to give the title compound (1350 mg, 10.921 mmol) as white solid.

ethyl 1-[(2S)-3-methylbutan-2-yl]-1H-imidazole-4-carboxylate

To a 5 mL microwave vial were added (2S)-3-methyl-2-butanamine (500 mg, 4.04 mmol), ethyl (2Z)-3-(dimethylamino)-2-isocyanoacrylate (680.27 mg, 4.04 mmol), 1-Butanol (3 mL) and Et$_3$N (0.84 mL, 6.07 mmol). The reaction mixture was irradiated with microwave at 130° C. for 1 hr to give a brown solution. H$_2$O (30 mL) was added and it was extracted with EtOAc (30 mL×2). The combined organic layer dried over Na$_2$SO$_4$ and concentrated in vacuum to give a yellow oil. The crude was purified by silica gel chromatography (PE/EA=10/1 to 3/2) to give the title compound (161 mg, 0.7657 mmol, 18.9310% yield) as brown oil.

LC-MS Method1 0.691 min, MS (m/z) 211.2 (M+H$^+$).

1-[(2S)-3-methylbutan-2-yl]-1H-imidazole-4-carboxylic acid

A stirred solution of ethyl 1-[(2S)-3-methylbutan-2-yl]-1H-imidazole-4-carboxylate (150.0 mg, 0.7600 mmol) in 1,4-Dioxane (3 mL) was added a solution of LiOH·H$_2$O (48.11 mg, 1.15 mmol). The reaction mixture was stirred at 20° C. for 4 hr to give a yellow solution. H$_2$O (10 mL) was added and it was extracted with EtOAc (10 mL×2). The H$_2$O phase was adjusted to 5 with 1M HCl aq. and lyophilized to give the title compound (110 mg, 0.6037 mmol, 78.98% yield) as brown solid.

LC-MS Method1 0.306 min, MS (m/z) 183.0 (M+H$^+$).

[(1R,5S,6S)-6-(5,5-dimethyl-4,5-dihydro-1,2-oxazol-3-yl)-3-azabicyclo[3.1.0]hex-3-yl]{1-[(2S)-3-methylbutan-2-yl]-1H-imidazol-4-yl}methanone To a stirred solution of 1-[(2S)-3-methylbutan-2-yl]-1H-imidazole-4-carboxylic acid (100 mg, 0.5500 mmol) and HATU (251.76 mg, 0.6600 mmol) in DMF (3 mL) was added N-ethyl-N-isopropylpropan-2-amine (0.47 mL, 2.74 mmol). After stirred for 30 mins, (1R,5S,6r)-6-(5,5-dimethyl-4,5-dihydro-1,2-oxazol-3-yl)-3-azabicyclo[3.1.0]hexane hydrochloride (138.94 mg, 0.5500 mmol) was added and the reaction was stirred at 20° C. for 16 hr to give a yellow solution. H$_2$O (30 mL) was added and it was extracted with EtOAc (30 mL×2). The combined organic layer dried over Na$_2$SO$_4$ and concentrated in vacuum to give a yellow oil. The crude was purified by Prep-HPLC (NH$_3$) and lyophilized to give the title compound (108.71 mg, 0.3156 mmol, 57.509% yield) as white solid.

LC-MS Method1: 345.3 [M+H$^+$]

$^1$H NMR (400 MHz, CHLOROFORM-d) δ 7.61 (d, J=1.00 Hz, 1H), 7.40 (d, J=1.25 Hz, 1H), 4.76 (br d, J=12.05 Hz, 1H), 4.18 (d, J=12.55 Hz, 1H), 3.94 (br dd, J=4.02, 11.80 Hz, 1H), 3.84 (quin, J=7.09 Hz, 1H), 3.61 (dd, J=4.27, 12.55 Hz, 1H), 2.64 (s, 2H), 2.07 (br dd, J=3.51, 7.28 Hz, 1H), 1.95-1.99 (m, 1H), 1.87-1.94 (m, 1H), 1.47 (d, J=6.78 Hz, 4H), 1.36 (s, 6H), 0.96 (d, J=6.78 Hz, 3H), 0.78 (d, J=6.53 Hz, 3H)

Example 11 {1-[(2R)-butan-2-yl]-1H-imidazol-4-yl}[(1R,5S,6R)-6-(5,5-dimethyl-4,5-dihydro-1,2-oxazol-3-yl)-3-azabicyclo[3.1.0]hex-3-yl]methanone ethyl 1-[(2R)-butan-2-yl]-1H-imidazole-4-carboxylate

A mixture of ethyl (2Z)-3-(dimethylamino)-2-isocyanoacrylate (300 mg, 1.78 mmol) and (2R)-2-butanamine (0.54 mL, 5.35 mmol) was stirred at 50° C. for 16 h to give brown mixture. TLC (PE:EA=1:1) showed new spot (Rf=0.2) was detected. The mixture was concentrated to give a residue. The residue was purified by flash column (PE:EA=1:0 to 1:4) to afford the title compound (240 mg, 1.2229 mmol, 68.562% yield) as brown solid.

LC-MS Method1 0.586 min, MS (m/z) 196.9 (M+H$^+$).

1-[(2R)-butan-2-yl]-1H-imidazole-4-carboxylic acid

To a mixture of ethyl 1-[(2R)-butan-2-yl]-1H-imidazole-4-carboxylate (240 mg, 1.22 mmol) in THF (3 mL) and H$_2$O (1.5 mL) was added LiOH·H$_2$O (0.11 mL, 1.83 mmol). The reaction mixture was stirred at 25° C. for 16 h to give yellow mixture. TLC (PE:EtOAc=1:1) showed most of the starting material was consumed. The reaction mixture was diluted with H$_2$O (15 mL) and extracted with EtOAc (8 mL×5). The aqueous phase was acidified with 1 N HCl aq. to pH=4. The resulting aqueous phase was dried in vacuum to afford the title compound (200 mg, 1.1891 mmol, 97.236% yield) (crude) as yellow oil.

{1-[(2R)-butan-2-yl]-1H-imidazol-4-yl}[(1R,5S,6R)-6-(5,5-dimethyl-4,5-dihydro-1,2-oxazol-3-yl)-3-azabicyclo[3.1.0]hex-3-yl]methanone To a mixture of (1R,5S,6r)-6-(5,5-dimethyl-4,5-dihydro-1,2-oxazol-3-yl)-3-azabicyclo[3.1.0]hexane hydrochloride (70 mg, 0.3900 mmol) in DMF (1 mL) were added 1-[(2R)-butan-2-yl]-1H-imidazole-4-carboxylic acid (65.32 mg, 0.3900 mmol), DIPEA (0.26 mL, 1.55 mmol) and HATU (178.16 mg, 0.4700 mmol). The reaction mixture was stirred at 25° C. for 16 h to give brown mixture. The reaction mixture was concentrated in vacuo to give a residue. The residue was purified by prep-HPLC (NH$_3$). The afforded flows were combined, concentrated to remove most of CH$_3$CN and lyophilized to afford the title compound (4.09 mg, 0.0108 mmol, 2.7864% yield) as yellow solid.

LC-MS Method1: 331.1 [M+H$^+$]

$^1$H NMR (400 MHz, DMSO-d6) δ ppm 8.91 (br s, 1H), 8.19 (br s, 1H), 4.31-4.44 (m, 1H), 4.15 (br d, J=11.3 Hz, 1H), 3.96 (br d, J=12.8 Hz, 1H), 3.90 (br d, J=9.0 Hz, 1H), 3.50-3.65 (m, 1H), 2.65 (s, 2H), 2.16 (br d, J=3.3 Hz, 1H), 2.07 (br d, J=3.5 Hz, 1H), 1.82 (quin, J=7.2 Hz, 2H), 1.55 (t, J=3.4 Hz, 1H), 1.48 (d, J=6.8 Hz, 3H), 1.26 (s, 6H), 0.76 (t, J=7.4 Hz, 3H)

Example 12 {1-[(2S)-butan-2-yl]-1H-imidazol-4-yl}[(1R,5S,6S)-6-(5,5-dimethyl-4,5-dihydro-1,2-oxazol-3-yl)-3-azabicyclo[3.1.0]hex-3-yl]methanone

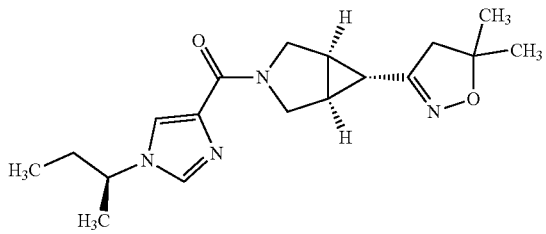 [SMILES: CC[C@H](C)n1cnc(C(=O)N2C[C@@H]3[C@H](C2)[C@H]3C2=NOC(C)(C)C2)c1]

ethyl 1-[(2S)-butan-2-yl]-1H-imidazole-4-carboxylate

A mixture of ethyl (2Z)-3-(dimethylamino)-2-isocyanoacrylate (300 mg, 1.78 mmol) and (S)-butan-2-amine (0.54 mL, 5.35 mmol) was stirred at 50° C. for 12 h to give brown mixture. TLC(PE:EA=1:1) showed new spot (Rf=0.2) was detected. The mixture was concentrated to give a residue. The residue was purified by flash column (PE:EA=1: 0 to 1:4) to afford the title compound (160 mg, 0.8153 mmol, 45.708% yield) as yellow solid.

LC-MS Method1 0.580 min, MS (m/z) 196.1 (M+H$^+$).

1-[(2S)-butan-2-yl]-1H-imidazole-4-carboxylic acid

To a mixture of ethyl 1-[(2S)-butan-2-yl]-1H-imidazole-4-carboxylate (160 mg, 0.8200 mmol) in THF (4 mL) and H$_2$O (2 mL) was added LiOH·H$_2$O (0.07 mL, 1.22 mmol). The reaction mixture was stirred at 20° C. for 16 h to give yellow mixture. The reaction mixture was diluted with H$_2$O (15 mL) and extracted with EtOAc (8 mL×5). The aqueous phase was acidified with 1 N HCl aq. to pH=4. The resulting aqueous phase was dried in vacuum to afford the title compound (150 mg, 0.8918 mmol, 109.39% yield) (crude) as yellow solid.

{1-[(2S)-butan-2-yl]-1H-imidazol-4-yl}[(1R,5S,6S)-6-(5,5-dimethyl-4,5-dihydro-1,2-oxazol-3-yl)-3-azabicyclo[3.1.0]hex-3-yl]methanone To a mixture of (1R,5S,6r)-6-(5,5-dimethyl-4,5-dihydro-1,2-oxazol-3-yl)-3-azabicyclo[3.1.0]hexane hydrochloride (70 mg, 0.3900 mmol) in DMF (1.5 mL) were added 1-[(2S)-butan-2-yl]-1H-imidazole-4-carboxylic acid (65.32 mg, 0.3900 mmol), DIPEA (0.26 mL, 1.55 mmol) and HATU (178.16 mg, 0.4700 mmol). The reaction mixture was stirred at 25° C. for 16 h to give brown mixture. LCMS showed the starting material was consumed. The reaction mixture was filtered. The filtrate was purified by prep-HPLC (NH$_3$). The afforded flows were combined, concentrated to remove most of CH$_3$CN and lyophilized to afford the title compound (34.59 mg, 0.1002 mmol, 25.797% yield) as white solid.

LC-MS Method2 1.516 min, MS (m/z) 331.2 [M+H$^+$]

$^1$H NMR (400 MHz, CHLOROFORM-d) δ ppm 7.64 (s, 1H), 7.44 (s, 1H), 4.76 (br d, J=12.0 Hz, 1H), 4.19 (br d, J=12.5 Hz, 1H), 4.02-4.10 (m, 1H), 3.95 (br d, J=7.8 Hz, 1H), 3.58-3.65 (m, 1H), 2.64 (s, 2H), 2.08 (br s, 1H), 1.93-2.01 (m, 1H), 1.93-2.01 (m, 1H), 1.74-1.84 (m, 2H), 1.49 (d, J=6.8 Hz, 3H), 1.47 (br s, 1H), 1.37 (s, 6H), 0.85 (t, J=7.4 Hz, 3H)

Example 13 [(1R,5S,6S)-6-(5,5-dimethyl-4,5-dihydro-1,2-oxazol-3-yl)-3-azabicyclo[3.1.0]hex-3-yl]{1-[(2S)-4-methylpentan-2-yl]-1H-imidazol-4-yl}methanone (R)-2-methyl-N-[(2E)-1,3-dimethylbutanylidene]-2-propanesulfinamide To a mixture of 4-methyl-2-pentanone (1.25 mL, 9.98 mmol) in THF (10 mL) were added (R)-2-methylpropane-2-sulfinamide (1210.06 mg, 9.98 mmol) and Ti(OEt)$_4$ (3414.54 mg, 14.98 mmol). The reaction mixture was stirred at 60° C. for 2 h to give colorless mixture. The reaction mixture was diluted with EtOAc (30 mL). The mixture was added to H$_2$O (10 mL) and stirred for 1 min to give yellow suspension. The suspension was filtered. The filtrate was washed with H$_2$O (20 mL×3), dried with anhydrous Na$_2$SO$_4$, filtered and concentrated in vacuum to afford the title compound (900 mg, 4.4261 mmol, 44.332% yield) as colorless oil.

LC-MS Method1 0.778 min, MS (m/z) 204.0 (M+H$^+$).

(R)-2-methyl-N-[(2S)-4-methylpentan-2-yl]-2-propanesulfinamide

To a mixture of (R)-2-methyl-N-[(2E)-1,3-dimethylbutanylidene]-2-propanesulfinamide (900 mg, 4.43 mmol) in THF (9 mL) was added L-selectride (13.28 mL, 13.28 mmol) at 0° C. The reaction mixture was stirred at 25° C. for 2 h to give colorless mixture. TLC (PE:EtOAc=2:1) showed one new spot (Rf=0.2) was detected. The reaction quenched by H$_2$O (3 mL). The reaction mixture was concentrated in vacuo to give a residue. The residue was purified by flash column (PE to 30% EtOAc in PE) to afford the title compound (260 mg, 1.026 mmol, 45.252% yield) as colorless oil.

$^1$H NMR (400 MHz, CHLOROFORM-d) δ ppm 3.50-3.30 (m, 1H), 2.81 (d, J=8.0 Hz, 1H), 1.80-1.60 (m, 1H), 1.60-1.30 (m, 2H), 1.28 (d, J=6.4 Hz, 3H), 1.21 (s, 9H), 0.90 (d, J=6.8 Hz, 3H), 0.88 (d, J=6.8 Hz, 3H).

(2S)-4-methyl-2-pentanamine hydrochloride

A solution of (R)-2-methyl-N-[(2S)-4-methylpentan-2-yl]-2-propanesulfinamide (610 mg, 2.97 mmol) in MeOH/HCl (10 mL, 2.97 mmol) was stirred at 25° C. for 2 h to give colorless mixture. The reaction mixture was concentrated in vacuo to give a residue. The residue was triturated with PE (20 mL) and dried in vacuo to give the title compound (240 mg, 1.7436 mmol, 58.698% yield) as white solid.

ethyl 1-[(2S)-4-methylpentan-2-yl]-1H-imidazole-4-carboxylate

To a mixture of (2S)-4-methyl-2-pentanamine hydrochloride (240 mg, 1.74 mmol) in 1-Butanol (2.5 mL) were added ethyl (2Z)-3-(dimethylamino)-2-isocyanoacrylate (293.25 mg, 1.74 mmol) and Et$_3$N (0.34 mL, 2.62 mmol). The reaction mixture was stirred at 130° C. for 1 h with a microwave system to give brown mixture. TLC (PE:EtOAc=1:1) showed one new spot (Rf=0.2) was detected. The reaction mixture was concentrated in vacuo to give a residue. The residue was purified by prep-TLC (PE:EtOAc=1:1) to afford the title compound (60 mg, 0.2675 mmol, 15.342% yield) as yellow oil.

LC-MS Method1 0.681 min, MS (m/z) 225.0 (M+H$^+$).

1-[(2S)-4-methylpentan-2-yl]-1H-imidazole-4-carboxylic acid

To a mixture of ethyl 1-[(2S)-4-methylpentan-2-yl]-1H-imidazole-4-carboxylate (60 mg, 0.2700 mmol) in THF (1.5 mL) and H$_2$O (0.50 mL) was added LiOH·H$_2$O (0.02 mL, 0.4000 mmol). The reaction mixture was stirred at 40° C. for 16 h to give a yellow mixture. TLC (PE:EtOAc=1:1) showed the starting material was consumed completely. The reaction mixture was diluted with H$_2$O (5 mL) and extracted with EtOAc (3 mL×2). The aqueous phase was acidified with 1 N HCl aq. to pH=5 and lyophilized to afford the title compound (50 mg, 0.2548 mmol, 95.244% yield) as yellow solid.

[(1R,5S,6S)-6-(5,5-dimethyl-4,5-dihydro-1,2-oxazol-3-yl)-3-azabicyclo[3.1.0]hex-3-yl]{1-[(2S)-4-methylpentan-2-yl]-1H-imidazol-4-yl}methanone To a mixture of 1-[(2S)-4-methylpentan-2-yl]-1H-imidazole-4-carboxylic acid (50 mg, 0.2500 mmol) in Pyridine (2.5 mL) was added EDCI (58.61 mg, 0.3100 mmol). The mixture was stirred at 25° C. for 10 min and followed by addition of (1R,5S,6r)-6-(5,5-dimethyl-4,5-dihydro-1,2-oxazol-3-yl)-3-azabicyclo[3.1.0]hexane hydrochloride (55.21 mg, 0.2500 mmol). The mixture was allowed to stirred at 25° C. for 16 h to give a yellow mixture. LCMS showed the starting material was consumed completely. The reaction mixture concentrated in vacuo to give a residue. The residue was purified by prep-HPLC (NH$_3$). The afforded flows were combined, concentrated to remove most of CH$_3$CN and lyophilized to afford the title compound (16.26 mg, 0.0449 mmol, 17.643% yield) as yellow solid.

LC-MS Method1: 359.2 [M+H$^+$]

$^1$H NMR (400 MHz, CHLOROFORM-d) δ ppm 7.64 (s, 1H), 7.46 (s, 1H), 4.76 (br d, J=12.0 Hz, 1H), 4.13-4.33 (m, 2H), 3.95 (dd, J=12.0, 3.8 Hz, 1H), 3.62 (dd, J=12.3, 4.0 Hz, 1H), 2.64 (s, 2H), 2.08 (br d, J=3.5 Hz, 1H), 1.98 (br d, J=3.5 Hz, 1H), 1.68-1.78 (m, 1H), 1.50-1.57 (m, 2H), 1.47 (d, J=6.8 Hz, 4H), 1.38 (s, 6H), 0.92 (d, J=6.5 Hz, 3H), 0.87 (d, J=6.8 Hz, 3H)

Example 14 (1-((S)-1-cyclopropylethyl)-1H-imidazol-4-yl)((1R,5S,6S)-6-(5,5-dimethyl-4,5-dihydroisoxazol-3-yl)-3-azabicyclo[3.1.0]hexan-3-yl)methanone ethyl 1-[(1S)-1-cyclopropylethyl]-1H-imidazole-4-carboxylate Around bottom flask was charged with (S)-1-cyclopropylethanamine hydrochloride (903.81 mg, 7.43 mmol), Et$_3$N (1.57 mL, 11.15 mmol), ethyl (2Z)-3-(dimethylamino)-2-isocyanoacrylate (250 mg, 1.49 mmol) and 1-Butanol (0.50 mL). The resulting mixture was stirred at 70° C. for 36 hours to give yellow solution. The reaction mixture was poured into H$_2$O (30 mL) and extracted with EtOAc (30 mL×2). The combined organic layers were washed with brine (30 mL×2), dried over Na$_2$SO$_4$, filtered and concentrated under reduced pressure to give a yellow oil. The crude product was purified by flash column (PE to 100% EtOAc in PE) to give the title compound (100 mg, 0.4802 mmol, 32.304% yield) as yellow oil.

LC-MS Method1 0.652 min, MS (m/z) 209.2 (M+H$^+$).

1-[(1S)-1-cyclopropylethyl]-1H-imidazole-4-carboxylic acid

To a solution of ethyl 1-[(1S)-1-cyclopropylethyl]-1H-imidazole-4-carboxylate (150 mg, 0.7200 mmol) in H$_2$O (0.50 mL), THF (0.50 mL), MeOH (0.50 mL) was added hydroxylithium hydrate (60.44 mg, 1.44 mmol). The resulting mixture was stirred at 20-25° C. for 14 hours to give white suspension. The reaction mixture was poured into H$_2$O and extracted with EtOAc (20 mL×4). The combined organic layers were washed with brine (20 mL×2), dried over Na$_2$SO$_4$, filtered and concentrated under reduced pressure to give the title compound (150 mg, crude product) as yellow oil.

LC-MS Method1 0.227 min, MS (m/z) 180.9 (M+H$^+$).

(1-((S)-1-cyclopropylethyl)-1H-imidazol-4-yl)((1R,5S,6S)-6-(5,5-dimethyl-4,5-dihydroisoxazol-3-yl)-3-azabicyclo[3.1.0]hexan-3-yl)methanone To a solution of 1-[(1S)-1-cyclopropylethyl]-1H-imidazole-4-carboxylic acid (70 mg, 0.3900 mmol) in DMF (3 mL) were added HATU (193.06 mg, 0.5000 mmol) and N-ethyl-N-isopropylpropan-2-amine (0.33 mL, 1.94 mmol) at 20° C. for 30 min. (1R,5S,6r)-6-(5,5-dimethyl-4,5-dihydro-1,2-oxazol-3-yl)-3-azabicyclo[3.1.0]hexane hydrochloride (98.35 mg, 0.3900 mmol) was added. The resulting mixture was stirred at 20-25° C. for 14 hours to give yellow solution. The reaction mixture was poured into sat. NH$_4$Cl aq. (50 mL) and extracted with EtOAc (50 mL×4). The combined organic layers were washed with brine (50 mL×2), dried over Na$_2$SO$_4$, filtered and concentrated under reduced pressure. The residue was purified by prep-HPLC (FA) to give the title compound (10.65 mg, 0.0311 mmol, 8.0061% yield) as yellow oil.

LC-MS Method1: 343.1 [M+H$^+$]

$^1$H NMR (400 MHz, CHLOROFORM-d) δ=7.70 (s, 1H), 7.64 (s, 1H), 4.63 (br d, J=10.0 Hz, 1H), 4.19 (br d, J=12.5 Hz, 1H), 3.95 (br dd, J=3.4, 11.2 Hz, 1H), 3.63 (br d, J=11.5 Hz, 1H), 3.48-3.43 (m, 1H), 2.64 (s, 2H), 2.08 (br s, 2H), 1.58 (d, J=6.8 Hz, 3H), 1.47 (t, J=3.4 Hz, 1H), 1.36 (s, 6H), 1.19-1.13 (m, 1H), 0.75-0.61 (m, 2H), 0.36 (q, J=4.9 Hz, 2H)

Example 15 {1-[(1R)-1-cyclopropylethyl]-1H-imidazol-4-yl}[(1R,5S,6R)-6-(5,5-dimethyl-4,5-dihydro-1,2-oxazol-3-yl)-3-azabicyclo[3.1.0]hex-3-yl]methanone ethyl 1-[(1R)-1-cyclopropylethyl]-1H-imidazole-4-carboxylate To a solution of ethyl (2Z)-3-(dimethylamino)-2-isocyanoacrylate (500 mg, 2.97 mmol) in 1-Butanol (1 mL) was added (1R)-1-cyclopropylethanamine (253.14 mg, 2.97 mmol) at 20° C. The reaction mixture was irradiated with microwave at 130° C. for 40 min to give a yellow solution. The reaction mixture was poured into sat. NH$_4$Cl aq. (50 mL) and extracted with EtOAc (50 mL×4). The combined organic layers were washed with sat. aq. (50 mL×2), dried over Na$_2$SO$_4$, filtered and concentrated under reduced pressure. The crude product was purified by silica column (PE to PE:EtOAc=1:1) to give the title compound (190 mg, 0.9123 mmol, 30.689% yield) as yellow oil.

LC-MS Method1 0.608 min, MS (m/z) 209.0 (M+H$^+$).

1-[(1R)-1-cyclopropylethyl]-1H-imidazole-4-carboxylic acid

To a solution of ethyl 1-[(1R)-1-cyclopropylethyl]-1H-imidazole-4-carboxylate (190 mg, 0.9100 mmol) in H$_2$O (1.9 mL), THF (1.9 mL), MeOH (1.9 mL) was added hydroxylithium hydrate (76.56 mg, 1.82 mmol) at 20° C. The resulting mixture was stirred at 20-25° C. for 2 hours to give white suspension. The reaction mixture was poured into H$_2$O and extracted with EtOAc (20 mL×4). The combined organic layers were washed with sat. aq. (20 mL×2), dried over Na$_2$SO$_4$, filtered and concentrated under reduced pressure to give the title compound (180 mg, 0.9989 mmol, 109.49% yield) as yellow oil.

LC-MS Method1 0.214 min, MS (m/z) 180.0 (M+H$^+$).

{1-[(1R)-1-cyclopropylethyl]-1H-imidazol-4-yl}[(1R,5S,6R)-6-(5,5-dimethyl-4,5-dihydro-1,2-oxazol-3-yl)-3-azabicyclo[3.1.0]hex-3-yl]methanone To a solution of 1-[(1R)-1-cyclopropylethyl]-1H-imidazole-4-carboxylic acid (70 mg, 0.3900 mmol) in DMF (2 mL) were added HATU (193.06 mg, 0.5000 mmol) and N-ethyl-N-isopropylpropan-2-amine (0.33 mL, 1.94 mmol) at 20° C. The reaction mixture was stirred for 30 min. (1R,5S,6r)-6-(5,5-dimethyl-4,5-dihydro-1,2-oxazol-3-yl)-3-azabicyclo[3.1.0]hexane hydrochloride (98.35 mg, 0.3900 mmol) was added. The resulting mixture was stirred at 20-25° C. for 14 hours to give yellow solution. The reaction mixture was poured into sat. NH$_4$Cl aq. (50 mL) and extracted with EtOAc (50 mL×4). The combined organic layers were washed with sat. aq. (50 mL×2), dried over Na$_2$SO$_4$, filtered and concentrated under reduced pressure. The residue was purified by prep-HPLC (FA) to give the title compound (14.08 mg, 0.0411 mmol, 10.585% yield) as yellow oil.

LC-MS Method1: 343.3 [M+H$^+$]

$^1$H NMR (400 MHz, CHLOROFORM-d) δ=7.70 (d, J=1.3 Hz, 1H), 7.64 (s, 1H), 4.65 (br d, J=11.5 Hz, 1H), 4.19 (br d, J=12.3 Hz, 1H), 3.94 (br dd, J=3.8, 11.8 Hz, 1H), 3.62 (br dd, J=4.1, 12.4 Hz, 1H), 3.45 (dd, J=6.8, 8.8 Hz, 1H), 2.64 (s, 2H), 2.11-2.05 (m, 2H), 1.58 (d, J=6.8 Hz, 3H), 1.46 (t, J=3.4 Hz, 1H), 1.36 (s, 6H), 1.19-1.13 (m, 1H), 0.77-0.70 (m, 1H), 0.65-0.60 (m, 1H), 0.36 (q, J=5.4 Hz, 2H)

Example 16 (1-((S)-1-cyclobutylethyl)-1H-imidazol-4-yl)((1R,5S,6S)-6-(5,5-dimethyl-4,5-dihydroisoxazol-3-yl)-3-azabicyclo[3.1.0]hexan-3-yl)methanone (R)—N-[(E)-cyclobutylmethylene]-2-methyl-2-propanesulfinamide To a mixture of cyclobutane aldehyde (1.07 mL, 11.89 mmol) in THF (15 mL) were added (R)-2-methylpropane-2-sulfinamide (1.44 g, 11.89 mmol) and Ti(OEt)$_4$ (4065.62 mg, 17.83 mmol). The reaction mixture was stirred at 60° C. for 2 h to give yellow mixture. TLC(PE:EtOAc=10: 1) showed the starting material was consumed completely, one new spot was (Rf=0.2) detected. The reaction mixture was diluted with EtOAc (40 mL). The mixture was added to H$_2$O (10 mL) and stirred for 1 min to give white suspension. The suspension was filtered. The filtrate was washed with H$_2$O (20 mL×3), dried with anhydrous Na$_2$SO$_4$, filtered and concentrated in vacuum to afford the title compound (1.77 g, 9.4501 mmol, 79.494% yield) as colorless oil.

$^1$H NMR (400 MHz, CHLOROFORM-d) δ=8.12 (d, J=4.8 Hz, 1H), 3.45-3.30 (m, 1H), 2.35-2.10 (m, 4H), 2.10-2.00 (m, 1H), 2.00-1.90 (m, 1H), 1.20 (s, 9H).

(R)—N-[(1S)-1-cyclobutylethyl]-2-methyl-2-propanesulfinamide

To a solution of (R)—N-[(E)-cyclobutylmethylene]-2-methyl-2-propanesulfinamide (0.5 g, 2.67 mmol) in THF (6 mL) was added chloro(methyl)magnesium (2.67 mL, 8.01 mmol) at −40° C. The reaction mixture was stirred at −40° C. for 2 h to give yellow mixture. TLC (DCM:EtOAc=1:1) showed the starting material was consumed completely, one new spot (Rf=0.3) was detected. The reaction mixture quenched with NH$_4$Cl (eq., 25 mL) and then extracted with EtOAc (15 mL×3). The combined organic phase was washed with brine (20 mL), dried over anhydrous Na$_2$SO$_4$, filtered and concentrated in vacuo to give a residue. The residue was purified by flash column (DCM to 20% EtOAc in DCM) to afford the title compound (360 mg, 1.7704 mmol, 66.32% yield) as colorless oil.

$^1$H NMR (400 MHz, CHLOROFORM-d) δ=3.35-3.15 (m, 1H), 2.84 (d, J=8.0 Hz, 1H), 2.40-2.20 (m, 1H), 2.10-1.90 (m, 1H), 2.00-1.90 (m, 1H), 1.90-1.60 (m, 4H), 1.20 (s, 9H), 1.18 (d, J=6.8 Hz, 3H).

(1S)-1-cyclobutylethanamine hydrochloride

A solution of (R)—N-[(1S)-1-cyclobutylethyl]-2-methyl-2-propanesulfinamide (360 mg, 1.77 mmol) in MeOH/HCl (0.44 mL, 1.77 mmol) was stirred at 25° C. for 2 h to give colorless mixture. TLC (DCM:EtOAc=1:1) showed the starting material was consumed completely. The reaction mixture was concentrated in vacuo to give the title compound (330 mg, 2.4329 mmol, 137.42% yield) as yellow solid.

ethyl 1-[(1S)-1-cyclobutylethyl]-1H-imidazole-4-carboxylate

To a mixture of (1S)-1-cyclobutylethanamine hydrochloride (240 mg, 1.77 mmol) in 1-Butanol (2 mL) were added ethyl (2Z)-3-(dimethylamino)-2-isocyanoacrylate (297.59 mg, 1.77 mmol) and Et$_3$N (0.37 mL, 2.65 mmol). The reaction mixture was stirred at 130° C. for 1 h used MW to give brown mixture. LCMS showed the starting material was consumed completely. TLC (PE:EtOAc=2:1) showed one new spot (Rf=0.2) was detected. The reaction mixture was concentrated in vacuo to give a residue. The residue was purified by prep-TLC (100% EtOAc) to afford the title compound (36 mg, 0.1620 mmol, 9.1533% yield) as brown solid.

$^1$H NMR (400 MHz, CHLOROFORM-d) δ=7.61 (s, 1H), 7.50 (s, 1H), 4.37 (q, J=6.8 Hz, 2H), 4.15-4.00 (m, 1H), 2.70-2.50 (m, 1H), 2.20-2.10 (m, 1H), 2.00-1.60 (m, 5H), 1.40 (d, J=6.8 Hz, 3H), 1.39 (t, J=6.8 Hz, 3H).

1-[(1S)-1-cyclobutylethyl]-1H-imidazole-4-carboxylic acid

To a mixture of ethyl 1-[(1S)-1-cyclobutylethyl]-1H-imidazole-4-carboxylate (36 mg, 0.1600 mmol) in THF (1.5 mL) and H$_2$O (0.50 mL) was added LiOH·H$_2$O (0.01 mL, 0.2400 mmol). The reaction mixture was stirred at 25° C. for 16 h to give brown mixture. TLC(PE:EtOAc=1:1) showed the starting material was consumed completely. The reaction mixture was diluted with H$_2$O (4 mL) and extracted with EtOAc (2 mL×2). The aqueous phase was acidified with 1 N HCl aq. to pH=4 and lyophilized to the title compound (31 mg, 0.1596 mmol, 98.547% yield) as brown solid.

$^1$H NMR (400 MHz, DMSO-d$_6$) δ=7.91 (s, 1H), 7.84 (s, 1H), 4.40-4.20 (m, 1H), 2.75-2.65 (m, 1H), 2.15-2.00 (m, 1H), 1.95-1.60 (m, 5H), 1.38 (d, J=6.8 Hz, 3H).

(1-((S)-1-cyclobutylethyl)-1H-imidazol-4-yl)((1R,5S,6S)-6-(5,5-dimethyl-4,5-dihydroisoxazol-3-yl)-3-azabicyclo[3.1.0]hexan-3-yl)methanone To a solution of 1-[(1S)-1-cyclobutylethyl]-1H-imidazole-4-carboxylic acid (30 mg, 0.1500 mmol) in DMF (1.5 mL) were added HATU (70.86 mg, 0.1900 mmol), DIPEA (99.81 mg, 0.7700 mmol). The mixture was stirred for 10 min. Then (1R,5S,6r)-6-(5,5-dimethyl-4,5-dihydro-1,2-oxazol-3-yl)-3-azabicyclo[3.1.0]hexane hydrochloride (39.1 mg, 0.1500 mmol) was added to the mixture. The mixture was stirred at 25° C. for 12 h to give brown solution. The reaction mixture was concentrated directly. The residue was purified by prep-HPLC (NH$_3$) to give the title compound (25.52 mg, 0.0716 mmol, 46.352% yield) as brown solid.

LC-MS Method1: 357.1 [M+H$^+$]

$^1$H NMR (400 MHz, CHLOROFORM-d) δ ppm 7.61 (1H, d, J=1.25 Hz), 7.42 (1H, d, J=1.25 Hz), 4.76 (1H, d, J=12.05 Hz), 4.19 (1H, d, J=12.55 Hz), 3.99-4.08 (1H, m), 3.94 (1H, dd, J=12.17, 4.14 Hz), 3.61 (1H, dd, J=12.55, 4.27 Hz), 2.64 (2H, s), 2.53-2.63 (1H, m), 2.05-2.18 (2H, m), 1.94-2.01 (1H, m), 1.85-1.94 (2H, m), 1.67-1.84 (3H, m), 1.46 (1H, br s), 1.36-1.41 (9H, m)

Example 17 {1-[(1R)-1-cyclobutylethyl]-1H-imidazol-4-yl}[(1R,5S,6R)-6-(5,5-dimethyl-4,5-dihydro-1,2-oxazol-3-yl)-3-azabicyclo[3.1.0]hex-3-yl]methanone ethyl 1-[(1R)-1-cyclobutylethyl]-1H-imidazole-4-carboxylate To a solution of ethyl (2Z)-3-(dimethylamino)-2-isocyanoacrylate (100 mg, 0.5900 mmol) in Et$_3$N (0.58 mL, 4.46 mmol) was added the mixture of (1R)-1-cyclobutylethanamine hydrochloride (241.94 mg, 1.78 mmol) in 1-Butanol (0.30 mL). The resulting mixture was stirred at 70° C. for 16 hours to give yellow mixture. TLC (PE:EtOAc=1:1) showed one new spot (Rf=0.3) was detected. The reaction mixture was concentrated in vacuo to give a residue. The residue was purified by prep-TLC (PE:EtOAc=1:1) to afford the title compound (25 mg, 0.1125 mmol, 18.916% yield) as yellow oil.

LC-MS Method1 0.667 min, MS (m/z) 222.9 (M+H$^+$).

1-[(1R)-1-cyclobutylethyl]-1H-imidazole-4-carboxylic acid

To a mixture of ethyl 1-[(1R)-1-cyclobutylethyl]-1H-imidazole-4-carboxylate (25 mg, 0.1100 mmol) in THF (0.75 mL) and H$_2$O (0.25 mL) was added LiOH·H$_2$O (0.01 mL, 0.1700 mmol). The reaction mixture was stirred at 40° C. for 16 h to give yellow mixture. TLC (PE:EtOAc=1:1) showed starting material was consumed completely. The reaction mixture was diluted with H$_2$O (6 mL) and concentrated to remove most of THF. The aqueous phase was acidified with 1 N HCl aq. to pH=5 and lyophilized to afford the title compound (21 mg, 0.1081 mmol, 96.131% yield) as yellow solid.

LC-MS Method1 0.414 min, MS (m/z) 194.9 (M+H⁺).

{1-[(1R)-1-cyclobutylethyl]-1H-imidazol-4-yl}[(1R,5S,6R)-6-(5,5-dimethyl-4,5-dihydro-1,2-oxazol-3-yl)-3-azabicyclo[3.1.0]hex-3-yl]methanone To a mixture of 1-[(1R)-1-cyclobutylethyl]-1H-imidazole-4-carboxylic acid (21 mg, 0.1100 mmol) in DMF (0.50 mL) were added HATU (49.6 mg, 0.1300 mmol) and DIPEA (0.09 mL, 0.5400 mmol). The mixture was stirred at 50° C. for 30 min and followed by addition of (1R,5S,6r)-6-(5,5-dimethyl-4,5-dihydro-1,2-oxazol-3-yl)-3-azabicyclo[3.1.0] hexane hydrochloride (29.23 mg, 0.1600 mmol). The mixture was stirred at 25° C. for 16 h to give a yellow mixture. The reaction mixture was purified by prep-HPLC (NH₃). The afforded flows were combined, concentrated to remove most of CH₃CN and lyophilized to afford the title compound (1.64 mg, 0.0046 mmol, 4.2553% yield) as yellow solid.

LC-MS Method1: 357.1 [M+H⁺]

¹H NMR (400 MHz, METHANOL-d4) δ ppm 7.73 (s, 1H), 7.68 (s, 1H), 4.42 (br d, J=11.3 Hz, 1H), 4.18-4.29 (m, 1H), 4.11 (br d, J=12.8 Hz, 1H), 3.94 (br dd, J=12.2, 3.9 Hz, 1H), 3.60 (br dd, J=12.4, 3.6 Hz, 1H), 2.73 (s, 2H), 2.62-2.71 (m, 1H), 2.10-2.20 (m, 2H), 2.03-2.10 (m, 1H), 1.78-1.94 (m, 4H), 1.72 (br t, J=8.5 Hz, 1H), 1.49 (t, J=3.4 Hz, 1H), 1.40 (d, J=6.5 Hz, 3H), 1.34 (s, 6H), 0.89 (br d, J=9.8 Hz, 1H)

Example 18 (1-((S)-1-cyclopentylethyl)-1H-imidazol-4-yl)((1R,5S,6S)-6-(5,5-dimethyl-4,5-dihydroisoxazol-3-yl)-3-azabicyclo[3.1.0]hexan-3-yl)methanone (1-((S)-1-cyclopentylethyl)-1H-imidazol-4-yl)((1R,5S,6S)-6-(5,5-dimethyl-4,5-dihydroisoxazol-3-yl)-3-azabicyclo[3.1.0]hexan-3-yl)methanone To a solution of 1-[(1S)-1-cyclopentylethyl]-1H-imidazole-4-carboxylic acid (50 mg, 0.2400 mmol, prepared with the same protocol described in Example 19 using (R)-2-methylpropane-2-sulfinamide instead of (S)-2-methylpropane-2-sulfinamide) in DMF (5 mL) were added HATU (137.68 mg, 0.3600 mmol) and Et₃N (0.12 mL, 0.9600 mmol). The mixture was stirred at 25° C. for 30 min. Then (1R,5S,6r)-6-(5,5-dimethyl-4,5-dihydro-1,2-oxazol-3-yl)-3-azabicyclo[3.1.0]hexane hydrochloride (43.28 mg, 0.2400 mmol) was added. The resulting mixture was stirred at 25° C. for 3 hours to give a brown solution. The reaction mixture was concentrated in vacuum to remove most of DMF. The crude product was purified by Prep-HPLC (NH₃) and lyophilized to give the title compound (70 mg, 0.1889 mmol, 78.697% yield) as a white solid.

LC-MS Method1: 371.3 [M+H⁺]

¹H NMR (400 MHz, CHLOROFORM-d) δ=7.65 (d, J=1.1 Hz, 1H), 7.44 (d, J=0.9 Hz, 1H), 4.76 (br d, J=11.9 Hz, 1H), 4.19 (br d, J=12.6 Hz, 1H), 3.95 (br dd, J=3.9, 11.9 Hz, 1H), 3.87 (qd, J=6.8, 9.5 Hz, 1H), 3.62 (br dd, J=4.1, 12.5 Hz, 1H), 3.66-3.57 (m, 1H), 2.64 (s, 2H), 2.20-2.04 (m, 2H), 2.02-1.94 (m, 1H), 1.88 (dtd, J=3.9, 7.6, 11.7 Hz, 1H), 1.64-1.55 (m, 3H), 1.49 (d, J=6.8 Hz, 6H), 1.38 (s, 6H), 1.23 (qd, J=8.8, 12.6 Hz, 1H), 1.14-1.01 (m, 1H)

Example 19 {1-[(1R)-1-cyclopentylethyl]-1H-imidazol-4-yl}[(1R,5S,6R)-6-(5,5-dimethyl-4,5-dihydro-1,2-oxazol-3-yl)-3-azabicyclo[3.1.0]hex-3-yl]methanone (S)—N-[(E)-cyclopentylmethylene]-2-methyl-2-propanesulfinamide To a mixture of cyclopentyl aldehyde in THF (20 mL) were added (S)-2-methylpropane-2-sulfinamide (2.47 g, 20.38 mmol), titanium(IV) ethanolate (6.97 g, 30.57 mmol). The suspension was stirred at 20° C. for 16 hr. The reaction mixture was diluted with EtOAc (60 mL). The mixture was added to H₂O (10 mL) and stirred for 1 min to give white suspension. The suspension was filtered. The filtrate was washed with H₂O (30 mL×3), dried with anhydrous Na₂SO₄, filtered and concentrated in vacuum to afford the title compound (3.6 g, crude) as yellow liquid.

LC-MS Method1: 0.833 min, MS (m/z): 201.9 (M+H⁺).

¹H NMR (400 MHz, CHLOROFORM-d) δ ppm 7.92 (t, d=4.8 Hz, 1H), 2.90-2.80 (m, 1H), 1.90-1.75 (m, 3H), 1.75-1.50 (m, 5H), 1.15 (s, 9H).

(S)—N-[(1R)-1-cyclopentylethyl]-2-methyl-2-propanesulfinamide

To a mixture of (S)—N-[(E)-cyclopentylmethylene]-2-methyl-2-propanesulfinamide in THF (20 mL) was added MeMgCl (742.96 mg, 9.93 mmol, 3.31 mL) dropwise for 10 min at −40° C. under N₂. The suspension was stirred at 20° C. for 16 hr. The residue was diluted with NH₄Cl (15 mL), extracted with EtOAc (30 mL×4), washed with saturated NaCl (30 mL×2), dried with anhydrous Na₂SO₄, filtered and concentrated in vacuum. The solution was purified by flash column (PE to 30% EtOAc in PE) to afford the title compound (595 mg, crude) as yellow liquid.

LC-MS Method1: 0.827 min, MS (m/z): 218 (M+H⁺).

¹H NMR (400 MHz, CHLOROFORM-d) δ ppm 3.20-3.05 (m, 1H), 2.82 (brd, J=8.4 Hz, 1H), 1.90-1.40 (m, 8H), 1.20 (d, J=7.2 Hz, 3H), 1.14 (s, 9H).

(1R)-1-cyclopentylethanamine hydrochloride

To a mixture of (S)—N-[(1R)-1-cyclopentylethyl]-2-methyl-2-propanesulfinamide was added MeOH/HCl (5 mL). The suspension was stirred at 25° C. for 1 hr. The residue was concentrated in vacuum to afford the title compound (257 mg, crude) as yellow solid.

ethyl 1-[(1R)-1-cyclopentylethyl]-1H-imidazole-4-carboxylate

To a mixture of (1R)-1-cyclopentylethanamine hydrochloride (52.0 mg, 0.35 mmol) was added 1-Butanol (0.5 mL). Then ethyl (2Z)-3-(dimethylamino)-2-isocyanoacrylate (58.44 mg, 0.35 mmol), Et₃N (52.64 mg, 0.52 mmol, 0.07 mL) was added into the solution. The suspension was subjected to reaction in microwave reactor (time: 1 hr, temp: 130° C.). The residue was concentrated in vacuum to afford the title compound (77 mg, crude) as yellow oil.

LC-MS Method1: 0.690 min, MS (m/z): 237.0 (M+H⁺).

¹H NMR (400 MHz, CHLOROFORM-d) δ ppm 7.57 (s, 1H), 7.43 (s, 1H), 4.30 (q, J=6.8 Hz, 2H), 3.80-3.70 (m, 1H), (q, J=7.2 Hz, 2H), 1.70-1.40 (m, 8H), 1.42 (d, J=6.8 Hz, 2H), 1.32 (t, J=7.2 Hz, 3H).

1-[(1R)-1-cyclopentylethyl]-1H-imidazole-4-carboxylic acid

To a mixture of ethyl 1-[(1R)-1-cyclopentylethyl]-1H-imidazole-4-carboxylate in H$_2$O (0.5 mL) and THF (1.5 mL) was added LiOH·H$_2$O (20.5 mg, 0.49 mmol, 1.5 eq). The suspension was stirred at 20° C. for 2 hr. The residue was diluted with H$_2$O (1 mL), extracted with EtOAc (5 mL×4). The afforded H$_2$O layer was acidified with 1 N HCl aq. to pH=5. The combined organic layers were concentrated and then lyophilized to afford the title compound (39 mg, crude) as yellow solid.

LC-MS Method1: 0.571 min, MS (m/z): 209 (M+H$^+$).

{1-[(1R)-1-cyclopentylethyl]-1H-imidazol-4-yl}[(1R,5S,6R)-6-(5,5-dimethyl-4,5-dihydro-1,2-oxazol-3-yl)-3-azabicyclo[3.1.0]hex-3-yl]methanone To a mixture of 1-[(1R)-1-cyclopentylethyl]-1H-imidazole-4-carboxylic acid (30.0 mg, 0.14 mmol) in Pyridine (0.5 mL) were added EDCI (27.6 mg, 0.14 mmol) and (1R,5S,6r)-6-(5,5-dimethyl-4,5-dihydro-1,2-oxazol-3-yl)-3-azabicyclo[3.1.0]hexane hydrochloride (26.0 mg, 0.14 mmol). The suspension was stirred at 20° C. for 16 hr. The reaction mixture was quenched with H$_2$O (10 mL). The residue was diluted with EtOAc (20 mL×3), washed with saturated NaCl (5 mL), dried with anhydrous Na$_2$SO$_4$, filtered and concentrated in vacuum. The solution was purified by prep-HPLC (NH$_3$) and lyophilized to afford the title compound (1.88 mg, 3.5% yield) as white solid.

LC-MS Method1: 3.486 min, MS (m/z): 371.3 (M+H$^+$).

$^1$H NMR (400 MHz, CHLOROFORM-d) δ ppm 7.58 (d, J=1.25 Hz, 1H), 7.36 (s, 1H), 4.70 (br d, J=12.30 Hz, 1H), 4.12 (d, J=12.30 Hz, 1H), 3.87 (br d, J=12.30 Hz, 1H), 3.79 (dd, J=9.41, 6.65 Hz, 1H), 3.54 (br d, J=8.53 Hz, 1H), 2.57 (s, 2H), 1.80-2.10 (m, 4H), 1.51-1.60 (m, 2H), 1.41 (br d, J=6.78 Hz, 9H), 1.30 (s, 7H), 1.18 (s, 7H).

Example 20 [(1R,5S,6S)-6-(5,5-dimethyl-4,5-dihydro-1,2-oxazol-3-yl)-3-azabicyclo[3.1.0]hex-3-yl]{1-[(1S)-1-(tetrahydro-2H-pyran-4-yl)ethyl]-1H-imidazol-4-yl}methanone

(R)-2-methyl-N-[(E)-tetrahydro-2H-pyran-4-ylmethylene]-2-propanesulfinamide A 100 mL round-bottom flask was charged with tetrahydro-2H-pyran-4-carbaldehyde (5000 mg, 43.81 mmol), (R)-2-methylpropane-2-sulfinamide (5309.27 mg, 43.81 mmol), Ti(OEt)$_4$ (13.5 mL, 65.71 mmol) and THF (25 mL). The reaction was heated at 60° C. for 30 min under N$_2$ protection to give a yellow solution. TLC (PE/EA=3/1, Rf=0.4) showed a new spot was detected. H$_2$O (3 mL) was added dropwise and it was stirred at 20° C. for 5 mins, then it was filtrated through a pad of celite and the filtrate concentrated in vacuum to give the title compound (8700 mg, 40.031 mmol, 91.383% yield) as white solid.

LC-MS Method1 0.745 min, MS (m/z) 218.1 (M+H$^+$).

(R)-2-methyl-N-[(1S)-1-(tetrahydro-2H-pyran-4-yl)ethyl]-2-propanesulfinamide A round-bottom flask charged with (R)-2-methyl-N-[(E)-tetrahydro-2H-pyran-4-ylmethylene]-2-propanesulfinamide (3000 mg, 13.8 mmol) and THF (30 mL) was cooled to −48° C., MeMgBr (5.06 mL, 15.18 mmol) was added dropwise to the mixture. The reaction was stirred at this temperature for 2 hr to give a yellow solution. H$_2$O (30 mL) was added and it was extracted with EtOAc (30 mL×2). The combined organic layer dried over Na$_2$SO$_4$ and concentrated in vacuum to give a yellow oil. The crude was purified by silica gel chromatography (DCM/EA=3/1 to 1/1) to give the title compound (1700 mg, 7.2846 mmol, 52.772% yield) as colorless oil.

$^1$H NMR (400 MHz, CHLOROFORM-d) δ ppm 4.05-3.95 (m, 2H), 3.40 (dt, J=4.0, 1.6 Hz, 2H), 3.25-3.10 (m, 1H), 2.90 (d, J=7.6 Hz, 1H), 1.85-1.75 (m, 1H), 1.70-1.20 (m, 4H), 1.29 (d, J=6.8 Hz, 3H), 1.25 (s, 9H).

(1S)-1-(tetrahydro-2H-pyran-4-yl)ethanamine hydrochloride

A 100 ml round-bottom flask was charged with (R)-2-methyl-N-[(1S)-1-(tetrahydro-2H-pyran-4-yl)ethyl]-2-propanesulfinamide (1700 mg, 7.28 mmol) and HCl/MeOH (10 mL, 7.28 mmol). The reaction mixture was stirred at 25° C. for 3 hr to give a colorless oil. It was evaporated in vacuum to give the title compound (1250 mg, 7.5456 mmol, 103.58% yield) as colorless oil.

ethyl 1-[(1S)-1-(tetrahydro-2H-pyran-4-yl)ethyl]-1H-imidazole-4-carboxylate A microwave tube was charged with ethyl (2Z)-3-(dimethylamino)-2-isocyanoacrylate (400.29 mg, 2.38 mmol), (1S)-1-(tetrahydro-2H-pyran-4-yl)ethanamine hydrochloride (394.27 mg, 2.38 mmol), triethylamine (0.5 mL, 3.57 mmol) and 1-Butanol (0.6004 mL). It was irradiated with microwave at 130° C. for 1 hr to give a brown solution. H$_2$O (15 mL) was added and it was extracted with EtOAc (15 mL×2). The combined organic layer dried over Na$_2$SO$_4$ and concentrated in vacuum to give a yellow oil. The crude was purified by silica gel chromatography (PE/EA=1/1 to 0/1) to give the title compound (135 mg, 0.5351 mmol, 22.481% yield) as yellow oil.

LC-MS Method1 0.638, MS (m/z) 253.2 (M+H$^+$).

1-[(1S)-1-(tetrahydro-2H-pyran-4-yl)ethyl]-1H-imidazole-4-carboxylic acid

A 100 mL round-bottom flask was charged with ethyl 1-[(1S)-1-(tetrahydro-2H-pyran-4-yl)ethyl]-1H-imidazole-4-carboxylate (130 mg, 0.5200 mmol), hydroxylithium hydrate (43.24 mg, 1.03 mmol), THF (3 mL). It was stirred at 20° C. for 3 hr to give a yellow solution. H$_2$O (15 mL) was added and it was extracted with EtOAc (15 mL×2). The aqueous phase was lyophilized to give the title compound (110 mg, 0.4905 mmol, 95.199% yield) as yellow solid. It was directly used in the next step.

[(1R,5S,6S)-6-(5,5-dimethyl-4,5-dihydro-1,2-oxazol-3-yl)-3-azabicyclo[3.1.0]hex-3-yl]{1-[(1S)-1-(tetrahydro-2H-pyran-4-yl)ethyl]-1H-imidazol-4-yl}methanone To a mixture of 1-[(1S)-1-(tetrahydro-2H-pyran-4-yl)ethyl]-1H-imidazole-4-carboxylic acid (110 mg, 0.4900 mmol) and HATU (243.77 mg, 0.6400 mmol) in DMF (5 mL) was added N-ethyl-N-isopropylpropan-2-amine (0.59 mL, 3.43 mmol). After stirred for 30 min, (1R,5S,6r)-6-(5,5-dimethyl-4,5-dihydro-1,2-oxazol-3-yl)-3-azabicyclo[3.1.0]hexane hydrochloride (384.3 mg, 0.7400 mmol) was added. The reaction mixture was stirred for another 16 hr to give a yellow solution. H$_2$O (30 mL) was added and it was extracted with EtOAc (30 mL×2). The combined organic layer dried over Na₂SO₄ and concentrated in vacuum to give a yellow oil. The crude was purified by Prep-HPLC (NH₃). The afforded flows were concentrated in vacuum to remove most of CH₃CN and lyophilized to give the title compound (9.57 mg, 0.0248 mmol, 5.0482% yield) as white solid.

LC-MS Method1: 387.3 [M+H$^+$]

$^1$H NMR (400 MHz, CHLOROFORM-d) δ ppm 1.12-1.17 (m, 1H) 1.23 (dd, J=12.30, 4.02 Hz, 1H) 1.37 (s, 6H) 1.46 (br d, J=3.01 Hz, 1H) 1.50 (d, J=6.78 Hz, 3H) 1.68 (br d, J=13.05 Hz, 1H) 1.78 (br d, J=8.78 Hz, 1H) 1.94-1.99 (m, 1H) 2.04-2.11 (m, 1H) 2.63 (s, 2H) 3.25 (td, J=11.80, 2.26 Hz, 1H) 3.36 (td, J=11.92, 2.01 Hz, 1H) 3.61 (dd, J=12.42, 3.89 Hz, 1H) 3.81-3.88 (m, 1H) 3.92 (br t, J=11.80 Hz, 2H) 4.02 (br dd, J=11.54, 3.76 Hz, 1H) 4.18 (br d, J=13.05 Hz, 1H) 4.75 (dd, J=12.05, 4.27 Hz, 1H) 7.40 (s, 1H) 7.62 (s, 1H)

Example 21 [(1R,5S,6S)-6-(5,5-dimethyl-4,5-dihydro-1,2-oxazol-3-yl)-3-azabicyclo[3.1.0]hex-3-yl]{1-[(1S)-1-phenylethyl]-1H-imidazol-4-yl}methanone ethyl 1-[(1S)-1-phenylethyl]-1H-imidazole-4-carboxylate A mixture of ethyl isocyanoacetate (1.0 g, 8.84 mmol) and 1,1-dimethoxy-N,N-dimethylmethanamine (1.53 mL, 11.49 mmol) was stirred at 0° C. for 3 h. TLC (PE:EA=3: 1) showed ethyl 2-isocyanoacetate (1. g, 8.84 mmol) (Rf=0.6) was consumed completely and new spot (Rf=0.4) was detected. (S)-1-phenylethanamine (4.5 mL, 35.36 mmol) was added to the mixture. The obtained mixture was stirred at 50° C. for 16 h to give brown mixture. TLC (PE:EA=1:1) showed new spot (Rf=0.1) was detected. The mixture was concentrated to give a residue. The residue was purified by flash column (PE:EA=1:0 to 0:1) to afford the title compound (0.9300 g, 3.807 mmol, 43.06% yield)(PE:EA=1:1, Rf=0.1) as a brown oil.

LC-MS Method1 0.685 min, MS (m/z) 244.9 (M+H$^+$).

1-[(1S)-1-phenylethyl]-1H-imidazole-4-carboxylic acid

To a mixture of ethyl 1-[(1S)-1-phenylethyl]-1H-imidazole-4-carboxylate (930 mg, 3.81 mmol) in THF (6 mL) and H₂O (3 mL) was added LiOH·H₂O (0.33 mL, 5.71 mmol). The reaction mixture was stirred at 20° C. for 16 h to give yellow mixture. TLC (PE:EtOAc=1:1) showed the starting material was consumed completely. The reaction mixture was diluted with H₂O (15 mL) and extracted with EtOAc (8 mL×5). The aqueous phase was acidified with 1 N HCl aq. to pH=4. The resulting aqueous phase was dried in vacuum to afford the title compound (900 mg, 4.162 mmol, 109.33% yield) (crude) as brown solid.

LC-MS Method1 0.539 min, MS (m/z) 216.9 (M+H$^+$).

[(1R,5S,6S)-6-(5,5-dimethyl-4,5-dihydro-1,2-oxazol-3-yl)-3-azabicyclo[3.1.0]hex-3-yl]{1-[(1S)-1-phenylethyl]-1H-imidazol-4-yl}methanone To a mixture of (1R,5S,6r)-6-(5,5-dimethyl-4,5-dihydro-1,2-oxazol-3-yl)-3-azabicyclo[3.1.0]hexane hydrochloride (100 mg, 0.5500 mmol) in DMF (2 mL) were added 1-[(1S)-1-phenylethyl]-1H-imidazole-4-carboxylic acid (143.96 mg, 0.6700 mmol), DIPEA (0.37 mL, 2.22 mmol) and HATU (254.51 mg, 0.6700 mmol). The reaction mixture was stirred at 25° C. for 16 h to give brown mixture. TLC (DCM:MeOH=40: 1, a drop of Et₃N) showed one new spot (Rf=0.5) was detected. The reaction mixture was diluted with H₂O (10 mL). The resulting mixture was extracted with EtOAc (5 mL×4). The combined organic phase was dried over anhydrous Na₂SO₄, filtered and concentrated in vacuo to give a residue. The residue was purified by prep-TLC (DCM:MeOH=40: 1, 1% Et₃N in the solvent) to give crude product. The crude product was purified by prep-HPLC (NH₃). The afforded flows were combined, concentrated to remove most of CH₃CN and lyophilized to afford the title compound (3.85 mg, 0.0102 mmol, 1.8336% yield) as white solid.

LC-MS Method1: 379.1 [M+H$^+$]

$^1$H NMR (400 MHz, CHLOROFORM-d) δ ppm 7.67 (br s, 1H), 7.48 (s, 1H), 7.31-7.40 (m, 3H), 7.18 (br d, J=6.5 Hz, 2H), 5.35 (q, J=6.9 Hz, 1H), 4.75 (br d, J=8.0 Hz, 1H), 4.18 (br d, J=12.3 Hz, 1H), 3.88-4.01 (m, 1H), 3.61 (br d, J=8.8 Hz, 1H), 2.64 (s, 2H), 2.07 (br s, 1H), 1.98 (br s, 1H), 1.88 (d, J=7.0 Hz, 3H), 1.46 (br s, 1H), 1.38 (s, 6H), 1.26 (s, 1H)

Example 22 2-[(1S)-1-(4-{[(1R,5S,6S)-6-(5,5-dimethyl-4,5-dihydro-1,2-oxazol-3-yl)-3-azabicyclo[3.1.0]hex-3-yl]carbonyl}-1H-imidazol-1-yl)ethyl]benzonitrile (R)—N-[(E)-(2-bromophenyl)methylene]-2-methyl-2-propanesulfinamide A 100 mL round-bottom flask was charged with 2-bromobenzaldehyde (2000 mg, 10.81 mmol), (R)-2-methylpropane-2-sulfinamide (1310.13 mg, 10.81 mmol), Ti(OEt)₄ (3.33 mL, 16.21 mmol) and THF (9.2536 mL). The reaction was heated at 60° C. for 30 min under N₂ protection to give a yellow solution. TLC (PE/EA=3/1, Rf=0.4) showed a new spot was detected. H₂O (3 mL) was added dropwise and it was stirred at 20° C. for 5 min, then it was filtrate through a pad of celite and concentrated in vacuum to give the title compound (3050 mg, 10.583 mmol, 97.903% yield) as white solid.

(R)—N-[(1S)-1-(2-bromophenyl)ethyl]-2-methyl-2-propanesulfinamide

A round-bottom flask charged with (R)—N-[(E)-(2-bromophenyl)methylene]-2-methyl-2-propanesulfinamide (3000 mg, 10.41 mmol) and THF (25 mL) was cooled to −48° C., and chloro(methyl)magnesium (4.16 mL, 12.49 mmol) was added dropwise to the mixture. The reaction was stirred at this temperature for 2 hr to give a yellow solution. H₂O (30 mL) was added and it was extracted with EtOAc (30 mL×2). The combined organic layer was dried over Na₂SO₄ and concentrated in vacuum to give a yellow oil. The crude was purified by silica gel chromatography (DCM/EA=10/1 to 3/1) to give the title compound (960 mg, 3.1553 mmol, 30.312% yield) as white solid.

$^1$H NMR (400 MHz, CHLOROFORM-d) δ ppm 7.54 (d, J=8.0 Hz, 1H), 7.43 (dd, J=8.0, 0.8 Hz, 1H), 7.40-7.20 (m, 1H), 7.20-7.10 (m, 1H), 5.05-4.95 (m, 1H), 3.37 (d, J=4.0 Hz, 1H), 1.54 (d, J=6.8 Hz, 3H), 1.21 (s, 9H).

(1S)-1-(2-bromophenyl)ethanamine hydrochloride

A solution of (R)—N-[(1S)-1-(2-bromophenyl)ethyl]-2-methyl-2-propanesulfinamide (900 mg, 2.96 mmol) in HCl/MeOH (105.31 mg, 2.96 mmol) was stirred at 30° C. for 16 hr to give a colorless solution. The reaction mixture was evaporated in vacuum to give the title compound (700 mg, 2.95 mmol, 100.04% yield) as yellow oil. It was used directly in the next step.
LC-MS Method1 0.592 min, MS (m/z) 202.1 (M+H$^+$).

ethyl 1-[(1S)-1-(2-bromophenyl)ethyl]-1H-imidazole-4-carboxylate

A 8 mL microwave vial was charged with (1S)-1-(2-bromophenyl)ethanamine hydrochloride (780 mg, 3.3 mmol), ethyl (2Z)-3-(dimethylamino)-2-isocyanoacrylate (554.61 mg, 3.3 mmol), Et$_3$N (0.69 mL, 4.95 mmol) and 1-Butanol (3 mL). The reaction was irradiated with microwave at 130° C. for 1 h to give a brown red solution. The reaction mixture was diluted with saturated Na$_2$CO$_3$ aq. (10 mL) and extracted with EtOAc (20 mL×2). The combined organic layer dried over Na$_2$SO$_4$ and concentrated in vacuum to give a yellow oil. The crude was purified by silica gel chromatography (DCM/EA=10/1 to 6/1) to give the title compound (230 mg, 0.7117 mmol, 21.581% yield) as yellow oil.
LC-MS Method1 0.726 min, MS (m/z) 324.9 (M+H$^+$).

ethyl 1-[(1S)-1-(2-cyanophenyl)ethyl]-1H-imidazole-4-carboxylate

A 50 mL round-bottom flask was charged with ethyl 1-[(1S)-1-(2-bromophenyl)ethyl]-1H-imidazole-4-carboxylate (180 mg, 0.5600 mmol), Zn(CN)$_2$ (130.78 mg, 1.11 mmol), Pd$_2$(dba)$_3$ (25.5 mg, 0.0300 mmol), P(t-Bu)$_3$·HBF$_4$ (32.32 mg, 0.1100 mmol), Zn (14.57 mg, 0.2200 mmol) and DMF (2 mL). The reaction mixture was stirred at 120° C. for 16 h to give a yellow solution. H$_2$O (15 mL) was added and it was extracted with EtOAc (20 mL×2). The combined organic layer dried over Na$_2$SO$_4$ and concentrated in vacuum to give a yellow oil. The reaction mixture was evaporated in vacuum to give the title compound (60 mg, 0.2228 mmol, 40.004% yield) as yellow oil. It was used directly in the next step.

1-[(1S)-1-(2-cyanophenyl)ethyl]-1H-imidazole-4-carboxylic acid

To a mixture of ethyl 1-[(1S)-1-(2-cyanophenyl)ethyl]-1H-imidazole-4-carboxylate (150 mg, 0.5600 mmol) in 1,4-Dioxane (5 mL) was added a solution of LiOH·H$_2$O (46.74 mg, 1.11 mmol) in H$_2$O (1.5 mL, 0.5600 mmol). It was reacted at 20° C. for 16 h to give a yellow solution. The reaction mixture was evaporated in vacuum to give the title compound (160 mg, 0.6632 mmol, 119.07% yield) as white solid.
LC-MS Method1 0.688 min, MS (m/z) 242.2 (M+H$^+$).

2-[(1S)-1-(4-{[(1R,5S,6S)-6-(5,5-dimethyl-4,5-dihydro-1,2-oxazol-3-yl)-3-azabicyclo[3.1.0]hex-3-yl]carbonyl}-1H-imidazol-1-yl)ethyl]benzonitrile To a solution of 1-[(1S)-1-(2-cyanophenyl)ethyl]-1H-imidazole-4-carboxylic acid (50 mg, 0.2100 mmol) in DMF (2 mL) were added N-ethyl-N-isopropylpropan-2-amine (0.18 mL, 1.04 mmol) and HATU (118.85 mg, 0.3100 mmol) at 20° C. After stirred for 30 min, (1R,5S,6r)-6-(5,5-dimethyl-4,5-dihydro-1,2-oxazol-3-yl)-3-azabicyclo[3.1.0]hexane hydrochloride (52.47 mg, 0.21 mmol) was added and stirred for 16 hr to give black suspension. H$_2$O (30 mL) was added and it was extracted with EtOAc (30 mL×2). The combined organic layer dried over Na$_2$SO$_4$ and concentrated in vacuum to give a yellow oil. The crude was purified by Prep-HPLC (NH$_3$). The afforded flows were concentrated in vacuum to remove most of CH$_3$CN and lyophilized to give the title compound (37.35 mg, 0.0926 mmol) as white solid.
LC-MS Method1: 404.3 [M+H$^+$]
$^1$H NMR (400 MHz, CHLOROFORM-d) δ 7.70 (dd, J=1.00, 7.53 Hz, 1H), 7.67 (d, J=1.51 Hz, 1H), 7.56-7.63 (m, 2H), 7.41-7.48 (m, 1H), 7.20 (d, J=8.03 Hz, 1H), 5.78 (q, J=7.03 Hz, 1H), 4.73 (dd, J=2.89, 12.17 Hz, 1H), 4.16 (d, J=12.55 Hz, 1H), 3.93 (br d, J=10.29 Hz, 1H), 3.60 (dd, J=4.14, 12.42 Hz, 1H), 2.63 (d, J=2.26 Hz, 2H), 2.07 (br d, J=3.51 Hz, 1H), 1.95-1.99 (m, 1H), 1.94 (d, J=7.03 Hz, 3H), 1.45 (br d, J=3.26 Hz, 1H), 1.36 (s, 6H)

Example 23 3-[(1S)-1-(4-{[(1R,5S,6S)-6-(5,5-dimethyl-4,5-dihydro-1,2-oxazol-3-yl)-3-azabicyclo[3.1.0]hex-3-yl]carbonyl}-1H-imidazol-1-yl)ethyl]benzonitrile (R)—N-[(E)-(3-cyanophenyl)methylene]-2-methyl-2-propanesulfinamide To a solution of (R)-2-methylpropane-2-sulfinamide (4621.37 mg, 38.13 mmol) in THF (20 mL) were added 3-formylbenzonitrile (5000 mg, 38.13 mmol) and tetraethoxytitanium (11.86 mL, 57.2 mmol) at 60° C. The resulting mixture was stirred at 60° C. for 0.5 hours to give yellow solution. H$_2$O (3 mL) was added dropwise and it was stirred for 5 min. Then solid was filtered through a pad of celite and the filtrate was concentrated in vacuum to afford the title compound (7630 mg, 32.562 mmol, 85.398% yield) as white solid. It was used directly for the next step without further purification.
LC-MS Method1 0.858 min, MS (m/z) 235.2 (M+H$^+$).

(R)—N-[(1S)-1-(3-cyanophenyl)ethyl]-2-methyl-2-propanesulfinamide

To a solution of (R)—N-[(E)-(3-cyanophenyl)methylene]-2-methyl-2-propanesulfinamide (3000 mg, 12.8 mmol) in THF (32.054 mL) was added chloro(methyl)magnesium (4.69 mL, 14.08 mmol) at −48° C. The resulting mixture was stirred at −40° C. for 14 hours to give yellow solution. The reaction mixture was poured into sat. NH$_4$Cl aq. (30 mL) and extracted with EtOAc (30 mL×4). The combined organic layers were washed with brine (30 mL×2), dried over Na$_2$SO$_4$, filtered and concentrated under reduced pressure to give the title compound (960 mg, 3.8345 mmol, 29.95% yield) as yellow solid.
LC-MS Method1 0.845 min, MS (m/z) 251.2 (M+H$^+$).

3-[(1S)-1-aminoethyl]benzonitrile hydrochloride

To (R)—N-[(1S)-1-(3-cyanophenyl)ethyl]-2-methyl-2-propanesulfinamide (960 mg, 3.83 mmol) was added HCl/MeOH (10 mL, 3.83 mmol) at 20° C. The resulting mixture was stirred at 20-25° C. for 0.5 hours to give yellow solution. The reaction mixture was evaporated in vacuum to give the title compound (643 mg, crude product) as yellow oil.
LC-MS Method1 0.258 min, MS (m/z) 147. (M−HCl+H$^+$).

ethyl 1-[(1S)-1-(3-cyanophenyl)ethyl]-1H-imidazole-4-carboxylate

To a solution of 3-[(1S)-1-aminoethyl]benzonitrile hydrochloride (250 mg, 1.49 mmol) in 1-Butanol (2.5 mL) were added Et₃N (0.31 mL, 2.23 mmol) and ethyl (2Z)-3-(dimethylamino)-2-isocyanoacrylate (271.49 mg, 1.49 mmol) The reaction mixture was irradiated with microwave at 130° C. for 60 min to give a yellow solution. The reaction mixture was poured into sat. NH₄Cl aq. (30 mL) and extracted with EtOAc (30 mL×2). The combined organic layers were washed with brine (30 mL×2), dried over Na₂SO₄, filtered and concentrated under reduced pressure to give the title compound (90 mg, 0.3342 mmol, 22.484% yield) as yellow oil.

LC-MS Method1 0.732 min, MS (m/z) 270.2 (M+H⁺).

1-[(1S)-1-(3-cyanophenyl)ethyl]-1H-imidazole-4-carboxylic acid

To a solution of ethyl 1-[(1S)-1-(3-cyanophenyl)ethyl]-1H-imidazole-4-carboxylate (90 mg, 0.3300 mmol) was added hydroxylithium hydrate (28.05 mg, 0.6700 mmol) in THF (0.90 mL), H₂O (0.90 mL) and MeOH (0.90 mL) at 20° C. The resulting mixture was stirred at 20-25° C. for 14 hours to give yellow solution. The reaction mixture was poured into H₂O and extracted with EtOAc (20 mL×4). The aqueous layers were concentrated and lyophilized to afford the title compound (132 mg, crude product) as white solid.

LC-MS Method1 0.468 min, MS (m/z) 241.9 (M+H⁺).

3-[(1S)-1-(4-{[(1R,5S,6S)-6-(5,5-dimethyl-4,5-dihydro-1,2-oxazol-3-yl)-3-azabicyclo[3.1.0]hex-3-yl]carbonyl}-1H-imidazol-1-yl)ethyl]benzonitrile To a solution of 1-[(1S)-1-(3-cyanophenyl)ethyl]-1H-imidazole-4-carboxylic acid (60 mg, 0.2500 mmol) in DMF (1.8 mL) were added HATU (123.6 mg, 0.3200 mmol) and N-ethyl-N-isopropylpropan-2-amine (0.3 mL, 1.74 mmol) at 20° C. The reaction mixture was stirred at 20° C. for 30 min. Then (1R,5S,6r)-6-(5,5-dimethyl-4,5-dihydro-1,2-oxazol-3-yl)-3-azabicyclo[3.1.0]hexane hydrochloride (62.96 mg, 0.2500 mmol) was added. The resulting mixture was stirred at 20-25° C. for 14 hours to give yellow solution. The reaction mixture was poured into sat. NH₄Cl aq. (80 mL) and extracted with EtOAc (50 mL×4). The combined organic layers were washed with sat. aq. (50 mL×2), dried over Na₂SO₄, filtered and concentrated under reduced pressure. The residue was purified by prep-HPLC (FA) to the title compound (10 mg, 0.0248 mmol, 9.9654% yield) as white solid.

LC-MS Method1: 404.2 [M+H⁺]
¹H NMR (400 MHz, CHLOROFORM-d) δ=7.63 (br d, J=7.8 Hz, 2H), 7.52-7.46 (m, 2H), 7.44 (s, 1H), 7.37 (br d, J=8.0 Hz, 1H), 5.40 (q, J=6.9 Hz, 1H), 4.73 (br d, J=12.3 Hz, 1H), 4.17 (br d, J=12.3 Hz, 1H), 3.98-3.91 (m, 1H), 3.64-3.58 (m, 1H), 2.64 (s, 2H), 2.08 (br s, 1H), 1.98 (br d, J=3.3 Hz, 1H), 1.90 (d, J=7.0 Hz, 3H), 1.46 (t, J=3.3 Hz, 1H), 1.36 (s, 6H)

Example 24 4-[(1S)-1-(4-{[(1R,5S,6S)-6-(5,5-dimethyl-4,5-dihydro-1,2-oxazol-3-yl)-3-azabicyclo[3.1.0]hex-3-yl]carbonyl}-1H-imidazol-1-yl)ethyl]benzonitrile (R)—N-[(E)-(4-cyanophenyl)methylene]-2-methyl-2-propanesulfinamide To a solution of (R)-2-methylpropane-2-sulfinamide (4621.37 mg, 38.13 mmol) in THF (20 mL) were added 4-formylbenzonitrile (5000 mg, 38.13 mmol) and tetraethoxytitanium (13.05 g, 57.2 mmol) at 60° C. The resulting mixture was stirred at 60° C. for 0.5 hours to give yellow solution. H₂O (3 mL) was added dropwise and it was stirred for 5 mins. Then the solid was removed by filtration through a pad of celite and the filtrate was concentrated in vacuum to give the title compound (8340 mg, 35.592 mmol, 93.345% yield) as white solid.

LC-MS Method1 0.858 min, MS (m/z) 234.8 (M+H⁺).

(R)—N-[(1S)-1-(4-cyanophenyl)ethyl]-2-methyl-2-propanesulfinamide

To a solution of (R)—N-[(E)-(4-cyanophenyl)methylene]-2-methyl-2-propanesulfinamide (2340 mg, 9.99 mmol) in THF (30 mL) was added chloro(methyl)magnesium (4.99 mL, 14.98 mmol) at −48° C. The resulting mixture was stirred at −40° C. for 14 hours to give yellow solution. The mixture was quenched with NH₄Cl and the aqueous layer was extracted with EA (30 mL×3). The combined organic layers were washed with brine, dried over Na₂SO₄ and then concentrated in vacuum. The crude product was purified by silica column (PE to PE:EtOAc=1:1). The afforded solid was triturated with EtOAc/hexane (20 mL/10 mL) and dried in air to give the title compound (1310 mg, 5.2325 mmol, 52.396% yield) as yellow solid.

LC-MS Method1 0.732 min, MS (m/z) 250.9 (M+H⁺).

4-[(1S)-1-aminoethyl]benzonitrile hydrochloride

To (R)—N-[(1S)-1-(4-cyanophenyl)ethyl]-2-methyl-2-propanesulfinamide (1310 mg, 5.23 mmol) was added HCl/MeOH (10 mL, 5.23 mmol) at 20° C. The resulting mixture was stirred at 20-25° C. for 0.5 hours to give yellow solution. The reaction mixture was evaporated in vacuum to give the title compound (1 g, crude product) as a yellow oil.

LC-MS Method1 0.302 min, MS (m/z) 146.8 (M+H⁺).

ethyl 1-[(1S)-1-(4-cyanophenyl)ethyl]-1H-imidazole-4-carboxylate

To a solution of ethyl (2Z)-3-(dimethylamino)-2-isocyanoacrylate (300 mg, 1.78 mmol) in 1-Butanol (3 mL) were added Et₃N (0.38 mL, 2.68 mmol) and 4-[(1S)-1-aminoethyl]benzonitrile hydrochloride (300 mg, 1.78 mmol). The reaction mixture was irradiated with microwave at 130° C. for 60 min to give a yellow solution. The reaction mixture was poured into sat. NH₄Cl aq. (30 mL) and extracted with EtOAc (30 mL×2). The combined organic layers were washed with sat. aq. (30 mL×2), dried over Na₂SO₄, filtered and concentrated under reduced pressure to give the title compound (110 mg, 0.4085 mmol, 22.9% yield) as yellow oil.

LC-MS Method1 0.732 min, MS (m/z) 270.2 (M+H⁺).

1-[(1S)-1-(4-cyanophenyl)ethyl]-1H-imidazole-4-carboxylic acid

To a solution of ethyl 1-[(1S)-1-(4-cyanophenyl)ethyl]-1H-imidazole-4-carboxylate (110 mg, 0.4100 mmol) in THF (1.1 mL), H₂O (1.1 mL) and MeOH (1.1 mL) was added hydroxylithium hydrate (34.28 mg, 0.8200 mmol) at 20° C. The resulting mixture was stirred at 20-25° C. for 14 hours to give yellow solution. The reaction mixture was poured into H₂O and extracted with EtOAc (20 mL×4). The aqueous layer was concentrated and lyophilized to afford the title compound (130 mg, crude product) as yellow solid.

LC-MS Method1 0.443 min, MS (m/z) 241.9 (M+H⁺).

4-[(1S)-1-(4-{[(1R,5S,6S)-6-(5,5-dimethyl-4,5-di-hydro-1,2-oxazol-3-yl)-3-azabicyclo[3.1.0]hex-3-yl]carbonyl}-1H-imidazol-1-yl)ethyl]benzonitrile To a solution of 1-[(1S)-1-(4-cyanophenyl)ethyl]-1H-imidazole-4-carboxylic acid (100 mg, 0.4100 mmol) in DMF (3 mL) were added HATU (206.01 mg, 0.5400 mmol) and N-ethyl-N-isopropylpropan-2-amine (0.5 mL, 2.9 mmol) at 20° C. The reaction mixture was stirred for 30 min. Then (1R,5S,6r)-6-(5,5-dimethyl-4,5-dihydro-1,2-oxazol-3-yl)-3-azabicyclo[3.1.0]hexane hydrochloride (104.94 mg, 0.4100 mmol) was added. The resulting mixture was stirred at 20-25° C. for 14 hours to give yellow solution. The reaction mixture was poured into sat. NH₄Cl aq. (20 mL) and extracted with EtOAc (20 mL×3). The crude product was purified by Prep-HPLC (FA) to give the title compound (2 mg, 0.0050 mmol, 1.1958% yield) as yellow solid.

LC-MS Method1: 404.2 [M+H⁺]

¹H NMR (400 MHz, CHLOROFORM-d) δ=7.66 (br d, J=8.0 Hz, 3H), 7.51 (br d, J=9.0 Hz, 1H), 7.23 (br s, 2H), 5.42 (br d, J=7.0 Hz, 1H), 4.72 (br s, 1H), 4.17 (br d, J=12.8 Hz, 1H), 3.93 (br d, J=12.0 Hz, 1H), 3.61 (br d, J=14.8 Hz, 1H), 2.63 (s, 2H), 2.08 (br s, 1H), 1.98 (br s, 1H), 1.90 (br d, J=7.0 Hz, 3H), 1.47 (br s, 1H), 1.37 (s, 6H)

Example 25 [(1R,5S,6S)-6-(5,5-dimethyl-4,5-di-hydro-1,2-oxazol-3-yl)-3-azabicyclo[3.1.0]hex-3-yl]{1-[(1S)-1-(2-pyridinyl)ethyl]-1H-imidazol-4-yl}methanone ethyl 1-[(1S)-1-(2-pyridinyl)ethyl]-1H-imidazole-4-carboxylate The mixture of (1S)-1-(2-pyridinyl)ethanamine (500 mg, 4.09 mmol) and ethyl (2Z)-3-(dimethylamino)-2-isocyanoacrylate (137.67 mg, 0.8200 mmol) was stirred at 50° C. for 16 h. The reaction mixture was concentrated directly. The residue was purified by prep-TLC (PE:EtOAc=0:1) to give the title compound as brown oil.

¹H NMR (400 MHz, CHLOROFORM-d) δ=8.61 (d, J=4.0 Hz, 1H), 7.78 (d, J=1.2 Hz, 1H), 7.70-7.60 (m, 2H), 7.30-7.20 (m, 1H), 7.02 (d, J=8.0 Hz, 1H), 5.50-5.35 (m, 1H), 4.36 (q, J=6.8 Hz, 2H), 1.94 (d, J=7.6 Hz, 3H), 1.38 (t, J=6.8 Hz, 3H).

1-[(1S)-1-(2-pyridinyl)ethyl]-1H-imidazole-4-carboxylic acid

To a solution of ethyl 1-[(1S)-1-(2-pyridinyl)ethyl]-1H-imidazole-4-carboxylate (160 mg, 0.6500 mmol) in THF (5 mL) and H₂O (1 mL, 55.56 mmol) was added LiOH·H₂O (0.11 mL, 1.96 mmol). The mixture was stirred at 20° C. for 12 h to give brown suspension. LCMS showed the starting material consumed up. The reaction mixture was concentrated. The afforded H₂O layer was acidified with 1 N HCl aq. to pH=5-7 and lyophilized to give the title compound (130 mg, 0.5985 mmol, 91.746% yield) as white solid.

[(1R,5S,6S)-6-(5,5-dimethyl-4,5-dihydro-1,2-oxazol-3-yl)-3-azabicyclo[3.1.0]hex-3-yl]{1-[(1S)-1-(2-pyridinyl)ethyl]-1H-imidazol-4-yl}methanone To a solution of 1-[(1S)-1-(2-pyridinyl)ethyl]-1H-imidazole-4-carboxylic acid (130 mg, 0.6000 mmol) in DMF (2 mL) were added HATU (274.55 mg, 0.7200 mmol), DIPEA (0.49 mL, 2.99 mmol), (1R,5S,6r)-6-(5,5-dimethyl-4,5-dihydro-1,2-oxazol-3-yl)-3-azabicyclo[3.1.0]hexane hydrochloride (108 mg, 0.6000 mmol). The mixture was stirred at 30° C. for 3 h to give brown solution. The reaction mixture was concentrated directly. The residue was purified by prep-HPLC (NH₃) and the afforded flows were combined, concentrated to remove most of CH₃CN and lyophilized to give the title compound (48.15 mg, 0.1269 mmol, 21.202% yield) as light yellow solid.

LC-MS Method1: 380.0 [M+H⁺]

¹H NMR (400 MHz, CHLOROFORM-d) δ ppm 8.60 (1H, d, J=4.63 Hz), 7.74 (1H, br d, J=2.38 Hz), 7.67 (1H, td, J=7.75, 1.50 Hz), 7.60 (1H, s), 7.24 (1H, dd, J=7.44, 4.82 Hz), 7.03 (1H, d, J=7.88 Hz), 5.43 (1H, q, J=7.00 Hz), 4.74 (1H, dd, J=12.07, 3.69 Hz), 4.18 (1H, d, J=12.51 Hz), 3.90-4.01 (1H, m), 3.61 (1H, dd, J=12.51, 4.13 Hz), 2.64 (2H, s), 2.07 (1H, br d, J=3.38 Hz), 1.97 (1H, br dd, J=7.13, 3.50 Hz), 1.92 (3H, d, J=7.00 Hz), 1.45 (1H, t, J=3.31 Hz), 1.31-1.43 (6H, m)

Example 26 [(1R,5S,6S)-6-(5,5-dimethyl-4,5-di-hydro-1,2-oxazol-3-yl)-3-azabicyclo[3.1.0]hex-3-yl]{1-[(1S)-1-(4-pyridinyl)ethyl]-1H-imidazol-4-yl}methanone (1R)-1-(4-pyridinyl)ethyl 4-methylbenzenesulfonate To a solution of (1R)-1-(4-pyridinyl)ethanol in THF (5 mL) was added NaH (148.11 mg, 6.17 mmol) at 0° C. The mixture was stirred at 0° C. for 0.5 h. 4-methylbenzene-1-sulfonyl chloride (0.29 mL, 1.95 mmol) was added and the mixture was stirred at 20-25° C. for 16 h. The reaction mixture was poured into H₂O (10 mL) and extracted with EtOAc (10 mL×4). The combined organic layers were dried over Na₂SO₄, filtered and concentrated under reduced pressure. The crude product was purified by flash column (PE to 30% EtOAc in PE) to afford the title compound (330 mg, 1.1899 mmol, 73.267% yield) as a white solid.

¹H NMR (400 MHz, CHLOROFORM-d) δ=8.54-8.48 (m, 2H), 7.69 (d, J=8.5 Hz, 2H), 7.25 (d, J=8.0 Hz, 2H), 7.13-7.10 (m, 2H), 5.54 (q, J=6.6 Hz, 1H), 2.42 (s, 3H), 1.59 (d, J=6.8 Hz, 3H)

ethyl 1-[(1S)-1-(4-pyridinyl)ethyl]-1H-imidazole-4-carboxylate

To a solution of (1R)-1-(4-pyridinyl)ethyl 4-methylbenzenesulfonate (280 mg, 1.01 mmol) in DMF (11.2 mL) were added methyl 1H-imidazole-5-carboxylate (127.32 mg, 1.01 mmol) and Cs₂CO₃ (164.47 mg, 0.50 mmol). The mixture was stirred at 40° C. for 16 h. The reaction mixture was poured into H₂O (10 mL) and extracted with EtOAc (15 mL×4). The combined organic layers were dried over Na₂SO₄, filtered and concentrated under reduced pressure. The residue was purified by prep-TLC (DCM:MeOH=10:1) to afford the title compound (28 mg, 0.1211 mmol, 11.993% yield) as a yellow oil.

LC-MS Method1: 232.1 [M+H]⁺

¹H NMR (400 MHz, CHLOROFORM-d) δ=8.64-8.60 (m, 2H), 7.68-7.59 (m, 2H), 7.05-7.01 (m, 2H), 5.39 (q, J=7.0 Hz, 1H), 3.95-3.84 (m, 3H), 1.91 (d, J=7.3 Hz, 3H)

1-[(1S)-1-(4-pyridinyl)ethyl]-1H-imidazole-4-carboxylic acid

To a solution of ethyl 1-[(1S)-1-(4-pyridinyl)ethyl]-1H-imidazole-4-carboxylate (50 mg, 0.22 mmol) in THF (2 mL)

and H$_2$O (1 mL) was added LiOH·H$_2$O (13.61 mg, 0.32 mmol). The mixture was stirred at 20-25° C. for 2 h. The reaction mixture was concentrated directly. The reaction mixture was acidified with 1 N HCl aq. to pH=6 and then lyophilized to afford the title compound (40 mg, 0.1841 mmol, 85.167% yield) as a yellow oil.

$^1$H NMR (400 MHz, DMSO-d$_6$) δ=8.59-8.50 (m, 2H), 7.95 (s, 1H), 7.83 (s, 1H), 7.25 (d, J=6.3 Hz, 2H), 5.66 (q, J=7.1 Hz, 1H), 1.81 (d, J=7.3 Hz, 3H)

[(1R,5S,6S)-6-(5,5-dimethyl-4,5-dihydro-1,2-oxazol-3-yl)-3-azabicyclo[3.1.0]hex-3-yl]{1-[(1S)-1-(4-pyridinyl)ethyl]-1H-imidazol-4-yl}methanone To a solution of 1-[(1S)-1-(4-pyridinyl)ethyl]-1H-imidazole-4-carboxylic acid (20 mg, 0.09 mmol) in Pyridine (1 mL) were added EDCI (26.48 mg, 0.14 mmol) and (1R,5S,6r)-6-(5,5-dimethyl-4,5-dihydro-1,2-oxazol-3-yl)-3-azabicyclo[3.1.0]hexane hydrochloride (19.95 mg, 0.0900 mmol). The resulting mixture was stirred at 20-25° C. for 16 h. The reaction mixture was concentrated directly. The residue was purified by prep-HPLC (NH$_3$). The afforded flows were combined, concentrated to remove most of CH$_3$CN and lyophilized to afford the title compound (24.99 mg, 0.0659 mmol, 71.527% yield) as a yellow solid.

LC-MS Method1: 380.1 [M+H]$^+$ $^1$H NMR (400 MHz, CHLOROFORM-d) δ=8.61 (d, J=5.8 Hz, 2H), 7.68 (s, 1H), 7.51 (s, 1H), 7.03 (d, J=5.8 Hz, 2H), 5.36 (q, J=6.9 Hz, 1H), 4.76 (dd, J=2.9, 12.2 Hz, 1H), 4.19 (br d, J=12.3 Hz, 1H), 4.02-3.89 (m, 1H), 3.62 (dd, J=4.1, 12.7 Hz, 1H), 2.64 (s, 2H), 2.13-1.96 (m, 2H), 1.90 (d, J=7.3 Hz, 3H), 1.48 (t, J=3.4 Hz, 1H), 1.38 (s, 6H)

Example 27 [(1R,5S,6S)-6-(5,5-dimethyl-4,5-dihydro-1,2-oxazol-3-yl)-3-azabicyclo[3.1.0]hex-3-yl]{1-[(1S)-1-(1,3-thiazol-2-yl)ethyl]-1H-imidazol-4-yl}methanone ethyl 1-[(1 S)-1-(1,3-thiazol-2-yl)ethyl]-1H-imidazole-4-carboxylate To a solution of (1S)-1-(1,3-thiazol-2-yl)ethanamine (131.19 mg, 0.7800 mmol) in 1-Butanol (1.4 mL) were added ethyl (2Z)-3-(dimethylamino)-2-isocyanoacrylate (100 mg, 0.7800 mmol) and Et$_3$N (0.16 mL, 1.17 mmol) at 25° C. The resulting mixture was subjected to reaction in microwave reactor (time: 1 h, temp: 130° C.). The reaction mixture was poured into H$_2$O (5 mL) and extracted with EA (5 mL×3). The combined organic layers were washed with brine (10 mL), dried over Na$_2$SO$_4$, filtered and concentrated under reduced pressure to give a crude product. The crude product was purified by Prep-TLC (EA) to give the title compound (50 mg, 0.1990 mmol, 25.507% yield) as a yellow oil.

1-[(1S)-1-(1,3-thiazol-2-yl)ethyl]-1H-imidazole-4-carboxylic acid

To a solution of ethyl 1-[(1S)-1-(1,3-thiazol-2-yl)ethyl]-1H-imidazole-4-carboxylate (50 mg, 0.2000 mmol) in THF (3 mL) and H$_2$O (1 mL) was added LiOH·H$_2$O (41.75 mg, 0.9900 mmol). The reaction mixture was stirred at 25° C. for 16 hours to give a yellow mixture. The reaction mixture was concentrated in vacuum to remove most of THF. The residue was diluted with H$_2$O (5 mL) and acidified with 0.5 M HCl aq. to pH=6. Then the solution was lyophilized to give the title compound as a yellow solid.

[(1R,5S,6S)-6-(5,5-dimethyl-4,5-dihydro-1,2-oxazol-3-yl)-3-azabicyclo[3.1.0]hex-3-yl]{1-[(1S)-1-(1,3-thiazol-2-yl)ethyl]-1H-imidazol-4-yl}methanone To a solution of 1-[(1S)-1-(1,3-thiazol-2-yl)ethyl]-1H-imidazole-4-carboxylic acid (44 mg, 0.2000 mmol) in Pyridine (2 mL) was added EDCI (56.67 mg, 0.3000 mmol). The mixture was stirred at 25° C. under N$_2$ for 10 min. Then (1R,5S,6r)-6-(5,5-dimethyl-4,5-dihydro-1,2-oxazol-3-yl)-3-azabicyclo[3.1.0]hexane hydrochloride (42.71 mg, 0.2000 mmol) was added. The resulting mixture was stirred at 25° C. for 2 hours to give a yellow solution. The reaction mixture was poured into H$_2$O (5 mL) and extracted with EA (5 mL×3). The combined organic layers were washed with brine (20 mL), dried over Na$_2$SO$_4$, filtered and concentrated under reduced pressure to give a residue. The crude product was purified by Prep-HPLC (NH$_3$) to give the title compound (60 mg, 0.1557 mmol, 78.975% yield) as a white solid.

LC-MS Method1: 386.2 [M+H]$^+$ $^1$H NMR (400 MHz, CHLOROFORM-d) δ=7.79 (d, J=3.3 Hz, 1H), 7.75 (s, 1H), 7.62 (s, 1H), 7.35 (d, J=3.3 Hz, 1H), 5.70 (q, J=6.9 Hz, 1H), 4.73 (dd, J=8.8, 11.9 Hz, 1H), 4.18 (br d, J=12.3 Hz, 1H), 3.99-3.91 (m, 1H), 3.61 (dd, J=4.2, 12.7 Hz, 1H), 2.64 (s, 2H), 2.11-2.06 (m, 1H), 2.03 (d, J=7.0 Hz, 3H), 2.00-1.95 (m, 1H), 1.37 (s, 6H)

Example 28 [(1R,5S,6S)-6-(5,5-dimethyl-4,5-dihydro-1,2-oxazol-3-yl)-3-azabicyclo[3.1.0]hex-3-yl]{1-[(1S)-1-(1,3-thiazol-5-yl)ethyl]-1H-imidazol-4-yl}methanone (R)-2-methyl-N-[(E)-1,3-thiazol-5-ylmethylene]-2-propanesulfinamide To a mixture of 5-formylthiazole (2.14 mL, 17.68 mmol) in THF (20 mL) were added (R)-2-methylpropane-2-sulfinamide (2142.48 mg, 17.68 mmol) and Ti(OEt)$_4$ (6045.61 mg, 26.52 mmol). The reaction mixture was stirred at 60° C. for 2 h to give yellow mixture. TLC (PE:EtOAc=2: 1) showed the starting material was consumed completely, and one new spot was (Rf=0.5) detected. The reaction mixture was diluted with EtOAc (30 mL). The mixture was added H$_2$O (10 mL) and stirred for 1 min to give yellow suspension. The suspension was filtered. The filtrate was washed with H$_2$O (20 mL×3), dried with anhydrous Na$_2$SO$_4$, filtered and concentrated in vacuum to afford the title compound (3.77 g, 17.428 mmol, 98.59% yield) as yellow solid.

(R)-2-methyl-N-[(1S)-1-(1,3-thiazol-5-yl)ethyl]-2-propanesulfinamide

To a mixture of (R)-2-methyl-N-[(E)-1,3-thiazol-5-ylmethylene]-2-propanesulfinamide (3.77 g, 17.43 mmol) in THF (37 mL) was added chloro(methyl)magnesium (9.88 mL, 29.63 mmol) at −40° C. The reaction mixture was stirred at 25° C. for 16 h to give black brown mixture. TLC (100% EtOAc) showed the starting material was consumed completely, and one new spot (Rf=0.3) was detected. The reaction mixture was quenched with NH$_4$Cl (60 mL). The resulting mixture was extracted with EtOAc (40 mL×4). The combined organic phase was washed with brine (80 mL×2), dried with anhydrous Na$_2$SO$_4$, filtered and concentrated in vacuum to give a residue. The residue was purified by flash column (10% EtOAc in PE to 100% EtOAc) to afford the title compound (1.7 g, 7.3159 mmol, 41.978% yield) as brown oil.

¹H NMR (400 MHz, CHLOROFORM-d) δ=8.77 (s, 1H), 7.84 (s, 1H), 5.00-4.60 (m, 1H), 3.52 (d, J=3.2 Hz, 1H), 1.69 (d, J=6.4 Hz, 3H), 1.23 (s, 9H).

(1S)-1-(1,3-thiazol-5-yl)ethanamine

A solution of (R)-2-methyl-N-[(1S)-1-(1,3-thiazol-5-yl)ethyl]-2-propanesulfinamide (500 mg, 2.15 mmol) in MeOH/HCl (8 mL, 2.15 mmol) was stirred at 25° C. for 2 h to give brown mixture. TLC (100% EtOAc) showed the starting material was consumed completely. The reaction mixture was concentrated in vacuo to give a residue. The residue was triturated with MTBE (20 mL) and dried in vacuo to give the title compound (504 mg, 3.0609 mmol, 142.25% yield) (crude) as brown solid.

ethyl 1-[(1S)-1-(1,3-thiazol-5-yl)ethyl]-1H-imidazole-4-carboxylate

To a mixture of (1S)-1-(1,3-thiazol-5-yl)ethanamine (350 mg, 2.13 mmol) in 1-Butanol (3.5 mL) were added ethyl (2Z)-3-(dimethylamino)-2-isocyanoacrylate (357.5 mg, 2.13 mmol) and Et₃N (0.41 mL, 3.19 mmol). The reaction mixture was stirred at 130° C. for 1 h used MW to give brown mixture. The reaction mixture was concentrated in vacuo to give a residue. The residue was purified by prep-TLC (100% EtOAc) to afford the title compound (46 mg, 0.1830 mmol, 8.6116% yield) as brown solid.

¹H NMR (400 MHz, CHLOROFORM-d) δ=8.83 (s, 1H), 7.81 (s, 1H), 7.66 (s, 1H), 7.62 (s, 1H), 5.75-5.60 (m, 1H), 4.37 (q, J=7.6 Hz, 2H), 2.00 (d, J=7.2 Hz, 3H), 1.39 (t, J=7.6 Hz, 3H).

1-[(1S)-1-(1,3-thiazol-5-yl)ethyl]-1H-imidazole-4-carboxylic acid

To a mixture ethyl 1-[(1S)-1-(1,3-thiazol-5-yl)ethyl]-1H-imidazole-4-carboxylate (46 mg, 0.1800 mmol) in THF (1.5 mL) and H₂O (0.50 mL) was added LiOH·H₂O (0.02 mL, 0.2700 mmol). The reaction mixture was stirred at 25° C. for 16 h to give yellow mixture. The reaction mixture was diluted with H₂O (4 mL) and extracted with EtOAc (2 mL×3). The aqueous phase was acidified with 1 N HCl aq. to pH=5 and lyophilized to afford the title compound (40 mg, 0.1792 mmol, 97.882% yield) as brown solid.

¹H NMR (400 MHz, DMSO-d₆) δ=9.06 (s, 1H), 7.93 (s, 1H), 7.90 (s, 1H), 7.76 (s, 1H), 6.05-5.95 (m, 1H), 1.89 (d, J=6.8 Hz, 3H).

[(1R,5S,6S)-6-(5,5-dimethyl-4,5-dihydro-1,2-oxazol-3-yl)-3-azabicyclo[3.1.0]hex-3-yl]{1-[(1S)-1-(1,3-thiazol-5-yl)ethyl]-1H-imidazol-4-yl}methanone To a mixture of 1-[(1S)-1-(1,3-thiazol-5-yl)ethyl]-1H-imidazole-4-carboxylic acid (40 mg, 0.1800 mmol) in DMF (0.8286 mL) were added HATU (82.2 mg, 0.2200 mmol) and DIPEA (0.15 mL, 0.9000 mmol). The mixture was stirred at 50° C. for 30 min and followed by addition of (1R,5S,6r)-6-(5,5-dimethyl-4,5-dihydro-1,2-oxazol-3-yl)-3-azabicyclo[3.1.0]hexane hydrochloride (48.44 mg, 0.2700 mmol). The mixture was stirred at 25° C. for 16 h to give a yellow mixture. The reaction mixture was purified by prep-HPLC (NH₃). The afforded flows were combined, concentrated to remove most of CH₃CN and lyophilized to afford the title compound (14.11 mg, 0.0366 mmol, 20.34% yield) as yellow solid.

LC-MS Method1: 386.1 [M+H⁺]

¹H NMR (400 MHz, CHLOROFORM-d) δ ppm 8.80 (s, 1H), 7.79 (s, 1H), 7.67 (s, 1H), 7.52 (d, J=1.4 Hz, 1H), 5.68 (d, J=7.0 Hz, 1H), 4.71 (t, J=11.3 Hz, 1H), 4.16 (dd, J=12.6, 1.9 Hz, 1H), 3.87-3.99 (m, 1H), 3.60 (dd, J=12.6, 4.2 Hz, 1H), 2.63 (s, 2H), 2.08 (dt, J=7.3, 3.7 Hz, 1H), 1.98 (d, J=7.0 Hz, 4H), 1.45 (br d, J=4.0 Hz, 1H), 1.37 (s, 6H).

Example 29 [(1R,5S,6S)-6-(5,5-dimethyl-4,5-dihydro-1,2-oxazol-3-yl)-3-azabicyclo[3.1.0]hex-3-yl]{1-[(2S)-1-phenylpropan-2-yl]-1H-imidazol-4-yl}methanone (2R)-1-phenyl-2-propanyl 4-methylbenzenesulfonate To a solution of (2R)-1-phenyl-2-propanol (400 mg, 2.94 mmol) in DCM (5 mL) were added Et₃N (0.45 mL, 3.23 mmol) and 4-methylbenzene-1-sulfonyl chloride (0.44 mL, 2.94 mmol). The reaction was stirred at 20° C. for 16 hr to give a yellow solution. TLC (PE/EA=10/1, rf=0.3) showed a new major spot. H₂O (30 mL) was added and it was extracted with DCM (30 mL×2). The combined organic layer was dried over Na₂SO₄ and concentrated in vacuum to give a yellow oil. The crude was purified by silica gel chromatography (PE/EA=1/0 to 10/1) to give the title compound (680 mg, 2.3418 mmol, 79.7310% yield) as a white solid.

methyl 1-[(2S)-1-phenylpropan-2-yl]-1H-imidazole-4-carboxylate

A solution of methyl 1H-imidazole-4-carboxylate (300 mg, 2.38 mmol) and (2R)-1-phenyl-2-propanyl 4-methylbenzenesulfonate (690.78 mg, 2.38 mmol) in DMF (4 mL) was stirred at 80° C. for 16 hr to give a yellow solution. H₂O (30 mL) was added and it was extracted with EtOAc (30 mL×2). The combined organic layer dried over Na₂SO₄ and concentrated in vacuum to give a yellow oil. The crude was purified by silica gel chromatography (DCM/EA=10/1 to 3/1) to give the title compound (120 mg, 0.4912 mmol, 20.649% yield)

¹H NMR (400 MHz, CHLOROFORM-d) δ ppm 7.61 (s, 1H), 7.35-7.15 (m, 5H), 6.95-6.85 (m, 2H), 4.45-4.35 (m, 1H), 3.88 (s, 3H), 3.10-2.90 (m, 2H), 1.56 (d, J=6.8 Hz, 3H).

1-[(2S)-1-phenylpropan-2-yl]-1H-imidazole-4-carboxylic acid

To a stirred solution of methyl 1-[(2S)-1-phenylpropan-2-yl]-1H-imidazole-4-carboxylate (120 mg, 0.4900 mmol) in 1,4-Dioxane (3 mL) was added a solution of LiOH·H₂O (41.22 mg, 0.9800 mmol) in H₂O (1 mL, 0.4900 mmol). The reaction mixture as stirred at 20° C. for 16 h to give a colorless oil. TLC (PE/EA=1/1, Rf=0) showed a new spot. The reaction mixture was evaporated in vacuum and lyophilized to give the title compound (110 mg, 0.4777 mmol, 97.252% yield) as white solid.

[(1R,5S,6S)-6-(5,5-dimethyl-4,5-dihydro-1,2-oxazol-3-yl)-3-azabicyclo[3.1.0]hex-3-yl]{1-[(2S)-1-phenylpropan-2-yl]-1H-imidazol-4-yl}methanone To a stirred solution of 1-[(2S)-1-phenylpropan-2-yl]-1H-imidazole-4-carboxylic acid (100 mg, 0.4300 mmol) and HATU (199.24 mg, 0.5200 mmol) in DMF (3 mL) was added N-ethyl-N-isopropylpropan-2-amine (0.37 mL, 2.17 mmol). After stirred for 30 mins, (1R,5S,6r)-6-(5,5-dimethyl-4,5-dihydro-1,2-oxazol-3-yl)-3-azabicyclo[3.1.0]

hexane hydrochloride (109.95 mg, 0.4300 mmol) was added and the reaction was stirred at 20° C. for 16 hr to give a yellow solution. H$_2$O (30 mL) was added and it was extracted with EtOAc (30 mL×2). The combined organic layer dried over Na$_2$SO$_4$ and concentrated in vacuum to give a yellow oil. The crude was purified by Prep-HPLC (NH$_3$). The afforded flows were concentrated in vacuum to remove most of CH$_3$CN and lyophilized to give the title compound (104.7 mg, 0.2668 mmol, 61.424% yield) as white solid.

LC-MS Method1: 393.3 [M+H$^+$]

$^1$H NMR (400 MHz, CHLOROFORM-d) δ 7.64 (s, 1H), 7.21-7.26 (m, 3H), 7.17 (br s, 1H), 6.96 (br d, J=7.03 Hz, 2H), 4.69 (br d, J=12.05 Hz, 1H), 4.30-4.38 (m, 1H), 4.18 (br d, J=10.54 Hz, 1H), 3.86-3.95 (m, 1H), 3.60 (br dd, J=3.89, 12.42 Hz, 1H), 2.94-3.04 (m, 2H), 2.63 (s, 2H), 2.06 (br d, J=3.51 Hz, 1H), 1.97 (br d, J=3.51 Hz, 1H), 1.54 (d, J=6.78 Hz, 3H), 1.46 (br d, J=11.29 Hz, 1H), 1.37 (s, 6H)

Example 30 [(1R,5S,6S)-6-(5,5-dimethyl-4,5-dihydro-1,2-oxazol-3-yl)-3-azabicyclo[3.1.0]hex-3-yl]{1-[(2S)-4-phenylbutan-2-yl]-1H-imidazol-4-yl}methanone (R)-2-methyl-N-[(1E)-1-methyl-3-phenylpropanylidene]-2-propanesulfinamide To a mixture of 4-phenyl-2-butanone (1.01 mL, 6.75 mmol) in THF (10 mL) were added (R)-2-methylpropane-2-sulfinamide (817.81 mg, 6.75 mmol) and Ti(OEt)$_4$ (2307.69 mg, 10.12 mmol). The reaction mixture was stirred at 60° C. for 16 h to give yellow mixture. The reaction mixture was diluted with EtOAc (30 mL). The mixture was added to H$_2$O (10 mL) and stirred for 1 min to give yellow suspension. The suspension was filtered. The filtrate was washed with H$_2$O (20 mL×3), dried with anhydrous Na$_2$SO$_4$, filtered and concentrated in vacuum to give a residue. The residue was purified by flash column (PE to 30% EtOAc in PE) to give the title compound (570 mg, 2.2674 mmol, 33.603% yield) as yellow oil.

LC-MS Method1 0.823 min, MS (m/z) 252 (M+H$^+$).

(R)-2-methyl-N-[(2S)-4-phenylbutan-2-yl]-2-propanesulfinamide

To a mixture of (R)-2-methyl-N-[(1E)-1-methyl-3-phenylpropanylidene]-2-propanesulfinamide (570 mg, 2.27 mmol) in THF (6 mL) was added L-selectride (6.8 mL, 6.8 mmol) at 0° C. The mixture was stirred at 25° C. for 3 h to give colorless mixture. TLC (PE:EtOAc=2: 1) showed one new spot (Rf=0.3) was detected. The reaction was quenched by H$_2$O (3 mL). The reaction mixture was concentrated in vacuo to give a residue. The residue was purified by flash column (PE to 30% EtOAc in PE) to afford the title compound (260 mg, 1.026 mmol, 45.252% yield) as yellow oil.

$^1$H NMR (400 MHz, CHLOROFORM-d) δ ppm 7.40-7.25 (m, 2H), 7.25-7.10 (m, 3H), 3.41 (qn, J=6.8 Hz, 1H), 2.93 (d, J=7.2 Hz, 1H), 2.80-2.55 (m, 2H), 1.95-1.75 (m, 2H), 1.33 (d, J=6.8 Hz, 3H), 1.24 (s, 9H).

(2S)-4-phenyl-2-butanamine

A solution of (R)-2-methyl-N-[(2S)-4-phenylbutan-2-yl]-2-propanesulfinamide (260 mg, 1.03 mmol) in MeOH/HCl (5 mL, 1.03 mmol) was stirred at 25° C. for 1 h to give yellow mixture. The reaction mixture was concentrated in vacuo to afford the title compound (190 mg, 1.0232 mmol, 99.724% yield) (crude) as yellow solid.

ethyl 1-[(2S)-4-phenylbutan-2-yl]-1H-imidazole-4-carboxylate

To a mixture of (2S)-4-phenyl-2-butanamine (190 mg, 1.02 mmol) in 1-Butanol (2 mL) were added ethyl (2Z)-3-(dimethylamino)-2-isocyanoacrylate (172.09 mg, 1.02 mmol) and Et$_3$N (0.2 mL, 1.53 mmol). The reaction mixture was heated in microwave system at 130° C. for 1 h to give brown mixture. TLC (PE:EtOAc=1:1) showed one new spot (Rf=0.2) was detected. The reaction mixture was concentrated in vacuo to give a residue. The residue was purified by prep-TLC (PE:EtOAc=1:1) to afford the title compound (40 mg, 0.1469 mmol, 14.354% yield) as brown oil.

LC-MS Method1 0.718 min, MS (m/z) 273 (M+H$^+$).

1-[(2S)-4-phenylbutan-2-yl]-1H-imidazole-4-carboxylic acid

To a mixture of ethyl 1-[(2S)-4-phenylbutan-2-yl]-1H-imidazole-4-carboxylate (40 mg, 0.1500 mmol) in THF (1.5 mL) and H$_2$O (0.50 mL) was added LiOH·H$_2$O (0.01 mL, 0.2200 mmol). The reaction mixture was stirred at 40° C. for 16 h to give yellow mixture. TLC (PE:EtOAc=1:1) showed the starting material was consumed completely. The reaction mixture was diluted with H$_2$O (5 mL) and extracted with EtOAc (3 mL×2). The aqueous phase was acidified with 1 N HCl aq. to pH=5 and lyophilized to afford the title compound (30 mg, 0.1228 mmol, 83.612% yield) as yellow solid.

LC-MS Method1 0.677 min, MS (m/z) 245 (M+H$^+$).

[(1R,5S,6S)-6-(5,5-dimethyl-4,5-dihydro-1,2-oxazol-3-yl)-3-azabicyclo[3.1.0]hex-3-yl]{1-[(2S)-4-phenylbutan-2-yl]-1H-imidazol-4-yl}methanone To a mixture of 1-[(2S)-4-phenylbutane-2-yl]1H-imidazole-4-carboxylic acid (30 mg, 0.1200 mmol) in Pyridine (1.5 mL) was added EDCI (28.25 mg, 0.1500 mmol). The mixture was stirred at 25° C. for 10 min and followed by addition of (1R,5S,6r)-6-(5,5-dimethyl-4,5-dihydro-1,2-oxazol-3-yl)-3-azabicyclo[3.1.0]hexane hydrochloride (26.61 mg, 0.1200 mmol). The mixture was stirred at 25° C. for 16 h to give a yellow mixture. LCMS showed the starting material was consumed completely. The reaction mixture was concentrated in vacuo to give a residue. The residue was purified by prep-HPLC (NH$_3$). The afforded flows were combined, concentrated to remove most of CH$_3$CN and lyophilized to afford the title compound (16.26 mg, 0.0449 mmol, 17.643% yield) as yellow solid.

LC-MS Method1: 407.2 [M+H$^+$]

$^1$H NMR (400 MHz, CHLOROFORM-d) δ ppm 7.68 (s, 1H), 7.43 (s, 1H), 7.28-7.32 (m, 2H), 7.19-7.24 (m, 1H), 7.12 (s, 1H), 7.10 (s, 1H), 4.78 (dd, J=11.8, 3.8 Hz, 1H), 4.21 (br d, J=12.5 Hz, 1H), 4.04-4.15 (m, 1H), 3.97 (br d, J=11.5 Hz, 1H), 3.63 (dd, J=12.4, 3.9 Hz, 1H), 2.65 (s, 2H), 2.39-2.60 (m, 2H), 2.05-2.19 (m, 3H), 1.99 (br d, J=3.5 Hz, 1H), 1.50 (d, J=6.8 Hz, 3H), 1.46-1.49 (m, 1H), 1.38 (s, 6H)

Example 31 [(1R,5S,6S)-6-(5,5-dimethyl-4,5-dihydro-1,2-oxazol-3-yl)-3-azabicyclo[3.1.0]hex-3-yl]{1-[(2S)-1-phenoxypropan-2-yl]-1H-imidazol-4-yl}methanone tert-butyl [(2S)-1-phenoxypropan-2-yl]carbamate To a solution of phenol (0.51 mL, 5.84 mmol), tert-butyl [(2S)-1-hydroxypropan-2-yl]carbamate (1024.08 mg, 5.84 mmol), PPh₃ (2299.32 mg, 8.77 mmol) in Toluene (12 mL) was slowly added DIAD (1.73 mL, 8.77 mmol). The reaction mixture was stirred at 20° C. for 16 hr to give a yellow solution. TLC (PE/EA=10/1, Rf=0.8) showed a new spot. H₂O (30 mL) was added and it was extracted with EtOAc (30 mL×2). The combined organic layer dried over Na₂SO₄ and concentrated in vacuum to give a yellow oil. The crude was purified by silica gel chromatography (PE/EA=10/1 to 3/1) to give the title compound (600 mg, 2.3874 mmol, 40.85% yield) as white solid.

(2S)-1-phenoxy-2-propanamine hydrochloride

To a solution of tert-butyl [(2S)-1-phenoxypropan-2-yl] carbamate (1100 mg, 4.38 mmol) in MeOH (1 mL) was added HCl/dioxane (5 mL, 20 mmol) and the reaction mixture was stirred at 20° C. for 3 hr to give a colorless solution. LCMS showed a new peak gives the desired ms. The reaction mixture was evaporated in vacuum to give the title compound (800 mg, 4.2628 mmol, 97.393% yield) as yellow solid. It was used directly in the next step.
LC-MS Method1 0.498 min, MS (m/z) 151.8 (M+H⁺).

ethyl 1-[(2S)-1-phenoxypropan-2-yl]-1H-imidazole-4-carboxylate

To a 5 mL MW vial were added (2S)-1-phenoxy-2-propanamine hydrochloride (1100 mg, 5.86 mmol), ethyl (2Z)-3-(dimethylamino)-2-isocyanoacrylate (985.82 mg, 5.86 mmol), 1-Butanol (3 mL) and Et₃N (1.22 mL, 8.79 mmol). The reaction was irradiated with microwave at 130° C. for 1 hr to give a brown solution. LCMS showed a new peak gives the desired ms. The reaction was diluted with sat. Na₂CO₃ aq. (20 mL). H₂O (30 mL) was added and it was extracted with EtOAc (30 mL×2). The combined organic layer dried over Na2SO4 and concentrated in vacuum to give a yellow oil. The crude was purified by silica gel chromatography (PE/EA=10/1 to 1/1) to give the title compound (310 mg, 1.1301 mmol, 19.28% yield) as white solid.
LC-MS Method1 0.765 min, MS (m/z) 275.2 (M+H⁺).

1-[(2S)-1-phenoxypropan-2-yl]-1H-imidazole-4-carboxylic acid

A stirred solution of ethyl 1-[(2S)-1-phenoxypropan-2-yl]-1H-imidazole-4-carboxylate (310 mg, 1.13 mmol) in 1,4-Dioxane (3 mL) was added a solution of LiOH·H₂O (61.64 mg, 1.47 mmol) in H₂O (ml, 1.13 mmol). The reaction mixture was stirred at 20° C. for 16 hr to give a yellow solution. LCMS showed a new peak give the desired ms. H₂O (30 mL) was added and it was extracted with EtOAc (30 mL). Then aqueous layer was acidified by 1M HCl aq. and lyophilized to give the title compound (240 mg, 0.9746 mmol, 86.241% yield) as a yellow solid.
LC-MS Method1 0.645 min, MS (m/z) 247.2 (M+H⁺).

[(1R,5S,6S)-6-(5,5-dimethyl-4,5-dihydro-1,2-oxazol-3-yl)-3-azabicyclo[3.1.0]hex-3-yl]{1-[(2S)-1-phenoxypropan-2-yl]-1H-imidazol-4-yl}methanone A stirred solution of 1-[(2S)-1-phenoxypropan-2-yl]-1H-imidazole-4-carboxylic acid (130 mg, 0.5300 mmol) and N-ethyl-N-isopropylpropan-2-amine (0.45 mL, 2.64 mmol) in DMF (2 mL) was added HATU (300.9 mg, 0.7900 mmol). After stirred for 30 mins, (1R,5S,6r)-6-(5,5-dimethyl-4,5-dihydro-1,2-oxazol-3-yl)-3-azabicyclo[3.1.0]hexane hydrochloride (114.4 mg, 0.5300 mmol) was added to give a brown solution. H₂O (30 mL) was added and it was extracted with EtOAc (30 mL×2). The combined organic layer dried over Na₂SO₄ and concentrated in vacuum to give a yellow oil. The crude was purified by prep-HPLC (NH₃). The afforded flows were concentrated in vacuum to remove most of CH₃CN and lyophilized to give the title compound (51.22 mg, 0.1254 mmol, 23.752% yield) as white solid.
LC-MS Method1: 409.3 [M+H⁺]
¹H NMR (400 MHz, CHLOROFORM-d) δ ppm 1.33 (s, 6H) 1.47 (br s, 1H) 1.64 (d, J=7.03 Hz, 3H) 2.00-2.15 (m, 2H) 2.72 (s, 2H) 3.53-3.67 (m, 1H) 3.92 (br d, J=8.53 Hz, 1H) 4.10 (br d, J=12.30 Hz, 1H) 4.15-4.28 (m, 2H) 4.37 (br d, J=10.79 Hz, 1H) 4.75 (br dd, J=11.04, 6.78 Hz, 1H) 6.88 (br d, J=8.03 Hz, 2H) 6.92 (br t, J=7.53 Hz, 1H) 7.24 (br t, J=7.65 Hz, 2H) 7.82 (br d, J=6.78 Hz, 2H)

Example 32 [(1R,5S,6r)-6-(5,5-dimethyl-4,5-dihydro-1,2-oxazol-3-yl)-3-azabicyclo[3.1.0]hex-3-yl][1-(pentan-3-yl)-1H-imidazol-4-yl]methanone ethyl 1-(pentan-3-yl)-1H-imidazole-4-carboxylate The mixture of pentan-3-amine (1.73 mL, 14.86 mmol) and ethyl (2Z)-3-(dimethylamino)-2-isocyanoacrylate (500 mg, 2.97 mmol) was stirred at 80° C. for 16 hours. The crude product was purified by flash column (PE:EA=2:1) to give the title compound (500 mg, 2.3779 mmol, 79.988% yield) as a brown oil.

1-(pentan-3-yl)-1H-imidazole-4-carboxylic acid

To a solution of ethyl 1-(pentan-3-yl)-1H-imidazole-4-carboxylate in THF (15 mL) and H₂O (5 mL) was added LiOH·H₂O (0.41 mL, 7.13 mmol). The reaction mixture was stirred at 40° C. for 16 hours to give a yellow mixture. The reaction mixture was concentrated in vacuum to remove most of THF. The residue was diluted with H₂O (5 mL) and acidified with 0.5 M HCl aq. to pH=6. Then the solution was lyophilized to give the title compound as a yellow solid.

[(1R,5S,6r)-6-(5,5-dimethyl-4,5-dihydro-1,2-oxazol-3-yl)-3-azabicyclo[3.1.0]hex-3-yl][1-(pentan-3-yl)-1H-imidazol-4-yl]methanone To a solution of 1-(pentan-3-yl)-1H-imidazole-4-carboxylic acid (50 mg, 0.2700 mmol) in DMF (5 mL) were added HATU (157.35 mg, 0.4100 mmol) and Et₃N (0.14 mL, 1.1 mmol) and the reaction mixture was stirred for 15 min at 25° C. Then (1R,5S,6r)-6-(5,5-dimethyl-4,5-dihydro-1,2-oxazol-3-yl)-3-azabicyclo[3.1.0]hexane hydrochloride (49.46 mg, 0.2700 mmol) was added. The resulting mixture was stirred for 2 hours at 25° C. to give a brown solution, and then concentrated in vacuum to remove most of DMF to give a crude product. The crude product was purified by Prep-HPLC (NH₃) to give the title compound as a white solid.
LC-MS Method1: 345.3 [M+H⁺]
¹H NMR (400 MHz, CHLOROFORM-d) δ=7.61 (d, J=1.3 Hz, 1H), 7.40 (d, J=1.3 Hz, 1H), 4.80 (d, J=12.0 Hz, 1H), 4.20 (d, J=12.5 Hz, 1H), 3.95 (dd, J=4.0, 11.8 Hz, 1H), 3.74 (tt, J=4.8, 9.5 Hz, 1H), 3.62 (dd, J=4.3, 12.3 Hz, 1H), 2.65 (s, 2H), 2.13-2.05 (m, 1H), 2.02-1.95 (m, 1H), 1.91-1.79 (m, 2H), 1.78-1.69 (m, 2H), 1.48 (t, J=3.4 Hz, 1H), 1.38 (s, 6H), 0.82 (t, J=7.3 Hz, 6H)

Example 33 [(1R,5S,6r)-6-(5,5-dimethyl-4,5-dihydro-1,2-oxazol-3-yl)-3-azabicyclo[3.1.0]hex-3-yl][1-(1-methylcyclopropyl)-1H-imidazol-4-yl]methanone

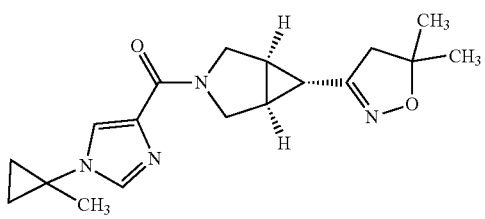 [SMILES: CC1(C)CC([C@H]2[C@@H]3CN(C(=O)c4cn(C5(C)CC5)cn4)C[C@@H]32)=NO1]

ethyl 1-(1-methylcyclopropyl)-1H-imidazole-4-carboxylate

To a solution of ethyl (2Z)-3-(dimethylamino)-2-isocyanoacrylate (469.02 mg, 2.79 mmol) in 1-Butanol (5.5 mL) were added 1-methylcyclopropanamine (300 mg, 2.79 mmol) and Et₃N (0.54 mL, 4.18 mmol). The resulting mixture was subjected to reaction in microwave reactor (time: 1 h, temp: 130° C.). TLC (PE:EtOAc=0:1) showed the reaction was completed (Rf=0.5). The reaction mixture was concentrated directly. The crude product was purified by flash column (PE to 40% EtOAc in PE) to afford the title compound (118 mg, 0.6075 mmol, 21.786% yield) as a brown oil.

LC-MS Method1: 0.568 min, MS (m/z) 194.9 [M+H]⁺

¹H NMR (400 MHz, CHLOROFORM-d) δ=7.71-7.69 (m, 1H), 7.60 (s, 1H), 4.36 (q, J=7.0 Hz, 2H), 1.58 (s, 3H), 1.38 (t, J=7.2 Hz, 3H), 1.17-1.12 (m, 2H), 0.96-0.91 (m, 2H)

1-(1-methylcyclopropyl)-1H-imidazole-4-carboxylic acid

To a solution of ethyl 1-(1-methylcyclopropyl)-1H-imidazole-4-carboxylate (118 mg, 0.61 mmol) in THF (1.5 mL) and H₂O (0.50 mL) was added LiOH·H₂O (0.05 mL, 0.79 mmol). The resulting mixture was stirred at 20-25° C. for 2 h. The reaction mixture was concentrated directly. The residue was acidified with 1 M HCl aq. to pH=6 and then lyophilized to afford the title compound (100 mg, 0.6018 mmol, 99.05% yield) as a yellow solid.

¹H NMR (400 MHz, DMSO-d₆) δ=7.81 (d, J=1.0 Hz, 1H), 7.65 (s, 1H), 1.55-1.47 (m, 3H), 1.13-1.07 (m, 2H), 0.91-0.85 (m, 2H)

[(1R,5S,6r)-6-(5,5-dimethyl-4,5-dihydro-1,2-oxazol-3-yl)-3-azabicyclo[3.1.0]hex-3-yl][1-(1-methylcyclopropyl)-1H-imidazol-4-yl]methanone To a solution of 1-(1-methylcyclopropyl)-1H-imidazole-4-carboxylic acid (100 mg, 0.60 mmol) in DMF (2 mL) were added HATU (276.06 mg, 0.72 mmol) and Et₃N (0.39 mL, 3.01 mmol). The mixture was stirred at 20-25° C. for 0.5 h. The mixture was added (1R,5S,6R)-6-(5,5-dimethyl-4,5-dihydro-1,2-oxazol-3-yl)-3-azabicyclo[3.1.0]hexane hydrochloride (108.47 mg, 0.60 mmol). The reaction mixture was stirred at 20-25° C. for 1 h. LCMS showed the desired MS (as a major peak). The residue was purified by prep-HPLC (NH₃). The afforded flows were combined, concentrated to remove most of CH₃CN and lyophilized to afford the title compound (60.45 mg, 0.1841 mmol, 30.589% yield) as a yellow solid.

¹H NMR (400 MHz, CHLOROFORM-d) δ=7.68 (d, J=1.5 Hz, 1H), 7.52 (d, J=1.3 Hz, 1H), 4.70 (d, J=11.8 Hz, 1H), 4.18 (d, J=12.5 Hz, 1H), 3.92 (dd, J=4.0, 12.0 Hz, 1H), 3.60 (dd, J=4.1, 12.4 Hz, 1H), 2.63 (s, 2H), 2.07 (br dd, J=3.5, 7.0 Hz, 1H), 2.01-1.92 (m, 1H), 1.57 (s, 3H), 1.45 (t, J=3.4 Hz, 1H), 1.37 (s, 6H), 1.16-1.10 (m, 2H), 0.95-0.89 (m, 2H)

LC-MS Method1 0.606 min, MS (m/z) 329.0 [M+H⁺]

Example 34 [(1R,5S,6r)-6-(5,5-dimethyl-4,5-dihydro-1,2-oxazol-3-yl)-3-azabicyclo[3.1.0]hex-3-yl][1-(1-methylcyclobutyl)-1H-imidazol-4-yl]methanone ethyl 1-(1-methylcyclobutyl)-1H-imidazole-4-carboxylate To a mixture of ethyl (2Z)-3-(dimethylamino)-2-isocyanoacrylate (200 mg, 1.19 mmol) in 1-Butanol (0.50 mL) were added 1-methylcyclobutanamine (583.25 mg, 4.76 mmol) and Et₃N (1.15 mL, 8.92 mmol). The resulting mixture was heated at 76° C. for 16 hr. The reaction mixture was diluted with H₂O (5 mL) and extracted with EtOAc (5 mL×3). The combined organic layers were separated, washed with brine (10 mL), dried over Na₂SO₄ and concentrated in vacuum to give crude oil. The crude oil was purified by prep-TLC (100% EA) to give the title compound (50 mg, 0.2401 mmol, 20.19% yield) as yellow oil.

LC-MS Method1 0.665 min, MS (m/z) 209.2 (M+H⁺).

1-(1-methylcyclobutyl)-1H-imidazole-4-carboxylic acid

To a mixture of ethyl 1-(1-methylcyclobutyl)-1H-imidazole-4-carboxylate (50 mg, 0.2400 mmol) in H₂O (0.4952 mL) and MeOH (0.3961 mL) was added LiOH·H₂O (0.04 mL, 0.7200 mmol). The resulting mixture was stirred at 25° C. for 5 hr. The aqueous phase was washed with DCM (3 mL×2) and acidified with 1N HCl to pH=2. The aqueous solution was lyophilized to give the title compound (50 mg, 0.2775 mmol, 115.57% yield) as pale yellow solid.

[(1R,5S,6r)-6-(5,5-dimethyl-4,5-dihydro-1,2-oxazol-3-yl)-3-azabicyclo[3.1.0]hex-3-yl][1-(1-methylcyclobutyl)-1H-imidazol-4-yl]methanone To a mixture of 1-(1-methylcyclobutyl)-1H-imidazole-4-carboxylic acid (48.08 mg, 0.2200 mmol) in DMF (0.40 mL) were added HATU (137.86 mg, 0.3600 mmol), DIPEA (0.18 mL, 1.11 mmol) and (1R,5S,6r)-6-(5,5-dimethyl-4,5-dihydro-1,2-oxazol-3-yl)-3-azabicyclo[3.1.0]hexane hydrochloride (40 mg, 0.2200 mmol). The resulting mixture was stirred at 20° C. for 4 hr. The reaction mixture was diluted with H₂O (5 mL) and extracted with EtOAc (5 mL×2), then washed with brine (8 mL). The combined organic layers were separated, then dried over Na₂SO₄ and concentrated in vacuum to give crude oil. The crude oil was purified by prep-HPLC (NH₃) and then lyophilized to give the title compound (3 mg, 0.0088 mmol, 3.9478% yield) as pale yellow solid.

¹H NMR (400 MHz, CD₃OD) δ=7.74 (s, 1H), 7.67 (s, 1H), 4.41 (br d, J=12.0 Hz, 1H), 4.09 (br d, J=12.3 Hz, 1H), 3.93 (br dd, J=3.8, 11.8 Hz, 1H), 3.59 (br dd, J=3.9, 12.4 Hz, 1H), 2.71 (s, 2H), 2.63-2.52 (m, 2H), 2.30 (tt, J=3.0, 8.9 Hz,

2H), 2.14-2.08 (m, 1H), 2.07-1.92 (m, 3H), 1.68 (s, 3H), 1.48 (t, J=3.4 Hz, 1H), 1.32 (s, 6H).

Example 35 [(1R,5S,6r)-6-(5,5-dimethyl-4,5-dihydro-1,2-oxazol-3-yl)-3-azabicyclo[3.1.0]hex-3-yl](1-propyl-1H-imidazol-4-yl)methanone ethyl 1-propyl-1H-imidazole-4-carboxylate To a solution of ethyl (2Z)-3-(dimethylamino)-2-isocyanoacrylate (500 mg, 2.97 mmol) in 1-Butanol (0.5 M, 64.98 mmol) were added propan-1-amine (2.97 mL, 1.78 mmol, 1.0 eq.) and Et₃N (0.25 mL, 1.78 mmol, 0.6 eq.). The mixture was stirred at 130° C. for 6 hr, and then concentrated to give a residue. The residue was purified by silica gel chromatography (n-hexane/EtOAc=60/40 to 0/100 and then MeOH/EtOAc=5/95) to give the title compound (214 mg, 1.17 mmol, 39.5% yield) as a brown oil.

LC-MS Method1 0.662 min, MS (m/z) 183.0 (M+H⁺).

¹H NMR (400 MHz, CHLOROFORM-d) δ 7.60 (d, J=1.2 Hz, 1H), 7.47 (d, J=1.2 Hz, 1H), 4.36 (q, J=7.2 Hz, 2H), 3.93 (t, J=6.9 Hz, 2H), 1.90-1.80 (m, 2H), 1.39 (t, J=6.9 Hz, 3H), 0.94 (t, J=9.6 Hz, 3H).

1-propyl-1H-imidazole-4-carboxylic acid

To a stirred solution of ethyl 1-propyl-1H-imidazole-4-carboxylate (214 mg, 1.17 mmol) in THF (1.7 mL, 660 mM) was added a solution of LiOH (70.3 mg, 2.94 mmol, 2.5 eq.) in H₂O (0.6 mL). The reaction mixture was stirred at 40° C. for 12 hr. The reaction mixture was diluted with H₂O and extracted with DCM. The aqueous phase was acidified with 1 N HCl (aq) to pH=5. The resulting aqueous phase was dried in vacuum to afford the title compound (133 mg, 0.86 mmol, 73.4% yield) (crude) as beige solid.

¹H NMR (400 MHz, DMSO-d₆) δ ppm 7.81 (d, J=1.5 Hz, 1H), 7.72 (d, J=1.5 Hz, 1H), 3.94 (t, J=6.9 Hz, 2H), 1.80-1.60 (m, 2H), 0.78 (t, J=7.5 Hz, 3H).

[(1R,5S,6r)-6-(5,5-dimethyl-4,5-dihydro-1,2-oxazol-3-yl)-3-azabicyclo[3.1.0]hex-3-yl](1-propyl-1H-imidazol-4-yl)methanone To a stirred solution of 1-propyl-1H-imidazole-4-carboxylic acid (45.0 mg, 0.14 mmol) and HATU (53.2 mg, 0.14 mmol, 1.0 eq.) in THF (0.7 mL, 200 mM) was added DIPEA (0.12 mL, 0.7 mmol, 5.0 eq.). After stirred at 50° C. for 30 min, (1R,5S,6r)-6-(5,5-dimethyl-4,5-dihydro-1,2-oxazol-3-yl)-3-azabicyclo[3.1.0]hexane hydrochloride (33.4 mg, 0.154 mmol, 1.1 eq.) was added and the reaction was stirred at 20° C. for 16 hr to give a yellow solution. H₂O was added and it was extracted with DCM. The combined organic layer dried over Na₂SO₄ and concentrated in vacuum to give a yellow oil. The crude was purified by silica gel chromatography (EtOAc/DCM=99/1 to 70/30) to give the title compound (23 mg, 0.072 mmol, 51.9% yield) as a beige powder.

LC-MS Method1 0.757 min, MS (m/z) 317.0 (M+H⁺).

¹H NMR (400 MHz, CHLOROFORM-d) δ 7.59 (d, J=1.5 Hz, 1H), 7.39 (d, J=1.5 Hz, 1H), 4.73 (d, J=11.2 Hz, 1H), 4.18 (d, J=11.2 Hz, 1H), 4.00-3.85 (m, 1H), 3.91 (t, J=7.2 Hz, 2H), 3.65-3.55 (m, 1H), 2.64 (s, 2H), 2.10-2.05 (m, 1H), 2.05-1.90 (m, 1H), 1.90-1.70 (m, 2H), 1.50-1.45 (m, 1H), 1.37 (s, 6H), 0.91 (t, 3H, J=7.2 Hz, 3H).

Example 36 [(1R,5S,6r)-6-(5,5-dimethyl-4,5-dihydro-1,2-oxazol-3-yl)-3-azabicyclo[3.1.0]hex-3-yl](1-isobutyl-1H-imidazol-4-yl)methanone ethyl 1-isobutyl-1H-imidazole-4-carboxylate To a solution of ethyl (2Z)-3-(dimethylamino)-2-isocyanoacrylate (1.50 g, 8.92 mmol) in 1-Butanol (17.8 mL, 0.5 M) were added 2-methylpropan-1-amine (1.0 mL, 9.8 mmol, 1.1 eq.) and Et₃N (0.74 mL, 5.35 mmol, 0.6 eq.). The mixture was stirred at 130° C. for 6 hr and then concentrated to give a residue. The residue was purified by silica gel chromatography (n-hexane/EtOAc=60/40 to 0/100 and then MeOH/EtOAc=5/95) to give the title compound (455 mg, 2.3 mmol, 26.0% yield) as a brown oil.

LC-MS Method1 0.743 min, MS (m/z) 197.0 (M+H⁺).

¹H NMR (300 MHz, CHLOROFORM-d) δ ppm 7.58 (d, J=1.2 Hz, 1H), 7.44 (d, J=1.2 Hz, 1H), 4.36 (q, J=7.2 Hz, 2H), 3.75 (d, J=7.8 Hz, 2H), 2.15-1.95 (m, 1H), 1.39 (t, J=7.2 Hz, 3H), 0.93 (d, J=6.6 Hz, 6H).

1-isobutyl-1H-imidazole-4-carboxylicacid

A stirred solution of ethyl 1-isobutyl-1H-imidazole-4-carboxylate (450 mg, 2.3 mmol) in THF (3.5 mL, 660 mM) was added a solution of LiOH (137 mg, 5.7 mmol, 2.5 eq.) in H₂O (1.2 mL). The reaction mixture was stirred at 40° C. for 12 hr, and then diluted with H₂O and extracted with DCM. The aqueous phase was acidified with 1 N HCl (aq) to pH=5. The resulting aqueous phase was dried in vacuum to afford the title compound (440 mg, 2.15 mmol, 93.8% yield) (crude) as yellow solid.

¹H NMR (400 MHz, DMSO-d₆) δ ppm 9.50 brs, 1H), 8.10 (d, J=1.2 Hz, 1H), 3.91 (d, J=6.9 Hz, 2H), 2.15-1.95 (m, 1H), 0.82 (d, J=6.6 Hz, 6H).

[(1R,5S,6r)-6-(5,5-dimethyl-4,5-dihydro-1,2-oxazol-3-yl)-3-azabicyclo[3.1.0]hex-3-yl](1-isobutyl-1H-imidazol-4-yl)methanone To a stirred solution of 1-isobutyl-1H-imidazole-4-carboxylicacid (65.0 mg, 0.15 mmol) and HATU (56.8 mg, 0.15 mmol, 1.0 eq.) in THF (0.7 mL, 200 mM) was added DIPEA (0.13 mL, 0.75 mmol, 5.0 eq.). After stirred at 50° C. for 30 min, (1R,5S,6r)-6-(5,5-dimethyl-4,5-dihydro-1,2-oxazol-3-yl)-3-azabicyclo[3.1.0]hexane hydrochloride (35.6 mg, 0.164 mmol, 1.1 eq.) was added and the reaction was stirred at 50° C. for 1 hr to give a yellow solution. H₂O was added and it was extracted with DCM. The combined organic layer dried over Na₂SO₄ and concentrated in vacuum to give a yellow oil. The crude was purified by silica gel chromatography (EtOAc/DCM=99/1 to 80/20) to give the title compound (36.2 mg, 0.11 mmol, 73.4% yield) as a white powder.

LC-MS Method1 0.800 min, MS (m/z) 331.1 (M+H⁺).

¹H NMR (300 MHz, CHLOROFORM-d) δ 7.57 (d, J=1.8 Hz, 1H), 7.36 (d, J=1.8 Hz, 1H), 4.74 (d, J=12.3 Hz, 1H), 4.18 (d, J=12.3 Hz, 1H), 3.93 (dd, J=12.3, 4.2 Hz, 1H), 3.73 (d, J=7.2 Hz, 2H), 3.61 (dd, J=12.3, 4.2 Hz, 1H), 2.64 (s, 2H), 2.15-1.95 (m, 3H), 1.50-1.40 (m, 1H), 1.37 (s, 6H), 0.92 (d, J=6.6 Hz, 6H).

Example 37 (1-isopropyl-1H-imidazol-4-yl)[(1R,5S,6r)-6-(5-methyl-4,5-dihydro-1,2-oxazol-3-yl)-3-azabicyclo[3.1.0]hex-3-yl]methanone tert-butyl (1R,5S,6r)-6-(5-methyl-4,5-dihydro-1,2-oxazol-3-yl)-3-azabicyclo[3.1.0]hexane-3-carboxylate The mixture of tert-butyl (1R,5S,6r)-6-[(Z)-chloro(hydroxyimino)methyl]-3-azabicyclo[3.1.0]hexane-3-carboxylate (200 mg, 0.77 mmol) in DMF (2 mL) were added prop-1-ene (4.6 mL, 2.3 mmol) and Et$_3$N (0.38 mL, 2.3 mmol). The resulting mixture was stirred at 20° C. for 16 hr to give pale yellow mixture. The reaction mixture was diluted with H$_2$O (10 mL), then extracted with EtOAc (10 mL×2). The combined organic layers were separated, then dried over Na$_2$SO$_4$ and concentrated in vacuum to give the title compound (130 mg, crude) as pale yellow oil.
LC-MS Method1 0.825 min, MS (m/z) 267.0 (M+H$^+$).

(1R,5S,6r)-6-(5-methyl-4,5-dihydro-1,2-oxazol-3-yl)-3-azabicyclo[3.1.0]hexane hydrochloride To tert-butyl (1R,5S,6r)-6-(5-methyl-4,5-dihydro-1,2-oxazol-3-yl)-3-azabicyclo[3.1.0]hexane-3-carboxylate (130 mg, 0.49 mmol) was added HCl/dioxane (3. mL, 0.49 mmol). The reaction mixture was stirred at 0° C. for 30 min to give pale yellow mixture. The reaction mixture was concentrated to dryness directly to give the title compound (90 mg, crude).

(1-isopropyl-1H-imidazol-4-yl)[(1R,5S,6r)-6-(5-methyl-4,5-dihydro-1,2-oxazol-3-yl)-3-azabicyclo[3.1.0]hex-3-yl]methanone To a mixture of (1R,5S,6r)-6-(5-methyl-4,5-dihydro-1,2-oxazol-3-yl)-3-azabicyclo[3.1.0]hexane hydrochloride (50 mg, 0.30 mmol) in DMF (0.50 mL) were added DIPEA (0.2 mL, 1.2 mmol), 1-isopropylimidazole-4-carboxylic acid (46.38 mg, 0.30 mmol) and HATU (148.6 mg, 0.39 mmol). The resulting mixture was stirred at 20° C. for 16 hr to give brown mixture. TLC (PE/EtOAc=0/1) showed a series of new spots and 1-isopropylimidazole-4-carboxylic acid (46.38 mg, 0.30 mmol) was consumed completely. LCMS detected desired MS. The reaction mixture was diluted with H$_2$O (5 mL) and extracted with EtOAc (5 mL×2), then washed with H$_2$O (5 mL) and brine (5 mL×2). The combined organic layers were separated, then dried over Na$_2$SO$_4$ and concentrated in vacuum to give crude product. The crude product was purified by prep-HPLC (NH$_3$) to give the title compound (5 mg, 0.0165 mmol, 5.4972% yield) as white solid.
$^1$H NMR (400 MHz, MeOH) δ=7.69 (br d, J=14.6 Hz, 2H), 4.76-4.73 (m, 1H), 4.74-4.73 (m, 1H), 4.42 (td, J=6.6, 13.4 Hz, 1H), 4.26 (br d, J=11.4 Hz, 1H), 4.08-3.98 (m, 1H), 3.86 (br dd, J=3.6, 11.6 Hz, 1H), 3.54 (br d, J=9.9 Hz, 1H), 3.02-2.89 (m, 1H), 2.44 (dd, J=8.1, 16.9 Hz, 1H), 2.13-1.95 (m, 2H), 1.42 (d, J=6.6 Hz, 6H), 1.18 (d, J=6.3 Hz, 3H)

Example 38 (1-isopropyl-1H-imidazol-4-yl)[(1R,5S, 6r)-6-(4-oxa-5-azaspiro[2.4]hept-5-en-6-yl)-3-azabicyclo[3.1.0]hex-3-yl]methanone tert-butyl (1R,5S,6r)-6-(4-oxa-5-azaspiro[2.4]hept-5-en-6-yl)-3-azabicyclo[3.1.0]hexane-3-carboxylate To a solution of tert-butyl (1R,5S,6r)-6-[(Z)-chloro(hydroxyimino)methyl]-3-azabicyclo[3.1.0]hexane-3-carboxylate (0.24 mL, 24.32 mmol) were added methylenecyclopropane (300 mg, 1.22 mmol) in THF (15 mL) and Et$_3$N (0.51 mL, 3.65 mmol). The reaction mixture was stirred at 0° C. for 16 hr to give a yellow solution. LCMS showed a new peak gives the desired MS. The reaction mixture was diluted with H$_2$O (30 mL) and extracted with EtOAc (30 mL×2). The combined organic layer dried over Na$_2$SO$_4$ and concentrated to give the title compound (260 mg, 0.9341 mmol, 76.809% yield) as yellow oil.

LC-MS Method1 0.845 min, MS (m/z) 279 (M+H$^+$).

6-[(1R,5S,6r)-3-azabicyclo[3.1.0]hex-6-yl]-4-oxa-5-azaspiro[2.4]hept-5-ene TFA Salt To a solution of tert-butyl (1R,5S,6r)-6-(4-oxa-5-azaspiro[2.4]hept-5-en-6-yl)-3-azabicyclo[3.1.0]hexane-3-carboxylate (260 mg, 0.93 mmol) in DCM (16.25 mL) was added 2,2,2-trifluoroacetic acid (0.07 mL, 0.93 mmol). The reaction mixture was stirred at 10° C. for 3 hr to give a yellow solution. LCMS showed a new peak give the desired MS. The reaction mixture was evaporated in vacuum to give the title compound (272 mg, 0.9307 mmol, 99.64% yield) as yellow oil. The product was used directly in the next step.
LC-MS Method1 0.178 min, MS (m/z) 179.1 (M+H$^+$).

(1-isopropyl-1H-imidazol-4-yl)[(1R,5S,6r)-6-(4-oxa-5-azaspiro[2.4]hept-5-en-6-yl)-3-azabicyclo[3.1.0]hex-3-yl]methanone A 100 ml round-bottom flask was charged with 1-isopropylimidazole-4-carboxylic acid (143.49 mg, 0.93 mmol), HATU (426.97 mg, 1.12 mmol), DMF (4.5916 mL) and N-ethyl-N-isopropylpropan-2-amine (0.48 mL, 2.79 mmol). After stirred for 30 min, 6-[(1R,5S,6r)-3-azabicyclo[3.1.0]hex-6-yl]-4-oxa-5-azaspiro[2.4]hept-5-ene TFA salt (272 mg, 0.93 mmol) was added. The reaction mixture was stirred at 10° C. for 16 hr to give a yellow solution. LCMS showed the reactant was completely consumed and the desired MS. The reaction mixture was diluted with H$_2$O (20 mL) and extracted with EtOAc (30 mL×2). The combined organic layer dried over Na$_2$SO$_4$ and concentrated to give yellow oil. The crude was purified by prep-HPLC (FA). The afford flows were concentrated in vacuum to remove most of CH$_3$CN and lyophilized to give the title compound (14.67 mg, 0.0467 mmol, 5.0137% yield) as white solid.
LC-MS Method1: 315.1 [M+H$^+$]
$^1$H NMR (400 MHz, CHLOROFORM-d) δ=7.67 (s, 1H), 7.48 (s, 1H), 4.73 (br d, J=12.0 Hz, 1H), 4.41-4.27 (m, 1H), 4.20 (br d, J=12.4 Hz, 1H), 3.95 (br dd, J=4.0, 12.0 Hz, 1H), 3.62 (br dd, J=4.0, 12.0 Hz, 1H), 2.96 (s, 2H), 2.80 (s, 1H), 2.12 (br d, J=3.0 Hz, 1H), 2.03 (br d, J=3.5 Hz, 1H), 1.50 (d, J=6.4 Hz, 6H), 1.14-1.08 (m, 2H), 0.73-0.67 (m, 2H)

Example 39 (1-isopropyl-1H-imidazol-4-yl)[(1R,5S, 6r)-6-(5-oxa-6-azaspiro[3.4]oct-6-en-7-yl)-3-azabicyclo[3.1.0]hex-3-yl]methanone tert-butyl (1R,5S,6r)-6-(5-oxa-6-azaspiro[3.4]oct-6-en-7-yl)-3-azabicyclo[3.1.0]hexane-3-carboxylate To a mixture of tert-butyl (1R,5S,6r)-6-[(E)-(hydroxyimino)methyl]-3-azabicyclo[3.1.0]hexane-3-carboxylate in DMF (1.5 mL) was added methylenecyclobutane (78.4 mg, 1.15 mmol). The suspension was stirred at 20° C. for 16 hr. The reaction mixture was quenched with H$_2$O (10 mL). The residue was diluted with EtOAc (20 mL×3), washed with saturated NaCl (5 mL), dried with anhydrous Na$_2$SO$_4$, filtered and concentrated in vacuum to afford the title compound (46 mg, crude) as yellow powder.
LC-MS Method1: 0.818 min, MS (m/z): 237.0 (M−56+H$^+$).

7-[(1R,5S,6r)-3-azabicyclo[3.1.0]hex-6-yl]-5-oxa-6-azaspiro[3.4]oct-6-ene TFA Salt A mixture of tert-butyl (1R,5S,6r)-6-(5-oxa-6-azaspiro[3.4]oct-6-en-7-yl)-3-azabicyclo[3.1.0]hexane-3-carboxylate (46.0 mg, 0.16 mmol) in DCM (1.5 mL) was added 2,2,2-trifluoroacetic acid (17.9 mg, 0.16 mmol). The suspension was stirred at 20° C. for 2 hr. The reaction mixture was concentrated under reduced pressure to give the title compound.

LC-MS Method1: 0.822 min, MS (m/z): 193.0 (M+H$^+$).

(1-isopropyl-1H-imidazol-4-yl)[(1R,5S,6r)-6-(5-oxa-6-azaspiro[3.4]oct-6-en-7-yl)-3-azabicyclo[3.1.0]hex-3-yl]methanone

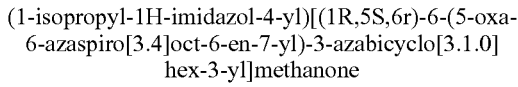

To a mixture of 7-[(1R,5S,6r)-3-azabicyclo[3.1.0]hex-6-yl]-5-oxa-6-azaspiro[3.4]oct-6-ene TFA salt (30.0 mg, 0.16 mmol) in Pyridine (0.5 mL) were added EDCI (29.9 mg, 0.16 mmol) and 1-isopropylimidazole-4-carboxylic acid (24.1 mg, 0.16 mmol). The suspension was stirred at 20° C. for 16 hr. The reaction mixture was quenched with H$_2$O (10 mL). The residue was diluted with EtOAc (20 mL×3), washed with saturated NaCl (5 mL), dried with anhydrous Na$_2$SO$_4$, filtered and concentrated in vacuum. The solution was purified by prep-HPLC (NH$_3$) and lyophilized to afford the title compound (6.49 mg, 12.7% yield) as yellow solid.

LC-MS Method1: 2.386 min, MS (m/z): 329.2 (M+H$^+$).

$^1$H NMR (400 MHz, CHLOROFORM-d) δ ppm 7.69 (d, J=1.51 Hz, 1H), 7.49 (d, J=1.51 Hz, 1H), 4.75 (d, J=12.05 Hz, 1H), 4.37 (dt, J=13.43, 6.84 Hz, 1H), 4.20 (d, J=12.80 Hz, 1H), 3.93-3.99 (m, 1H), 3.63 (dd, J=12.92, 3.89 Hz, 1H), 2.96 (s, 2H), 2.48 (dt, J=12.55, 9.66 Hz, 2H), 2.07-2.18 (m, 4H), 2.02 (br d, J=9.03 Hz, 1H), 1.76-1.85 (m, 1H), 1.52 (d, J=6.78 Hz, 7H), 1.49 (t, J=3.51 Hz, 1H).

Example 40 {(1R,5S,6r)-6-[5-(difluoromethyl)-5-methyl-4,5-dihydro-1,2-oxazol-3-yl]-3-azabicyclo[3.1.0]hex-3-yl}(1-isopropyl-1H-imidazol-4-yl)methanone tert-butyl (1R,5S,6r)-6-[5-(dihydroxymethyl)-5-methyl-4,5-dihydro-1,2-oxazol-3-yl]-3-azabicyclo[3.1.0]hexane-3-carboxylate

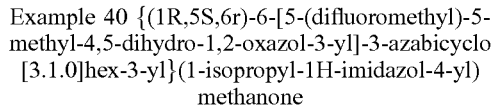

To a solution of tert-butyl (1R,5S,6r)-6-[(Z)-chloro(hydroxyimino)methyl]-3-azabicyclo[3.1.0]hexane-3-carboxylate (200 mg, 0.77 mmol) and methacrylaldehyde (0.32 mL, 3.84 mmol) in DMF (3 mL) was added Et$_3$N (0.22 mL, 1.53 mmol). The reaction was stirred at 20° C. for 12 h to give pale yellow solution. The reaction was diluted with EtOAc (15 mL), stirred with saturated NaHCO$_3$ (10 mL) for 5 min. The aqueous layer was extracted with EtOAc (10 mL×2). The combined DCM layer was dried over Na$_2$SO$_4$ and concentrated in vacuum to give the title compound (240 mg, 0.7683 mmol, crude) as pale brown oil.

tert-butyl (1R,5S,6r)-6-[5-(difluoromethyl)-5-methyl-4,5-dihydro-1,2-oxazol-3-yl]-3-azabicyclo[3.1.0]hexane-3-carboxylate

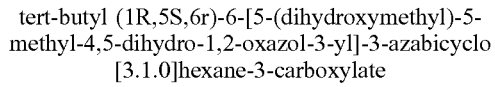

To a solution of tert-butyl (1R,5S,6r)-6-[5-(dihydroxymethyl)-5-methyl-4,5-dihydro-1,2-oxazol-3-yl]-3-azabicyclo[3.1.0]hexane-3-carboxylate (240 mg, 0.77 mmol) in DCM (10 mL) was added DAST (371.11 mg, 2.31 mmol) at −78° C. The reaction was allowed to warm to 20° C. and stirred for further 12 h to give pale brown solution. The reaction was re-cooled to −78° C., treated with additional DAST (300 mg) and then allowed to warm to 20° C. and stirred for further 12 h to give pale brown solution. The reaction was cooled to 0° C., diluted with DCM (20 mL), and quenched with saturated NaHCO$_3$ (8 mL). The organic layer was collected, dried over Na$_2$SO$_4$, and concentrated in vacuum to give crude oil, which was purified by prep-HPLC (HCl). The afforded eluent was treated with saturated NaHCO$_3$ (2 mL) and concentrated to remove MeCN. The residue was extracted with EtOAC (10 mL×2). The combined EtOAc layer was dried over Na$_2$SO$_4$ and concentrated in vacuum to give the title compound (55 mg, 0.1739 mmol, 22.628% yield) as pale brown gum.

$^1$H NMR (400 MHz, CHLOROFORM-d) δ=5.58 (t, J=56 Hz, 1H), 3.65 (d, J=11.2 Hz, 1H), 3.56 (d, J=11.2 Hz, 1H), 3.36-3.32 (m, 2H), 3.04 (dd, J=17.2, 6.0 Hz, 1H), 2.60 (d, J=17.2 Hz, 1H), 2.00-1.85 (m, 3H), 1.37 (s, 9H), 1.37 (s, 3H).

{(1R,5S,6r)-6-[5-(difluoromethyl)-5-methyl-4,5-dihydro-1,2-oxazol-3-yl]-3-azabicyclo[3.1.0]hex-3-yl}(1-isopropyl-1H-imidazol-4-yl)methanone

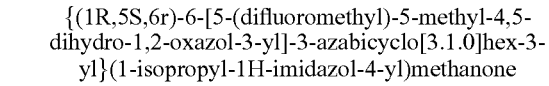

To a solution of tert-butyl (1R,5S,6r)-6-[5-(difluoromethyl)-5-methyl-4,5-dihydro-1,2-oxazol-3-yl]-3-azabicyclo[3.1.0]hexane-3-carboxylate (55 mg, 0.17 mmol) in DCM (2 mL) was added MeSO$_3$H (33.38 mg, 0.35 mmol). The reaction was stirred at 20° C. for 1 h to give pale yellow solution. DMF (1 mL) was added, followed by 1-isopropylimidazole-4-carboxylic acid (32.17 mg, 0.21 mmol), HATU (66.47 mg, 0.17 mmol) and Et$_3$N (0.12 mL, 0.87 mmol). The resultant mixture was stirred at 20° C. for 12 h to give yellow mixture. The reaction was concentrated and purified by prep-HPLC (NH$_3$). The afforded eluent was concentrated and lyophilized to give the title compound (7.01 mg, 0.0199 mmol, 11.442% yield) as a pale yellow solid.

LC-MS Method1: 353.0 [M+H$^+$]

$^1$H NMR (400 MHz, CHLOROFORM-d) δ=7.60 (d, J=1.4 Hz, 1H), 7.40 (d, J=1.4 Hz, 1H), 5.78-5.37 (m, 1H), 4.70 (d, J=12.1 Hz, 1H), 4.28 (quin, J=6.7 Hz, 1H), 4.13 (d, J=12.4 Hz, 1H), 3.87 (br d, J=10.0 Hz, 1H), 3.54 (dd, J=3.9, 12.4 Hz, 1H), 3.05 (d, J=17.4 Hz, 1H), 2.61 (br dd, J=7.8, 17.6 Hz, 1H), 2.04 (br s, 1H), 1.99-1.89 (m, 1H), 1.43 (d, J=6.6 Hz, 6H), 1.38 (m, 3H)

Example 41 [(1R,5S,6r)-6-(5-ethyl-5-methyl-4,5-dihydro-1,2-oxazol-3-yl)-3-azabicyclo[3.1.0]hex-3-yl](1-isopropyl-1H-imidazol-4-yl)methanone tert-butyl (1R,5S,6r)-6-(5-ethyl-5-methyl-4,5-dihydro-1,2-oxazol-3-yl)-3-azabicyclo[3.1.0]hexane-3-carboxylate

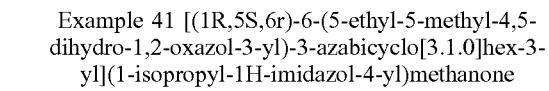

To a solution of tert-butyl (1R,5S,6r)-6-[(Z)-chloro(hydroxyimino)methyl]-3-azabicyclo[3.1.0]hexane-3-carboxylate in DMF (1.5 mL) were added 2-methylbut-1-ene (403.48 mg, 5.75 mmol), Et$_3$N (116.4 mg, 1.15 mmol, 0.16 mL). The suspension was stirred at 20° C. for 16 hr. The reaction mixture was quenched with H$_2$O (10 mL). The residue was extracted with EtOAc (20 mL×3). The combined organic layers were washed with saturated NaCl (5 mL), dried with anhydrous Na$_2$SO$_4$, filtered and concentrated in vacuum. The residue was purified by prep-TLC (PE:EtOAc=2:1, Rf=0.5) to afford the title compound (76 mg, crude) as yellow powder.

LC-MS Method1: 0.833 min, MS (m/z): 239.0 (M−56+H$^+$).

(1R,5S,6r)-6-(5-ethyl-5-methyl-4,5-dihydro-1,2-oxazol-3-yl)-3-azabicyclo[3.1.0]hexane TFA salt

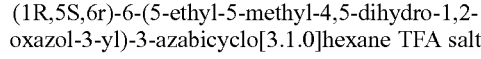

A mixture of compound tert-butyl (1R,5S,6r)-6-(5-ethyl-5-methyl-4,5-dihydro-1,2-oxazol-3-yl)-3-azabicyclo[3.1.0]

hexane-3-carboxylate (76.0 mg, 0.26 mmol), 2,2,2-trifluoroacetic acid (29.4 mg, 0.16 mmol) in DCM (1 mL) was stirred at 20° C. for 2 hr. The reaction mixture was concentrated under reduced pressure to afford the title compound as brown oil.

LC-MS Method1: 0.357 min, MS (m/z): 195.0 (M+H$^+$).

[(1R,5S,6r)-6-(5-ethyl-5-methyl-4,5-dihydro-1,2-oxazol-3-yl)-3-azabicyclo[3.1.0]hex-3-yl](1-isopropyl-1H-imidazol-4-yl)methanone A solution of (1R,5S,6r)-6-(5-ethyl-5-methyl-4,5-dihydro-1,2-oxazol-3-yl)-3-azabicyclo[3.1.0]hexane TFA salt (50.0 mg, 0.26 mmol) in Pyridine (2 mL) were added EDCI (49.3 mg, 0.26 mmol), 1-isopropylimidazole-4-carboxylic acid (39.7 mg, 0.26 mmol). The suspension was stirred at 20° C. for 16 hr. The reaction mixture was quenched with H$_2$O (10 mL). The residue was extracted with EtOAc (20 mL×3), washed with saturated NaCl (5 mL), dried with anhydrous Na$_2$SO$_4$, filtered and concentrated in vacuum. The residue was purified by prep-HPLC (NH$_3$) and lyophilized to afford the title compound (5.77 mg, 6.8% yield) as yellow solid.

LC-MS Method1: 2.693 min, MS (m/z): 331.2 (M+H$^+$).
$^1$H NMR (400 MHz, CHLOROFORM-d) δ ppm 7.59 (s, 1H), 7.40 (s, 1H), 4.64 (s, 1H), 4.28 (s, 1H), 4.12 (br d, J=12.63 Hz, 1H), 3.86 (br d, J=12.38 Hz, 1H), 3.51-3.57 (m, 1H), 2.59-2.65 (m, 1H), 2.44-2.51 (m, 1H), 2.00 (br s, 1H), 1.90 (br s, 1H), 1.54-1.61 (m, 3H), 1.46-1.50 (m, 7H), 1.43 (d, J=6.63 Hz, 7H), 1.38 (t, J=3.25 Hz, 1H), 1.25 (s, 4H), 1.18 (s, 3H), 0.85 (t, J=7.44 Hz, 4H).

Example 42 {(1R,5S,6r)-6-[(5R)-5-ethyl-5-methyl-4,5-dihydro-1,2-oxazol-3-yl]-3-azabicyclo[3.1.0]hex-3-yl}(1-isopropyl-1H-imidazol-4-yl)methanone Example 43 {(1R,5S,6r)-6-[(5S)-5-ethyl-5-methyl-4,5-dihydro-1,2-oxazol-3-yl]-3-azabicyclo[3.1.0]hex-3-yl}(1-isopropyl-1H-imidazol-4-yl)methanone The compounds in Examples 42 and 43 were obtained during the course of the preparation in Example 41, respectively. They were isolated from the final step of Example 41 by SFC purification, which are {(1R,5S,6r)-6-[(5R)-5-ethyl-5-methyl-4,5-dihydro-1,2-oxazol-3-yl]-3-azabicyclo[3.1.0]hex-3-yl}(1-isopropyl-1H-imidazol-4-yl)methanone (63.41 mg, 0.19 mmol, 9.3% yield) and {(1R,5S,6r)-6-[(5S)-5-ethyl-5-methyl-4,5-dihydro-1,2-oxazol-3-yl]-3-azabicyclo[3.1.0]hex-3-yl}(1-isopropyl-1H-imidazol-4-yl)methanone (69.78 mg, 0.21 mmol, 10.2% yield) as white solid.

$^1$H NMR (400 MHz, CHLOROFORM-d) δ=7.66 (s, 1H), 7.48 (s, 1H), 4.74 (br d, J=11.8 Hz, 1H), 4.36 (spt, J=6.7 Hz, 1H), 4.19 (d, J=12.5 Hz, 1H), 3.94 (dd, J=4.0, 12.0 Hz, 1H), 3.61 (dd, J=4.1, 12.4 Hz, 1H), 2.74-2.63 (m, 1H), 2.60-2.48 (m, 1H), 2.15-2.02 (m, 1H), 2.01-1.90 (m, 1H), 1.66-1.58 (m, 2H), 1.50 (d, J=6.8 Hz, 6H), 1.45 (t, J=3.4 Hz, 1H), 1.32 (s, 3H), 0.92 (t, J=7.5 Hz, 3H)

Example 44 (1-isopropyl-1H-imidazol-4-yl)[(1R,5S,6r)-6-(2-oxa-3-azabicyclo[3.1.0]hex-3-en-4-yl)-3-azabicyclo[3.1.0]hex-3-yl]methanone ethyl (1R,5S,6r)-3-azabicyclo[3.1.0]hexane-6-carboxylate hydrochloride To 6-ethyl 3-(tert-butyl) (1R,5S,6r)-3-azabicyclo[3.1.0]hexane-3,6-dicarboxylate (3.5 g, 13.71 mmol) was added HCl/dioxane (50. mL, 3 mmol). The mixture was stirred at 30° C. for 2 h to give brown solution. TLC (PE:EtOAc=5:1) showed a new spot. The reaction mixture was concentrated directly to give the title compound (2.5 g, 13.044 mmol, 95.15% yield) as a black solid.

6-ethyl 3-[2-(trimethylsilyl)ethyl](1R,5S,6r)-3-azabicyclo[3.1.0]hexane-3,6-dicarboxylate To a solution of ethyl (1R,5S,6r)-3-azabicyclo[3.1.0]hexane-6-carboxylate hydrochloride (2.5 g, 13.04 mmol) in DCM (20.27 mL) was added DIPEA (10.78 mL, 65.22 mmol) at 0° C. Then 2,5-dioxopyrrolidin-1-yl (2-(trimethylsilyl)ethyl) carbonate (4.06 g, 15.65 mmol) in DCM (20.27 mL) was added to the mixture, which was stirred at 30° C. for 12 h to give brown suspension. TLC (PE:EtOAc=3:1) showed a new spot. The reaction mixture was concentrated directly. The crude product was purified by flash column (PE to 20% EtOAc in PE) to give the title compound (3.5 g, 11.688 mmol, 89.609% yield) as yellow oil.

$^1$H NMR (400 MHz, CHLOROFORM-d) δ=4.20-4.10 (m, 4H), 3.73 (d, J=11.2 Hz, 1H), 3.65 (d, J=11.2 Hz, 1H), 3.49 (t, J=11.2 Hz, 2H), 2.12 (s, 2H), 1.48 (d, J=3.2 Hz, 1H), 1.28 (t, J=6.8 Hz, 3H), 1.00-0.90 (, 2H), 0.03 (s, 9H).

2-(trimethylsilyl)ethyl (1R,5S,6r)-6-(hydroxymethyl)-3-azabicyclo[3.1.0]hexane-3-carboxylate To a solution of 6-ethyl 3-[2-(trimethylsilyl)ethyl] (1R,5S,6r)-3-azabicyclo[3.1.0]hexane-3,6-dicarboxylate (3.5 g, 11.69 mmol) in THF (40 mL) was added LiAlH$_4$ (0.67 g, 17.53 mmol) at 0° C. The mixture was stirred at 0° C. for 20 min to give white suspension. TLC (PE:EtOAc=1:1) showed the reaction was completed. The reaction mixture was poured into H$_2$O (0.6 mL), 1N NaOH aq (0.6 mL), H$_2$O (1.8 ml) and filtered. The filtrate was concentrated to give yellow oil. The crude product was purified by flash column (PE to 40% EtOAc in PE) to give the title compound (1.2 g, 4.662 mmol, 39.885% yield) as colorless oil.

$^1$H NMR (400 MHz, CHLOROFORM-d) δ=4.15 (dd, J=8.8, 7.6 Hz, 2H), 3.67 (d, J=10.8 Hz, 1H), 3.60 (d, J=10.8 Hz, 1H), 3.60-3.45 (m, 2H), 3.41 (dt, J=8.0, 4.0 Hz, 2H), 1.50-1.40 (m, 3H), 1.00-0.85 (m, 3H), 0.03 (s, 9H).

2-(trimethylsilyl)ethyl (1R,5S,6r)-6-formyl-3-azabicyclo[3.1.0]hexane-3-carboxylate To a solution of 2-(trimethylsilyl)ethyl (1R,5S,6r)-6-(hydroxymethyl)-3-azabicyclo[3.1.0]hexane-3-carboxylate (1.2 g, 4.66 mmol) in DCM (15 mL) was added DMP (2.97 g, 6.99 mmol), NaHCO$_3$ (979.14 mg, 11.66 mmol) at 0° C. The mixture was stirred at 30° C. for 2 h. TLC (PE:EtOAc=1:1) showed the reaction was completed. The reaction mixture were poured into H$_2$O (40 mL) and extracted with EtOAc (30 mL×4). The combined organic layers were washed with NaHCO$_3$.aq. (50 mL) and Na$_2$SO$_3$.aq. (50 mL), dried over Na$_2$SO$_4$, filtered and concentrated under reduced pressure. The crude product was purified by flash column (PE to 30% EtOAc in PE) to give the title compound (0.8200 g, 3.2108 mmol, 68.871% yield) as brown oil.

$^1$H NMR (400 MHz, CHLOROFORM-d) δ=9.46 (d, J=4.0 Hz, 1H), 4.17 (dd, J=7.6, 4.0 Hz, 2H), 3.80 (d, J=11.6 Hz, 1H), 3.60 (d, J=11.6 Hz, 1H), 3.54 (t, J=11.6 Hz, 2H), 2.24 S, 2H), 1.83 (dd, J=6.4, 3.2 Hz, 1H), 0.99 (dd, J=7.6, 4.0 Hz, 2H), 0.03 (s, 9H).

2-(trimethylsilyl)ethyl (1R,5S,6r)-6-[(E)-(hydroxyimino)methyl]-3-azabicyclo[3.1.0]hexane-3-carboxylate To a solution of 2-(trimethylsilyl)ethyl (1R,5S,6r)-6-formyl-3-azabicyclo[3.1.0]hexane-3-carboxylate (820 mg, 3.21 mmol) in EtOH (10 mL) were added KOAc (315.11 mg, 3.21 mmol), HOAc (0.18 mL, 3.21 mmol), NH₂OH HCl (0.17 mL, 4.17 mmol). The mixture was stirred at 25° C. for 3 h to give white suspension. TLC (PE:EtOAc=2:1) showed the reaction was completed. The reaction mixture was removed under reduced pressure. H₂O (40 mL) was added to the residue and the mixture was extracted with EtOAc (30 mL×4). The combined organic phases were washed with saturated sodium hydrogen carbonate (30 mL×2) and saturated brine (40 mL×2) and dried over Na2SO4. The solvent was removed under reduced pressure to give the title compound (850 mg, 3.1435 mmol, 97.904% yield) as brown oil.

2-(trimethylsilyl)ethyl (1R,5S,6r)-6-[(Z)-chloro(hydroxyimino)methyl]-3-azabicyclo[3.1.0]hexane-3-carboxylate To a solution of 2-(trimethylsilyl)ethyl (1R,5S,6r)-6-[(E)-(hydroxyimino)methyl]-3-azabicyclo[3.1.0]hexane-3-carboxylate (850 mg, 3.14 mmol) in DMF (9 mL) was added NCS (503.7 mg, 3.77 mmol). The mixture was stirred at 25° C. for 3 h to give brown solution. TLC (PE:EtOAc=2:1) showed the reaction was completed. The reaction mixture was poured into H₂O (40 mL) and extracted with EtOAc (30 mL×4). The combined organic layers were washed with brine (50 mL×2), dried over Na₂SO₄, filtered and concentrated under reduced pressure. The crude product was purified by flash column (PE to 30% EtOAc in PE) to give the title compound (750 mg, 2.4602 mmol, 78.264% yield) as colorless oil.

2-(trimethylsilyl)ethyl (1R,5S,6r)-6-[5-(chloromethyl)-4,5-dihydro-1,2-oxazol-3-yl]-3-azabicyclo[3.1.0]hexane-3-carboxylate To a solution of 2-(trimethylsilyl)ethyl (1R,5S,6r)-6-[(Z)-chloro(hydroxyimino)methyl]-3-azabicyclo[3.1.0]hexane-3-carboxylate (400 mg, 1.31 mmol) in DMF (5.3333 mL) were added 3-chloroprop-1-ene (0.54 mL, 6.56 mmol) and Et₃N (0.51 mL, 3.94 mmol). The mixture was stirred at 25° C. for 12 h to give brown solution. TLC (PE:EtOAc=3:1) showed the reaction was completed. H₂O (40 mL) was added to the mixture, which was extracted with EtOAc (30 mL×4). The combined organic phases were washed with saturated brine (40 mL×2) and dried over Na₂SO₄. The solvent was removed under reduced pressure. The crude product was purified by flash column (PE to 20% EtOAc in PE) to give the title compound (160 mg, 0.4639 mmol, 35.354% yield) as colorless oil.

$^1$H NMR (400 MHz, CHLOROFORM-d) δ=4.85-4.75 (m, 1H), 4.16 (dd, J=9.2, 7.2 Hz, 2H), 3.76 (d, J=11.2 Hz, 1H), 3.70 (d, J=11.2 Hz, 1H), 3.61 (dd, J=7.2, 4.0 Hz, 1H), 3.55-3.40 (m, 3H), 3.15-3.05 (m, 1H), 2.95-2.80 (m, 1H), 52.00 (brs, 2H), 1.50 (brs, 1H), 1.00 (dd, J=9.2, 7.2 Hz, 2H), 0.05 (s, 9H).

4-[(1R,5S,6r)-3-azabicyclo[3.1.0]hex-6-yl]-2-oxa-3-azabicyclo[3.1.0]hex-3-ene To a solution of 2-(trimethylsilyl)ethyl (1R,5S,6r)-6-[5-(chloromethyl)-4,5-dihydro-1,2-oxazol-3-yl]-3-azabicyclo[3.1.0]hexane-3-carboxylate (20 mg, 0.06 mmol) in DMSO (1 mL) was added t-BuOK (13.01 mg, 0.12 mmol). The mixture was stirred at 20° C. for 30 min to give brown solution. The reaction mixture was lyophilized directly to give the title compound (8 mg, 0.0487 mmol, 84.022% yield) as brown solid.

$^1$H NMR (400 MHz, CHLOROFORM-d) δ=4.90-4.80 (m, 1H), 4.04 (d, J=12.4 Hz, 1H), 3.80-3.60 (m, 2H), 3.40-3.30 (m, 1H), 2.40-2.30 (m, 1H), 2.20-1.90 (m, 2H), 1.60-1.50 (m, 1H), 1.00-0.85 (m, 2H), 0.40-0.30 (m, 1H).

(1-isopropyl-1H-imidazol-4-yl)[(1R,5S,6r)-6-(2-oxa-3-azabicyclo[3.1.0]hex-3-en-4-yl)-3-azabicyclo[3.1.0]hex-3-yl]methanone To a solution of 4-[(1R,5S,6r)-3-azabicyclo[3.1.0]hex-6-yl]-2-oxa-3-azabicyclo[3.1.0]hex-3-ene (30 mg, 0.18 mmol) and 1-isopropylimidazole-4-carboxylic acid (27.75 mg, 0.18 mmol) in Pyridine (2.9557 mL) was added EDCI (44.86 mg, 0.23 mmol). The mixture was stirred at 25° C. for 3 h to give yellow solution. LCMS showed the desire MS as a major peak. The reaction mixture was concentrated directly. The residue was purified by prep-HPLC (NH₃) to give the title compound (7.58 mg, 0.0252 mmol, 14.02% yield) as yellow solid.

LC-MS Method1: 301.2 [M+H$^+$]

$^1$H NMR (400 MHz, CHLOROFORM-d) δ ppm 7.68 (1H, d, J=1.51 Hz), 7.48 (1H, d, J=1.25 Hz), 4.85 (1H, td, J=5.33, 2.13 Hz), 4.78 (1H, br d, J=10.79 Hz), 4.36 (1H, m, J=13.49, 6.68 Hz), 4.23 (1H, br d, J=11.80 Hz), 3.98 (1H, br dd, J=12.05, 4.52 Hz), 3.60-3.70 (1H, m), 2.36 (1H, dt, J=8.85, 4.49 Hz), 1.98-2.15 (2H, m), 1.66 (1H, br d, J=3.51 Hz), 1.51 (6H, d, J=6.78 Hz), 0.85-0.89 (1H, m), 0.31 (1H, br s)

Example 45 (1-isopropyl-1H-imidazol-4-yl)[(1R,5S,6r)-6-(1-methyl-2-oxa-3-azabicyclo[3.1.0]hex-3-en-4-yl)-3-azabicyclo[3.1.0]hex-3-yl]methanone

2-(trimethylsilyl)ethyl (1R,5S,6r)-6-[5-(chloromethyl)-5-methyl-4,5-dihydro-1,2-oxazol-3-yl]-3-azabicyclo[3.1.0]hexane-3-carboxylate To a solution of 2-(trimethylsilyl)ethyl (1R,5S,6r)-6-[(Z)-chloro(hydroxyimino)methyl]-3-azabicyclo[3.1.0]hexane-3-carboxylate (150 mg, 0.49 mmol) in DMF (2 mL) were added 3-chloro-2-methylprop-1-ene (0.24 mL, 2.46 mmol) and Et₃N (0.19 mL, 1.48 mmol). The mixture was stirred at 25° C. for 12 h to give brown mixture. The reaction mixture was poured into H₂O (10 mL) and extracted with EtOAc (15 mL×4). The combined organic layers were washed with brine (50 mL), dried over Na₂SO₄, filtered and concentrated under reduced pressure to give the title compound (150 mg, 0.4179 mmol, 84.931% yield) as brown oil.

$^1$H NMR (400 MHz, CHLOROFORM-d) δ=4.25-4.10 (m, 2H), 3.80-3.60 (m, 2H), 3.55-3.45 (m, 4H), 3.05 (d, J=9.2 Hz, 1H), 2.65 (d, J=9.2 Hz, 1H), 2.00-1.90 (m, 1H), 1.55-1.45 (m, 2H), 1.05 (s, 3H), 1.50-1.40 (m, 1H), 0.99 (t, J=8.0 Hz, 2H), 0.04 (s, 9H).

4-[(1R,5S,6r)-3-azabicyclo[3.1.0]hex-6-yl]-1-methyl-2-oxa-3-azabicyclo[3.1.0]hex-3-ene To a solution of 2-(trimethylsilyl)ethyl (1R,5S,6r)-6-[5-(chloromethyl)-5-methyl-4,5-dihydro-1,2-oxazol-3-yl]-3-azabicyclo[3.1.0]hexane-3-carboxylate (130 mg, 0.36 mmol) in DMSO (4 mL) was added t-BuOK (81.28 mg, 0.72 mmol). The mixture was stirred at 20° C. for 30 min to give brown solution. The reaction mixture was lyophilized directly to give the title compound (60 mg, 0.3366 mmol, 92.95% yield) as brown solid.

(1-isopropyl-1H-imidazol-4-yl)[(1R,5S,6r)-6-(1-methyl-2-oxa-3-azabicyclo[3.1.0]hex-3-en-4-yl)-3-azabicyclo[3.1.0]hex-3-yl]methanone To a solution of 4-[(1R,5S,6r)-3-azabicyclo[3.1.0]hex-6-yl]-1-methyl-2-oxa-3-azabicyclo[3.1.0]hex-3-ene (60 mg, 0.34 mmol) and 1-isopropylimidazole-4-carboxylic acid (51.9 mg, 0.34 mmol) in Pyridine (5 mL) was added EDCI (129.07 mg, 0.67 mmol). The mixture was stirred at 25° C. for 3 h to give yellow solution. The mixture was concentrated directly. The residue was purified by prep-HPLC (NH$_3$). The afforded solid was purified by prep-TLC (DCM:MeOH=15:1) to give the title compound (11.96 mg, 0.0380 mmol, 11.301% yield) as light yellow solid.

LC-MS Method1: 315.2 [M+H$^+$]

$^1$H NMR (400 MHz, CHLOROFORM-d) δ ppm 7.67 (1H, s), 7.48 (1H, s), 4.75 (1H, br d, J=12.05 Hz), 4.36 (1H, m, J=13.43, 6.84 Hz), 4.22 (1H, br d, J=12.30 Hz), 3.97 (1H, br d, J=12.05 Hz), 3.64 (1H, br d, J=12.30 Hz), 2.08 (2H, br d, J=3.76 Hz), 2.01 (1H, br s), 1.67 (3H, s), 1.51 (6H, d, J=6.78 Hz), 0.90 (1H, dd, J=9.41, 5.14 Hz), 0.33-0.43 (1H, m)

Example 46 (1-isopropyl-1H-imidazol-4-yl)[(1R,5S,6r)-6-(4,5,5-trimethyl-4,5-dihydro-1,2-oxazol-3-yl)-3-azabicyclo[3.1.0]hex-3-yl]methanone tert-butyl (1R,5S,6r)-6-(4,5,5-trimethyl-4,5-dihydro-1,2-oxazol-3-yl)-3-azabicyclo[3.1.0]hexane-3-carboxylate To a solution of Et$_3$N (0.36 mL, 2.18 mmol) and 2-methylbut-2-ene (1.16 mL, 10.92 mmol) in THF was added tert-butyl (1R,5S,6r)-6-[(Z)-chloro(hydroxyimino)methyl]-3-azabicyclo[3.1.0]hexane-3-carboxylate (200 mg, 0.73 mmol). The mixture was stirred at 20° C. for 16 hr. The mixture was diluted with H$_2$O (15 mL) and extracted with EtOAc (15 mL×3). The organic phase was washed with brine (50 mL), dried over anhydrous Na$_2$SO$_4$ and concentrated to give a residue. The residue was purified by flash column (PE:EtOAc=1:0-0:1) to afford the title compound (100 mg, 0.3397 mmol, 46.663% yield) as a yellow oil.

(1R,5S,6r)-6-(4,5,5-trimethyl-4,5-dihydro-1,2-oxazol-3-yl)-3-azabicyclo[3.1.0]hexane TFA salt A mixture of tert-butyl (1R,5S,6r)-6-(4,5,5-trimethyl-4,5-dihydro-1,2-oxazol-3-yl)-3-azabicyclo[3.1.0]hexane-3-carboxylate (160 mg, 0.54 mmol) in TFA (0.5 mL, 0.54 mmol) and DCM (2 mL) was stirred at 20° C. for 40 min. The reaction mixture was concentrated in vacuum and then lyophilized to give the title compound (100 mg, crude product) as yellow oil.

$^1$H NMR (400 MHz, CHLOROFORM-d) δ=3.60-3.40 (m, 4H), 2.30-2.20 (m, 2H), 2.00-1.70 (m, 2H), 1.24 (s, 3H), 1.15 (s, 3H), 0.95 (d, J=7.6 Hz, 3H).

(1-isopropyl-1H-imidazol-4-yl)[(1R,5S,6r)-6-(4,5,5-trimethyl-4,5-dihydro-1,2-oxazol-3-yl)-3-azabicyclo[3.1.0]hex-3-yl]methanone To a mixture of 1-isopropylimidazole-4-carboxylic acid (39.68 mg, 0.26 mmol) in DMF (1 mL) were added HATU (127.91 mg, 0.33 mmol) and DIPEA (0.21 mL, 1.29 mmol). The mixture was heated at 50° C. for 30 min. (1R,5S,6r)-6-(4,5,5-trimethyl-4,5-dihydro-1,2-oxazol-3-yl)-3-azabicyclo[3.1.0]hexane TFA salt (50 mg, 0.26 mmol) was added the mixture. The resulting mixture was stirred at 20° C. for 4 hr. The reaction mixture was diluted with H$_2$O (10 mL) and extracted with EtOAc (10 mL×2), then washed with brine (10 mL). The combined organic layers were separated, then dried over Na$_2$SO$_4$ and concentrated in vacuum to give crude oil. The crude oil was purified by prep-HPLC (NH$_3$) and lyophilized to give the title compound (6 mg, 0.0182 mmol, 7.0554% yield) as white solid.

$^1$H NMR (400 MHz, DMSO) δ=7.98 (d, J=2.8 Hz, 2H), 4.79 (br d, J=12.5 Hz, 1H), 4.65 (td, J=6.8, 13.2 Hz, 1H), 4.17-4.10 (m, 1H), 4.01 (br d, J=13.1 Hz, 1H), 3.65 (br s, 1H), 3.02 (br d, J=6.5 Hz, 1H), 2.30-2.07 (m, 2H), 1.60 (d, J=6.5 Hz, 6H), 1.47 (br s, 1H), 1.48-1.45 (m, 1H), 1.40 (s, 3H), 1.31 (s, 3H), 1.22 (d, J=7.5 Hz, 3H)

Example 47 (1-isopropyl-1H-imidazol-4-yl){(1R,5S,6r)-6-[(4S)-4,5,5-trimethyl-4,5-dihydro-1,2-oxazol-3-yl]-3-azabicyclo[3.1.0]hex-3-yl}methanone Example 48 (1-isopropyl-1H-imidazol-4-yl){(1R,5S,6r)-6-[(4R)-4,5,5-trimethyl-4,5-dihydro-1,2-oxazol-3-yl]-3-azabicyclo[3.1.0]hex-3-yl}methanone To a solution of 1-isopropylimidazole-4-carboxylic acid (476.15 mg, 3.09 mmol) in Pyridine (8 mL) were added EDCI (592.06 mg, 3.09 mmol) and (1R,5S,6r)-6-(4,5,5-trimethyl-4,5-dihydro-1,2-oxazol-3-yl)-3-azabicyclo[3.1.0] hexane (400 mg, 2.06 mmol). The resulting mixture was stirred at 20-25° C. for 2 h. LCMS showed the desired MS (as a major peak). The reaction mixture was concentrated directly. The residue was purified by prep-HPLC (NH$_3$). The afforded flows were combined, concentrated to remove most of CH$_3$CN and lyophilized. The product was chirally separated by SFC and lyophilized to afford (1-isopropyl-1H-imidazol-4-yl){(1R,5S,6r)-6-[(4S)-4,5,5-trimethyl-4,5-dihydro-1,2-oxazol-3-yl]-3-azabicyclo[3.1.0]hex-3-yl}methanone (48.84 mg, 0.15 mmol, 7.2% yield) and (1-isopropyl-1H-imidazol-4-yl){(1R,5S,6r)-6-[(4R)-4,5,5-trimethyl-4,5-dihydro-1,2-oxazol-3-yl]-3-azabicyclo[3.1.0]hex-3-yl}methanone (52.66 mg, 0.1594 mmol, 7.7403% yield) both as yellow gum.

$^1$H NMR (400 MHz, CHLOROFORM-d) δ=7.68 (br s, 1H), 7.49 (s, 1H), 4.85-4.64 (m, 1H), 4.48-4.29 (m, 1H), 4.27-4.12 (m, 1H), 4.03-3.88 (m, 1H), 3.71-3.54 (m, 1H), 2.78 (quin, J=7.2 Hz, 1H), 2.30-1.95 (m, 2H), 1.65 (br s, 3H), 1.52 (s, 6H), 1.31 (d, J=2.8 Hz, 3H), 1.28-1.18 (m, 4H), 1.10 (br d, J=7.3 Hz, 3H)

Example 49 (1-isopropyl-1H-imidazol-4-yl)[(1R,5S,6r)-6-(4-methoxy-5,5-dimethyl-4,5-dihydro-1,2-oxazol-3-yl)-3-azabicyclo[3.1.0]hex-3-yl]methanone tert-butyl (1R,5S,6s)-6-ethynyl-3-azabicyclo[3.1.0]hexane-3-carboxylate To a solution of tert-butyl (1R,5S,6r)-6-formyl-3-azabicyclo[3.1.0]hexane-3-carboxylate (2000 mg, 9.47 mmol) in MeOH (8 mL) were added K$_2$CO$_3$ (2616.87 mg, 18.93 mmol) and 1-diazo-1-dimethoxyphosphoryl-propan-2-one (1818.71 mg, 9.47 mmol). The reaction mixture was stirred at 20° C. for 16 hr to give a light yellow mixture. TLC (PE/EtOAc=3:1) showed a new spot. The reaction mixture was diluted with H$_2$O (300 mL) and extracted with EtOAc (100 mL×2). The organic layer was washed with brine (100 mL×2) and dried over anhydrous sodium sulfate to give a residue. The residue was purified by silica column (PE/EtOAc=3:1) to give the title compound (1800 mg, 8.6843 mmol, 91.733% yield) as white solid.

$^1$H NMR (400 MHz, CHLOROFORM-d) δ=3.35 (d, J=11.2 Hz, 1H), 3.57 (d, J=11.2 Hz, 1H), 3.36-3.30 (m, 2H), 1.88 (s, 1H), 1.84-1.80 (m, 2H), 1.42 (s, 9H), 1.12-1.09 (m, 1H).

tert-butyl (1R,5S,6s)-6-(3-hydroxy-3-methyl-1-butyn-1-yl)-3-azabicyclo[3.1.0]hexane-3-carboxylate To a solution of tert-butyl (1R,5S,6s)-6-ethynyl-3-azabicyclo[3.1.0]hexane-3-carboxylate (1800 mg, 8.68 mmol) in THF (90 mL) was added n-BuLi (0.2 mL, 9.55 mmol) at −78° C. The reaction mixture was stirred for 30 min at −78° C. The acetone (1109.65 mg, 19.11 mmol) was added to the reaction mixture. Then the reaction mixture was stirred at 25° C. for 16 hr to give a yellow mixture. The reaction mixture was quenched with H$_2$O (100 mL) and extracted with EtOAc (100 mL×2). The organic layer was washed with brine (100 mL) and dried over anhydrous sodium sulfate to give a residue. The residue was purified by silica column (PE/EtOAc=3:1) to give the title compound as white solid.

$^1$H NMR (400 MHz, CHLOROFORM-d) δ=3.63 (d, J=11.2 Hz, 1H), 3.55 (d, J=11.2 Hz, 1H), 3.40-3.10 (m, 2H), 1.83 (s, 1H), 1.78-1.60 (m, 2H), 1.47 (s, 6H), 1.42 (s, 9H), 1.10-1.09 (m, 1H).

tert-butyl (1R,5S,6r)-6-(5,5-dimethyl-2-oxido-4-oxo-4,5-dihydro-1,2-oxazol-3-yl)-3-azabicyclo[3.1.0]hexane-3-carboxylate To a solution of tert-butyl (1R,5S,6s)-6-(3-hydroxy-3-methyl-1-butyn-1-yl)-3-azabicyclo[3.1.0]hexane-3-carboxylate (900 mg, 3.39 mmol) in MeCN (36 mL) were added t-BuONO (699.11 mg, 6.78 mmol) and Pd(OAc)$_2$ (152.3 mg, 0.68 mmol). The reaction mixture was stirred at 25° C. for 16 hr to give a yellow mixture. TLC (PE/EtOAc=3:1) showed a new spot. The reaction mixture was diluted with H$_2$O (200 mL) and extracted with EtOAc (100 mL×2). The organic layer was washed with brine (200 mL), filtered and dried over anhydrous sodium sulfate to give a residue. The residue was purified by silica column (PE/EtOAc=3:1) to give the title compound (600 mg, 1.9333 mmol, 57% yield) as yellow solid.

$^1$H NMR (400 MHz, CHLOROFORM-d) δ=3.72 (d, J=11.2 Hz, 1H), 3.65 (d, J=11.2 Hz, 1H), 3.47-3.40 (m, 2H), 2.40-2.20 (m, 2H), 1.60 (s, 1H), 1.49 (s, 6H), 1.44 (s, 9H).

tert-butyl (1R,5S,6r)-6-(4-hydroxy-5,5-dimethyl-2-oxido-4,5-dihydro-1,2-oxazol-3-yl)-3-azabicyclo[3.1.0]hexane-3-carboxylate To a solution of tert-butyl (1R,5S,6r)-6-(5,5-dimethyl-2-oxido-4-oxo-4,5-dihydro-1,2-oxazol-3-yl)-3-azabicyclo[3.1.0]hexane-3-carboxylate (650 mg, 2.09 mmol) in THF (10 mL) was added a solution of NaBH$_4$ (87.15 mg, 2.3 mmol) in MeOH (3 mL) at 0° C. The reaction mixture was stirred at 0° C. for 2 hr to give a white mixture. The reaction mixture was quenched with H$_2$O (100 mL) and extracted with EtOAc (100 mL×2). The organic layer was dried over anhydrous sodium sulfate to give the title compound (570 mg, 1.8248 mmol, 87.128% yield) as colorless oil.

$^1$H NMR (400 MHz, CHLOROFORM-d) δ=4.25 (d, J=11.2 Hz, 1H), 4.20 (d, J=11.2 Hz, 1H), 3.70-3.50 (m, 2H), 3.50-3.40 (m, 2H), 2.25-2.15 (m, 1H), 2.15-2.00 (m, 1H), 1.70 (d, J=3.2 Hz, 1H), 1.43 (s, 9H), 1.43 (s, 3H), 1.35 (s, 3H).

tert-butyl (1R,5S,6r)-6-(4-methoxy-5,5-dimethyl-2-oxido-4,5-dihydro-1,2-oxazol-3-yl)-3-azabicyclo[3.1.0]hexane-3-carboxylate To a solution of tert-butyl (1R,5S,6r)-6-(4-hydroxy-5,5-dimethyl-2-oxido-4,5-dihydro-1,2-oxazol-3-yl)-3-azabicyclo[3.1.0]hexane-3-carboxylate (400 mg, 1.28 mmol) in THF (20 mL) was added NaH (36.88 mg, 1.54 mmol) at 0° C. and stirred at 0° C. for 0.5 hr to give a yellow mixture. MeI (0.11 mL, 1.79 mmol) was added to the reaction mixture. The reaction mixture was stirred at 20° C. for 16 hr to give a light yellow mixture. TLC (PE/EtOAc=1:1) showed a new spot. The reaction mixture was quenched with H$_2$O (100 mL) and extracted with EtOAc (50 mL×3). The organic layer was concentrated to give a residue. The residue was purified by silica column (PE/EtOAc=1:1) to give the title compound (380 mg, 1.1643 mmol, 90.916% yield) as colorless oil.

$^1$H NMR (400 MHz, CHLOROFORM-d) δ=4.02 (d, J=4.0 Hz, 1H), 3.80-3.60 (m, 2H), 3.50-3.35 (m, 2H), 3.41 (s, 3H), 2.15-2.00 (m, 2H), 1.69 (s, 1H), 1.43 (s, 9H), 1.39 (s, 3H), 1.37 (s, 3H).

tert-butyl (1R,5S,6r)-6-(4-methoxy-5,5-dimethyl-4,5-dihydro-1,2-oxazol-3-yl)-3-azabicyclo[3.1.0]hexane-3-carboxylate A solution of tert-butyl (1R,5S,6r)-6-(4-methoxy-5,5-dimethyl-2-oxido-4,5-dihydro-1,2-oxazol-3-yl)-3-azabicyclo[3.1.0]hexane-3-carboxylate (380 mg, 1.16 mmol) in P(MeO)$_3$ (1. mL, 1.16 mmol) was stirred at 110° C. for 16 hr to give a yellow mixture. TLC (PE/EtOAc=1:1) showed a new spot. The reaction mixture was diluted with EtOAc (200 mL) and washed with H2O (100 mL×3). The organic layer was concentrated to give a residue. The residue was purified by silica column (PE/EtOAc=1:1) to give the title compound (320 mg, 1.031 mmol, 88.551% yield) as colorless oil.

$^1$H NMR (400 MHz, CHLOROFORM-d) δ=4.01 (d, J=11.2 Hz, 1H), 3.80-3.60 (m, 2H), 3.46 (s, 3H), 3.46-3.30 (m, 2H), 2.20-2.00 (m, 2H), 1.64 (s, 1H), 1.46 (s, 9H), 1.35 (s, 3H), 1.29 (s, 3H).

(1R,5S,6r)-6-(4-methoxy-5,5-dimethyl-4,5-dihydro-1,2-oxazol-3-yl)-3-azabicyclo[3.1.0]hexane TFA Salt To a solution of tert-butyl (1R,5S,6r)-6-(4-methoxy-5,5-dimethyl-4,5-dihydro-1,2-oxazol-3-yl)-3-azabicyclo[3.1.0]hexane-3-carboxylate (200 mg, 0.64 mmol) in DCM (4 mL) was added TFA (0.8 mL, 0.64 mmol). The reaction mixture was stirred at 25° C. for 1 hr to give a colorless mixture. The reaction mixture was removed the solvent to give a residue. The residue was used for the next step directly.

LC-MS Method1 0.323 min, MS (m/z) 211.0 (M+H$^+$).

(1-isopropyl-1H-imidazol-4-yl)[(1R,5S,6r)-6-(4-methoxy-5,5-dimethyl-4,5-dihydro-1,2-oxazol-3-yl)-3-azabicyclo[3.1.0]hex-3-yl]methanone To a solution of 1-isopropylimidazole-4-carboxylic acid (49.12 mg, 0.32 mmol), HATU (91.62 mg, 0.48 mmol) in DMF (2.393 mL) was added DIPEA (0.16 mL, 0.96 mmol). The reaction mixture was stirred at 15° C. for 30 min. Then (1R,5S,6r)-6-(4-methoxy-5,5-dimethyl-4,5-dihydro-1,2-oxazol-3-yl)-3-azabicyclo[3.1.0]hexane TFA salt (67 mg, 0.32 mmol) was added to the reaction. The reaction mixture was stirred at 15° C. for 0.5 hr to give a yellow mixture. LCMS showed the desired MS. The reaction mixture was purified by prep-HPLC (NH$_3$) to give the title compound (65.26 mg, 0.1884 mmol, 59.122% yield) as white powder $^1$H NMR (400 MHz, CHLOROFORM-d) δ=7.67 (s, 1H), 7.47 (s, 1H), 4.75 (dd, J=12.0, 16.8 Hz, 1H), 4.35 (m, 1H), 4.21 (m, 1H), 4.05-3.92 (m, 2H), 3.66-3.58 (m, 1H), 2.25-2.17 (m, 1H), 2.07 (m, 1H), 1.50 (d, J=6.8 Hz, 6H), 1.47 (m, 1H), 1.35 (s, 3H), 1.28 (d, J=4.4 Hz, 3H)

Example 50 [(1R,5S,6r)-6-(4-isobutyl-5,5-dimethyl-4,5-dihydro-1,2-oxazol-3-yl)-3-azabicyclo[3.1.0]hex-3-yl](1-isopropyl-1H-imidazol-4-yl)methanone tert-butyl (1R,5S,6r)-6-(4-isobutyl-5,5-dimethyl-4,5-dihydro-1,2-oxazol-3-yl)-3-azabicyclo[3.1.0]hexane-3-carboxylate To a solution of tert-butyl (1R,5S,6r)-6-[(Z)-chloro(hydroxyimino)methyl]-3-azabicyclo[3.1.0]hexane-3-carboxylate (200 mg, 0.77 mmol) and Et$_3$N (0.3 mL, 2.3 mmol) in DMF (2.8571 mL) was added 2,5-dimethylhex-2-ene (258.23 mg, 2.3 mmol). The mixture was stirred at 25° C. for 12 h. LCMS showed the desired mass was detected. The reaction mixture was poured into H$_2$O (50 mL), extracted by EtOAc (40 mL×3). The organic phase was washed with H$_2$O (30 mL×3) and brine (50 mL), dried over anhydrous Na$_2$SO$_4$, concentrated to give the title compound (150 mg, 58.1% yield) as colorless oil.

(1R,5S,6r)-6-(4-isobutyl-5,5-dimethyl-4,5-dihydro-1,2-oxazol-3-yl)-3-azabicyclo[3.1.0]hexane TFA Salt The solution of tert-butyl (1R,5S,6r)-6-(4-isobutyl-5,5-dimethyl-4,5-dihydro-1,2-oxazol-3-yl)-3-azabicyclo[3.1.0] hexane-3-carboxylate (150 mg, 0.45 mmol) in HCl/Dioxane (10. mL, 0.45 mmol) was stirred at 15° C. for 1 h. TLC (PE:EtOAc=3: 1) showed the starting material (Rf=0.3) was consumed completely and a new spot (Rf=0) was found. LCMS showed the desired MS. The reaction mixture was concentrated under reduced pressure to give the title compound (105 mg, 0.3110 mmol, 69.757% yield, crude) as a white solid. The crude product was used directly for next step.

LC-MS Method1 0.725, MS (m/z) 237.1 (M+H$^+$).

[(1R,5S,6r)-6-(4-isobutyl-5,5-dimethyl-4,5-dihydro-1,2-oxazol-3-yl)-3-azabicyclo[3.1.0]hex-3-yl](1-isopropyl-1H-imidazol-4-yl)methanone To a solution of (1R,5S,6r)-6-(4-isobutyl-5,5-dimethyl-4,5-dihydro-1,2-oxazol-3-yl)-3-azabicyclo[3.1.0]hexane TFA salt (105 mg, 0.44 mmol) and DIPEA (0.22 mL, 1.33 mmol) in DMF (3 mL) were added HATU (202.58 mg, 0.53 mmol) and 1-isopropylimidazole-4-carboxylic acid (68.49 mg, 0.44 mmol). The mixture was stirred at 20° C. for 12 h. LCMS showed the desired mass was detected. The reaction mixture was poured into H$_2$O (30 mL), extracted by EtOAc (20 mL×3). The organic phase was washed by brine, dried over anhydrous Na$_2$SO$_4$ and concentrated to give a residue. The residue was purified by prep-HPLC (NH$_3$) to give the title compound (4.86 mg, 0.0130 mmol, 2.9368% yield) as an off-white solid.

LC-MS Method1: 372.0 [M+H$^+$]

$^1$H NMR (400 MHz, METHANOL-d$_4$) δ=9.11 (s, 1H), 8.21 (br s, 1H), 4.77-4.69 (m, 2H), 4.13-4.00 (m, 3H), 3.72 (br dd, J=4.4, 12.4 Hz, 1H), 3.01-2.92 (m, 1H), 2.36-2.25 (m, 1H), 2.20-2.06 (m, 1H), 1.79-1.71 (m, 1H), 1.63 (d, J=6.8 Hz, 6H), 1.36 (d, J=2.4 Hz, 3H), 1.21 (s, 3H), 0.97 (br d, J=6.5 Hz, 6H), 0.90-0.87 (m, 3H)

Example 51 (1-cyclopropyl-1H-imidazol-4-yl)[(1R, 5S,6r)-6-(4-oxa-5-azaspiro[2.4]hept-5-en-6-yl)-3-azabicyclo[3.1.0]hex-3-yl]methanone

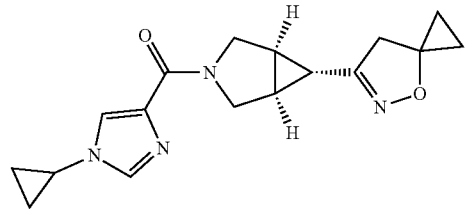 [SMILES: O=C(c1cn(C2CC2)cn1)N1C[C@@H]2[C@H](C1)[C@H]2C1=NOC2(CC2)C1]

(1-cyclopropyl-1H-imidazol-4-yl)[(1R,5S,6r)-6-(4-oxa-5-azaspiro[2.4]hept-5-en-6-yl)-3-azabicyclo[3.1.0]hex-3-yl]methanone To the mixture of 6-[(1R,5S,6r)-3-azabicyclo[3.1.0]hex-6-yl]-4-oxa-5-azaspiro[2.4]hept-5-ene hydrochloride (49.0 mg, 0.27 mmol) in Pyridine (1.5 mL) were added EDCI (52.7 mg, 0.27 mmol) and 1-cyclopropylimidazole-4-carboxylic acid (41.83 mg, 0.27 mmol). The suspension was stirred at 20° C. for 16 hr. The solution was purified by prep-HPLC (NH$_3$) and lyophilized to afford the title compound (6.79 mg, 7.9% yield) as yellow solid.

LC-MS Method1: 2.058 min, MS (m/z): 313.2 (M+H$^+$).

$^1$H NMR (400 MHz, CHLOROFORM-d) δ ppm 7.56 (d, J=1.38 Hz, 1H) 7.43 (d, J=1.25 Hz, 1H) 4.63 (d, J=12.01 Hz, 1H) 4.12 (d, J=12.38 Hz, 1H) 3.87 (dd, J=11.82, 3.94 Hz, 1H) 3.55 (dd, J=12.88, 4.38 Hz, 1H) 3.26-3.33 (m, 1H) 2.89 (s, 2H) 2.05 (br d, J=3.50 Hz, 1H) 1.93-1.99 (m, 1H) 1.45 (br d, J=3.63 Hz, 1H) 1.18 (s, 3H) 1.02-1.07 (m, 2H) 0.95-0.99 (m, 3H) 0.90-0.94 (m, 2H) 0.61-0.66 (m, 2H)

Example 52 [1-(1-methylcyclopropyl)-1H-imidazol-4-yl][(1R,5S,6r)-6-(4-oxa-5-azaspiro[2.4]hept-5-en-6-yl)-3-azabicyclo[3.1.0]hex-3-yl]methanone

[1-(1-methylcyclopropyl)-1H-imidazol-4-yl][(1R,5S, 6r)-6-(4-oxa-5-azaspiro[2.4]hept-5-en-6-yl)-3-azabicyclo[3.1.0]hex-3-yl]methanone To a solution of 1-(1-methylcyclopropyl)-1H-imidazole-4-carboxylic acid (37.3 mg, 0.22 mmol) in DMF (1.5 mL) were added HATU (110.87 mg, 0.29 mmol) and Et$_3$N (0.09 mL, 0.67 mmol). The mixture was stirred at 20-25° C. for 0.5 h. To the mixture was added 6-[(1R,5S,6r)-3-azabicyclo [3.1.0]hex-6-yl]-4-oxa-5-azaspiro[2.4]hept-5-ene hydrochloride (40 mg, 0.22 mmol). The resulting mixture was stirred for 2 h. The residue was purified by prep-HPLC (NH$_3$). The afforded flows were combined, concentrated to remove most of CH₃CN and lyophilized to afford the title compound (11.21 mg, 0.0343 mmol, 15.303% yield) as a yellow solid.

LC-MS Method1: 327.2 [M+H⁺]

$^1$H NMR (400 MHz, CHLOROFORM-d) δ=7.69 (d, J=1.3 Hz, 1H), 7.53 (d, J=1.3 Hz, 1H), 4.73 (br d, J=12.0 Hz, 1H), 4.21 (br d, J=12.3 Hz, 1H), 3.95 (br dd, J=4.0, 12.0 Hz, 1H), 3.62 (br dd, J=4.0, 12.5 Hz, 1H), 2.97 (s, 2H), 2.13 (br d, J=3.5 Hz, 1H), 2.07-2.01 (m, 1H), 1.58 (s, 3H), 1.53 (t, J=3.4 Hz, 1H), 1.18-1.08 (m, 4H), 0.98-0.89 (m, 2H), 0.75-0.68 (m, 2H)

Example 53 (1-isopropyl-1H-imidazol-4-yl){(1R,5S,6r)-6-[(1S,5S)-1-methyl-2-oxa-3-azabicyclo[3.1.0]hex-3-en-4-yl]-3-azabicyclo[3.1.0]hex-3-yl}methanone Example 54 (1-isopropyl-1H-imidazol-4-yl){(1R,5S,6r)-6-[(1R,5R)-1-methyl-2-oxa-3-azabicyclo[3.1.0]hex-3-en-4-yl]-3-azabicyclo[3.1.0]hex-3-yl}methanone The compound produced in Example 45 was applied for SFC chiral separation to afford (1-isopropyl-1H-imidazol-4-yl){(1R,5S,6r)-6-[(1S,5S)-1-methyl-2-oxa-3-azabicyclo[3.1.0]hex-3-en-4-yl]-3-azabicyclo[3.1.0]hex-3-yl}methanone (22.30 mg), and (1-isopropyl-1H-imidazol-4-yl){(1R,5S,6r)-6-[(1R,5R)-1-methyl-2-oxa-3-azabicyclo[3.1.0]hex-3-en-4-yl]-3-azabicyclo[3.1.0]hex-3-yl}methanone (21.47 mg) as white solid.

(1-isopropyl-1H-imidazol-4-yl) {(1R,5S,6r)-6-[(1S,5S)-1-methyl-2-oxa-3-azabicyclo[3.1.0]hex-3-en-4-yl]-3-azabicyclo[3.1.0]hex-3-yl}methanone LC-MS Method1: 315.2 [M+H⁺]

$^1$H NMR (400 MHz, CHLOROFORM-d) δ ppm 7.67 (1H, s), 7.48 (1H, s), 4.75 (1H, br d, J=12.05 Hz), 4.36 (1H, m, J=13.43, 6.84 Hz), 4.22 (1H, br d, J=12.30 Hz), 3.97 (1H, br d, J=12.05 Hz), 3.64 (1H, br d, J=12.30 Hz), 2.08 (2H, br d, J=3.76 Hz), 2.01 (1H, br s), 1.67 (3H, s), 1.51 (6H, d, J=6.78 Hz), 0.90 (1H, dd, J=9.41, 5.14 Hz), 0.33-0.43 (1H, m)

(1-isopropyl-1H-imidazol-4-yl) {(1R,5S,6r)-6-[(1R,5R)-1-methyl-2-oxa-3-azabicyclo[3.1.0]hex-3-en-4-yl]-3-azabicyclo[3.1.0]hex-3-yl}methanone LS-MS method1: 315.2 [M+H⁺]

$^1$H NMR (400 MHz, CHLOROFORM-d) δ ppm 7.67 (1H, s), 7.48 (1H, s), 4.75 (1H, br d, J=12.05 Hz), 4.36 (1H, m, J=13.43, 6.84 Hz), 4.22 (1H, br d, J=12.30 Hz), 3.97 (1H, br d, J=12.05 Hz), 3.64 (1H, br d, J=12.30 Hz), 2.08 (2H, br d, J=3.76 Hz), 2.01 (1H, br s), 1.67 (3H, s), 1.51 (6H, d, J=6.78 Hz), 0.90 (1H, dd, J=9.41, 5.14 Hz), 0.33-0.43 (1H, m)

Example 55 (1-isopropyl-1H-imidazol-4-yl)[(1R,5S,6r)-6-(5-methyl-4-phenyl-1,2-oxazol-3-yl)-3-azabicyclo[3.1.0]hex-3-yl]methanone tert-butyl (1R,5S,6r)-6-(4-bromo-5-methyl-1,2-oxazol-3-yl)-3-azabicyclo[3.1.0]hexane-3-carboxylate To a solution of tert-butyl (1R,5S,6r)-6-(5-methyl-1,2-oxazol-3-yl)-3-azabicyclo[3.1.0]hexane-3-carboxylate (2.46 g, 9.31 mmol, from Example 56) in DMF (25 mL) was added NBS (1.66 g, 9.31 mmol) at 0 to 5° C. The reaction was stirred at 15° C. for 5 hours to give a yellow solution. LCMS showed the reaction was completed. The reaction was diluted with H₂O (150 mL) and extracted with EA (40 mL×3). The combined organic layers were washed with NH₄Cl aq. (40 mL×2), NaHCO₃aq. (40 mL) and brine (40 mL), dried over Na₂SO₄, filtered and concentrated to afford the title compound (2.9 g, 90.786% yield) as light yellow oil.

$^1$H NMR (400 MHz, CHLOROFORM-d) δ 3.75-3.60 (m, 2H), 3.55-3.40 (m, 2H), 2.38 (s, 3H), 2.20-2.00 (m, 2H), 1.70-1.65 (m, 1H), 1.46 (s, 9H).

tert-butyl (1R,5S,6r)-6-(5-methyl-4-phenyl-1,2-oxazol-3-yl)-3-azabicyclo[3.1.0]hexane-3-carboxylate A mixture of tert-butyl (1R,5S,6r)-6-(4-bromo-5-methyl-1,2-oxazol-3-yl)-3-azabicyclo[3.1.0]hexane-3-carboxylate (100 mg, 0.29 mmol), phenylboronic acid (42.63 mg, 0.35 mmol) and NaHCO₃ (73.43 mg, 0.87 mmol) in DMF (1.5 mL) and H₂O (0.2 mL) was purged with N₂. Then, Pd(dppf)Cl₂ (21.32 mg, 0.03 mmol) was added and the mixture was purged with N₂ and heated at 90° C. under N₂ atmosphere for 12 h to give black mixture. The mixture was diluted with EtOAc (20 mL) and H₂O (10 mL). The solid was filtered off. The organic layer was washed with H₂O (10 mL) and brine (10 mL), then, dried over Na₂SO₄ and concentrated in vacuum to give brown oil. The brown oil was purified by prep-TLC (PE/EtOAc=6/1) to give the title compound (50 mg, 0.1469 mmol, 50.411% yield) as a white solid.

LC-MS Method1 0.943 min, MS (m/z) 340.9 (M+H⁺).

(1R,5S,6r)-6-(5-methyl-4-phenyl-1,2-oxazol-3-yl)-3-azabicyclo[3.1.0]hexane hydrochloride A mixture of tert-butyl (1R,5S,6r)-6-(5-methyl-4-phenyl-1,2-oxazol-3-yl)-3-azabicyclo[3.1.0]hexane-3-carboxylate (50 mg, 0.15 mmol) in 4M HCl/dioxane (5. mL, 0.15 mmol) was stirred at 0° C. for 50 min to give colorless solution. The reaction was concentrated in vacuum to give the title compound (50 mg, 0.1807 mmol, 123% yield) as pale yellow gum, which was used directly in the next step.

(1-isopropyl-1H-imidazol-4-yl)[(1R,5S,6r)-6-(5-methyl-4-phenyl-1,2-oxazol-3-yl)-3-azabicyclo[3.1.0]hex-3-yl]methanone To a solution of 1-isopropylimidazole-4-carboxylic acid (36.21 mg, 0.23 mmol) in DMF (2 mL) were added HATU (82.88 mg, 0.22 mmol), Et₃N (0.06 mL, 0.45 mmol) and (1R,5S,6r)-6-(5-methyl-4-phenyl-1,2-oxazol-3-yl)-3-azabicyclo[3.1.0]hexane hydrochloride (50 mg, 0.18 mmol) at 20° C. The reaction was stirred at 20° C. for 4 h to give pale brown solution. The reaction was concentrated in vacuum to give pale brown gum, which was purified by prep-HPLC (NH₃). The fluent was concentrated and lyophilized to give the title compound (32.53 mg, 0.0864 mmol, 47.831% yield) as pale yellow solid.

LC-MS Method1: 377.0 [M+H⁺]

$^1$H NMR (400 MHz, CHLOROFORM-d) δ=7.57 (d, J=1.3 Hz, 1H), 7.40-7.33 (m, 3H), 7.28 (d, J=7.4 Hz, 1H), 7.25-7.21 (m, 2H), 4.59 (d, J=12.1 Hz, 1H), 4.26 (spt, J=6.8 Hz, 1H), 4.07 (d, J=12.6 Hz, 1H), 3.96 (dd, J=4.4, 11.9 Hz, 1H), 3.62 (dd, J=4.2, 12.6 Hz, 1H), 2.33 (s, 3H), 2.32-2.28 (m, 1H), 2.13-2.06 (m, 1H), 1.53-1.53 (m, 1H), 1.41 (d, J=6.6 Hz, 6H)

Example 56 (1-isopropyl-1H-imidazol-4-yl)[(1R,5S, 6r)-6-(5-methyl-1,2-oxazol-3-yl)-3-azabicyclo[3.1.0] hex-3-yl]methanone tert-butyl (1R,5S,6r)-6-(5-methyl-1,2-oxazol-3-yl)-3-azabicyclo[3.1.0]hexane-3-carboxylate To a solution of tert-butyl (1R,5S,6r)-6-[(Z)-chloro(hydroxyimino)methyl]-3-azabicyclo[3.1.0]hexane-3-carboxylate (0.5 g, 1.92 mmol) and prop-1-en-2-yl acetate (1.04 mL, 9.59 mmol) in DCM (6 mL) was added Et$_3$N (0.8 mL, 5.75 mmol) drop-wise at 0° C. The reaction was then stirred at 20° C. for 12 h to give pale yellow solution. LCMS showed the desired MS. The solution was diluted with DCM (30 mL) and washed with H$_2$O (15 mL×2), saturated NaHCO$_3$ (15 mL) and brine (15 mL). The organic layer was dried over Na$_2$SO$_4$ and concentrated in vacuum to give the title compound (460 mg, 1.7403 mmol, 90.747% yield) as pale yellow oil, which was used directly in the next step.

(1R,5S,6r)-6-(5-methyl-1,2-oxazol-3-yl)-3-azabicyclo[3.1.0]hexane TFA Salt

To a solution of tert-butyl (1R,5S,6r)-6-(5-methyl-1,2-oxazol-3-yl)-3-azabicyclo[3.1.0]hexane-3-carboxylate (235 mg, 0.89 mmol) in DCM (5 mL) was added 2,2,2-trifluoroacetic acid (1. mL, 13.06 mmol). The reaction mixture was stirred at 20° C. for 3 hr to give a yellow solution. The reaction mixture was evaporated in vacuum to give the title compound (260 mg, 0.9345 mmol, 105.11% yield) as yellow oil. It used directly in the next step.

(1-isopropyl-1H-imidazol-4-yl)[(1R,5S,6r)-6-(5-methyl-1,2-oxazol-3-yl)-3-azabicyclo[3.1.0]hex-3-yl]methanone A 100 mL round-bottom flask was charged with 1-isopropylimidazole-4-carboxylic acid (70 mg, 0.45 mmol), N-ethyl-N-isopropylpropan-2-amine (0.24 mL, 1.41 mmol), HATU (190.94 mg, 0.50 mmol) and DMF (3 mL). After stirring for 30 min, (1R,5S,6r)-6-(5-methyl-1,2-oxazol-3-yl)-3-azabicyclo[3.1.0]hexane TFA salt (126.33 mg, 0.45 mmol) was added. The reaction mixture was stirred at 20° C. for 16 hr to give a yellow solution. H$_2$O (30 mL) was added and it was extracted with EtOAc (30 mL×2). The combined organic layer was dried over Na$_2$SO$_4$ and concentrated in vacuum to give a yellow oil. The crude was purified by prep-HPLC (NH$_3$). The afforded flows were concentrated in vacuum to remove most of CH$_3$CN and lyophilized to give the title compound (13.06 mg, 0.0383 mmol, 8.4313% yield) as white solid.

LC-MS Method1: 301.1 [M+H$^+$]

$^1$H NMR (400 MHz, DMSO-d$_6$) δ 9.22 (br s, 1H), 8.35 (s, 1H), 6.07 (s, 1H), 4.66 (td, J=6.64, 13.35 Hz, 1H), 4.11 (br d, J=10.76 Hz, 1H), 4.02 (br d, J=12.63 Hz, 1H), 3.98 (br dd, J=4.06, 10.82 Hz, 1H), 3.63 (br dd, J=4.19, 12.57 Hz, 1H), 2.34 (s, 3H), 2.14-2.20 (m, 1H), 2.05-2.10 (m, 1H), 1.84 (t, J=3.38 Hz, 1H), 1.51 (d, J=6.63 Hz, 6H)

Example 57 [(1R,5S,6r)-6-(1,2-benzoxazol-3-yl)-3-azabicyclo[3.1.0]hex-3-yl](1-isopropyl-1H-imidazol-4-yl)methanone N-phenoxyacetamide To a solution of (aminooxy)benzene (200 mg, 1.37 mmol) in THF (3 mL) was added Ac$_2$O (280.49 mg, 2.75 mmol) at 0° C. The mixture was stirred at 20° C. for 3 h to give brown suspension. The reaction mixture was concentrated directly. The crude product was purified by flash column (PE to 20% EtOAc in PE) to give the title compound (170 mg, 1.1246 mmol, 81.868% yield) as white solid.

$^1$H NMR (400 MHz, DMSO-d6) δ=11.67 (brs, 1H), 7.35-7.25 (m, 2H), 7.05-6.95 (m, 3H), 1.92 (s, 3H).

tert-butyl (1R,5S,6r)-6-(1,2-benzoxazol-3-yl)-3-azabicyclo[3.1.0]hexane-3-carboxylate To a solution of N-phenoxyacetamide (50 mg, 0.33 mmol) in tert-Amyl alcohol (1.5 mL, 0.33 mmol) were added Pd(TFA)$_2$ (9.92 mg, 0.03 mmol), tert-butyl 6-formyl-3-azabicyclo[3.1.0]hexane-3-carboxylate (139.76 mg, 0.66 mmol) and TBHP (0.17 mL, 0.83 mmol). The mixture was stirred at 60° C. under N$_2$ for 12 h to give brown solution. The reaction mixture was poured into NaHSO$_3$ aq. (20 mL) and extracted with EtOAc (20 mL×4). The combined organic layers were washed with brine (50 mL), dried over Na$_2$SO$_4$, filtered and concentrated under reduced pressure. The residue was purified by prep-TLC (PE:EtOAc=6:1) to give the title compound (20 mg, 0.0666 mmol, 20.131% yield) as white gum.

3-[(1R,5S,6r)-3-azabicyclo[3.1.0]hex-6-yl]-1,2-benzoxazole hydrochloride

To a solution of tert-butyl (1R,5S,6r)-6-(1,2-benzoxazol-3-yl)-3-azabicyclo[3.1.0]hexane-3-carboxylate (20 mg, 0.07 mmol) was added HCl/dioxane (2.0 mL, 8 mmol). The mixture was stirred at 20° C. for 1 h to give colorless solution. TLC (PE:EtOAc=5:1) showed the reaction was completed. The reaction mixture was concentrated directly to give the title compound (15 mg, 0.0634 mmol, 95.168% yield) as brown gum.

[(1R,5S,6r)-6-(1,2-benzoxazol-3-yl)-3-azabicyclo [3.1.0]hex-3-yl](1-isopropyl-1H-imidazol-4-yl) methanone To a solution of 1-isopropylimidazole-4-carboxylic acid (22.08 mg, 0.14 mmol) in DMF (1.5 mL) were added HATU (43.79 mg, 0.11 mmol), IEA (0.06 mL, 0.38 mmol) and 3-[(1R,5S,6r)-3-azabicyclo[3.1.0]hex-6-yl]-1,2-benzoxazole hydrochloride (30 mg, 0.10 mmol).

The mixture was stirred at 20° C. for 1 h to give brown solution. LCMS showed the desire MS and a part of 3-[(1R, 5S,6r)-3-azabicyclo[3.1.0]hex-6-yl]-1,2-benzoxazole hydrochloride was remained. The mixture was stirred at 20° C. for 12 h to give brown solution. LCMS showed the desire MS as major peak. The mixture was poured into H$_2$O (15 mL) and extracted with EtOAc (15 mL×5). The combined organic layer was washed with brine (50 mL), dried over Na$_2$SO$_4$ and concentrated to dryness. The residue was purified by prep-TLC (MeOH:EtOAc=1:11) and the afforded solid was triturated with MTBE (2 mL) and dried in air to give as brown solid. The residue was purified by prep-HPLC (NH$_3$). The afforded flows were combined, concentrated to remove most of CH3CN and lyophilized to give the title compound (10 mg, 0.0297 mmol, 31.14% yield) as white solid.

LC-MS Method1: 336.9 [M+H$^+$]

$^1$H NMR (400 MHz, CHLOROFORM-d) δ ppm 7.73 (1H, d, J=1.25 Hz), 7.68 (1H, d, J=8.03 Hz), 7.47-7.57 (3H, m), 7.31 (1H, dd, J=7.91, 3.89 Hz), 4.91 (1H, br d, J=12.05 Hz), 4.34-4.40 (2H, m), 4.08 (1H, br dd, J=12.05, 3.76 Hz), 3.74 (1H, br dd, J=12.55, 4.02 Hz), 2.45-2.53 (1H, m), 2.31-2.41 (1H, m), 2.07 (1H, t, J=3.26 Hz), 1.53 (6H, d, J=6.53 Hz)

Example 58 [(1R,5S,6r)-6-(4-cyclopropyl-5,5-dimethyl-4,5-dihydro-1,2,4-oxadiazol-3-yl)-3-azabicyclo [3.1.0]hex-3-yl](1-isopropyl-1H-imidazol-4-yl) methanone N-cyclopropyl-2-propanimine To a solution of cyclopropylamine (0.24 mL, 3.5 mmol) and acetone (1017.34 mg, 17.52 mmol) in DMF (2.5 mL) was added 4A MS (2000 mg, 3.5 mmol). The mixture was stirred at 110° C. for 4 hr without monitor. The mixture was filtered to give the title compound (2000 mg, 2.0585 mmol, 58.759% yield). The crude product was used directly for next step.

tert-butyl (1R,5S,6r)-6-(4-cyclopropyl-5,5-dimethyl-4,5-dihydro-1,2,4-oxadiazol-3-yl)-3-azabicyclo [3.1.0]hexane-3-carboxylate To a solution of $Et_3N$ (0.36 mL, 2.18 mmol) and N-cyclopropyl-2-propanimine (5000 mg, 5.15 mmol) was added tert-butyl (1R,5S,6r)-6-[(Z)-chloro(hydroxyimino)methyl]-3-azabicyclo[3.1.0]hexane-3-carboxylate (200 mg, 0.73 mmol). The mixture was stirred at 20° C. for 16 hr. LCMS showed the desired mass. The mixture was diluted with $H_2O$ (50 mL) and extracted by EtOAc (30 mL×2). The organic phase was washed with brine (50 mL), dried over anhydrous $Na_2SO_4$ and concentrated to give a residue. The residue was purified by flash column (PE:EtOAc=1:0-0:1) to afford the title compound (80 mg, 0.2489 mmol, 34.192% yield) as a yellow oil
$^1$H NMR (400 MHz, DMSO-d6) δ=11.67 (brs, 1H), 7.35-7.25 (m, 2H), 7.05-6.95 (m, 3H), 1.92 (s, 3H).

(1R,5S,6r)-6-(4-cyclopropyl-5,5-dimethyl-4,5-dihydro-1,2,4-oxadiazol-3-yl)-3-azabicyclo[3.1.0] hexane TFA Salt To a solution of tert-butyl (1R,5S,6r)-6-(4-cyclopropyl-5,5-dimethyl-4,5-dihydro-1,2,4-oxadiazol-3-yl)-3-azabicyclo [3.1.0]hexane-3-carboxylate (80 mg, 0.25 mmol) in DCM (4.4444 mL) was added TFA (0.44 mL, 5.98 mmol). The mixture was stirred at 20° C. for 4 h. TLC (PE:EtOAc=1:1) showed a new spot (Rf=0) was detected. The mixture was concentrated to afford the title compound (55 mg, 0.2485 mmol, 99.851% yield) as yellow oil. The crude was used for next step directly.

[(1R,5S,6r)-6-(4-cyclopropyl-5,5-dimethyl-4,5-dihydro-1,2,4-oxadiazol-3-yl)-3-azabicyclo[3.1.0]hex-3-yl](1-isopropyl-1H-imidazol-4-yl)methanone To a solution of (1R,5S,6r)-6-(4-cyclopropyl-5,5-dimethyl-4,5-dihydro-1,2,4-oxadiazol-3-yl)-3-azabicyclo[3.1.0] hexane TFA salt (55 mg, 0.25 mmol), 1-isopropylimidazole-4-carboxylic acid (42.15 mg, 0.27 mmol) and DIPEA (0.14 mL, 0.87 mmol) in DMF (2.4444 mL) was added HATU (142.52 mg, 0.37 mmol). The mixture was stirred at 20° C. for 1 hr to give a brown mixture. LCMS showed the starting material was consumed and the desired peak was detected. The reaction mixture was diluted with $H_2O$ (50 mL) and extracted by EtOAc (25 mL×3). The organic phase was washed with brine (50 mL×3), dried over anhydrous $Na_2SO_4$ and concentrated to give a residue. The residue was purified by Prep-HPLC ($NH_3$) to afford the title compound (7.32 mg, 0.0205 mmol, 8.2398% yield) as white solid.
LC-MS Method1: 358.0 [M+H$^+$]
$^1$H NMR (400 MHz, CHLOROFORM-d) δ=7.68 (d, J=1.6 Hz, 1H), 7.47 (d, J=1.2 Hz, 1H), 4.75 (d, J=12.0 Hz, 1H), 4.35 (spt, J=6.7 Hz, 1H), 4.16 (d, J=12.6 Hz, 1H), 3.96 (dd, J=4.3, 11.9 Hz, 1H), 3.64 (dd, J=4.4, 12.8 Hz, 1H), 2.32-2.26 (m, 1H), 2.23 (td, J=3.8, 7.3 Hz, 1H), 2.03 (td, J=3.8, 7.4 Hz, 1H), 1.50 (d, J=6.8 Hz, 6H), 1.46 (d, J=6.0 Hz, 6H), 1.43 (t, J=3.6 Hz, 1H), 0.75-0.68 (m, 4H)

Example 59 (1-isopropyl-1H-imidazol-4-yl)[(1R,5S, 6r)-6-(4,5,5-trimethyl-4,5-dihydro-1,2,4-oxadiazol-3-yl)-3-azabicyclo[3.1.0]hex-3-yl]methanone N-methyl-2-propanimine To a solution of methylamine (1.3 mL, 32.2 mmol) and acetone (9349.65 mg, 160.98 mmol) in DMF (22.976 mL) was added 4A MS (3000 mg, 32.2 mmol). The mixture was stirred at 110° C. for 4 h. The mixture was filtered to give the title compound (2000 mg, 2.8121 mmol, 8.7345% yield). The crude product was used directly for next step.

tert-butyl (1R,5S,6r)-6-(4,5,5-trimethyl-4,5-dihydro-1,2,4-oxadiazol-3-yl)-3-azabicyclo[3.1.0]hexane-3-carboxylate To a solution of $Et_3N$ (0.36 mL, 2.18 mmol) and N-methyl-2-propanimine (258.86 mg, 3.64 mmol) was added tert-butyl (1R,5S,6r)-6-[(Z)-chloro(hydroxyimino) methyl]-3-azabicyclo[3.1.0]hexane-3-carboxylate (200 mg, 0.73 mmol).
The mixture was stirred at 20° C. for 16 hr. LCMS showed desired mass. The mixture was diluted with $H_2O$ (50 mL) and extracted by EtOAc (30 ml×2). The organic phase was washed with brine (50 mL), dried over anhydrous $Na_2SO_4$ and concentrated to give a residue. The residue was purified by flash column (PE:EtOAc=1:0-0:1) to afford the title compound (140 mg, 0.4740 mmol, 65.109% yield) (PE: EtOAc=1:1, Rf=0.3) as a yellow oil.
$^1$H NMR (400 MHz, CHLOROFORM-d) δ=3.70 (d, J=11.2 Hz, 1H), 3.60 (d, J=11.2 Hz, 1H), 3.50-3.40 (m, 2H), 2.78 (s, 3H), 2.10-2.00 (m, 1H), 2.00-1.90 (m, 1H), 1.44 (s, 9H), 1.41 (s, 6H). 1.16-1.14 (m, 1H).

(1R,5S,6r)-6-(4,5,5-trimethyl-4,5-dihydro-1,2,4-oxadiazol-3-yl)-3-azabicyclo[3.1.0]hexane TFA Salt To a solution of tert-butyl (1R,5S,6r)-6-(4,5,5-trimethyl-4,5-dihydro-1,2,4-oxadiazol-3-yl)-3-azabicyclo[3.1.0] hexane-3-carboxylate (140 mg, 0.47 mmol) in DCM (2.8 mL) was added TFA (0.56 mL, 7.54 mmol). The reaction mixture was stirred at 15° C. for 16 hr to give a brown mixture. LCMS showed the starting material was consumed up. The reaction mixture was concentrated to give the title compound as a brown oil. The residue was used for the next step directly.
LC-MS Method1 0.214 min, MS (m/z) 195.9 (M+H$^+$).

(1-isopropyl-1H-imidazol-4-yl)[(1R,5S,6r)-6-(4,5,5-trimethyl-4,5-dihydro-1,2,4-oxadiazol-3-yl)-3-azabicyclo[3.1.0]hex-3-yl]methanone To a solution of 5-isopropyl-1H-pyrazole-3-carboxylic acid (72.64 mg, 0.47 mmol) in DMF (3.5385 mL) were added HATU (135.48 mg, 0.71 mmol) and DIPEA (182.7 mg, 1.41 mmol). The reaction mixture was stirred at 15° C. for 30 min. Then (1R,5S,6r)-6-(4,5,5-trimethyl-4,5-dihydro-1,2,4-oxadiazol-3-yl)-3-azabicyclo[3.1.0]hexane TFA salt (92 mg, 0.47 mmol) was added to the reaction. The reaction mixture was stirred at 15° C. for 0.5 hr to give a yellow mixture. LCMS showed the desired MS. The reaction mixture was purified by prep-HPLC (NH₃) to give the title compound (18.72 mg, 0.0565 mmol, 11.989% yield) as white powder.

LC-MS Method1: 331.9 [M+H⁺]

¹H NMR (400 MHz, CHLOROFORM-d) δ=7.67 (d, J=1.2 Hz, 1H), 7.47 (d, J=1.2 Hz, 1H), 4.75 (d, J=12.0 Hz, 1H), 4.35 (spt, J=6.7 Hz, 1H), 4.19 (d, J=12.4 Hz, 1H), 3.94 (dd, J=4.3, 12.0 Hz, 1H), 3.62 (dd, J=4.4, 12.8 Hz, 1H), 2.76 (s, 3H), 2.20 (td, J=3.7, 7.3 Hz, 1H), 2.06-2.00 (m, 1H), 1.50 (d, J=6.4 Hz, 6H), 1.40 (d, J=4.0 Hz, 6H), 1.15 (t, J=3.4 Hz, 1H)

Example 60 [(1R,5S,6r)-6-(4-ethyl-5,5-dimethyl-4,5-dihydro-1,2,4-oxadiazol-3-yl)-3-azabicyclo[3.1.0]hex-3-yl](1-isopropyl-1H-imidazol-4-yl)methanone tert-butyl (1R,5S,6r)-6-(4-ethyl-5,5-dimethyl-4,5-dihydro-1,2,4-oxadiazol-3-yl)-3-azabicyclo[3.1.0]hexane-3-carboxylate To a solution of Et₃N (0.36 mL, 2.18 mmol) and N-ethylpropan-2-imine (309.93 mg, 3.64 mmol) was added tert-butyl (1R,5S,6r)-6-[(Z)-chloro(hydroxyimino)methyl]-3-azabicyclo[3.1.0]hexane-3-carboxylate (200 mg, 0.73 mmol). The mixture was stirred at 20° C. for 16 hr. LCMS showed the desired mass. The mixture was diluted with H₂O (50 mL) and extracted by EtOAc (30 mL×2). The organic phase was washed with brine (50 mL), dried over anhydrous Na₂SO₄ and concentrated to give a residue. The residue was purified by flash column (PE:EtOAc=1:0-0:1) to afford the title compound (140 mg, 0.4525 mmol, 62.158% yield) (PE:EtOAc=1:1, Rf=0.3) as a yellow oil.

¹H NMR (400 MHz, CHLOROFORM-d) δ=3.68 (d, J=11.2 Hz, 1H), 3.58 (d, J=11.2 Hz, 1H), 3.45-3.30 (m, 2H), 3.18 (q, J=6.8 Hz, 2H), 2.30-2.20 (m, 1H), 2.00-1.90 (m, 1H), 1.45 (s, 9H), 1.42 (s, 3H), 1.21 (t, J=6.8 Hz, 3H), 1.14-1.13 (m, 1H).

(1R,5S,6r)-6-(4-ethyl-5,5-dimethyl-4,5-dihydro-1,2,4-oxadiazol-3-yl)-3-azabicyclo[3.1.0]hexane TFA Salt To a solution of tert-butyl (1R,5S,6r)-6-(4-ethyl-5,5-dimethyl-4,5-dihydro-1,2,4-oxadiazol-3-yl)-3-azabicyclo[3.1.0]hexane-3-carboxylate (140 mg, 0.45 mmol) in DCM (2.6731 mL) was added TFA (0.53 mL, 7.2 mmol). The reaction mixture was stirred at 15° C. for 16 hr to give a brown mixture. LCMS showed the starting material was consumed up. The reaction mixture was concentrated to give the title compound as brown oil. The residue was used for the next step directly.

LC-MS Method1 0.785 min, MS (m/z) 309.9 (M+H⁺).

[(1R,5S,6r)-6-(4-ethyl-5,5-dimethyl-4,5-dihydro-1,2,4-oxadiazol-3-yl)-3-azabicyclo[3.1.0]hex-3-yl](1-isopropyl-1H-imidazol-4-yl)methanone To a solution of 1-isopropylimidazole-4-carboxylic acid (69.24 mg, 0.45 mmol) in DMF (3.373 mL) were added HATU (129.15 mg, 0.67 mmol) and DIPEA (0.22 mL, 1.35 mmol). The reaction mixture was stirred at 15° C. for 30 min. Then the (1R,5S,6r)-6-(4-ethyl-5,5-dimethyl-4,5-dihydro-1,2,4-oxadiazol-3-yl)-3-azabicyclo[3.1.0]hexane TFA salt (94 mg, 0.45 mmol) was added to the reaction. The reaction mixture was stirred at 15° C. for 0.5 hr to give a yellow mixture. LCMS showed the desired MS. The reaction mixture was purified by prep-HPLC (NH₃) to give the title compound (9.9 mg, 0.0287 mmol, 6.3809% yield) as off-white solid.

LC-MS Method1: 346.0 [M+H⁺]

¹H NMR (400 MHz, CHLOROFORM-d) δ=7.67 (d, J=1.2 Hz, 1H), 7.47 (d, J=1.2 Hz, 1H), 4.73 (d, J=12.0 Hz, 1H), 4.35 (m, 1H), 4.17 (d, J=12.6 Hz, 1H), 3.96 (dd, J=4.0, 12.0 Hz, 1H), 3.64 (dd, J=4.0, 12.6 Hz, 1H), 3.16 (m, 2H), 2.24 (m, 1H), 2.05 (m, 1H), 1.50 (d, J=6.8 Hz, 6H), 1.42 (d, J=5.6 Hz, 6H), 1.19 (t, J=7.2 Hz, 3H), 1.14 (t, J=3.4 Hz, 1H)

Example 61 (1-isopropyl-1H-imidazol-4-yl)[(1R,5S,6r)-6-([1,2,4]triazolo[4,3-a]pyridin-3-yl)-3-azabicyclo[3.1.0]hex-3-yl]methanone tert-butyl (1R,5S,6r)-6-{[2-(2-pyridinyl)hydrazino]carbonyl}-3-azabicyclo[3.1.0]hexane-3-carboxylate To a mixture of (1R,5S,6r)-3-{[(tert-butyl)oxy]carbonyl}-3-azabicyclo[3.1.0]hexane-6-carboxylic acid (300 mg, 1.32 mmol) in DMF (5 mL) were added 2-hydrazinylpyridine (144.06 mg, 1.32 mmol), Et₃N (0.2 mL, 1.45 mmol), and HATU (555.13 mg, 1.45 mmol). The reaction mixture was stirred at 15° C. for 16 h to give brown mixture. The reaction mixture was concentrated in vacuo to give a residue. The residue was purified by silica column (SiO₂, petroleum ether:Ethyl acetate=6:1 to 0:1) to give the title compound (418 mg, 1.3129 mmol, 99.459% yield) as yellow gum.

¹H NMR (400 MHz, CHLOROFORM-d) δ=8.55 (dd, J=4.4, 1.6 Hz, 1H), 8.27 (dd, J=9.2, 1.2 Hz, 1H), 8.03 (d, J=4.8 Hz, 1H), 7.57 (t, J=9.2 Hz, 1H), 7.29 (dd, J=8.4, 4.4 Hz, 1H), 6.80-6.70 (m, 1H), 3.60-3.50 (m, 2H), 3.40-3.30 (m, 3H), 2.10-2.00 (m, 2H), 1.47-1.46 (m, 1H), 1.35 (s, 9H).

tert-butyl (1R,5S,6r)-6-([1,2,4]triazolo[4,3-a]pyridin-3-yl)-3-azabicyclo[3.1.0]hexane-3-carboxylate To a mixture of tert-butyl (1R,5S,6r)-6-{[2-(2-pyridinyl)hydrazino]carbonyl}-3-azabicyclo[3.1.0]hexane-3-carboxylate (200 mg, 0.63 mmol) in MeCN (4 mL) was added Burgess Reagent (149.7 mg, 0.63 mmol). The reaction mixture was stirred at 90° C. for 12 h to give yellow mixture. TLC (DCM/MeOH=10/1) showed the starting materials was consumed completely and a new spot was detected. The reaction mixture was concentrated in vacuo to give residue. The residue was purified by prep-TLC (DCM/MeOH=10/1) to afford the title compound (64 mg, 0.2131 mmol, 33.919% yield) as yellow solid.

LC-MS Method1 0.668, MS (m/z) 300.9 (M+H⁺).

3-[(1R,5S,6r)-3-azabicyclo[3.1.0]hex-6-yl][1,2,4]triazolo[4,3-a]pyridine TFA Salt To a solution of tert-butyl (1R,5S,6r)-6-([1,2,4]triazolo[4,3-a]pyridin-3-yl)-3-azabicyclo[3.1.0]hexane-3-carboxylate (66.2 mg, 0.22 mmol) in DCM (2 mL) was added TFA (0.2 mL, 2.61 mmol). The reaction mixture was stirred at 25° C. for 2 h to give yellow mixture. The reaction mixture was concentrated in vacuo to give the title compound. The crude product was used directly in the next step.

(1-isopropyl-1H-imidazol-4-yl)[(1R,5S,6r)-6-([1,2,4]triazolo[4,3-a]pyridin-3-yl)-3-azabicyclo[3.1.0]hex-3-yl]methanone To a mixture of 3-[(1R,5S,6r)-3-azabicyclo[3.1.0]hex-6-yl][1,2,4]triazolo[4,3-a]pyridine TFA salt (40 mg, 0.20 mmol) in DMF (2 mL) were added 1-isopropylimidazole-4-carboxylic acid (30.8 mg, 0.20 mmol), Et$_3$N (0.11 mL, 0.80 mmol), and HATU (114.55 mg, 0.30 mmol). The reaction mixture was stirred at 25° C. for 12 h to give yellow mixture. The crude product was purified by prep-HPLC (NH$_3$) to give the title compound (8.6 mg, 12.8% yield) as yellow gum.

$^1$H NMR (400 MHz, CDCl$_3$) δ=7.97 (d, J=7.0 Hz, 1H), 7.68-7.62 (m, 2H), 7.44 (s, 1H), 7.18-7.14 (m, 1H), 6.79 (t, J=6.8 Hz, 1H), 4.90 (d, J=12.0 Hz, 1H), 4.40-4.19 (m, 2H), 4.00 (dd, J=4.1, 12.1 Hz, 1H), 3.69 (dd, J=4.1, 12.5 Hz, 1H), 2.50 (td, J=3.7, 7.3 Hz, 1H), 2.31 (td, J=3.7, 7.2 Hz, 1H), 1.88 (t, J=3.3 Hz, 1H), 1.45 (d, J=6.8 Hz, 6H).

Example 62 (1-isopropyl-1H-imidazol-4-yl)[(1R,5S,6r)-6-([1,2,3]triazolo[1,5-a]pyridin-3-yl)-3-azabicyclo[3.1.0]hex-3-yl]methanone tert-butyl (1R,5S,6r)-6-[hydroxy(2-pyridinyl)methyl]-3-azabicyclo[3.1.0]hexane-3-carboxylate To a solution of tert-butyl (1R,5S,6r)-6-formyl-3-azabicyclo[3.1.0]hexane-3-carboxylate (0.61 mL, 1.42 mmol) in THF (6 mL) was added bromo(2-pyridyl)magnesium (3.2 mL, 2.13 mmol) at 15° C. The reaction mixture was stirred at 0° C. for 4 hr to give a brown mixture. LCMS showed the desired MS. TLC (PE/EtOAc=1:2) showed anew spot. The reaction mixture was quenched with H$_2$O (30 mL) and extracted with EtOAc (30 mL×2). The organic layer was washed with brine (30 mL×2), dried over anhydrous Na$_2$SO$_4$, filtrated and concentrated under reduced pressure to give a residue. The residue was purified by silica gel column (PE/EtOAc=1:2) to give the title compound (200 mg, 0.6888 mmol, 48.505% yield) as light yellow gum.

$^1$H NMR (400 MHz, CHLOROFORM-d) δ=8.53 (d, J=8.4 Hz, 1H), 7.75-7.65 (m, 1H), 7.40-7.30 (m, 1H), 7.25-7.20 (m, 1H), 4.60-4.25 (m, 2H), 3.60-3.45 (m, 2H), 3.40-3.30 (m, 2H), 1.80-1.60 (m, 2H), 1.43 (s, 9H), 1.00-0.90 (m, 1H).

tert-butyl (1R,5S,6r)-6-(2-pyridinylcarbonyl)-3-azabicyclo[3.1.0]hexane-3-carboxylate To a solution of tert-butyl (1R,5S,6r)-6-[hydroxy(2-pyridinyl)methyl]-3-azabicyclo[3.1.0]hexane-3-carboxylate (200 mg, 0.69 mmol) in DCM (4.1931 mL) was added DMP (292.15 mg, 0.69 mmol) at 15° C. The reaction mixture was stirred at 15° C. for 20 min to give a white mixture. TLC (PE/EtOAc=1:1) showed a new spot. The reaction mixture was quenched with NaHCO$_3$ (30 mL) and extracted with DCM (30 mL×2). The organic layer was washed with brine (30 mL×2), dried over anhydrous Na$_2$SO$_4$, filtrated and concentrated under reduced pressure to give a residue. The residue was purified by silica gel column (PE/EtOAc=1:1) to give the title compound (200 mg, 0.6936 mmol, 100.7% yield) as white solid.

$^1$H NMR (400 MHz, CHLOROFORM-d) δ=8.77 (d, J=4.0 Hz, 1H), 8.10-7.90 (m, 2H), 7.70 (dd, J=4.8, 3.6 Hz, 1H), 3.57 (d, J=11.2 Hz, 2H), 3.50-3.40 (m, 2H), 3.24 (s, 1H), 2.23 (s, 2H), 1.41 (s, 3H).

tert-butyl (1R,5S,6r)-6-([1,2,3]triazolo[1,5-a]pyridin-3-yl)-3-azabicyclo[3.1.0]hexane-3-carboxylate To a solution of tert-butyl (1R,5S,6r)-6-(2-pyridinylcarbonyl)-3-azabicyclo[3.1.0]hexane-3-carboxylate (100 mg, 0.35 mmol) in EtOH (2.0973 mL) was added hydrazine hydrate (26.04 mg, 0.52 mmol). The reaction mixture was stirred at 60° C. for 6 hr to give a colorless mixture. Then copper acetate (3.45 mg, 0.02 mmol), ethyl acetate (10 mL) was added to the reaction mixture. Then the reaction mixture was stirred at 20° C. for 1 hr to give a colorless mixture. LCMS showed the desired MS. The reaction mixture was concentrated to give a residue. The residue was purified by prep-TLC (PE/EtOAc=1:1) to give the title compound (20 mg, 0.0666 mmol, 19.2% yield) as colorless oil LC-MS Method1 0.832 min, MS (m/z) 301.2 (M+H$^+$).

$^1$H NMR (400 MHz, CHLOROFORM-d) δ 8.65 (d, J=7.2 Hz, 1H), 7.69 (dd, J=7.6, 1.2 Hz, 1H), 7.19 (dd, J=8.0, 5.6 Hz, 1H), 6.95 (t, J=6.0 Hz, 1H), 3.84 (d, J=11.2 Hz, 1H), 3.75 (d, J=11.2 Hz, 1H), 3.60-3.50 (m, 2H), 2.35-2.25 (m, 1H), 2.20-2.10 (m, 1H), 1.95-1.90 (m, 1H), 1.48 (s, 9H).

3-[(1R,5S,6r)-3-azabicyclo[3.1.0]hex-6-yl][1,2,3]triazolo[1,5-a]pyridine TFA Salt To a solution of tert-butyl (1R,5S,6r)-6-([1,2,3]triazolo[1,5-a]pyridin-3-yl)-3-azabicyclo[3.1.0]hexane-3-carboxylate (30 mg, 0.10 mmol) in DCM (3.14 mL) was added TFA (0.01 mL, 0.10 mmol). The reaction mixture was stirred at 20° C. for 16 hr to give a colorless mixture. TLC (PE/EtOAc=1:1) showed a new spot. The reaction mixture was removed the solvent to give the title compound. The residue was used for the next step directly.

LC-MS Method1 0.289 min, MS (m/z) 200.9 (M+H$^+$).

(1-isopropyl-1H-imidazol-4-yl)[(1R,5S,6r)-6-([1,2,3]triazolo[1,5-a]pyridin-3-yl)-3-azabicyclo[3.1.0]hex-3-yl]methanone To a solution of 1-isopropylimidazole-4-carboxylic acid (23.1 mg, 0.15 mmol) in DMF (1.1251 mL) were added HATU (43.08 mg, 0.22 mmol) and DIPEA (0.07 mL, 0.45 mmol). The reaction mixture was stirred at 15° C. for 30 min. Then 3-[(1R,5S,6r)-3-azabicyclo[3.1.0]hex-6-yl][1,2,3]triazolo[1,5-a]pyridine TFA salt (30 mg, 0.15 mmol) was added to the reaction. The reaction mixture was stirred at 15° C. for 0.5 hr to give a yellow mixture. LCMS showed the desired MS. The reaction mixture was purified by prep-HPLC (FA) to give the title compound (14.4 mg, 0.0428 mmol, 28.573% yield) as white powder.

LC-MS Method1: 337.1 [M+H$^+$]

$^1$H NMR (400 MHz, DMSO-d$_6$) δ=8.94 (d, J=7.2 Hz, 1H), 8.12-7.73 (m, 3H), 7.35-7.22 (m, 1H), 7.10 (m, 1H), 4.77-4.41 (m, 2H), 4.22-3.85 (m, 2H), 3.60 (br s, 1H), 2.35-2.24 (m, 1H), 2.20-2.08 (m, 2H), 1.44 (br d, J=5.6 Hz, 6H)

Example 63 (1-isopropyl-1H-imidazol-4-yl)[(1R,5S,6r)-6-(1H-tetrazol-5-yl)-3-azabicyclo[3.1.0]hex-3-yl]methanone tert-butyl (1R,5S,6r)-6-carbamoyl-3-azabicyclo[3.1.0]hexane-3-carboxylate A solution of (1R,5S,6r)-3-{[(tert-butyl)oxy]carbonyl}-3-azabicyclo[3.1.0]hexane-6-carboxylic acid (1000 mg, 4.4 mmol), 1H-benzo[d][1,2,3]triazol-1-ol (713.47 mg, 5.28 mmol), N-ethyl-N-isopropylpropan-2-amine (0.91 mL, 5.28 mmol) and EDCI (1012.23 mg, 5.28 mmol) in DCM (10 mL) was stirred at 10° C. for 30 min. Then it was cooled to 0° C. and NH$_3$/EtOH (5 mL, 40 mmol) was added drop-wise to stirred for 16 hr to give a white suspension. TLC (DCM/ MeOH=10/1 Rf=0.1) showed a new spot was detected. H$_2$O (10 mL) was added and it was extracted with EtOAc (10 mL×2). The combined organic layer dried over Na$_2$SO$_4$ and concentrated in vacuum to give the title compound (1050 mg, 4.6405 mmol, 105.46% yield) as white solid.

$^1$H NMR (400 MHz, CHLOROFORM-d) δ=5.59 (brs, 1H), 5.29 (brs, 1H), 3.61 (d, J=11.2 Hz, 1H), 3.59 (d, J=11.2 Hz, 1H), 3.45-3.35 (m, 2H), 2.27 (t, J=7.2 Hz, 1H), 2.01 (brs, 2H), 1.37 (s, 9H).

tert-butyl (1R,5S,6r)-6-cyano-3-azabicyclo[3.1.0] hexane-3-carboxylate

To a solution of tert-butyl (1R,5S,6r)-6-carbamoyl-3-azabicyclo[3.1.0]hexane-3-carboxylate (620 mg, 2.74 mmol) in DMF (12.4 mL) was added 2,4,6-trichloro-1,3,5-triazine (0.57 mL, 5.48 mmol). The reaction mixture was stirred at 15° C. for 16 hr to give a yellow solution. TLC (PE/EA=3/1 Rf=0.2) showed a new spot was detected. H$_2$O (30 mL) was added and it was extracted with EtOAc (30 mL×2). The combined organic layer dried over Na2SO4 and concentrated in vacuum to give the title compound as a yellow oil. The crude was purified by silica gel chromatography (PE/EA=10/1 to 3/1) to give the title compound (380 mg, 1.8246 mmol, 66.591% yield) as colorless oil.

tert-butyl (1R,5S,6r)-6-(1H-tetrazol-5-yl)-3-azabicyclo[3.1.0]hexane-3-carboxylate A mixture of tert-butyl (1R,5S,6r)-6-cyano-3-azabicyclo [3.1.0]hexane-3-carboxylate (330 mg, 1.58 mmol), ammonia hydrochloride (169.52 mg, 3.17 mmol) and NaN$_3$ (206.02 mg, 3.17 mmol) in DMF (7.3333 mL) was stirred at 120° C. for 24 hr to give a yellow solution. TLC (EA, Rf=0.1) showed anew spot was detected. H$_2$O (10 mL) was added and it was extracted with EtOAc (15 mL×3). The combined organic layer was dried over Na$_2$SO$_4$ and concentrated in vacuum to give the title compound (380 mg, 1.5123 mmol, 95.437% yield) as yellow oil.

$^1$H NMR (400 MHz, DMSO-d$_6$) δ ppm 7.95 (brs, 1H), 3.70-3.40 (m, 4H), 2.15 (brs, 2H), 1.96 (t, J=3.2 Hz, 1H), 1.40 (s, 9H).

(1R,5S,6r)-6-(1H-tetrazol-5-yl)-3-azabicyclo[3.1.0] hexane TFA Salt tert-butyl (1R,5S,6r)-6-(1H-tetrazol-5-yl)-3-azabicyclo [3.1.0]hexane-3-carboxylate (120 mg, 0.4800 mmol) was dissolved in HCl/dioxane (2 mL, 0.4800 mmol) and it was stirred at 15° C. for 2 hr to give a colorless solution. The reaction was evaporated in vacuum to give the title compound as a colorless oil. It was directly used in the next step.

(1-isopropyl-1H-imidazol-4-yl)[(1R,5S,6r)-6-(1H-tetrazol-5-yl)-3-azabicyclo[3.1.0]hex-3-yl]methanone A 100 mL round-bottom flask was charged with 1-isopropylimidazole-4-carboxylic acid (60 mg, 0.39 mmol), HATU (163.66 mg, 0.43 mmol), N-ethyl-N-isopropylpropan-2-amine (0.27 mL, 1.56 mmol) and DMF (3 mL). After stirred for 30 min, (1R,5S,6r)-6-(1H-tetrazol-5-yl)-3-azabicyclo[3.1.0]hexane TFA salt (103.21 mg, 0.39 mmol) was added. The reaction mixture was stirred at 20° C. for 16 hr to give a yellow solution. H$_2$O (10 mL) was added and it was extracted with EtOAc (10 mL×2). The H$_2$O layer was purified by Prep-HPLC (NH$_3$). The afforded flows were concentrated in vacuum to remove most of CH$_3$CN and lyophilized to give the title compound (37.35 mg, 0.13 mmol, 33.402% yield) as white solid.

LC-MS Method1: 288.0 [M+H$^+$]

$^1$H NMR (400 MHz, DMSO-d$_6$) δ 9.14 (br s, 1H), 8.32 (s, 1H), 4.65 (td, J=6.64, 13.35 Hz, 1H), 4.17 (br d, J=10.88 Hz, 1H), 3.98-4.08 (m, 2H), 2.42 (br d, J=3.25 Hz, 1H), 2.32 (br d, J=3.75 Hz, 1H), 2.13 (t, J=3.31 Hz, 1H), 1.50 (d, J=6.63 Hz, 6H)

Example 64 (1R,5S,6r)-N-(propan-2-yl)-3-[1-(propan-2-yl)-1H-imidazole-4-carbonyl]-3-azabicyclo [3.1.0]hexane-6-carboxamide tert-butyl (1R,5S,6r)-6-(isopropylcarbamoyl)-3-azabicyclo[3.1.0]hexane-3-carboxylate To a solution of (1R,5S,6r)-3-{[(tert-butyl)oxy]carbonyl}-3-azabicyclo[3.1.0]hexane-6-carboxylic acid (100 mg, 0.44 mmol) in DMF (1.5 mL) were added HATU (201.87 mg, 0.5300 mmol), Et$_3$N (0.22 mL, 1.32 mmol) and propan-2-amine (52.02 mg, 0.8800 mmol). The mixture was stirred at 20° C. for 12 h to give yellow solution. TLC (PE: EtOAc=1:1) showed a new spot (Rf=0, 0.7). The reaction mixture was poured into H$_2$O (10 mL) and extracted with EtOAc (10 mL×4). The combined organic layers were washed with brine (20 mL), dried over Na$_2$SO$_4$, filtered and concentrated under reduced pressure to afford the title compound (110 mg 0.4099 mmol, 93.157% yield) (crude) as a white solid.

(1R,5S,6r)-N-isopropyl-3-azabicyclo[3.1.0]hexane-6-carboxamide TFA Salt

To a solution of (1R,5S,6r)-3-{[(tert-butyl)oxy]carbonyl}-3-azabicyclo[3.1.0]hexane-6-carboxylic acid (110 mg, 0.4100 mmol) in DCM (2.8947 mL) was added TFA (0.58 mL, 7.79 mmol). The resulting mixture was stirred at 20 to 25° C. for 30 min to give yellow solution. TLC (PE: EtOAc=1:1) showed a new spot (Rf=0, 0.4). The reaction mixture was filtered and concentrated under reduced pressure to afford the title compound (110 mg, 0.3897 mmol, 95.072% yield) (crude) as yellow oil.

(1R,5S,6r)-N-(propan-2-yl)-3-[1-(propan-2-yl)-1H-imidazole-4-carbonyl]-3-azabicyclo[3.1.0]hexane-6-carboxamide To a solution of 1-isopropylimidazole-4-carboxylic acid (120.16 mg, 0.78 mmol) in DMF (2 mL) were added HATU (193.68 mg, 0.51 mmol), Et$_3$N (0.19 mL, 1.17 mmol) and (1R,5S,6r)-N-isopropyl-3-azabicyclo[3.1.0]hexane-6-carboxamide TFA salt (110 mg, 0.39 mmol). The resulting mixture was stirred at 20 to 25° C. for 12 hours to give yellow solution. The reaction mixture was poured into H$_2$O (10 mL) and extracted with EtOAc (10 mL×4). The combined organic layers were dried over Na$_2$SO$_4$, filtered and concentrated under reduced pressure. The residue was purified by prep-HPLC (NH$_3$). The afforded flows were combined and concentrated to remove most of CH$_3$CN and lyophilized to afford the title compound (50.32 mg, 0.1653 mmol, 42.42% yield) as white solid.

LC-MS Method1: 305.2 [M+H⁺]

¹H NMR (400 MHz, CHLOROFORM-d) δ=7.65 (d, J=1.3 Hz, 1H), 7.47 (d, J=1.3 Hz, 1H), 5.41 (br d, J=7.8 Hz, 1H), 4.74 (d, J=11.8 Hz, 1H), 4.35 (spt, J=6.7 Hz, 1H), 4.17-4.02 (m, 2H), 3.90 (dd, J=4.0, 12.0 Hz, 1H), 3.61 (dd, J=4.0, 12.5 Hz, 1H), 2.19 (td, J=3.7, 7.2 Hz, 1H), 2.10 (td, J=3.4, 7.3 Hz, 1H), 1.50 (d, J=6.8 Hz, 6H), 1.16-1.13 (m, 6H)

Example 65 (1R,5S,6r)-N-tert-butyl-3-[1-(propan-2-yl)-1H-imidazole-4-carbonyl]-3-azabicyclo[3.1.0]hexane-6-carboxamide tert-butyl (1R,5S,6r)-6-[(tert-butyl)carbamoyl]-3-azabicyclo[3.1.0]hexane-3-carboxylate To a solution of (1R,5S,6r)-3-{[(tert-butyl)oxy]carbonyl}-3-azabicyclo[3.1.0]hexane-6-carboxylic acid (200 mg, 0.88 mmol) in Pyridine (2 mL) was added 2-methylpropan-2-amine (0.11 mL, 1.06 mmol). The reaction mixture was stirred at 20° C. for 0.5 hr to give a mixture. Then the EDCI (337.41 mg, 1.76 mmol) was added to the reaction mixture. The reaction mixture was stirred at 20° C. for 2 hr to give a brown mixture. TLC (PE/EtOAc=1:1) showed a new spot. The reaction mixture was diluted with H2O (10 mL) and extracted with EtOAc (20 mL×2). The organic layer was dried over anhydrous Na₂SO₄, filtrated and concentrated under reduced pressure to give a residue. The residue was purified by prep-TLC (PE/EtOAc=1:1) to give the title compound (200 mg, 0.7083 mmol, 80.48% yield) as white solid.

¹H NMR (400 MHz, CHLOROFORM-d) δ=5.43 (brs, 1H), 3.64 (d, J=11.2 Hz, 1H), 3.55 (d, J=11.2 Hz, 1H), 3.45-3.35 (m, 2H), 1.99 (s, 2H), 1.43 (s, 9H), 1.34 (s, 9H), 1.10-1.05 (m, 1H).

(1R,5S,6r)-N-(tert-butyl)-3-azabicyclo[3.1.0]hexane-6-carboxamide TFA Salt

To a solution of tert-butyl (1R,5S,6r)-6-[(tert-butyl)carbamoyl]-3-azabicyclo[3.1.0]hexane-3-carboxylate (100 mg, 0.35 mmol) in DCM (1.3333 mL) was added TFA (0.01 mL, 0.07 mmol). The reaction mixture was stirred at 20° C. for 16 hr to give a colorless mixture. LCMS showed the desired MS. The reaction mixture was removed the solvent to give the title compound. The compound was used for the next step directly.

LC-MS Method1 0.293 min, MS (m/z) 182.9 (M+H⁺).

(1R,5S,6r)-N-tert-butyl-3-[1-(propan-2-yl)-1H-imidazole-4-carbonyl]-3-azabicyclo[3.1.0]hexane-6-carboxamide To a solution of 1-isopropylimidazole-4-carboxylic acid (54.14 mg, 0.35 mmol) in Pyridine (2.6371 mL) was added EDCI (134.63 mg, 0.70 mmol). The reaction mixture was stirred at 15° C. for 30 min. Then (1R,5S,6r)-N-(tert-butyl)-3-azabicyclo[3.1.0]hexane-6-carboxamide TFA salt (64 mg, 0.35 mmol) was added to the reaction. The reaction mixture was stirred at 15° C. for 0.5 hr to give a yellow mixture. The reaction mixture was quenched with H₂O and the resulting residue was purified by prep-HPLC (NH₃) to give the title compound (37.57 mg, 0.1180 mmol, 33.602% yield) as light yellow solid.

LC-MS Method1: 319.0 [M+H⁺]

¹H NMR (400 MHz, CHLOROFORM-d) δ=7.63 (d, J=1.2 Hz, 1H), 7.46 (d, J=1.2 Hz, 1H), 5.44 (s, 1H), 4.72 (d, J=11.2 Hz, 1H), 4.34 (spt, J=6.7 Hz, 1H), 4.11 (d, J=12.4 Hz, 1H), 3.87 (dd, J=3.6, 11.8 Hz, 1H), 3.58 (dd, J=4.4, 12.8 Hz, 1H), 2.16-2.09 (m, 1H), 2.04 (td, J=3.5, 7.3 Hz, 1H), 1.49 (d, J=6.8 Hz, 6H), 1.33 (s, 9H), 1.10 (t, J=3.1 Hz, 1H)

Example 66 (1R,5S,6r)-N-tert-butyl-N-methyl-3-[1-(propan-2-yl)-1H-imidazole-4-carbonyl]-3-azabicyclo[3.1.0]hexane-6-carboxamide tert-butyl (1R,5S,6r)-6-[methyl(tert-butyl)carbamoyl]-3-azabicyclo[3.1.0]hexane-3-carboxylate To a solution of tert-butyl (1R,5S,6r)-6-[(tert-butyl)carbamoyl]-3-azabicyclo[3.1.0]hexane-3-carboxylate (50 mg, 0.18 mmol) in DMF (2.4909 mL) was added NaH (8.5 mg, 0.35 mmol) at 20° C. Then the reaction mixture was stirred at 20° C. for 1 hr. Then MeI (0.04 mL, 0.71 mmol) in DMF (2.4909 mL) was added. The reaction mixture was stirred at 50° C. for 2 hr to give a light yellow mixture. TLC (PE/EtOAc=1:1) showed the new spot. The reaction mixture was quenched with H₂O (10 mL) and extracted with EtOAc (10 mL). The organic layer was dried over anhydrous Na₂SO₄, filtrated and concentrated under reduced pressure to give the title compound (52 mg, 0.1754 mmol, 99.077% yield) as brown oil ¹H NMR (400 MHz, CHLOROFORM-d) δ=3.66 (d, J=11.2 Hz, 1H), 3.60 (d, J=11.2 Hz, 1H), 3.50-3.40 (m, 2H), 3.02 (s, 3H), 2.10-2.00 (m, 1H), 2.00-1.90 (m, 1H), 1.50-1.40 (m, 1H), 1.44 (s, 9H), 1.38 (s, 9H), (1R,5S,6r)-N-methyl-N-(tert-butyl)-3-azabicyclo[3.1.0]hexane-6-carboxamide TFA Salt To a solution of tert-butyl (1R,5S,6r)-6-[methyl(tert-butyl)carbamoyl]-3-azabicyclo[3.1.0]hexane-3-carboxylate (52 mg, 0.18 mmol) in DCM (1 mL) was added TFA (0.1 mL, 1.35 mmol). The reaction mixture was stirred at 20° C. for 16 hr to give a brown mixture. TLC (PE/EtOAc=1:1) showed a new spot. The reaction mixture was concentrated under reduced pressure to give the title compound and it was used for the next step directly.

(1R,5S,6r)-N-tert-butyl-N-methyl-3-[1-(propan-2-yl)-1H-imidazole-4-carbonyl]-3-azabicyclo[3.1.0]hexane-6-carboxamide To a solution of 1-isopropylimidazole-4-carboxylic acid (78.54 mg, 0.51 mmol) in Pyridine (3.826 mL) was added EDCI (195.32 mg, 1.02 mmol). The reaction mixture was stirred at 15° C. for 30 min. Then (1R,5S,6r)-N-methyl-N-(tert-butyl)-3-azabicyclo[3.1.0]hexane-6-carboxamide TFA salt (100 mg, 0.51 mmol) was added to the reaction. The reaction mixture was stirred at 15° C. for 0.5 hr to give a yellow mixture. LCMS showed the desired MS. The reaction mixture was purified by prep-HPLC (NH₃) to give the title compound (16.42 mg, 0.0494 mmol, 9.6952% yield) as light yellow solid.

LC-MS Method1: 333.0 [M+H⁺]

¹H NMR (400 MHz, CHLOROFORM-d) δ=7.66 (d, J=1.2 Hz, 1H), 7.47 (d, J=1.2 Hz, 1H), 4.66 (d, J=12.0 Hz, 1H), 4.40-4.31 (m, 1H), 4.11 (d, J=12.8 Hz, 1H), 3.97 (dd, J=4.3, 12.0 Hz, 1H), 3.65 (dd, J=4.3, 12.8 Hz, 1H), 3.00 (s, 3H), 2.20 (td, J=3.8, 7.5 Hz, 1H), 2.05 (td, J=3.8, 7.4 Hz, 1H), 1.50 (d, J=6.8 Hz, 6H), 1.38 (s, 9H)

Example 67 (1R,5S,6r)-N-methyl-N-(1-methylcyclopropyl)-3-[1-(propan-2-yl)-1H-imidazole-4-carbonyl]-3-azabicyclo[3.1.0]hexane-6-carboxamide tert-butyl (1R,5S,6r)-6-[(1-methylcyclopropyl)carbamoyl]-3-azabicyclo[3.1.0]hexane-3-carboxylate To a mixture of (1R,5S,6r)-3-{[(tert-butyl)oxy]carbonyl}-3-azabicyclo[3.1.0]hexane-6-carboxylic acid (500 mg, 2.2 mmol) in DCM (20 mL) were added Et$_3$N (0.73 mL, 4.4 mmol) and HATU (1.26 g, 3.3 mmol). After 10 min, 1-methylcyclopropanamine hydrochloride (236.69 mg, 2.2 mmol) was added. The resulting mixture was stirred at 20° C. for 6 hours to give brown mixture. LCMS showed the desired peak was found. The reaction was diluted with H$_2$O (20 mL) and extracted with EtOAc (30 mL×3). The combined organic layers were separated, then dried over Na$_2$SO$_4$ and concentrated in vacuum to give brown oil. The crude oil was purified by prep-TLC (PE/EtOAc=1/1) to give the title compound (590 mg, 2.1044 mmol, 95.651% yield) as white solid.

LC-MS Method1: 227.0 [M+H$^+$].

$^1$H NMR (400 MHz, CHLOROFORM-d) δ=6.15-5.95 (m, 1H), 3.70-3.59 (m, 1H), 3.58-3.48 (m, 1H), 3.45-3.25 (m, 2H), 2.07-1.96 (m, 2H), 1.46-1.40 (m, 9H), 1.36 (s, 3H), 1.13-1.04 (m, 1H), 0.78-0.70 (m, 2H), 0.65-0.57 (m, 2H)

tert-butyl (1R,5S,6r)-6-[methyl(1-methylcyclopropyl)carbamoyl]-3-azabicyclo[3.1.0]hexane-3-carboxylate To a mixture of tert-butyl (1R,5S,6r)-6-[(1-methylcyclopropyl)carbamoyl]-3-azabicyclo[3.1.0]hexane-3-carboxylate (100 mg, 0.4000 mmol) in THF (5 mL) was added NaH (23.78 mg, 0.5900 mmol). The reaction mixture was then stirred at 0° C. for 15 min. Then MeI (0.03 mL, 0.4800 mmol) was added. The reaction mixture was stirred at 15° C. for 16 hr. TLC (PE/EA=1/1) showed a new spot (Rf=0.5) and the reaction was completed. The mixture was diluted with H$_2$O (20 mL), extracted with EA (10 mL×2), and then washed with H$_2$O (10 mL) and NH$_4$Cl (10 mL). The combined organic layers were dried over Na$_2$SO$_4$ and concentrated in vacuum to give crude oil. The crude oil was purified by prep-TLC (PE/EA=1/1) to give the title compound (100 mg, 0.3755 mmol, 94.732% yield) as off-white solid.

LC-MS Method1 0.825 min, MS (m/z) 295 (M+H$^+$).

(1R,5S,6r)-N-methyl-N-(1-methylcyclopropyl)-3-azabicyclo[3.1.0]hexane-6-carboxamide TFA Salt To a solution of tert-butyl (1R,5S,6r)-6-[methyl(1-methylcyclopropyl)carbamoyl]-3-azabicyclo[3.1.0]hexane-3-carboxylate (100 mg, 0.34 mmol) in DCM (2 mL) was added TFA (0.15 mL, 2.04 mmol) at 20° C. The mixture was stirred at 20° C. for 2 hours. LCMS showed the desired peak was found. The reaction mixture was concentrated under reduced pressure to give the title compound (100 mg, crude product) as yellow oil.

LC-MS Method1: 195.0 [M+H$^+$].

(1R,5S,6r)-N-methyl-N-(1-methylcyclopropyl)-3-[1-(propan-2-yl)-1H-imidazole-4-carbonyl]-3-azabicyclo[3.1.0]hexane-6-carboxamide To a mixture of 1-isopropylimidazole-4-carboxylic acid (75 mg, 0.49 mmol) in DCM (5 mL) were added HATU (278.97 mg, 0.73 mmol) and Et$_3$N (0.16 mL, 0.97 mmol). The mixture was stirred at 20° C. for 10 min under N$_2$. Then (1R,5S,6r)-N-methyl-N-(1-methylcyclopropyl)-3-azabicyclo[3.1.0]hexane-6-carboxamide TFA salt (94.51 mg, 0.49 mmol) in DCM (3 mL) was added. The resulting mixture was stirred at 20° C. for 16 hr to give brown mixture. LCMS showed the desired peak was found. The reaction was diluted with H$_2$O (20 mL) and extracted with DCM (20 mL). The combined organic layers were separated, then dried over Na$_2$SO$_4$ and concentrated in vacuum to give brown oil. The brown oil was purified by prep-HPLC (FA). The afforded flows were combined, concentrated to remove most of CH$_3$CN, added NH$_3$H$_2$O (0.5 mL) and lyophilized to afford the title compound (20 mg, 0.0605 mmol, 12.442% yield) as yellow solid.

LC-MS Method1: 331.1 [M+H$^+$].

$^1$H NMR (400 MHz, DMSO-d$_6$) δ=7.80 (br s, 2H), 4.66-4.37 (m, 2H), 4.00-3.78 (m, 2H), 3.50 (br d, J=5.1 Hz, 1H), 2.77 (s, 3H), 2.13-1.92 (m, 2H), 1.91-1.83 (m, 1H), 1.40 (d, J=6.6 Hz, 6H), 1.28 (s, 3H), 1.09-0.54 (m, 4H)

Example 68 (1R,5S,6r)-N-(1-cyanocyclopropyl)-3-[1-(propan-2-yl)-1H-imidazole-4-carbonyl]-3-azabicyclo[3.1.0]hexane-6-carboxamide ethyl (1R,5S,6r)-3-azabicyclo[3.1.0]hexane-6-carboxylate TFA Salt To a mixture of 6-ethyl 3-(tert-butyl) (1R,5S,6r)-3-azabicyclo[3.1.0]hexane-3,6-dicarboxylate (600 mg, 2.35 mmol) in DCM (10 mL) was added TFA (1 mL, 13.46 mmol).

The reaction was stirred at 25° C. for 3 h to give brown mixture. The reaction mixture was concentrated in vacuo to give the title compound (300 mg, crude).

ethyl (1R,5S,6r)-3-[(1-isopropyl-1H-imidazol-4-yl)carbonyl]-3-azabicyclo[3.1.0]hexane-6-carboxylate To a solution of ethyl (1R,5S,6r)-3-azabicyclo[3.1.0]hexane-6-carboxylate TFA salt (300 mg, 1.18 mmol) in THF (4 mL) were added Et$_3$N (0.81 mL, 5.88 mmol), 1-isopropylimidazole-4-carboxylic acid (181.16 mg, 1.18 mmol) and HATU (583.98 mg, 1.53 mmol). The resulting mixture was stirred at 20° C. for 12 h to give yellow mixture. The reaction mixture was concentrated and purified by silica column to give the title compound (170 mg, crude) as light yellow gum.

LC-MS Method1 0.598 min, MS (m/z) 291.9 (M+H$^+$).

(1R,5S,6r)-3-[(1-isopropyl-1H-imidazol-4-yl)carbonyl]-3-azabicyclo[3.1.0]hexane-6-carboxylic acid To a mixture of ethyl (1R,5S,6r)-3-[(1-isopropyl-1H-imidazol-4-yl)carbonyl]-3-azabicyclo[3.1.0]hexane-6-carboxylate (170 mg, 0.58 mmol) in THF/H$_2$O (4 mL, 3/1) was added hydroxylithium hydrate (31.83 mg, 0.76 mmol). The reaction was stirred at 25° C. for 12 h to give yellow mixture. TLC showed the starting material was consumed up. The reaction mixture was concentrated in vacuo to give the title compound (153 mg, crude) as light yellow solid.

LC-MS Method1 0.218 min, MS (m/z) 263.9 (M+H$^+$).

(1R,5S,6r)-N-(1-cyanocyclopropyl)-3-[1-(propan-2-yl)-1H-imidazole-4-carbonyl]-3-azabicyclo[3.1.0]hexane-6-carboxamide To a solution (1R,5S,6r)-3-[(1-isopropyl-1H-imidazol-4-yl)carbonyl]-3-azabicyclo[3.1.0]hexane-6-carboxylic acid (153 mg, 0.58 mmol) in DMF (2 mL) were added HATU (244.37 mg, 0.64 mmol), Et₃N (0.3 mL, 2.32 mmol) and 1-aminocyclopropanecarbonitrile hydrochloride (82.68 mg, 0.70 mmol). The reaction mixture was stirred at 25° C. for 12 h to give yellow mixture. The reaction mixture was concentrated in vacuo to give residue. The crude product was purified by prep-HPLC (NH₃) to give the title compound (5.98 mg) as a white solid LC-MS Method1: 328.1 [M+H⁺]

¹H NMR (400 MHz, CDCl₃) δ=7.56 (d, J=1.0 Hz, 1H), 7.40 (d, J=1.1 Hz, 1H), 6.69 (s, 1H), 4.63 (d, J=12.1 Hz, 1H), 4.37-4.23 (m, 1H), 4.02 (d, J=12.5 Hz, 1H), 3.81 (dd, J=3.9, 11.9 Hz, 1H), 3.52 (dd, J=4.1, 12.6 Hz, 1H), 2.22-2.15 (m, 1H), 2.11-2.03 (m, 1H), 1.46 (br d, J=2.5 Hz, 2H), 1.43 (d, J=6.8 Hz, 6H), 1.18 (br d, J=4.1 Hz, 2H), 1.13 (t, J=3.1 Hz, 1H)

Example 69 (1R,5S,6r)-N-(1-cyanocyclopropyl)-N-methyl-3-[1-(propan-2-yl)-1H-imidazole-4-carbonyl]-3-azabicyclo[3.1.0]hexane-6-carboxamide (1R,5S,6r)-N-(1-cyanocyclopropyl)-N-methyl-3-[1-(propan-2-yl)-1H-imidazole-4-carbonyl]-3-azabicyclo[3.1.0]hexane-6-carboxamide To a mixture of (1R,5S,6r)-N-(1-cyanocyclopropyl)-3-[(1-isopropyl-1H-imidazol-4-yl)carbonyl]-3-azabicyclo[3.1.0]hexane-6-carboxamide (15 mg, 0.05 mmol) in DMF (0.50 mL)/THF (0.50 ml) was added NaH (2.75 mg, 0.07 mmol) under ice-cooling. The reaction mixture was stirred for 0.3 h. Then MeI (19.51 mg, 0.14 mmol) was added. The mixture was stirred at 30° C. for 3 h. The reaction mixture was concentrated directly. Then the residue was purified by prep-HPLC (NH₃) to afford the title compound (2.8 mg, 0.0176 mmol, 38.356% yield) as white solid.

LC-MS Method1: 341.9 [M+H⁺]

¹H NMR (400 MHz, CHLOROFORM-d) δ=7.63 (br s, 1H), 7.41 (s, 1H), 4.64 (br s, 1H), 4.34-4.22 (m, 1H), 4.11-3.92 (m, 2H), 3.66 (br s, 1H), 3.00-2.85 (m, 3H), 2.28 (br s, 1H), 2.12 (br s, 1H), 1.84 (br s, 1H), 1.44 (d, J=6.8 Hz, 7H), 1.18 (s, 4H)

Example 70 (1R,5S,6r)-3-[1-(propan-2-yl)-1H-imidazole-4-carbonyl]-N-[1-(trifluoromethyl)cyclopropyl]-3-azabicyclo[3.1.0]hexane-6-carboxamide tert-butyl (1R,5S,6r)-6-{[1-(trifluoromethyl)cyclopropyl]carbamoyl}-3-azabicyclo[3.1.0]hexane-3-carboxylate To a solution of (1R,5S,6r)-3-{[(tert-butyl)oxy]carbonyl}-3-azabicyclo[3.1.0]hexane-6-carboxylic acid (200 mg, 0.88 mmol) in DMF (3 mL) were added HATU (370.09 mg, 0.97 mmol), Et₃N (0.34 mL, 2.64 mmol) and 1-(trifluoromethyl)cyclopropanamine hydrochloride (170.61 mg, 1.06 mmol). The resulting mixture was stirred at 25° C. for 12 h. TLC (PE:EtOAc=1:1) showed the reaction was completed. The reaction mixture was poured into H₂O (10 ml) and extracted with EtOAc (10 ml×3). The combined organic layers were dried over Na₂SO₄, filtered and concentrated under reduced pressure. The residue was purified by flash column (PE to 40% EtOAc in PE) to afford the title compound (328 mg, 0.9811 mmol, 111.48% yield, crude product) as a white solid.

¹H NMR (400 MHz, CHLOROFORM-d) δ=6.47 (s, 1H), 3.68-3.53 (m, 2H), 3.41 (br d, J=11.3 Hz, 2H), 2.12-2.03 (m, 2H), 1.48-1.46 (m, 1H), 1.44 (s, 9H), 1.31 (br s, 2H), 1.19 (t, J=3.1 Hz, 1H), 1.10 (br d, J=5.5 Hz, 2H)

(1R,5S,6r)-N-[1-(trifluoromethyl)cyclopropyl]-3-azabicyclo[3.1.0]hexane-6-carboxamide TFA Salt To a solution of tert-butyl (1R,5S,6r)-6-{[1-(trifluoromethyl)cyclopropyl]carbamoyl}-3-azabicyclo[3.1.0]hexane-3-carboxylate (50 mg, 0.15 mmol) in DCM (2 mL) was added 2,2,2-trifluoroacetic acid (0.3 mL, 3.92 mmol). The resulting mixture was stirred at 20 to 25° C. for 2 h. TLC (PE:EtOAc=1:1) showed the reaction was completed. The mixture was concentrated by purging with N₂ to afford the title compound (30 mg, 0.1281 mmol, 85.645% yield) as a white solid.

(1R,5S,6r)-3-[1-(propan-2-yl)-1H-imidazole-4-carbonyl]-N-[1-(trifluoromethyl)cyclopropyl]-3-azabicyclo[3.1.0]hexane-6-carboxamide To a solution of 1-isopropylimidazole-4-carboxylic acid (19.75 mg, 0.13 mmol) in DMF (2 mL) were added Et₃N (0.08 mL, 0.64 mmol), HATU (58.76 mg, 0.15 mmol) and (1R,5S,6r)-N-[1-(trifluoromethyl)cyclopropyl]-3-azabicyclo[3.1.0]hexane-6-carboxamide TFA salt (30 mg, 0.13 mmol). The resulting mixture was stirred at 20 to 25° C. for 16 h. The mixture was filtered and the filtrate was purified by prep-HPLC (NH₃). The afforded flows were combined, concentrated to remove most of CH₃CN and lyophilized to afford the title compound (3.97 mg, 0.0107 mmol, 8.3687% yield) as a white solid.

LC-MS Method1: 371.1 [M+H⁺]

¹H NMR (400 MHz, CHLOROFORM-d) δ=7.67 (s, 1H), 7.49 (s, 1H), 6.13 (br s, 1H), 4.77 (br d, J=12.0 Hz, 1H), 4.43-4.31 (m, 1H), 4.16 (br d, J=12.8 Hz, 1H), 3.90 (dd, J=3.9, 12.3 Hz, 1H), 3.62 (dd, J=3.5, 13.3 Hz, 1H), 2.23 (br d, J=3.8 Hz, 1H), 2.15 (br d, J=3.3 Hz, 1H), 1.52 (d, J=6.6 Hz, 7H), 1.37-1.32 (m, 2H), 1.27 (s, 2H), 1.21 (br s, 2H), 1.13 (br d, J=7.6 Hz, 2H)

Example 71 (1R,5S,6r)-N-methyl-3-[1-(propan-2-yl)-1H-imidazole-4-carbonyl]-N-[1-(trifluoromethyl)cyclopropyl]-3-azabicyclo[3.1.0]hexane-6-carboxamide tert-butyl (1R,5S,6r)-6-{methyl[1-(trifluoromethyl)cyclopropyl]carbamoyl}-3-azabicyclo[3.1.0]hexane-3-carboxylate To a mixture of tert-butyl (1R,5S,6r)-6-{[1-(trifluoromethyl)cyclopropyl]carbamoyl}-3-azabicyclo[3.1.0]hexane-3-carboxylate (180 mg, 0.54 mmol) in DMF (2.52 mL) was added NaH (19.38 mg, 0.81 mmol) under ice-cooling after stirring for 0.5 h. Then MeI (382.1 mg, 2.69 mmol) was added. The mixture was stirred at 30° C. for 3 h. TLC (PE:EtOAc=5:1) showed the reaction was completed (Rf=0.2). The reaction mixture was poured into H₂O (10 mL) and extracted with EtOAc (10 mL×4). The combined organic layers were washed with sat. aq. (10 mL×4), dried over Na₂SO₄, filtered and concentrated under reduced pressure to afford the title compound (180 mg, 0.5167 mmol, 95.973% yield) as a yellow oil.

(1R,5S,6r)-N-methyl-N-[1-(trifluoromethyl)cyclopropyl]-3-azabicyclo[3.1.0]hexane-6-carboxamide TFA Salt To a solution of tert-butyl (1R,5S,6r)-6-{methyl[1-(trifluoromethyl)cyclopropyl]carbamoyl}-3-azabicyclo[3.1.0]

hexane-3-carboxylate (220 mg, 0.63 mmol) in DCM (3 mL) was added 2,2,2-trifluoroacetic acid (0.3 mL, 3.92 mmol). The resulting mixture was stirred at 20 to 25° C. for 2 h. TLC (PE:EtOAc=5:1) showed the reaction was completed. The mixture was concentrated by purging with $N_2$ to afford the title compound (150 mg, 0.6043 mmol, 95.681% yield) as a brown solid.

(1R,5S,6r)-N-methyl-3-[1-(propan-2-yl)-1H-imidazole-4-carbonyl]-N-[1-(trifluoromethyl)cyclopropyl]-3-azabicyclo[3.1.0]hexane-6-carboxamide To a solution of 1-isopropylimidazole-4-carboxylic acid (93.16 mg, 0.60 mmol) in DMF (2 mL) were added HATU (277.21 mg, 0.73 mmol) and $Et_3N$ (0.39 mL, 3.02 mmol). The mixture was stirred at 20 to 25° C. for 0.5 h. (1R,5S,6r)-N-methyl-N-[1-(trifluoromethyl)cyclopropyl]-3-azabicyclo[3.1.0]hexane-6-carboxamide TFA salt (150 mg, 0.60 mmol) was added and the reaction mixture was stirred at 20-25° C. for 16 h. The mixture was then filtered and the filtrate was concentrated. The residue was purified by prep-HPLC ($NH_3$). The afforded flows were combined, concentrated to remove most of $CH_3CN$ and lyophilized to afford the title compound (36.84 mg, 0.0958 mmol, 15.86% yield) as a yellow solid.
LC-MS Method1: 385.0 [M+H$^+$]
$^1$H NMR (400 MHz, DMSO-d$_6$) δ=7.79 (br d, J=8.3 Hz, 2H), 4.59-4.39 (m, 2H), 3.94-3.74 (m, 2H), 3.52 (br d, J=12.0 Hz, 1H), 3.15 (s, 1H), 2.89 (s, 3H), 2.17 (br s, 1H), 2.06 (br s, 1H), 1.95 (br s, 1H), 1.80 (br s, 1H), 1.72-1.51 (m, 2H), 1.40 (d, J=6.8 Hz, 7H)

Example 72 (1R,5S,6r)-3-[1-(propan-2-yl)-1H-imidazole-4-carbonyl]-N-(1,1,1-trifluoro-2-methylpropan-2-yl)-3-azabicyclo[3.1.0]hexane-6-carboxamide tert-butyl (1R,5S,6r)-6-[(1,1,1-trifluoro-2-methylpropan-2-yl)carbamoyl]-3-azabicyclo[3.1.0]hexane-3-carboxylate To a solution of (1R,5S,6r)-3-{[(tert-butyl)oxy]carbonyl}-3-azabicyclo[3.1.0]hexane-6-carboxylic acid (100 mg, 0.44 mmol) and HATU (126.53 mg, 0.66 mmol) in DMF (3.3046 mL) was added DIPEA (0.22 mL, 1.32 mmol). The reaction mixture was stirred at 15° C. for 30 min. Then 1,1,1-trifluoro-2-methyl-propan-2-amine (55.93 mg, 0.44 mmol) was added. The reaction mixture was stirred at 15° C. for 0.5 hr to give a yellow mixture. LCMS showed the desired MS. TLC (PE/EtOAc=1:1) showed a new spot. The reaction mixture was diluted with $H_2O$ (50 mL) and extracted with EtOAc (30 mL×2). The organic layer was dried over anhydrous sodium sulfate, filtered and concentrated to give a residue. The residue was purified by silica column (PE/EtOAc=1:1) to give the title compound (90 mg, 0.2676 mmol, 60.81% yield) as white solid.
$^1$H NMR (400 MHz, CHLOROFORM-d) δ=5.75 (s, 1H), 3.65 (d, J=11.2 Hz, 1H), 3.57 (d, J=11.2 Hz, 1H), 3.45-3.35 (m, 2H), 2.02 (brs, 2H), 1.59 (s, 6H), 1.45 (s, 9H).

(1R,5S,6r)-N-(1,1,1-trifluoro-2-methylpropan-2-yl)-3-azabicyclo[3.1.0]hexane-6-carboxamide TFA Salt To a solution of tert-butyl (1R,5S,6r)-6-[(1,1,1-trifluoro-2-methylpropan-2-yl)carbamoyl]-3-azabicyclo[3.1.0]hexane-3-carboxylate (90 mg, 0.27 mmol) in DCM (2 mL) was added TFA (9.53 mg, 0.27 mmol). The reaction mixture was stirred at 25° C. for 0.5 hr to give a colorless mixture. TLC (PE/EtOAc=1:1) showed a new spot. The solvent was removed by evaporation to afford the title compound as yellow oil.

(1R,5S,6r)-3-[1-(propan-2-yl)-1H-imidazole-4-carbonyl]-N-(1,1,1-trifluoro-2-methylpropan-2-yl)-3-azabicyclo[3.1.0]hexane-6-carboxamide To a solution of 1-isopropylimidazole-4-carboxylic acid (41.12 mg, 0.27 mmol) and HATU (76.69 mg, 0.40 mmol) in DMF (2.0028 mL) was added DIPEA (0.13 mL, 0.80 mmol). The reaction mixture was stirred at 15° C. for 30 min. Then (1R,5S,6r)-N-(1,1,1-trifluoro-2-methylpropan-2-yl)-3-azabicyclo[3.1.0]hexane-6-carboxamide TFA salt (63 mg, 0.27 mmol) was added to the reaction. The reaction mixture was stirred at 15° C. for 0.5 hr to give a yellow mixture. LCMS showed the desired MS. The reaction mixture was purified by prep-HPLC ($NH_3$) to give the title compound (37.38 mg, 0.1004 mmol, 37.639% yield) as light yellow solid.
LC-MS Method1: 373.2 [M+H$^+$]
$^1$H NMR (400 MHz, CHLOROFORM-d) δ=7.64 (d, J=1.2 Hz, 1H), 7.46 (d, J=1.2 Hz, 1H), 5.70 (s, 1H), 4.74 (d, J=12.0 Hz, 1H), 4.35 (m, 1H), 4.14 (d, J=12.3 Hz, 1H), 3.87 (dd, J=3.9, 11.9 Hz, 1H), 3.58 (dd, J=3.9, 12.4 Hz, 1H), 2.19-2.01 (m, 2H), 1.57 (d, J=5.5 Hz, 6H), 1.49 (d, J=6.8 Hz, 6H), 1.20 (t, J=3.0 Hz, 1H)

Example 73 (1R,5S,6r)-N-methyl-3-[1-(propan-2-yl)-1H-imidazole-4-carbonyl]-N-(1,1,1-trifluoro-2-methylpropan-2-yl)-3-azabicyclo[3.1.0]hexane-6-carboxamide tert-butyl (1R,5S,6r)-6-[methyl(1,1,1-trifluoro-2-methylpropan-2-yl)carbamoyl]-3-azabicyclo[3.1.0]hexane-3-carboxylate To a solution of tert-butyl (1R,5S,6r)-6-[(1,1,1-trifluoro-2-methylpropan-2-yl)carbamoyl]-3-azabicyclo[3.1.0]hexane-3-carboxylate (160 mg, 0.48 mmol) in THF (7.4294 mL) was added NaH (13.7 mg, 0.57 mmol) at 0° C. and the mixture was stirred at 0° C. for 0.5 hr to give a yellow mixture. MeI (0.04 mL, 0.67 mmol) was added to the reaction mixture. The reaction mixture was stirred at 20° C. for 16 hr to give a light yellow mixture. TLC (PE/EtOAc=1:1) showed a new spot. LCMS showed the desired MS. The reaction mixture was quenched with $H_2O$ (100 mL) and extracted with EtOAc (50 mL×3). The organic layer was concentrated to give a residue. The residue was purified by silica column (PE/EtOAc=1:1) to give the title compound (150 mg, 0.4281 mmol, 89.996% yield) as colorless oil.
$^1$H NMR (400 MHz, CHLOROFORM-d) δ=3.66 (d, J=11.2 Hz, 1H), 3.55 (d, J=11.2 Hz, 1H), 3.50-3.40 (m, 2H), 3.15 (s, 3H), 2.20-2.10 (m, 1H), 2.10-2.00 (m, 1H), 1.66 (s, 6H), 1.60-1.50 (m, 1H), 1.44 (s, 9H).

(1R,5S,6r)-N-methyl-N-(1,1,1-trifluoro-2-methylpropan-2-yl)-3-azabicyclo[3.1.0]hexane-6-carboxamide TFA Salt To a solution of tert-butyl (1R,5S,6r)-6-[methyl(1,1,1-trifluoro-2-methylpropan-2-yl)carbamoyl]-3-azabicyclo[3.1.0]hexane-3-carboxylate (100 mg, 0.29 mmol) in DCM (2.1332 mL) was added TFA (10.16 mg, 0.29 mmol). The reaction mixture was stirred at 25° C. for 0.5 hr to give a colorless mixture. TLC (PE/EtOAc=1:1) showed anew spot.

The reaction mixture was removed the solvent to give the title compound. It was used for the next step directly.

(1R,5S,6r)-N-methyl-3-[1-(propan-2-yl)-1H-imidazole-4-carbonyl]-N-(1,1,1-trifluoro-2-methylpropan-2-yl)-3-azabicyclo[3.1.0]hexane-6-carboxamide To a solution of 1-isopropylimidazole-4-carboxylic acid (43.74 mg, 0.28 mmol), HATU (81.58 mg, 0.43 mmol) in DMF (2.1306 mL) was added DIPEA (0.14 mL, 0.85 mmol). The reaction mixture was stirred at 15° C. for 30 min. Then (1R,5S,6r)-N-methyl-N-(1,1,1-trifluoro-2-methylpropan-2-yl)-3-azabicyclo[3.1.0]hexane-6-carboxamide TFA salt (71 mg, 0.28 mmol) was added to the reaction. The reaction mixture was stirred at 15° C. for 0.5 hr to give a yellow mixture. LCMS showed the desired MS. The reaction mixture was purified by prep-HPLC ($NH_3$) to give the title compound (72.14 mg, 0.1867 mmol, 65.805% yield) as white powder.
LC-MS Method1: 387.2 [M+H$^+$]
$^1$H NMR (400 MHz, CHLOROFORM-d) δ=7.67 (d, J=1.6 Hz, 1H), 7.47 (d, J=1.2 Hz, 1H), 4.71 (d, J=12.3 Hz, 1H), 4.35 (m, 1H), 4.13 (d, J=12.5 Hz, 1H), 3.96 (dd, J=4.4, 12.2 Hz, 1H), 3.65 (dd, J=4.4, 12.7 Hz, 1H), 3.12 (s, 3H), 2.24 (m, 1H), 2.11 (m, 1H), 1.65 (s, 6H), 1.56 (t, J=3.1 Hz, 1H), 1.50 (d, J=6.8 Hz, 6H)

Example 74 [(1R,5S,6r)-6-(2,2-dimethyl-2,3-dihydro-1H-indole-1-carbonyl)-3-azabicyclo[3.1.0]hexan-3-yl][1-(propan-2-yl)-1H-imidazol-4-yl]methanone 2,2-dimethylindoline To a solution of 2,2-dimethyl-1,2-dihydro-3H-indol-3-one (270 mg, 1.67 mmol) and trichloroalumane (223.33 mg, 1.67 mmol) in THF (5 mL) was added $LiAlH_4$ (95.47 mg, 2.51 mmol) at 0° C. under $N_2$. The reaction mixture was stirred at 20° C. under $N_2$ for 2 hours. TLC (PE:EtOAc=4:1) showed the reaction was completed. The reaction mixture was basified with $NaHCO_3$aq. to pH=8, extracted with EtOAC (10 mL×3), dried over $Na_2SO_4$, filtered and concentrated under reduced pressure to give a residue. The residue was purified by prep-TLC (PE:EtOAc=4:1) to afford the title compound (60 mg, 0.4076 mmol, 24.333% yield) (crude) as yellow oil.

tert-butyl (1R,5S,6r)-6-[(2,2-dimethyl-2,3,3a7a-tetrahydro-1H-indol-1-yl)carbonyl]-3-azabicyclo[3.1.0]hexane-3-carboxylate To a solution of (1R,5S,6r)-3-{[(tert-butyl)oxy]carbonyl}-3-azabicyclo[3.1.0]hexane-6-carboxylic acid (92.62 mg, 0.41 mmol) in DCM (1 mL) were added HATU (233.71 mg, 0.61 mmol) and $Et_3N$ (0.11 mL, 0.82 mmol). The mixture was stirred at 20° C. for 10 minute under $N_2$. Then 2,2-dimethylindoline (60 mg, 0.41 mmol) was added. The resulting mixture was stirred at 20° C. for 16 h to give brown mixture. The reaction mixture was poured into $H_2O$ (10 mL) and extracted with EtOAc (10 mL×4). The combined organic layers were washed with brine (10 mL), dried over $Na_2SO_4$, filtered and concentrated under reduced pressure to give brown oil. The residue was purified by prep-TLC (PE:EtOAc=4:1) to afford the title compound (45 mg, 0.1262 mmol, 30.975% yield) as a brown oil.

(1R,5S,6r)-3-azabicyclo[3.1.0]hex-6-yl(2,2-dimethyl-2,3,3a,7a-tetrahydro-1H-indol-1-yl)methanone TFA Salt To a solution of tert-butyl (1R,5S,6r)-6-[(2,2-dimethyl-2,3,3a,7a-tetrahydro-1H-indol-1-yl)carbonyl]-3-azabicyclo[3.1.0]hexane-3-carboxylate (45 mg, 0.13 mmol) in DCM (4 mL) was added TFA (1 mL, 13.46 mmol). The resulting mixture was stirred at 20 to 25° C. for 1 h. The reaction mixture was purged with $N_2$ to remove the solvent to afford the title compound (32 mg, 0.1248 mmol, 98.884% yield) as brown oil.

[(1R,5S,6r)-6-(2,2-dimethyl-2,3-dihydro-1H-indole-1-carbonyl)-3-azabicyclo[3.1.0]hexan-3-yl][1-(propan-2-yl)-1H-imidazol-4-yl]methanone To a solution of 1-isopropylimidazole-4-carboxylic acid (25.02 mg, 0.16 mmol) in DMF (1.5 mL) were added HATU (57.27 mg, 0.15 mmol), $Et_3N$ (0.07 mL, 0.50 mmol) and (1R,5S,6r)-3-azabicyclo[3.1.0]hex-6-yl(2,2-dimethyl-2,3,3a,7a-tetrahydro-1H-indol-1-yl)methanone TFA salt (32 mg, 0.12 mmol). The resulting mixture was stirred at 20 to 25° C. for 12 hours to give green solution. The reaction mixture was poured into $H_2O$ (10 mL) and extracted with EtOAc (10 mL×4). The combined organic layers were dried over $Na_2SO_4$, filtered and concentrated under reduced pressure. The residue was purified by prep-HPLC ($NH_3$). The afforded flows were combined, concentrated to remove most of $CH_3CN$ and lyophilized to afford the title compound (18 mg, 0.0459 mmol, 36.738% yield) as white solid.
LC-MS Method1: 393.0 [M+H$^+$]
$^1$H NMR (400 MHz, CHLOROFORM-d) δ=7.68 (s, 1H), 7.48 (s, 1H), 7.26-7.20 (m, 1H), 7.18-7.13 (m, 2H), 7.00-6.95 (m, 1H), 4.78 (d, J=12.4 Hz, 1H), 4.36 (td, J=6.8, 13.5 Hz, 1H), 4.22 (br d, J=12.5 Hz, 1H), 4.07 (dd, J=4.5, 12.3 Hz, 1H), 3.77 (dd, J=4.2, 13.3 Hz, 1H), 2.97 (br s, 2H), 2.46 (dd, J=3.6, 7.2 Hz, 1H), 2.30 (br d, J=3.3 Hz, 1H), 1.93 (br s, 1H), 1.56 (br s, 2H), 1.56-1.52 (m, 4H), 1.50 (d, J=6.6 Hz, 6H)

Example 75 cyclopropyl{(1R,5S,6r)-3-[(1-isopropyl-1H-imidazol-4-yl)carbonyl]-3-azabicyclo[3.1.0]hex-6-yl}methanone tert-butyl (1R,5S,6r)-6-[cyclopropyl(hydroxy)methyl]-3-azabicyclo[3.1.0]hexane-3-carboxylate To a solution of tert-butyl (1R,5S,6r)-6-formyl-3-azabicyclo[3.1.0]hexane-3-carboxylate (500 mg, 2.37 mmol) in THF (5 mL) was drop wise added bromo(cyclopropyl)magnesium (7.1 mL, 3.55 mmol) at 0° C. The mixture was stirred at 0° C. for 45 min. The mixture was poured into $H_2O$ (40 mL) slowly and extracted by EtOAc (20 mL×3). The organic phase was washed with brine (50 mL), dried over anhydrous $Na_2SO_4$, filtered and concentrated to give the title compound (600 mg, 2.36 mmol) as yellow oil.
$^1$H NMR (400 MHz, CHLOROFORM-d) δ=3.75-3.50 (m, 2H), 3.45-3.30 (m, 2H), 2.75-2.55 (m, 2H), 1.57 (s, 2H), 1.44 (s, 9H), 1.10-0.90 (m, 1H), 1.90-1.80 (m, 1H), 0.60-0.45 (m, 2H), 0.30-0.20 (m, 2H).

tert-butyl (1R,5S,6r)-6-(cyclopropylcarbonyl)-3-azabicyclo[3.1.0]hexane-3-carboxylate To a solution of tert-butyl (1R,5S,6r)-6-[cyclopropyl(hydroxy)methyl]-3-azabicyclo[3.1.0]hexane-3-carboxylate (550 mg, 2.17 mmol) in DCM (11 mL) was added DMP (1.01 g, 2.39 mmol) at 0° C. The mixture was stirred at 20° C. for 2 h. TLC (PE:EtOAc=3:1) showed the starting material (Rf=0.3) was consumed completely and a new spot (Rf=0.6) was detected. The mixture was poured into $H_2O$ (30 mL) slowly, extracted by DCM (25 mL×3). The organic phase was washed with saturated NaHCO$_3$ (30 mL×2) and brine (35 mL×1), dried over anhydrous Na$_2$SO$_4$ and concentrated to give a residue. The residue was purified by SiO$_2$ flash column (PE:EtOAc=10:1-1:1) to afford the title compound (280 mg, 1.11 mmol, 51.3% yield) as a white solid.

$^1$H NMR (400 MHz, CHLOROFORM-d) δ=3.70 (d, J=11.2 Hz, 1H), 3.61 (d, J=11.2 Hz, 1H), 3.45-3.40 (m, 2H), 2.10 (s, 2H), 2.10-2.00 (m, 1H), 1.92 (s, 1H), 1.46 (s, 9H), 1.10-1.00 (m, 2H), 0.95-0.90 (m, 2H).

(1R,5S,6r)-3-azabicyclo[3.1.0]hex-6-yl(cyclopropyl) methanone

To a solution of tert-butyl (1R,5S,6r)-6-(cyclopropylcarbonyl)-3-azabicyclo[3.1.0]hexane-3-carboxylate (80 mg, 0.32 mmol) in DCM (5 mL) was added TFA (1 mL, 13.4 mmol). The mixture was stirred at 25° C. for 2 h. TLC (PE:EtOAc=3:1) showed a new spot (Rf=0) was detected. The mixture was concentrated to afford the title compound (80 mg, 0.52 mmol) as a yellow oil. The crude was used for next directly.

cyclopropyl {(1R,5S,6r)-3-[(1-isopropyl-1H-imidazol-4-yl)carbonyl]-3-azabicyclo[3.1.0]hex-6-yl}methanone To a solution of (1R,5S,6r)-3-azabicyclo[3.1.0]hex-6-yl (cyclopropyl)methanone (75 mg, 0.5 mmol) and DIPEA (0.41 mL, 2.48 mmol) in DMF (2 mL) was added HATU (189 mg, 0.5 mmol) and 1-isopropylimidazole-4-carboxylic acid (76.4 mg, 0.5 mmol). The mixture were stirred at 20° C. for 16 h. The mixture was diluted with H2O (50 mL), extracted by EtOAc (25 mL×3). The organic phase was washed by brine (50 mL×3), dried over anhydrous Na$_2$SO$_4$, filtered and concentrated to give a residue. The residue was purified by Prep-HPLC (NH$_3$) to afford the title compound (7 mg, 0.024 mmol, 4.91% yield) as a white solid.

LC-MS Method1: 288.1 [M+H$_+$]

$^1$H NMR (400 MHz, CHLOROFORM-d) δ ppm 7.68 (d, J=1.5 Hz, 1H) 7.48 (d, J=1.4 Hz, 1H) 4.75 (d, J=12.1 Hz, 1H) 4.36 (dt, J=13.4, 6.7 Hz, 1H) 4.17 (d, J=12.8 Hz, 1H) 3.95 (dd, J=12.2, 3.9 Hz, 1H) 3.63 (dd, J=12.6, 4.1 Hz, 1H) 2.26 (dt, J=7.1, 3.5 Hz, 1H) 2.16 (dt, J=7.2, 3.5 Hz, 1H) 1.98-2.06 (m, 1H) 1.93 (t, J=3.0 Hz, 1H) 1.51 (d, J=6.6 Hz, 6H) 1.02-1.08 (m, 2H) 0.88-0.94 (m, 2H)

Example 76 (1-isopropyl-1H-imidazol-4-yl)[(1R,5S, 6r)-6-(2-thienylcarbonyl)-3-azabicyclo[3.1.0]hex-3-yl]methanone tert-butyl (1R,5S,6r)-6-(2-thienylcarbonyl)-3-azabicyclo[3.1.0]hexane-3-carboxylate To a mixture of 2-bromothiophene (0.28 mL, 2.84 mmol) in THF (5 mL) was added n-BuLi (1.42 mL, 3.55 mmol) dropwise at −78° C. The reaction mixture was stirred at −78° C. for 1 h. Then tert-butyl (1R,5S,6r)-6-formyl-3-azabicyclo[3.1.0]hexane-3-carboxylate (500 mg, 2.37 mmol) was added at −78° C. The resulting mixture was stirred at 25° C. for 30 min. The reaction mixture was diluted with H$_2$O (10 mL) and then extracted with EtOAc (10 mL×2). The combined organic layers were dried over Na$_2$SO$_4$ and concentrated in vacuum to give crude oil. The crude oil was purified by flash column (0-30% EtOAc in PE) to give the title compound (30 mg, 0.1023 mmol, 4.3205% yield) as pale yellow oil.

$^1$H NMR (400 MHz, CHLOROFORM-d) δ=7.75 (s, 1H), 7.60 (s, 1H), 7.09 (s, 1H), 3.80-3.50 (m, 2H), 3.50-3.40 (m, 2H), 2.31 (s, 1H), 2.23 (brs, 2H), 1.40 (s, 9H).

(1R,5S,6r)-3-azabicyclo[3.1.0]hex-6-yl(2-thienyl) methanone TFA Salt

The mixture of tert-butyl (1R,5S,6r)-6-(2-thienylcarbonyl)-3-azabicyclo[3.1.0]hexane-3-carboxylate (30 mg, 0.10 mmol) in DCM (0.50 mL) and TFA (0.1 mL, 0.10 mmol) was stirred at 25° C. for 2 hr. The reaction mixture was concentrated to dryness to give the title compound (19 mg, 0.0983 mmol, 96.139% yield) as yellow oil.

(1-isopropyl-1H-imidazol-4-yl)[(1R,5S,6r)-6-(2-thienylcarbonyl)-3-azabicyclo[3.1.0]hex-3-yl]methanone To a mixture of (1R,5S,6r)-3-azabicyclo[3.1.0]hex-6-yl (2-thienyl)methanone TFA salt (19 mg, 0.10 mmol) in Pyridine (0.50 mL) were added EDCI (22.61 mg, 0.12 mmol) and 1-isopropylimidazole-4-carboxylic acid (15.16 mg, 0.10 mmol). The resulting mixture was stirred at 20° C. for 16 hr. The reaction mixture was diluted with H$_2$O (5 mL) and then extracted with EtOAc (5 mL×3). The combined organic layers were washed with brine (10 mL), then dried over Na$_2$SO$_4$ and concentrated in vacuum to give the residue. The residue was purified by prep-TLC (EtOAc/ MeOH=20/1, 0.05% NH$_3$·H$_2$O) to afford the title compound (5 mg, 0.0152 mmol, 15.439% yield) as white solid.

$^1$H NMR (400 MHz, CD$_3$OD) δ=8.02 (d, J=3.0 Hz, 1H), 7.84 (d, J=4.8 Hz, 1H), 7.77 (br d, J=7.5 Hz, 2H), 7.22-7.18 (m, 1H), 4.50 (br d, J=8.3 Hz, 2H), 4.14 (br d, J=13.1 Hz, 1H), 4.01 (br s, 1H), 3.71 (br s, 1H), 2.59 (s, 1H), 2.38 (br d, J=17.8 Hz, 2H), 1.51 (d, J=6.5 Hz, 6H), 1.46 (s, 1H), 1.44-1.42 (m, 1H).

Example 77 (1-isopropyl-1H-imidazol-4-yl){(1R, 5S,6r)-6-[(4-methyl-2-thienyl)carbonyl]-3-azabicyclo[3.1.0]hex-3-yl}methanone tert-butyl (1R,5S,6r)-6-[hydroxy(4-methyl-2-thienyl) methyl]-3-azabicyclo[3.1.0]hexane-3-carboxylate (compound 1) and tert-butyl(1R,5S,6r)-3-azabicyclo [3.1.0]hex-6-yl(4-methyl-2-thienyl)methanone (compound 2)

To a solution of 3-methylthiophene (0.24 mL, 2.55 mmol) in THF (5 mL) was dropwise added 2.5 M n-BuLi in n-Hexane (1.02 mL, 2.55 mmol) at −78° C. The mixture was stirred at −78° C. for 0.5 hour under N$_2$. Then, tert-butyl (1R,5S,6r)-6-formyl-3-azabicyclo[3.1.0]hexane-3-carboxylate (742.43 mg, 3.51 mmol) was added at −78° C. The resulting solution was warmed to 25° C. and stirred for 1 hour to give a brown solution. The reaction mixture was diluted with EtOAc and quenched with saturated NH$_4$Cl solution carefully. The resulting mixture was poured into H$_2$O (10 mL) and extracted with EtOAc (10 mL×3). The combined organic layers were washed with brine (10 mL), dried over Na$_2$SO$_4$, filtered and concentrated under reduced pressure. The crude product was purified by flash column (PE:EtOAc=30:1) to give the title compound 1 (660 mg, 2.133 mmol, 83.76% yield) as a yellow oil and the title compound 2 (100 mg, 0.3253 mmol, 12.774% yield) as a yellow solid.

tert-butyl (1R,5S,6r)-6-[(4-methyl-2-thienyl)carbonyl]-3-azabicyclo[3.1.0]hexane-3-carboxylate To a solution of tert-butyl (1R,5S,6r)-6-[hydroxy(4-methyl-2-thienyl)methyl]-3-azabicyclo[3.1.0]hexane-3-carboxylate (660 mg, 2.13 mmol) in DCM (8 mL) was added DMP (1357.05 mg, 3.2 mmol) at 0° C. The mixture was stirred at 25° C. for 2 hours to give a white suspension. The reaction mixture was poured into H$_2$O (10 mL) and extracted with EtOAc (10 mL×3). The combined organic layers were washed with NaHCO$_3$.aq. (20 mL) and Na$_2$SO$_3$ aq. (10 mL), dried over Na$_2$SO$_4$, filtered and concentrated under reduced pressure to give the crude product. The crude product was purified by flash column chromatography (PE:EtOAc=30:1) to give the title compound (500 mg, 1.6265 mmol, 76.253% yield).

(1R,5S,6r)-3-azabicyclo[3.1.0]hex-6-yl(4-methyl-2-thienyl)methanone TFA Salt To a solution of tert-butyl (1R,5S,6r)-6-[(4-methyl-2-thienyl)carbonyl]-3-azabicyclo[3.1.0]hexane-3-carboxylate (100 mg, 0.33 mmol) in DCM (5 mL) was added TFA (0.75 mL, 9.76 mmol). The resulting mixture was stirred at 25° C. for 2 hours to give a yellow solution. The reaction mixture was evaporated in vacuum to give the title compound (60 mg, 0.2894 mmol, 88.98% yield) as a yellow oil. It was directly used in the next step.

(1-isopropyl-1H-imidazol-4-yl){(1R,5S,6r)-6-[(4-methyl-2-thienyl)carbonyl]-3-azabicyclo[3.1.0]hex-3-yl}methanone To a solution of (1R,5S,6r)-3-azabicyclo[3.1.0]hex-6-yl (4-methyl-2-thienyl)methanone TFA salt (130 mg, 0.63 mmol) in DMF (4 mL) were added HATU (359.63 mg, 0.94 mmol) and Et$_3$N (0.16 mL, 1.25 mmol). The mixture was stirred at 25° C. for 10 min under N$_2$. Then, 1-isopropylimidazole-4-carboxylic acid (193.37 mg, 1.25 mmol) in DMF (2 mL) was added, the resulting mixture was stirred at 25° C. for 16 hours to give a yellow mixture. The reaction mixture was poured into H$_2$O (10 mL) and extracted with EtOAc (10 mL×3). The combined organic layers were washed with brine (10 mL), dried over Na$_2$SO$_4$, filtered and concentrated under reduced pressure to give the crude product. The crude product was purified by Prep-HPLC (NH$_3$) and lyophilized to give the title compound (200 mg, 0.5823 mmol, 92.857% yield) as a yellow solid.

LC-MS Method1: 344.2 [M+H$^+$]

$^1$H NMR (400 MHz, CHLOROFORM-d) δ=7.72 (d, J=1.3 Hz, 1H), 7.59 (d, J=1.0 Hz, 1H), 7.49 (d, J=1.3 Hz, 1H), 7.24 (s, 1H), 4.79 (d, J=12.3 Hz, 1H), 4.38 (spt, J=6.7 Hz, 1H), 4.23 (d, J=12.8 Hz, 1H), 4.03 (dd, J=4.0, 12.3 Hz, 1H), 3.71 (dd, J=3.8, 12.8 Hz, 1H), 2.51-2.41 (m, 1H), 2.37-2.31 (m, 2H), 2.29 (s, 3H), 1.52 (d, J=6.8 Hz, 6H)

Example 78 (1-isopropyl-1H-imidazol-4-yl){(1R,5S,6r)-6-[(4-methoxy-2-thienyl)carbonyl]-3-azabicyclo[3.1.0]hex-3-yl}methanone tert-butyl (1R,5S,6r)-6-[hydroxy(4-methoxy-2-thienyl)methyl]-3-azabicyclo[3.1.0]hexane-3-carboxylate To a solution of 3-methoxy thiophen (0.18 mL, 2.13 mmol) in THF (3 mL) was added 2.5 M n-BuLi in n-Hexane (0.85 mL, 2.13 mmol) at −78° C. The mixture was stirred at −78° C. for 0.5 h under N$_2$. tert-butyl (1R,5S,6r)-6-formyl-3-azabicyclo[3.1.0]hexane-3-carboxylate (300 mg, 1.42 mmol) was added at −78° C. The resulting mixture was stirred at 20 to 25° C. for 2 h. The reaction mixture was poured into sat. NH$_4$Cl aq. (2 mL) and the aqueous layer was extracted with EtOAc (10 mL×4). The combined organic layers were washed with sat. aq. (10 mL×2), dried over Na$_2$SO$_4$, filtered and concentrated under reduced pressure. The crude product was purified by flash column (PE to 30% EtOAc in PE) to afford the title compound (380 mg, 1.1677 mmol, 82.231% yield) as a yellow gum.

tert-butyl (1R,5S,6r)-6-[(4-methoxy-2-thienyl)carbonyl]-3-azabicyclo[3.1.0]hexane-3-carboxylate To a solution of tert-butyl (1R,5S,6r)-6-[hydroxy(4-methoxy-2-thienyl)methyl]-3-azabicyclo[3.1.0]hexane-3-carboxylate (380 mg, 1.17 mmol) in THF (4 mL) was added MnO$_2$ (507.61 mg, 5.84 mmol). The mixture was stirred at 50° C. for 16 h. TLC (PE:EtOAc=2:1) showed new spots and the starting material was remained. The mixture was then filtered and the filtrate was concentrated in vacuum. The residue was purified by prep-TLC (PE:EtOAc=2:1) to afford the title compound (60 mg, 0.1855 mmol, 15.888% yield) as a colorless oil.

$^1$H NMR (400 MHz, CHLOROFORM-d) δ=7.43 (d, J=1.8 Hz, 1H), 6.64 (d, J=1.6 Hz, 1H), 3.85 (s, 3H), 3.75 (br d, J=11.4 Hz, 1H), 3.65 (br d, J=10.9 Hz, 1H), 3.50 (br d, J=8.9 Hz, 2H), 2.29 (s, 3H), 1.48 (s, 9H)

(1R,5S,6r)-3-azabicyclo[3.1.0]hex-6-yl(4-methoxy-2-thienyl)methanone TFA Salt To a solution of tert-butyl (1R,5S,6r)-6-[(4-methoxy-2-thienyl)carbonyl]-3-azabicyclo[3.1.0]hexane-3-carboxylate (70 mg, 0.22 mmol) in DCM (3.5 mL) was added 2,2,2-trifluoroacetic acid (0.35 mL, 4.57 mmol). The resulting mixture was stirred at 20 to 25° C. for 1 h. TLC (PE:EtOAc=2:1) showed the reaction was completed (Rf=0). The mixture was concentrated by purging with N$_2$ to afford the title compound (48 mg, 0.2150 mmol, 99.318% yield) as a purple solid.

(1-isopropyl-1H-imidazol-4-yl){(1R,5S,6r)-6-[(4-methoxy-2-thienyl)carbonyl]-3-azabicyclo[3.1.0]hex-3-yl}methanone To a solution of 1-isopropylimidazole-4-carboxylic acid (33.14 mg, 0.21 mmol) in Pyridine (2 mL) were added EDCI (61.81 mg, 0.32 mmol) and (1R,5S,6r)-3-azabicyclo[3.1.0] hex-6-yl(4-methoxy-2-thienyl)methanone TFA salt (48 mg, 0.21 mmol) at 20 to 25° C. for 2 h. The reaction mixture was concentrated directly. The residue was purified by prep-HPLC (NH$_3$) to afford crude product. The crude product was purified by prep-TLC (DCM:MeOH=10:1) to afford the title compound (5.73 mg, 0.0159 mmol, 7.4158% yield) as a white solid.

LC-MS Method1: 360.0 [M+H$^+$]

$^1$H NMR (400 MHz, CHLOROFORM-d) δ=7.72 (s, 1H), 7.54-7.48 (m, 1H), 7.40 (d, J=1.5 Hz, 1H), 6.63 (d, J=1.8 Hz, 1H), 4.79 (d, J=12.3 Hz, 1H), 4.38 (td, J=6.9, 13.3 Hz, 1H), 4.23 (d, J=12.5 Hz, 1H), 4.04 (dd, J=4.0, 12.0 Hz, 1H), 3.83 (s, 3H), 3.71 (dd, J=3.8, 12.5 Hz, 1H), 2.46 (br d, J=3.3 Hz, 1H), 2.35 (br d, J=6.3 Hz, 1H), 2.32-2.27 (m, 1H), 1.52 (d, J=6.5 Hz, 8H)

Example 79 (1-isopropyl-1H-imidazol-4-yl){(1R, 5S,6r)-6-[(4-methyl-1,3-thiazol-2-yl)carbonyl]-3-azabicyclo[3.1.0]hex-3-yl}methanone tert-butyl (1R,5S,6r)-6-[hydroxy(4-methyl-1,3-thiazol-2-yl)methyl]-3-azabicyclo[3.1.0]hexane-3-carboxylate To a solution of 2-bromo-4-methyl-1,3-thiazole (74.48 uL, 0.71 mmol) in THF (2 mL) was added 2.5 M n-BuLi in n-Hexane (0.34 mL, 0.86 mmol) at −78° C. The mixture was stirred at −78° C. for 0.5 h under $N_2$. Then to the reaction mixture added tert-butyl (1R,5S,6r)-6-formyl-3-azabicyclo[3.1.0]hexane-3-carboxylate (210.89 mg, 1 mmol) at −78° C. The resulting solution was warmed to 25° C. and stirred for 1 h to give a brown solution. LCMS showed the desire MS. The reaction mixture was poured into $NH_4Cl$ aq. (20 mL) and extracted with EtOAc (20 mL×4). The combined organic layers were washed with brine (50 mL×2), dried over $Na_2SO_4$, filtered and concentrated under reduced pressure. The crude product was purified by flash column (PE to 20% EtOAc in PE) to give the title compound (220 mg, 0.7087 mmol, 99.396% yield) as brown oil.
$^1$H NMR (400 MHz, CHLOROFORM-d) δ=7.68 (s, 1H), 5.00-4.85 (m, 1H), 4.06 (t, J=10.8 Hz, 2H), 3.90-3.75 (m, 2H), 2.85 (s, 3H), 2.25-2.00 (m, 2H), 1.84 (s, 9H), 1.70-1.60 (m, 1H), 1.55-1.50 (m, 1H).

tert-butyl (1R,5S,6r)-6-[(4-methyl-1,3-thiazol-2-yl)carbonyl]-3-azabicyclo[3.1.0]hexane-3-carboxylate To a solution of tert-butyl (1R,5S,6r)-6-[hydroxy(4-methyl-1,3-thiazol-2-yl)methyl]-3-azabicyclo[3.1.0]hexane-3-carboxylate (220 mg, 0.71 mmol) in DCM (4 mL) was added DMP (450.91 mg, 1.06 mmol) at 0° C. The mixture was stirred at 25° C. for 3 h to give white suspension. The reaction mixture was filtered. The filtrate was washed with $NaHCO_3$.aq. (50 mL×2) and $Na_2SO_3$.aq. (50 mL×2), dried over $Na_2SO_4$, filtered and concentrated under reduced pressure to give the title compound (220 mg, 0.7134 mmol, 100.65% yield) as brown oil.
$^1$H NMR (400 MHz, CHLOROFORM-d) δ=7.27 (s, 1H), 3.78 (d, J=11.2 Hz, 1H), 3.72 (d, J=11.2 Hz, 1H), 3.55-3.45 (m, 2H), 3.15-3.10 (m, 1H), 2.57 (s, 3H), 2.35 (brs, 2H), 1.48 (s, 9H).

(1R,5S,6r)-3-azabicyclo[3.1.0]hex-6-yl(4-methyl-1,3-thiazol-2-yl)methanone TFA Salt To a solution of tert-butyl (1R,5S,6r)-6-[(4-methyl-1,3-thiazol-2-yl)carbonyl]-3-azabicyclo[3.1.0]hexane-3-carboxylate (100 mg, 0.32 mmol) in DCM (5 mL) was added TFA (1. mL, 0.32 mmol). The mixture was stirred at 25° C. for 30 min to give brown solution. TLC (PE:EtOAc=3:1) showed the reaction was completed. The reaction mixture was concentrated directly to give the title compound (100 mg, 0.3103 mmol, 95.687% yield, TFA salt) as brown oil.

(1-isopropyl-1H-imidazol-4-yl){(1R,5S,6r)-6-[(4-methyl-1,3-thiazol-2-yl)carbonyl]-3-azabicyclo[3.1.0]hex-3-yl}methanone To a solution of 1-isopropylimidazole-4-carboxylic acid (47.83 mg, 0.31 mmol) in DMF (2 mL) were added HATU (142.34 mg, 0.37 mmol) and DIPEA (200.5 mg, 1.55 mmol). The mixture was stirred at 25° C. for 20 min. Then (1R,5S,6r)-3-azabicyclo[3.1.0]hex-6-yl(4-methyl-1,3-thiazol-2-yl)methanone TFA salt (100 mg, 0.31 mmol, TFA salt) was added. The mixture was stirred at 25° C. for 2 h to give brown solution. The mixture was stirred at 25° C. for 12 h to give brown solution. The reaction mixture was concentrated directly. The residue was purified by prep-HPLC ($NH_3$) to give the title compound (20.22 mg, 0.0587 mmol, 18.921% yield) as yellow solid.
$^1$H NMR (400 MHz, CHLOROFORM-d) δ ppm 7.72 (1H, d, J=1.51 Hz), 7.48 (1H, d, J=1.51 Hz), 7.24 (1H, d, J=0.75 Hz), 4.81 (1H, d, J=12.30 Hz), 4.33-4.43 (1H, m), 4.28 (1H, d, J=13.05 Hz), 4.07 (1H, dd, J=12.30, 4.02 Hz), 3.72 (1H, dd, J=12.80, 4.02 Hz), 3.12 (1H, t, J=3.14 Hz), 2.53 (4H, d, J=0.75 Hz), 2.40 (1H, dt, J=7.09, 3.61 Hz), 1.52 (6H, d, J=6.53 Hz)

Example 80 (1-isopropyl-1H-imidazol-4-yl)[(1R,5S,6r)-6-(2-pyridinylcarbonyl)-3-azabicyclo[3.1.0]hex-3-yl]methanone bromo(2-pyridinyl)magnesium To a solution of 2-bromopyridine (0.61 mL, 6.33 mmol) in THF (10 mL) was added chloro(isopropyl)magnesium (3.2 mL, 6.33 mmol) at 15° C. The reaction mixture was stirred at 0° C. for 4 hr to give the title compound as a mixture. The reaction mixture was used for the next step without further purification.

tert-butyl (1R,5S,6r)-6-[hydroxy(2-pyridinyl)methyl]-3-azabicyclo[3.1.0]hexane-3-carboxylate To a solution of tert-butyl (1R,5S,6r)-6-formyl-3-azabicyclo[3.1.0]hexane-3-carboxylate (0.61 mL, 1.42 mmol) in THF (6 mL) was added bromo(2-pyridinyl)magnesium (3.2 mL, 2.13 mmol) at 15° C. The reaction mixture was stirred at 0° C. for 4 hr to give a brown mixture. TLC (PE/EA=1:2) showed a new spot. The reaction mixture was quenched with $H_2O$ (30 mL) and extracted with EtOAc (30 mL×2). The organic layer was washed with brine (30 mL×2), dried over anhydrous $Na_2SO_4$, filtered and concentrated under reduced pressure to give a residue. The residue was purified by silica gel column (PE/EA=1:2) to give the title compound (460 mg, 1.5842 mmol, 111.56% yield) as light yellow gum.
$^1$H NMR (400 MHz, DMSO-$d_6$) δ 8.47 (dd, J=4.4, 0.8 Hz, 1H), 7.78 (t, J=5.6 Hz, 1H), 7.47 (d, J=8.0 Hz, 1H), 7.30-7.20 (m, 1H), 5.41 (d, J=4.8 Hz, 1H), 4.27 (t, J=5.6 Hz, 1H), 3.40-3.20 (m, 4H), 1.62 (brs, 2H), 1.37 (s, 9H), 1.85-1.75 (m, 1H).

tert-butyl (1R,5S,6r)-6-[(2-pyridinyl)carbonyl]-3-azabicyclo[3.1.0]hexane-3-carboxylate To a solution of tert-butyl (1R,5S,6r)-6-[hydroxy(2-pyridinyl)methyl]-3-azabicyclo[3.1.0]hexane-3-carboxylate (460 mg, 1.58 mmol) in DCM (9.6442 mL) was added DMP (671.94 mg, 1.58 mmol) at 15° C. The reaction mixture was stirred at 15° C. for 20 min to give a white mixture. TLC (PE/EA=1:1) showed a new spot. The reaction mixture was quenched with $NaHCO_3$ (30 mL) and extracted with DCM (30 mL×2). The organic layer was washed with brine (30 mL×2), dried over anhydrous $Na_2SO_4$, filtered and concentrated under reduced pressure to give a residue. The residue was purified by silica gel column (PE/EA=1:1) to give the title compound (340 mg, 1.1792 mmol, 74.431% yield) as white solid.
$^1$H NMR (400 MHz, DMSO-$d_6$) δ 8.77 (dd, J=4.4, 0.8 Hz, 1H), 8.02 (t, J=5.6 Hz, 1H), 7.95 (d, J=8.0 Hz, 1H), 7.70-7.60 (m, 1H), 3.57 (d, J=11.4 Hz, 1H), 3.50-3.25 (m, 3H), 3.25-3.20 (m, 1H), 2.22 (brs, 2H), 1.41 (s, 9H), 1.85-1.75 (m, 1H).

(1R,5S,6r)-3-azabicyclo[3.1.0]hex-6-yl(2-pyridinyl)methanone TFA Salt

To a solution of tert-butyl (1R,5S,6r)-6-[(2-pyridinyl)carbonyl]-3-azabicyclo[3.1.0]hexane-3-carboxylate (58 mg, 0.20 mmol) in DCM (1.5 mL) was added TFA (0.02 mL, 0.20 mmol). The reaction mixture was stirred at 20° C. for 2 hr to give a colorless mixture. The reaction mixture was concentrated under reduced pressure to give the title compound. It was used for the next step directly.
LC-MS Method1: 0.268 min, MS (m/z): 189.0 (M+H⁺).

(1-isopropyl-1H-imidazol-4-yl)[(1R,5S,6r)-6-(2-pyridinylcarbonyl)-3-azabicyclo[3.1.0]hex-3-yl]methanone To a solution of (1R,5S,6r)-3-azabicyclo[3.1.0]hex-6-yl (2-pyridinyl)methanone TFA salt (37 mg, 0.20 mmol) in Pyridine (1.5 mL) were added 1-isopropylimidazole-4-carboxylic acid (45.46 mg, 0.29 mmol) and EDCI (56.52 mg, 0.29 mmol). The reaction mixture was stirred at 20° C. for 16 hr. The solution was purified by prep-HPLC (NH₃) and lyophilized to afford the title compound (7.52 mg, 11.79% yield) as yellow solid.
LC-MS Method1: 0.363 min, MS (m/z): 325.2 (M+H⁺).
¹H NMR (400 MHz, CHLOROFORM-d) δ ppm 8.68 (d, J=4.77 Hz, 1H), 8.02 (d, J=7.78 Hz, 1H), 7.81-7.86 (m, 1H), 7.71 (s, 1H), 7.45-7.49 (m, 2H), 4.79 (d, J=12.30 Hz, 1H), 4.37 (dt, J=13.36, 6.74 Hz, 1H), 4.28 (d, J=12.80 Hz, 1H), 4.08 (dd, J=12.17, 3.89 Hz, 1H), 3.73 (dd, J=12.80, 4.02 Hz, 1H), 3.45 (t, J=3.01 Hz, 1H), 2.44-2.49 (m, 1H), 2.36 (dt, J=7.28, 3.64 Hz, 1H), 1.52 (d, J=6.53 Hz, 6H)

Example 81 [(1R,5S,6r)-6-(5,5-dimethyl-4,5-dihydro-1,2-oxazol-3-yl)-6-methyl-3-azabicyclo[3.1.0]hex-3-yl](1-isopropyl-1H-imidazol-4-yl)methanone

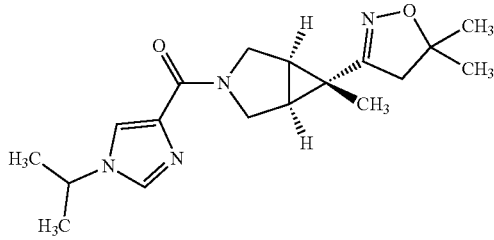 [SMILES: CC(C)n1cnc(C(=O)N2C[C@@H]3[C@H](C2)[C@@]3(C)C2=NOC(C)(C)C2)c1]

ethyl (2E)-2-hydrazonopropanoate

Hydrazine hydrate (0.86 g, 17.22 mmol) was slowly added to a mixture of glacial HOAc (1.4 mL, 24.5 mmol) and H₂O (1.4 mL, 77.78 mmol) at 0° C. Then ethyl 2-oxopropanoate (0.95 mL, 8.61 mmol) was added at room temperature. MeOH (0.5 mL) was added in order to obtain a homogeneous solution. The mixture was stirred at 25° C. for 6 h to give yellow solution. TLC (PE:EtOAc=1:1) showed the reaction was completed. The reaction mixture was removed under reduced pressure. H₂O (40 mL) was added to the residued and the mixture was extracted with EtOAc (30 mL×4). The combined organic phases were washed with saturated sodium hydrogen carbonate (30 mL×2), saturated brine (40 mL×2) and dried over Na₂SO₄. The solvent was removed under reduced pressure. The crude product was purified by flash column chromatography (PE to 20% EtOAc in PE) to give the title compound (930 mg, 7.1456 mmol, 82.975% yield) as colorless oil.
LC-MS Method1 0.348 min, MS (m/z) 130.8 [M+H⁺].
¹H NMR (400 MHz, CHLOROFORM-d) δ=5.93 (brs, 2H), 4.28 (q, J=6.8 Hz, 2H), 1.99 (s, 3H), 1.37 (t, J=6.8 Hz, 3H).

ethyl 3-benzyl-6-methyl-2,4-dioxo-3-azabicyclo[3.1.0]hexane-6-carboxylate

To a solution of ethyl (2E)-2-hydrazonopropanoate (2.5 g, 19.21 mmol) in 1,4-Dioxane (30 mL) was added MnO₂ (10.02 g, 115.25 mmol). The mixture was stirred at 20° C. for 1.5 h and then filtered through a pad of Celite. To the filtrate was added 1-benzyl-1H-pyrrole-2,5-dione (3.6 g, 19.21 mmol). The reaction was stirred at 20° C. for 2 h and at 100° C. for 16 h to give yellow solution. TLC (PE:EtOAc=5:1) showed the reaction was completed. The reaction mixture was concentrated directly. The crude product was purified by flash column (PE to 10% EtOAc in PE). The afforded solid was triturated with EtOAc/PE (2 mL/20 mL) and dried in air to give the title compound (1.28 g, 4.4551 mmol, 23.193% yield) as colorless solid.
LC-MS Method1 0.827 min, MS (m/z) 287.9 [M+H⁺].
¹H NMR (400 MHz, CHLOROFORM-d) δ=7.45-7.25 (m, 5H), 4.57 (s, 2H), 4.15 (q, J=6.8 Hz, 2H), 2.89 (s, 2H), 1.25 (t, J=6.8 Hz, 3H), 1.14 (s, 3H).

ethyl 3-benzyl-6-methyl-3-azabicyclo[3.1.0]hexane-6-carboxylate

To a solution of ethyl 3-benzyl-6-methyl-2,4-dioxo-3-azabicyclo[3.1.0]hexane-6-carboxylate (2.5 g, 8.7 mmol) (crude) in THF (25 mL) was added BORANE DIMETHYL SULFIDE COMPLEX (3.48 mL, 34.81 mmol) at 25° C. The mixture was stirred at 70° C. for 2 h to give colorless suspension. TLC (PE:EtOAc=5:1) showed the reaction was completed. The reaction mixture was added dropwise into MeOH/HCl (12 N) (8:1=5 mL) and the mixture was stirred for 30 min. Then the mixture was concentrated directly. The crude product was purified by flash column (PE to 10% EtOAc in PE) to the title compound (600 mg, 2.3136 mmol, 26.588% yield) as colorless oil.
LC-MS Method1 0.781 min, MS (m/z) 260.1 [M+H⁺].
¹H NMR (400 MHz, CHLOROFORM-d) δ=7.50-7.30 (m, 5H), 4.10 (q, J=6.8 Hz, 2H), 4.05 (s, 2H), 3.36 (dt, J=12.0, 1.2 Hz, 2H), 2.98 (d, J=5.2 Hz, 1H), 2.88 (d, J=5.2 Hz, 1H), 2.45-2.40 (m, 1H), 2.20-2.10 (m, 1H), 1.40 (s, 9H), 1.25 (t, J=6.8 Hz, 3H), 0.70 (s, 1H).

[(1R,5S,6r)-3-benzyl-6-methyl-3-azabicyclo[3.1.0]hex-6-yl]methanol

To a solution of ethyl 3-benzyl-6-methyl-3-azabicyclo[3.1.0]hexane-6-carboxylate (600 mg, 2.31 mmol) in THF (8 mL) was added LiAlH4 (131.87 mg, 3.47 mmol) at 0° C. The mixture was stirred at 0° C. for 10 min to give white suspension. TLC (PE:EtOAc=5:1) showed the reaction was completed. To the reaction mixture was added H₂O (0.15 mL), 1N NaOH aq (0.15 mL), H₂O (0.5 ml) continuously and filtered. The filtrate was concentrated to give colorless oil. The crude product was purified by flash column chromatography (PE to 30% EtOAc in PE) to give the title compound (270 mg, 1.2425 mmol, 53.703% yield) colorless oil.

LC-MS Method1 1.643 min, MS (m/z) 218.2 [M+H$^+$].

$^1$H NMR (400 MHz, CHLOROFORM-d) δ=7.55-7.50 (m, 2H), 7.45-7.40 (m, 3H), 4.03 (s, 2H), 3.40-3.25 (m, 2H), 3.30 (s, 2H), 3.00-2.90 (m, 2H), 1.60-1.55 (m, 2H), 1.27 (s, 3H). The relative configuration was determined by NoE experiments.

tert-butyl (1R,5S,6r)-6-(hydroxymethyl)-6-methyl-3-azabicyclo[3.1.0]hexane-3-carboxylate To a solution of [(1R,5S,6r)-3-benzyl-6-methyl-3-azabicyclo[3.1.0]hex-6-yl]methanol (100 mg, 0.4600 mmol) in MeOH (3 mL) was added Pd(OH)$_2$ (30 mg, 0.4600 mmol). The mixture was stirred at 20° C. under H$_2$ (15 psi) for 12 h to give black solution. TLC (PE:EtOAc=1:1) showed the reaction was completed. The reaction mixture was filtered and the filtrate was concentrated. The residue was diluted with DCM (3 mL) and di-tert-butyl dicarbonate (150.65 mg, 0.6900 mmol) was added into the solution. The mixture was stirred at 20° C. for 30 min to give colorless solution. The reaction mixture was concentrated directly. The crude product was purified by flash column (PE to 30% EtOAc in PE) to give the title compound (35 mg, 0.1540 mmol, 33.462% yield) as white solid.

LC-MS Method1 0.710 min, MS (m/z) 171.8 [M-tBu+H$^+$].

$^1$H NMR (400 MHz, CHLOROFORM-d) δ=3.60-3.45 (m, 2H), 3.45-3.35 (m, 2H), 1.50-1.45 (m, 2H), 1.49 (s, 9H), 1.04 (s, 3H).

tert-butyl (1R,5S,6r)-6-formyl-6-methyl-3-azabicyclo[3.1.0]hexane-3-carboxylate

To a solution of tert-butyl (1R,5S,6r)-6-(hydroxymethyl)-6-methyl-3-azabicyclo[3.1.0]hexane-3-carboxylate (70 mg, 0.3100 mmol) in DCM (2 mL) was added DMP (143.68 mg, 0.3400 mmol) at 0° C. The mixture was stirred at 20° C. for 2 h to give white suspension. TLC (PE:EtOAc=1:1) showed the reaction was completed. The reaction mixture was poured into H$_2$O (20 mL) and extracted with EtOAc (20 mL×4). The combined organic layers were washed with NaHCO$_3$.aq. (50 mL), Na$_2$SO$_3$.aq. (50 mL), dried over Na$_2$SO$_4$, filtered and concentrated under reduced pressure to give the title compound (62 mg, 0.2752 mmol, 89.366% yield) as yellow gum.

$^1$H NMR (400 MHz, CHLOROFORM-d) δ=8.96 (s, 1H), 3.70-3.55 (m, 2H), 3.48 (d, J=11.4 Hz, 1H), 3.40 (d, J=11.4 Hz, 1H), 2.15 (d, J=2.0 Hz, 1H), 1.45 (s, 9H), 1.72 (s, 3H).

tert-butyl (1R,5S,6r)-6-[(E)-(hydroxyimino)methyl]-6-methyl-3-azabicyclo[3.1.0]hexane-3-carboxylate To a solution of tert-butyl (1R,5S,6r)-6-formyl-6-methyl-3-azabicyclo[3.1.0]hexane-3-carboxylate (62 mg, 0.2800 mmol) in EtOH (1.5 mL) were added HOAc (15.73 uL, 0.2800 mmol), KOAc (26.97 mg, 0.2800 mmol) and hydroxylamine hydrochloride (0.01 mL, 0.3300 mmol). The mixture was stirred at 20° C. for 2 h to give yellow suspension. TLC (PE:EtOAc=3:1) showed the reaction was completed. The reaction mixture was poured into H$_2$O (20 mL) and extracted with EtOAc (15 mL×4). The combined organic layers were washed with brine (50 mL), dried over Na$_2$SO$_4$, filtered and concentrated under reduced pressure to give the title compound (65 mg, 0.2705 mmol, 98.286% yield) as yellow solid.

LC-MS Method1 0.727 min, MS (m/z) 185.0 [M-tBu+H$^+$].

$^1$H NMR (400 MHz, CHLOROFORM-d) δ=7.03 (s, 1H), 3.65-3.50 (m, 2H), 3.46 (d, J=11.2 Hz, 1H), 3.39 (d, J=11.2 Hz, 1H), 1.80 (d, J=2.4 Hz, 2H), 1.45 (s, 9H), 1.15 (s, 3H).

tert-butyl (1R,5S,6r)-6-[(Z)-chloro(hydroxyimino)methyl]-6-methyl-3-azabicyclo[3.1.0]hexane-3-carboxylate To a solution of tert-butyl (1R,5S,6r)-6-[(E)-(hydroxyimino)methyl]-6-methyl-3-azabicyclo[3.1.0]hexane-3-carboxylate (65 mg, 0.2700 mmol) in DMF (1.5 mL) was added NCS (39.73 mg, 0.3000 mmol). The mixture was stirred at 20° C. for 14 h to give brown solution. The mixture was poured into H$_2$O (15 mL) and extracted with EtOAc (15 mL×5).

The combined organic layer was washed with brine (50 mL), dried over Na$_2$SO$_4$ and concentrated to dryness to give the title compound (70 mg, 0.2548 mmol, 94.193% yield) as yellow oil.

LC-MS Method1 0.802 min, MS (m/z) 218.9 [M-tBu+H$^+$].

$^1$H NMR (400 MHz, CHLOROFORM-d) δ=8.55 (s, 1H), 3.66-3.55 (m, 2H), 3.47 (d, J=9.0 Hz, 1H), 3.39 (d, J=9.0 Hz, 1H), 2.15-2.08 (m, 2H), 1.44 (s, 9H), 1.22 (s, 3H).

tert-butyl (1R,5S,6r)-6-(5,5-dimethyl-4,5-dihydro-1,2-oxazol-3-yl)-6-methyl-3-azabicyclo[3.1.0]hexane-3-carboxylate To a solution of tert-butyl (1R,5S,6r)-6-[(Z)-chloro(hydroxyimino)methyl]-6-methyl-3-azabicyclo[3.1.0]hexane-3-carboxylate (70 mg, 0.2500 mmol) in DMF (1.5 mL) were added Et$_3$N (0.13 mL, 0.7600 mmol) and 2-methylprop-1-ene (0.48 mL, 0.7600 mmol, 2.4 M in THF). The mixture was stirred at 20° C. for 12 h to give brown solution. The mixture was poured into H$_2$O (15 mL) and extracted with EtOAc (15 mL×5). The combined organic layer was washed with brine (50 mL), dried over Na$_2$SO$_4$ and concentrated to dryness to give the title compound (70 mg, 0.2378 mmol, 93.325% yield) as yellow oil.

LC-MS Method1 0.810 min, MS (m/z) 295.1 [M+H$^+$].

$^1$H NMR (400 MHz, CHLOROFORM-d) δ=3.60-3.55 (m, 2H), 3.46 (d, J=8.7 Hz, 1H), 3.38 (d, J=8.7 Hz, 1H), 2.64 (s, 2H), 2.00-1.92 (m, 2H), 1.45 (s, 9H), 1.36 (s, 6H), 1.16 (s, 3H).

(1R,5S,6r)-6-(5,5-dimethyl-4,5-dihydro-1,2-oxazol-3-yl)-6-methyl-3-azabicyclo[3.1.0]hexane TFA Salt To a solution of tert-butyl (1R,5S,6r)-6-(5,5-dimethyl-4,5-dihydro-1,2-oxazol-3-yl)-6-methyl-3-azabicyclo[3.1.0]hexane-3-carboxylate (70 mg, 0.2400 mmol) in DCM (5 mL) was added TFA (1 mL, 13.46 mmol). The mixture was stirred at 20° C. for 30 min to give yellow solution. The reaction mixture was concentrated directly to give the title compound (70 mg crude) as yellow oil.

LC-MS Method1 0.268 min, MS (m/z) 194.9 [M+H$^+$].

$^1$H NMR (400 MHz, DIMETHYL SULFOXIDE-d6) δ ppm 9.58 (brs, 1H), 8.85 (brs, 1H), 3.65-3.50 (m, 2H), 3.20-3.10 (m, 2H), 2.68 (s, 2H), 2.25 (m, 2H), 1.25 (s, 6H), 1.18 (s, 3H).

[(1R,5S,6r)-6-(5,5-dimethyl-4,5-dihydro-1,2-oxazol-3-yl)-6-methyl-3-azabicyclo[3.1.0]hex-3-yl](1-isopropyl-1H-imidazol-4-yl)methanone To a solution of 1-isopropylimidazole-4-carboxylic acid (61.11 mg, 0.4000 mmol) in DMF (2 mL) were added HATU (179.08 mg, 0.4700 mmol), Et₃N (0.2 mL, 1.44 mmol), (1R,5S,6r)-6-(5,5-dimethyl-4,5-dihydro-1,2-oxazol-3-yl)-6-methyl-3-azabicyclo[3.1.0]hexane TFA salt (70 mg, 0.3600 mmol). The mixture was stirred at 20° C. for 12 h to give brown solution. The reaction mixture was concentrated directly. The residue was purified by prep-HPLC (NH₃). The afforded flows were combined, concentrated to remove most of CH₃CN and lyophilized to give the title compound (11.6 mg, 0.0351 mmol, 9.7431% yield) as brown solid.

LC-MS Method1 0.610 min, MS (m/z) 331.1 [M+H⁺]

¹H NMR (400 MHz, CHLOROFORM-d) δ ppm 7.69 (1H, s), 7.48 (1H, s), 4.17-4.44 (3H, m), 3.79-3.95 (2H, m), 2.66 (2H, d, J=1.63 Hz), 2.12-2.19 (1H, m), 1.99-2.05 (1H, m), 1.51 (6H, dd, J=6.69, 1.56 Hz), 1.38 (6H, s), 1.19 (3H, d, J=1.75 Hz)

Example 82 (1-cyclopropyl-1H-imidazol-4-yl)[(1R,5S,6r)-6-(5,5-dimethyl-4,5-dihydro-1,2-oxazol-3-yl)-6-methyl-3-azabicyclo[3.1.0]hex-3-yl]methanone

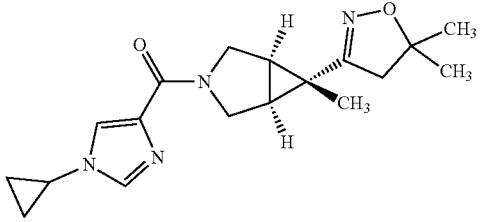 [SMILES: CC1(C)CC([C@@]2(C)[C@@H]3CN(C(=O)c4cn(C5CC5)cn4)C[C@@H]32)=NO1]

(1-cyclopropyl-1H-imidazo-4-yl)[1R,5S,6r)-6-(5,5-dimethyl-4,5-dihydro-1,2-oxazol-3-yl)-6-methyl-3-azabicyclo[3.1.0]hex-3-yl]methanone To a solution of 1-cyclopropyl-1H-imidazole-4-carboxylic acid (14.81 mg, 0.10 mmol) in Pyridine (0.75 mL) was added EDCI (27.98 mg, 0.15 mmol). The mixture was stirred for 20 minute. Then (1R,5S,6r)-6-(5,5-dimethyl-4,5-dihydro-1,2-oxazol-3-yl)-6-methyl-3-azabicyclo[3.1.0]hexane TFA salt; (30 mg, 0.10 mmol) was added. The mixture was stirred at 25° C. for 1 h. The reaction mixture was concentrated directly. The residue was purified by prep-HPLC (NH₃). The afforded flows were combined, concentrated to remove most of CH₃CN and lyophilized to afford the title compound (9.93 mg, 0.0302 mmol, 31.073% yield) as a yellow gum.

LC-MS Method2 3.650 min, MS (m/z) 329.2 [M+H]⁺

¹H NMR (400 MHz, CHLOROFORM-d) δ=7.66 (d, J=1.5 Hz, 1H), 7.51 (d, J=1.3 Hz, 1H), 4.32-4.19 (m, 2H), 3.91-3.78 (m, 2H), 3.37 (tt, J=3.8, 7.2 Hz, 1H), 2.66 (s, 2H), 2.14 (dd, J=4.9, 8.2 Hz, 1H), 2.06-1.96 (m, 1H), 1.38 (s, 7H), 1.18 (s, 3H), 1.09-0.96 (m, 4H)

Example 83 [(1R,5S,6r)-6-(5,5-dimethyl-4,5-dihydro-1,2-oxazol-3-yl)-6-methyl-3-azabicyclo[3.1.0]hex-3-yl][1-(1-methylcyclopropyl)-1H-imidazol-4-yl]methanone

[(1R,5S,6r)-6-(5,5-dimethyl-4,5-dihydro-1,2-oxazol-3-yl)-6-methyl-3-azabicyclo[3.1.0]hex-3-yl][1-(1-methylcyclopropyl)-1H-imidazol-4-yl]methanone To a solution of 1-(1-methylcyclopropyl)-1H-imidazole-4-carboxylic acid (42.77 mg, 0.2600 mmol) in DMF (1.5 mL) were added HATU (127.14 mg, 0.3300 mmol) and DIPEA (0.21 mL, 1.29 mmol). The mixture was stirred for 30 min. Then (1R,5S,6r)-6-(5,5-dimethyl-4,5-dihydro-1,2-oxazol-3-yl)-6-methyl-3-azabicyclo[3.1.0]hexane TFA salt (50 mg, 0.2600 mmol) was added. The mixture was stirred at 25° C. for 3 h to give brown solution. The reaction mixture was concentrated directly. The residue was purified by prep-HPLC (NH₃) to give the title compound (33.31 mg, 0.0973 mmol, 37.794% yield) as brown solid.

LC-MS Method1: 343.3 [M+H⁺]

¹H NMR (400 MHz, DMSO-d₆) δ=7.71 (s, 1H), 7.53 (d, J=1.2 Hz, 1H), 4.32-4.20 (m, 2H), 3.89-3.80 (m, 2H), 2.66 (s, 3H), 2.16-1.99 (m, 2H), 1.57 (s, 3H), 1.37 (s, 6H), 1.17 (s, 3H), 1.33-1.31 (m, 2H), 0.94-0.91 (m, 2H).

Example 84 (1-isopropyl-1H-imidazol-4-yl)[(1R,5S,6r)-6-methyl-6-(4-oxa-5-azaspiro[2.4]hept-5-en-6-yl)-3-azabicyclo[3.1.0]hex-3-yl]methanone tert-butyl (1R,5S,6r)-6-methyl-6-(4-oxa-5-azaspiro[2.4]hept-5-en-6-yl)-3-azabicyclo[3.1.0]hexane-3-carboxylate tert-butyl (1R,5S,6r)-6-[(Z)-chloro(hydroxyimino)methyl]-6-methyl-3-azabicyclo[3.1.0]hexane-3-carboxylate (300 mg, 1.09 mmol) was added gradually to a solution of methylenecyclopropane (0.24 mL, 9.96 mmol) in THF (13.469 mL). Then, Et₃N (0.46 mL, 3.28 mmol) was added. The reaction mixture was stirred at 0° C. for 16 hr to give a yellow solution. The reaction mixture was diluted with H₂O (30 mL) and extracted with EtOAc (30 mL×2). The combined organic layer was dried over Na₂SO₄ and concentrated in vacuum to give a residue. The residue was purified by silica column (PE/EA=2:1) to give the title compound (200 mg, 0.6841 mmol, 62.647% yield) as white solid.

¹H NMR (400 MHz, CHLOROFORM-d) δ=3.65-3.55 (m, 2H), 3.47 (d, J=11.2 Hz, 1H), 3.39 (d, J=11.2 Hz, 1H), 2.96 (s, 2H), 2.10-1.95 (m, 2H), 1.48 (s, 9H), 1.20 (s, 3H), 1.15-1.05 (m, 2H), 0.75-0.65 (m, 2H).

6-[(1R,5S,6r)-6-methyl-3-azabicyclo[3.1.0]hex-6-yl]-4-oxa-5-azaspiro[2.4]hept-5-ene TFA Salt To a solution of tert-butyl (1R,5S,6r)-6-methyl-6-(4-oxa-5-azaspiro[2.4]hept-5-en-6-yl)-3-azabicyclo[3.1.0]hexane-3-carboxylate (200 mg, 0.6800 mmol) in DCM (11.901 mL) was added 2,2,2-trifluoroacetic acid (0.05 mL, 0.6800 mmol). The reaction mixture was stirred at 10° C. for 1 hr to give a yellow solution. TLC (PE/EA=1:1) showed a new spot. The reaction mixture was evaporated in vacuum to give the title compound (200 mg, 0.6530 mmol, 95.458% yield) as yellow oil.

(1-isopropyl-1H-imidazol-4-yl)[(1R,5S,6r)-6-methyl-6-(4-oxa-5-azaspiro[2.4]hept-5-en-6-yl)-3-azabicyclo[3.1.0]hex-3-yl]methanone A 100 ml round-bottom flask was charged with 1-isopropylimidazole-4-carboxylic acid (50.34 mg, 0.3300 mmol), HATU (149.78 mg, 0.3900 mmol), N-ethyl-N-isopropylpropan-2-amine (0.17 mL, 0.9800 mmol) and DMF (1.6108 mL). After stirred for 30 min, 6-[(1R,5S,6r)-6-methyl-3-azabicyclo[3.1.0]hex-6-yl]-4-oxa-5-azaspiro[2.4]hept-5-ene TFA salt (100 mg, 0.3300 mmol) was added. The reaction mixture was stirred at 10° C. for 1 hr to give a yellow solution. LCMS showed reactant was completely consumed and the desired MS. The reaction mixture was diluted with $H_2O$ (20 mL) and extracted with EtOAc (30 mL×2). The combined organic layer was dried over $Na_2SO_4$ and concentrated in vacuum to give a residue as yellow oil. The crude was purified by Prep-HPLC ($NH_3$). The afford flows was concentrated in vacuum to remove most of $CH_3CN$ and lyophilized to give the title compound (52.53 mg, 0.1600 mmol, 48.99% yield) as white solid.

LC-MS Method1: 329.2 [M+H$^+$]

$^1$H NMR (400 MHz, CHLOROFORM-d) δ=7.69 (d, J=1.6 Hz, 1H), 7.48 (d, J=1.2 Hz, 1H), 4.39-4.22 (m, 3H), 3.89-3.84 (m, 2H), 2.98 (s, 2H), 2.20 (m, 1H), 2.06 (m, 1H), 1.50 (d, J=6.4 Hz, 6H), 1.22 (s, 3H), 1.16-1.07 (m, 2H), 0.74-0.67 (m, 2H)

Example 85 (1-cyclopropyl-1H-imidazol-4-yl)[(1R,5S,6r)-6-methyl-6-(4-oxa-5-azaspiro[2.4]hept-5-en-6-yl)-3-azabicyclo[3.1.0]hex-3-yl]methanone

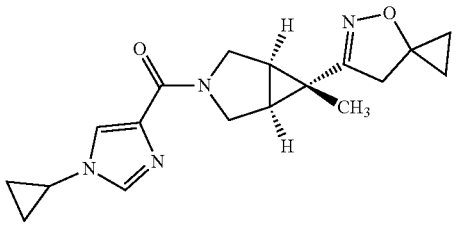 [SMILES: C[C@]1(C2=NOC3(CC3)C2)[C@@H]2CN(C(=O)c3cn(C4CC4)cn3)C[C@@H]21]

(1-cyclopropyl-1H-imidazol-4-yl)[(1R,5S,6r)-6-methyl-6-(4-oxa-5-azaspiro[2.4]hept-5-en-6-yl)-3-azabicyclo[3.1.0]hex-3-yl]methanone To a solution of 1-cyclopropylimidazole-4-carboxylic acid (25.12 mg, 0.1700 mmol) in DMF (1 mL) were added HATU (71.11 mg, 0.1900 mmol) and DIPEA (100.16 mg, 0.7800 mmol). The mixture was stirred at 25° C. for 0.5 h. Then 6-[(1R,5S,6r)-6-methyl-3-azabicyclo[3.1.0]hex-6-yl]-4-oxa-5-azaspiro[2.4]hept-5-ene TFA salt (50 mg, 0.1600 mmol) was added to the mixture. The mixture was stirred at 25° C. for 12 h to give brown solution. LCMS showed the desire MS as a major peak. The reaction mixture was concentrated directly. The residue was purified by prep-HPLC ($NH_3$) to give the title compound (11.52 mg, 0.0353 mmol, 20% yield) as brown solid.

LC-MS Method2 1.763 min, MS (m/z) 327.2 [M+H$^+$]

$^1$H NMR (400 MHz, CHLOROFORM-d) δ ppm 7.66 (1H, d, J=1.25 Hz), 7.51 (1H, d, J=1.25 Hz), 4.18-4.35 (2H, m), 3.82-3.92 (2H, m), 3.37 (1H, tt, J=7.31, 3.73 Hz), 2.99 (2H, s), 2.20 (1H, dd, J=8.16, 5.14 Hz), 2.01-2.12 (1H, m), 1.19-1.24 (3H, m), 1.09-1.17 (2H, m), 0.96-1.08 (4H, m), 0.67-0.76 (2H, m)

Example 86 [1-(1-methylcyclopropyl)-1H-imidazol-4-yl][(1R,5S,6r)-6-methyl-6-(4-oxa-5-azaspiro[2.4]hept-5-en-6-yl)-3-azabicyclo[3.1.0]hex-3-yl]methanone

[1-(1-methylcyclopropyl)-1H-imidazol-4-yl][(1R,5S,6r)-6-methyl-6-(4-oxa-5-azaspiro[2.4]hept-5-en-6-yl)-3-azabicyclo[3.1.0]hex-3-yl]methanone To a solution of 1-(1-methylcyclopropyl) imidazole-4-carboxylic acid (37.98 mg, 0.2300 mmol) in DMF (2 mL) were added HATU (104.22 mg, 0.2700 mmol) and DIPEA (0.19 mL, 1.14 mmol). The mixture was stirred at 25° C. for 30 min. Then 6-[(1R,5S,6r)-6-methyl-3-azabicyclo[3.1.0]hex-6-yl]-4-oxa-5-azaspiro[2.4]hept-5-ene TFA salt (70 mg, 0.2300 mmol) was added to the mixture. The mixture was stirred at 25° C. for 3 h to give brown solution. The reaction mixture was concentrated directly. The residue was purified by prep-HPLC ($NH_3$) to give the title compound (15.64 mg, 0.0459 mmol, 20.102% yield) as brown solid.

LC-MS Method1: 341.3 [M+H$^+$]

$^1$H NMR (400 MHz, CHLOROFORM-d) δ ppm 7.65 (2H, br d, J=6.25 Hz) 4.10-4.26 (2H, m) 3.77-3.92 (2H, m) 3.00 (2H, s) 2.20-2.29 (1H, m) 2.07-2.15 (1H, m) 1.59 (3H, s) 1.17-1.23 (3H, m) 1.08-1.17 (4H, m) 0.93-1.00 (2H, m) 0.69-0.76 (2H, m)

Example 87 (1R,5S,6r)-N-tert-butyl-6-methyl-3-[1-(propan-2-yl)-1H-imidazole-4-carbonyl]-3-azabicyclo[3.1.0]hexane-6-carboxamide (1R,5S,6r)-6-methyl-3-{[(tert-butyl)oxy]carbonyl}-3-azabicyclo[3.1.0]hexane-6-carboxylic acid To a solution of tert-butyl (1R,5S,6r)-6-formyl-6-methyl-3-azabicyclo[3.1.0]hexane-3-carboxylate (100 mg, 0.44 mmol) in 1-BuOH (1.7 mL, 0.44 mmol), THF (1.7 mL), and $H_2O$ (0.60 mL) were added 2-methylbut-2-ene (0.94 mL, 8.88 mmol), $NaClO_2$ (160.58 mg, 1.78 mmol) and $NaH_2PO_4$ (490.02 mg, 3.55 mmol). The resulting mixture was stirred at 20 to 25° C. for 16 h. TLC (PE:EtOAc=2:1) showed the reaction was completed (Rf=0.5). The reaction mixture was poured into $H_2O$ (10 mL) and extracted with EtOAc (10 mL×4). The combined organic layers were dried over $Na_2SO_4$, filtered and concentrated under reduced pressure to afford the title compound (167 mg, 0.6921 mmol, 155.93% yield) as a white solid.

$^1$H NMR (400 MHz, CHLOROFORM-d) δ=3.66-3.56 (m, 2H), 3.47-3.34 (m, 2H), 2.26-2.18 (m, 2H), 1.47-1.42 (m, 9H), 1.17 (s, 3H)

tert-butyl (1R,5S,6r)-6-methyl-6-[(tert-butyl)carbamoyl]-3-azabicyclo[3.1.0]hexane-3-carboxylate To a solution of (1R,5S,6r)-6-methyl-3-1{[(tert-butyl)oxy]carbonyl}-3-azabicyclo[3.1.0]hexane-6-carboxylic acid (100 mg, 0.41 mmol) in Pyridine (1 mL) was added EDCI (119.18 mg, 0.62 mmol). The mixture was stirred at 20 to 25° C. for 0.5 h. Then 2-methylpropan-2-amine (0.04 mL, 0.41 mmol) was added. The resulting mixture stirred at 20 to 25° C. for 16 h. TLC (PE:EA=1:1) showed the reaction was completed. The crude product was purified by flash column (PE to 30% EtOAc in PE) to afford the title compound (50 mg, 0.1687 mmol, 40.7% yield) as a brown solid.

$^1$H NMR (400 MHz, CHLOROFORM-d) δ=3.67-3.55 (m, 2H), 3.36 (d, J=11.9 Hz, 1H), 3.28 (d, J=11.8 Hz, 1H), 2.15-2.04 (m, 2H), 1.48-1.42 (m, 9H), 1.48-1.42 (m, 1H), 1.39-1.30 (m, 9H), 1.13 (s, 3H)

(1R,5S,6r)-6-methyl-N-(tert-butyl)-3-azabicyclo[3.1.0]hexane-6-carboxamide TFA Salt A solution of tert-butyl (1R,5S,6r)-6-methyl-6-[(tert-butyl)carbamoyl]-3-azabicyclo[3.1.0]hexane-3-carboxylate (50 mg, 0.17 mmol) in DCM (1 mL) and 2,2,2-trifluoroacetic acid (0.1 mL, 1.31 mmol) was stirred at 20 to 25° C. for 1 h. TLC (PE:EtOAc=1:1) showed the reaction was completed (Rf=0.3). The reaction mixture was concentrated by purging with $N_2$ to afford the title compound (30 mg, 0.1528 mmol, 90.604% yield) as a brown oil.

(1R,5S,6r)-N-tert-butyl-6-methyl-3-[1-(propan-2-yl)-1H-imidazole-4-carbonyl]-3-azabicyclo[3.1.0]hexane-6-carboxamide To a solution of 1-isopropylimidazole-4-carboxylic acid (23.56 mg, 0.15 mmol) in DMF (0.50 mL) were added HATU (75.96 mg, 0.20 mmol) and Et$_3$N (0.06 mL, 0.46 mmol). The mixture was stirred at 20 to 25° C. for 0.5 h. Then (1R,5S,6r)-6-methyl-N-(tert-butyl)-3-azabicyclo[3.1.0]hexane-6-carboxamide TFA salt (30 mg, 0.15 mmol) was added to the mixture. The resulting mixture was stirred at 20 to 25° C. for 2 h. LCMS showed the desired MS (as a major peak). The residue was purified by prep-HPLC (NH$_3$). The afforded flows were combined, concentrated to remove most of CH$_3$CN and lyophilized to afford the title compound (10.28 mg, 0.0309 mmol, 20.233% yield) as an off-white solid.

LC-MS Method1: 333.1 [M+H$^+$]

$^1$H NMR (400 MHz, CHLOROFORM-d) δ=7.69 (s, 1H), 7.48 (s, 1H), 5.58 (s, 1H), 4.36 (td, J=6.7, 13.4 Hz, 1H), 4.24 (d, J=2.3 Hz, 2H), 3.94-3.85 (m, 1H), 3.74 (d, J=13.3 Hz, 1H), 2.30-2.25 (m, 1H), 2.12 (dd, J=5.4, 8.2 Hz, 1H), 1.51 (d, J=6.8 Hz, 6H), 1.36 (s, 9H), 1.15 (s, 3H)

Example 88 [(1R,5S,6r)-6-(5,5-dimethyl-4,5-dihydro-1,2-oxazol-3-yl)-3-azabicyclo[3.1.0]hex-3-yl](5-isopropyl-1H-pyrazol-3-yl)methanone

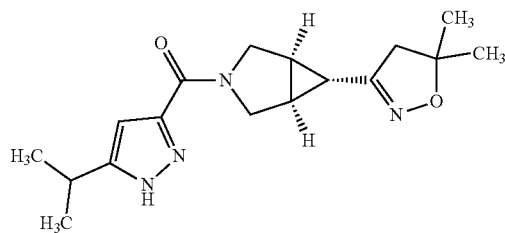 [SMILES: CC(C)c1cc(C(=O)N2C[C@@H]3[C@H](C2)[C@H]3C2=NOC(C)(C)C2)n[nH]1]

[(1R,5S,6r)-6-(5,5-dimethyl-4,5-dihydro-1,2-oxazol-3-yl)-3-azabicyclo[3.1.0]hex-3-yl](5-isopropyl-1H-pyrazol-3-yl)methanone To a solution of 5-isopropyl-1H-pyrazole-3-carboxylic acid (21.34 mg, 0.1400 mmol) in DMF (1 mL) were added HATU (63.13 mg, 0.1700 mmol), DIPEA (0.08 mL, 0.4800 mmol) and (1R,5S,6r)-6-(5,5-dimethyl-4,5-dihydro-1,2-oxazol-3-yl)-3-azabicyclo[3.1.0]hexane hydrochloride (30 mg, 0.1400 mmol). The mixture was stirred at 25° C. for 12 h to give brown solution. TLC (PE:EtOAc=1:3) showed a new spot. The reaction mixture was poured into H$_2$O (10 mL) and extracted with EtOAc (20 mL×3). The combined organic layers were washed with brine (30 mL), dried over Na$_2$SO$_4$, filtered and concentrated under reduced pressure. The residue was purified by prep-TLC (PE:EtOAc=1:3) and lyophilized to give the title compound (18.42 mg, 0.0570 mmol, 41.171% yield) as white powder.

LC-MS Method1 0.781 min, MS (m/z) 317.0 [M+H$^+$]

$^1$H NMR (400 MHz, CHLOROFORM-d) δ ppm 6.41 (s, 1H), 4.13-4.28 (m, 2H), 3.95 (br dd, J=11.17, 4.14 Hz, 1H), 3.69 (br dd, J=12.92, 4.39 Hz, 1H), 3.06 (quin, J=6.84 Hz, 1H), 2.66 (s, 2H), 2.15 (br dd, J=7.40, 3.39 Hz, 1H), 2.02-2.08 (m, 1H), 1.47 (t, J=3.26 Hz, 1H), 1.38 (s, 6H), 1.27-1.31 (m, 6H)

Example 89 (5-sec-butyl-1H-pyrazol-3-yl)[(1R,5S,6r)-6-(5,5-dimethyl-4,5-dihydro-1,2-oxazol-3-yl)-3-azabicyclo[3.1.0]hex-3-yl]methanone ethyl 5-methyl-2,4-dioxoheptanoate To a solution of 3-methylpentan-2-one (0.61 mL, 4.99 mmol) and diethyl oxalate (0.81 mL, 5.99 mmol) in THF (20 mL) was added NaH (239.62 mg, 5.99 mmol) at 0° C. The reaction was allowed to warm to 20° C. and stirred for further 6 h to give pale brown solution. The reaction was cooled to 0° C., treated with H$_2$O (30 mL), acidified with 2M HCl to pH=6 and extracted with EA (20 mL×2). The combined organic layer was dried over Na$_2$SO$_4$ and concentrated in vacuum to give the title compound (1000 mg, 4.9943 mmol) as pale brown liquid.

$^1$H NMR (400 MHz, CHLOROFORM-d) δ=14.60 (brs, 1H), 6.40 (s, 1H), 4.26 (q, J=6.8 Hz, 2H), 2.55-2.40 (m, 1H), 1.60-1.50 (m, 1H), 1.50-1.35 (m, 1H), 1.38 (t, J=6.8 Hz, 3H), 1.10 (d, J=7.4 Hz, 3H), 0.82 (t, J=6.8 Hz, 3H).

ethyl 5-sec-butyl-1H-pyrazole-3-carboxylate

To a solution of ethyl 5-methyl-2,4-dioxoheptanoate (1000 mg, 4.99 mmol) in EtOH (20 mL) was added hydrazine hydrate (275.01 mg, 5.49 mmol) at 20° C. After stirred for 20 min, the reaction was heated at 60° C. for further 4 h to give yellow mixture. The mixture was concentrated in vacuum to give crude oil. The oil was diluted with EA (40 mL), washed with H$_2$O (30 mL×2) and brine (30 mL), then, dried over Na$_2$SO$_4$ and concentrated in vacuum to give the title compound (950 mg, 4.8408 mmol, 96.927% yield) as pale yellow oil.

$^1$H NMR (400 MHz, CHLOROFORM-d) δ=6.55 (s, 1H), 4.31 (q, J=6.8 Hz, 2H), 2.80-2.35 (m, 1H), 1.70-1.50 (m, 2H), 1.37 (t, J=6.8 Hz, 3H), 1.31 (d, J=7.4 hz, 3H), 0.82 (t, J=6.8 Hz, 3H).

5-sec-butyl-1H-pyrazole-3-carboxylic acid

To a solution of ethyl 5-sec-butyl-1H-pyrazole-3-carboxylate (950 mg, 4.84 mmol) in MeOH (15 mL) and H$_2$O (5 mL) was added LiOH·H$_2$O (0.42 mL, 7.26 mmol). The reaction was stirred at 20° C. for 12 h to give yellow mixture. The mixture was concentrated to remove MeOH. The residue was diluted with H$_2$O (5 mL) and washed with DCM (5 mL×2). The aqueous layer was cooled to 0° C. and acidified with 2M HCl to pH=6. The precipitate was collected and concentrated in vacuum to give the title compound (420 mg, 2.4972 mmol, 51.586% yield) as a white solid.

(5-sec-butyl-1H-pyrazol-3-yl)[(1R,5S,6r)-6-(5,5-dimethyl-4,5-dihydro-1,2-oxazol-3-yl)-3-azabicyclo[3.1.0]hex-3-yl]methanone To a solution of 5-sec-butyl-1H-pyrazole-3-carboxylic acid (50 mg, 0.3000 mmol) in DMF (1.5 mL) were added HATU (125.02 mg, 0.3300 mmol), (1R,5S,6r)-6-(5,5-dimethyl-4,5-dihydro-1,2-oxazol-3-yl)-3-azabicyclo[3.1.0]hexane TFA salt (70.87 mg, 0.3300 mmol) and Et$_3$N (0.1 mL, 0.7400 mmol). The reaction was stirred at 20° C. for 12 h to give pale yellow mixture. The mixture was concentrated in vacuum and purified by prep-HPLC (HCl). The afforded eluent was concentrated and lyophilized to give the title compound (10.38 mg, 0.0314 mmol, 10.567% yield) as pale yellow solid.

LC-MS Method1: 331.0 [M+H$^+$]

$^1$H NMR (400 MHz, DMSO-d$_6$) δ=6.51-6.28 (m, 1H), 4.30 (br d, J=11.9 Hz, 1H), 3.94 (d, J=12.3 Hz, 1H), 3.83 (dd, J=4.2, 11.8 Hz, 1H), 2.80-2.71 (m, 1H), 2.65 (s, 2H), 2.08 (td, J=3.7, 7.4 Hz, 1H), 2.00 (td, J=3.8, 7.3 Hz, 1H), 1.65-1.51 (m, 2H), 1.47-1.41 (m, 1H), 1.25 (s, 6H), 1.20 (d, J=6.9 Hz, 3H), 0.80 (t, J=7.4 Hz, 3H)

Example 90 [5-(1-cyclopropylethyl)-1H-pyrazol-3-yl][(1R,5S,6r)-6-(5,5-dimethyl-4,5-dihydro-1,2-oxazol-3-yl)-3-azabicyclo[3.1.0]hex-3-yl]methanone methyl 5-acetyl-1-{[2-(trimethylsilyl)ethoxy]methyl}-1H-pyrazole-3-carboxylate A solution of methyl 5-bromo-1-{[2-(trimethylsilyl)ethoxy]methyl}-1H-pyrazole-3-carboxylate (1500 mg, 4.47 mmol, Tetrahedron 2015, 71(39), 7250), tributyl(1-ethoxyvinyl)stannane (1938.94 mg, 5.37 mmol) and PdCl$_2$(dppf) (163.68 mg, 0.2200 mmol) in 1,4-Dioxane (25 mL) was heated to 9° C. for 16 hr give a yellow solution. 1M HCl aq. (3 mL) was added to be stirred for 10 min. Then the reaction was diluted with H$_2$O (20 mL) and it was extracted with EtOAc (30 mL×2). The combined organic layer was dried over Na$_2$SO$_4$ and concentrated in vacuum to give a yellow oil. The crude was purified by silica gel chromatography (PE/EA=10/1 to 3/1) to give the title compound (580 mg, 1.9436 mmol, 43.443% yield) as white solid.

LC-MS Method1 0.972 min, MS (m/z) 299.0 (M+H$^+$).

methyl 5-{(1E)-N-[(4-methylphenyl)sulfonyl]ethanehydrazonoyl}-1-{[2-(trimethylsilyl)ethoxy]methyl}-1H-pyrazole-3-carboxylate A 100 mL round-bottom flask was charged with methyl 5-acetyl-1-{[2-(trimethylsilyl)ethoxy]methyl}-1H-pyrazole-3-carboxylate (810 mg, 2.71 mmol), 4-methylbenzenesulfonohydrazide (505.5 mg, 2.71 mmol), 4-methylbenzenesulfonic acid (0.02 mL, 0.1400 mmol) and MeOH (10 mL). The reaction was stirred at 40° C. for 16 hr to give a yellow solution. The reaction mixture was evaporated in vacuum to give the title compound (1250 mg, 2.6788 mmol, 98.688% yield) as yellow oil. It used directly in the next step.

LC-MS Method1 1.012 min, MS (m/z) 467.1 (M+H$^+$).

methyl 5-(1-cyclopropylethyl)-1-{[2-(trimethylsilyl)ethoxy]methyl}-1H-pyrazole-3-carboxylate A round-bottom flask was charged with methyl 5-{(1E)-N-[(4-methylphenyl)sulfonyl]ethanehydrazonoyl}-1-{[2-(trimethylsilyl)ethoxy]methyl}-1H-pyrazole-3-carboxylate (500 mg, 1.07 mmol), cyclopropylboronic acid (138.06 mg, 1.61 mmol), K$_2$CO$_3$ (222.14 mg, 1.61 mmol) and 1,4-Dioxane (10 mL). The reaction was heated to 110° C. for 2 hr to give a white suspension. TLC (PE/EA=10/1, Rf=0.7) showed a new spot. The reaction mixture was filtered through a pad of celite and the filtrate was concentrated in vacuum to give a colorless oil. The crude was purified by silica gel chromatography (PE/EA=10/1 to 3/1) to give the title compound (230 mg, 0.6904 mmol, 64.43% yield) as colorless oil.

LC-MS Method1 1.105 min, MS (m/z) 325.2 (M+H$^+$).

methyl 5-(1-cyclopropylethyl)-1H-pyrazole-3-carboxylate

A round-bottom flask was charged with methyl 5-(1-cyclopropylethyl)-1-{[2-(trimethylsilyl)ethoxy]methyl}-1H-pyrazole-3-carboxylate (230 mg, 0.7100 mmol), 2,2,2-trifluoroacetic acid (0.05 mL, 0.7100 mmol) and DCM (10 mL). The reaction mixture was stirred at 20° C. for 2 hr to give a yellow solution. The reaction mixture was evaporated in vacuum to give the title compound (130 mg, 0.6693 mmol, 94.428% yield) as yellow oil.

LC-MS Method1 0.785 min, MS (m/z) 195.2 (M+H$^+$).

5-(1-cyclopropylethyl)-1H-pyrazole-3-carboxylic acid

A 100 mL round-bottom flask was charged with methyl 5-(1-cyclopropylethyl)-1H-pyrazole-3-carboxylate (130 mg, 0.6700 mmol), hydroxylithium hydrate (84.25 mg, 2.01 mmol), H$_2$O (1.3 mL), THF (1.3 mL) and MeOH (1.3 mL). The reaction mixture was stirred under N$_2$ atmosphere for 3 hr to give a yellow solution. H$_2$O (30 mL) was added and pH value was adjusted to 3 with 1M HCl. It was extracted with EtOAc (30 mL×2). The combined organic layer was dried over Na$_2$SO$_4$ and concentrated in vacuum to give the title compound (120 mg, 0.6659 mmol, 99.495% yield) as yellow oil.

LC-MS Method1 0.732 min, MS (m/z) 181.2 (M+H$^+$).

[5-(1-cyclopropylethyl)-1H-pyrazol-3-yl][(1R,5S,6r)-6-(5,5-dimethyl-4,5-dihydro-1,2-oxazol-3-yl)-3-azabicyclo[3.1.0]hex-3-yl]methanone To a solution of 5-(1-cyclopropylethyl)-1H-pyrazole-3-carboxylic acid (80 mg, 0.4400 mmol) in DMF (2 mL) were added HATU (203.67 mg, 0.5300 mmol) and N-ethyl-N-isopropylpropan-2-amine (0.46 mL, 2.66 mmol). After stirred for 30 min, (1R,5S,6r)-6-(5,5-dimethyl-4,5-dihydro-1,2-oxazol-3-yl)-3-azabicyclo[3.1.0]hexane TFA salt (278.26 mg, 0.5300 mmol) was added. The reaction mixture was stirred for 16 hr to give a yellow solution. H$_2$O (30 mL) was added and it was extracted with EtOAc (30 mL×2). The combined organic layer was dried over Na$_2$SO$_4$ and concentrated in vacuum to give a yellow oil. The crude was purified by Prep-TLC (DCM/EA=3/1) and lyophilized to give the title compound (16.86 mg, 0.0459 mmol, 10.346% yield) as white solid.

LC-MS Method1: 343.0 [M+H$^+$]

¹H NMR (400 MHz, CDCl₃) δ ppm 6.55 (s, 1H), 3.33 (d, J=11.2 Hz, 1H), 3.20 (d, J=11.2 Hz, 1H), 3.95-3.85 (m, 1H), 3.70-3.60 (m, 1H), 2.65 (s, 2H), 2.20-2.10 (m, 2H), 2.05-2.00 (m, 1H), 1.45-1.40 (m, 1H), 1.38 (s, 9H), 0.95-0.85 (m, 1H), 0.58 (d, J=7.6 Hz, 2H), 0.30-0.20 (m, 2H).

Example 91 [5-(1-cyclobutylethyl)-1H-pyrazol-3-yl][(1R,5S,6r)-6-(5,5-dimethyl-4,5-dihydro-1,2-oxazol-3-yl)-3-azabicyclo[3.1.0]hex-3-yl]methanone N'-[(1E)-1-cyclobutylethylidene]-4-methylbenzenesulfonohydrazide A solution of 1-cyclobutylethanone (350 mg, 3.57 mmol) and TsNHNH₂ (664.16 mg, 3.57 mmol) in MeOH (7 mL) was stirred at 25° C. for 4 hr. The solvent was concentrated by reduce pressure to give the crude product. The crude product was triturated by (PE:EtOAc=10:1, 10 mL) to afford the title compound (820 mg, 3.0785 mmol, 86.322% yield) as a white solid.

¹H NMR (400 MHz, CDCl₃) δ ppm 7.86 (d, J=8.0 Hz, 2H), 7.30 (d, J=8.0 Hz, 2H), 3.10-2.90 (m, 1H), 2.43 (s, 3H), 2.10-2.00 (m, 6H), 1.68 (s, 3H).

3-(1-cyclobutylvinyl)-1-{[2-(trimethylsilyl)ethoxy]methyl}-1H-pyrazole-5-carboxylic acid To a solution of methyl 3-bromo-1-{[2-(trimethylsilyl)ethoxy]methyl}-1H-pyrazole-5-carboxylate (300 mg, 0.89 mmol), N'-[(1E)-1-cyclobutylethylidene]-4-methylbenzenesulfonohydrazide (238.34 mg, 0.89 mmol) and t-BuOLi (214.89 mg, 2.68 mmol) in 1,4-Dioxane (5 mL) were added XPhos (42.66 mg, 0.09 mmol) and Pd₂(dba)₃ (40.97 mg, 0.04 mmol) at 25° C. under N₂. The mixture was stirred at 110° C. for 12 hr. The mixture was poured into H₂O (10 mL), and then adjusted pH to 4 to 5 by 1M HCl and extracted by EtOAc (10 mL×3). The organic phase was washed by brine (15 mL), then dried over anhydrous Na₂SO₄ and the solvent was removed. The residue was purified by SiO₂ column chromatography (PE:EtOAc=1:0-5:1, 0.5% FA) to afford the title compound (200 mg, 0.6202 mmol, 69.313% yield) as a yellow oil.

¹H NMR (400 MHz, CDCl₃) δ ppm 7.23 (s, 1H), 7.05 (s, 1H), 5.81 (s, 2H), 5.81 (s, 1H), 3.70-3.60 (m, 2H), 3.00-2.80 (m, 2H), 2.30-1.90 (m, 6H), 1.00-0.90 (m, 2H), 0.03 (s, 9H).

3-(1-cyclobutylethyl)-1-{[2-(trimethylsilyl)ethoxy]methyl}-1H-pyrazole-5-carboxylic acid To a solution of 3-(1-cyclobutylvinyl)-1-{[2-(trimethylsilyl)ethoxy]methyl}-1H-pyrazole-5-carboxylic acid (200 mg, 0.62 mmol) in MeOH (4 mL) was added Pd/C (100 mg) under N₂. The mixture was stirred at 25° C. under H₂ (15 psi) for 12 hr. The mixture was filtered through Celite and the filtrate was concentrated to give the title compound (200 mg, 0.6164 mmol, 99.377% yield) as a colorless oil. The crude was used directly for next step.

¹H NMR (400 MHz, CDCl₃) δ ppm 6.77 (s, 2H), 5.80-5.70 (m, 2H), 3.60-3.50 (m, 2H), 2.80-2.70 (m, 1H), 2.45-2.30 (m, 1H), 2.20-2.00 (m, 1H), 1.80-1.60 (m, 5H), 1.43 (d, J=6.8 Hz, 3H), 0.80-0.70 (m, 2H), 0.06 (s, 9H).

methyl 3-(1-cyclobutylethyl)-1H-pyrazole-5-carboxylate

To a solution of 3-(1-cyclobutylethyl)-1-{[2-(trimethylsilyl)ethoxy]methyl}-1H-pyrazole-5-carboxylic acid (100 mg, 0.310 mmol) in MeOH (4 mL) was added TFA (175.69 mg, 1.54 mmol) at 25° C. The mixture was stirred at 60° C. for 12 hr. The mixture was stirred at 70° C. for 6 hr. The mixture was concentrated to give the crude title compound (100 mg, 0.2881 mmol, 93.486% yield) as yellow oil. The crude was used directly for next step.

LC-MS Method1: 0.818 min, MS (m/z) 209.1 (M+H⁺).

3-(1-cyclobutylethyl)-1H-pyrazole-5-carboxylic acid

To a solution of methyl 3-(1-cyclobutylethyl)-1H-pyrazole-5-carboxylate (100 mg, 0.480 mmol) in THF (1 mL) and H₂O (2 mL) was added LiOH·H₂O (80.59 mg, 1.92 mmol). The mixture was stirred at 20° C. for 2 hr. The mixture was diluted with H₂O (10 mL), adjusted pH to 4 to 5 by 1M HCl and extracted by EA (10 mL×3). The combined organic layer was dried over Na₂SO₄ and the solvent was removed to give the title compound (80 mg, 0.4119 mmol, 85.779% yield) as a yellow oil.

¹H NMR (400 MHz, CDCl₃) δ ppm 0.66 (s, 1H), 2.90-2.70 (m, 1H), 2.50-2.30 (m, 1H), 2.00-1.50 (m, 6H), 1.25 (d, J=6.8 Hz, 3H).

[5-(1-cyclobutylethyl)-1H-pyrazol-3-yl][(1R,5S,6r)-6-(5,5-dimethyl-4,5-dihydro-1,2-oxazol-3-yl)-3-azabicyclo[3.1.0]hex-3-yl]methanone To a solution of 3-(1-cyclobutylethyl)-1H-pyrazole-5-carboxylic acid (120 mg, 0.62 mmol) and EDCI (130 mg, 0.68 mmol) in Pyridine (5 mL) was added (1R,5S,6r)-6-(5,5-dimethyl-4,5-dihydro-1,2-oxazol-3-yl)-3-azabicyclo[3.1.0]hexane TFA salt (120 mg, 0.67 mmol). The mixture was stirred at 20° C. for 2 h. The reaction mixture was concentrated to give a residue. The residue was purified by Prep-HPLC (NH₃) to give the title compound (10 mg, 0.028 mmol) as a white solid.

LC-MS Method1: 357.1 [M+H⁺]

¹H NMR (400 MHz, CDCl₃) δ ppm 6.44 (s, 1H) 4.32 (d, J=11.6 Hz, 1H) 4.20 (d, J=12.6 Hz, 1H) 3.92 (dd, J=11.4, 4.3 Hz, 1H) 3.65 (dd, J=12.6, 4.3 Hz, 1H) 3.60-3.70 (m, 1H) 2.82-2.78 (m, 1H) 2.66 (s, 2H) 2.35-2.46 (m, 1H) 1.73-2.17 (m, 8H) 1.44 (t, J=3.4 Hz, 1H) 1.38 (s, 6H) 1.18 (d, J=7.0 Hz, 3H)

Example 92 (5-cyclopropyl-1H-pyrazol-3-yl)[(1R,5S,6r)-6-(5,5-dimethyl-4,5-dihydro-1,2-oxazol-3-yl)-3-azabicyclo[3.1.0]hex-3-yl]methanone (5-cyclopropyl-1H-pyrazol-3-yl)[(1R,5S,6r)-6-(5,5-dimethyl-4,5-dihydro-1,2-oxazol-3-yl)-3-azabicyclo[3.1.0]hex-3-yl]methanone To a stirred solution of 5-cyclopropyl-1H-pyrazole-3-carboxylic acid (23.0 mg, 0.151 mmol) and HATU (57.5 mg, 0.151 mmol) in THF (0.76 mL) was added DIPEA (0.13 mL, 0.756 mmol). After stirred at 50° C. for 30 min, (1R,5S,6r)-6-(5,5-dimethyl-4,5-dihydro-1,2-oxazol-3-yl)-3-azabicyclo[3.1.0]hexane hydrochloride (36.0 mg, 0.166 mmol) was added and the reaction was stirred at 50° C. for 1 hr to give a yellow solution. H₂O was added and it was extracted with DCM. The combined organic layer was dried over Na₂SO₄ and concentrated in vacuum to give a yellow oil. The crude was purified by silica gel chromatography (EtOAc/DCM=99/1 to 80/20) to give the title compound (14.7 mg, 0.047 mmol, 47.5% yield) as a beige powder.

LC-MS Method1: 315.0[M+H⁺]

¹H NMR (400 MHz, CHLOROFORM-d) δ=6.30 (s, 1H), 4.23 (d. J=11.7 Hz, 1H), 4.18 (d. J=12.9 Hz, 1H), 3.88 (dd, J=11.1, 4.2 Hz, 1H), 3.64 (dd, J=12.9, 4.5 Hz, 1H), 2.65 (s, 2H), 2.15-2.01 (m, 2H), 1.92-1.87 (m, 1H), 1.42 (t, J=3.0 Hz, 1H), 1.37 (s, 6H), 0.99-0.94 (m, 2H), 0.77-0.72 (m, 2H)

Example 93 (5-isopropyl-1H-pyrazol-3-yl)[(1R,5S, 6r)-6-(5-methyl-4,5-dihydro-1,2-oxazol-3-yl)-3-azabicyclo[3.1.0]hex-3-yl]methanone (5-isopropyl-1H-pyrazol-3-yl)[(1R,5S,6r)-6-(5-methyl-4,5-dihydro-1,2-oxazol-3-yl)-3-azabicyclo [3.1.0]hex-3-yl]methanone To a mixture of (1R,5S,6r)-6-(5-methyl-4,5-dihydro-1,2-oxazol-3-yl)-3-azabicyclo[3.1.0]hexane hydrochloride (50 mg, 0.3000 mmol) in DMF (0.50 mL) were added DIPEA (0.2 mL, 1.2 mmol), 5-isopropyl-1H-pyrazole-3-carboxylic acid (46.38 mg, 0.3000 mmol) and HATU (148.6 mg, 0.3900 mmol). The resulting mixture was stirred at 20° C. for 16 hr to give brown mixture. TLC (PE/EA=0/1) showed new spots and the reactant was consumed completed. The reaction mixture was diluted with H₂O (5 mL), extracted with EtOAc (5 mL×2), and then washed with H₂O (5 mL) and brine (5 mL×2). The combined organic layers were separated, then dried over Na₂SO₄ and concentrated in vacuum to give crude product. The crude product was purified by prep-HPLC (NH₃) to give the title compound (2.11 mg, 0.0070 mmol, 2.3198% yield) as white solid.

¹H NMR (400 MHz, CDCl₃) δ=6.40 (s, 1H), 4.63-4.56 (m, 1H), 4.23 (br d, J=11.3 Hz, 1H), 4.13 (d, J=12.8 Hz, 1H), 3.84 (dd, J=4.3, 11.5 Hz, 1H), 3.58 (dd, J=4.0, 12.8 Hz, 1H), 2.98-2.88 (m, 2H), 2.47-2.38 (m, 1H), 2.08 (br d, J=3.5 Hz, 1H), 1.98 (br s, 1H), 1.28-1.20 (m, 12H)

Example 94 {(1R,5S,6r)-6-[5,5-dimethyl-4-(3-methylphenyl)-4,5-dihydro-1,2-oxazol-3-yl]-3-azabicyclo [3.1.0]hex-3-yl}(5-isopropyl-1H-pyrazol-3-yl) methanone tert-butyl (1R,5S,6r)-6-[5,5-dimethyl-4-(3-methylphenyl)-4,5-dihydro-1,2-oxazol-3-yl]-3-azabicyclo [3.1.0]hexane-3-carboxylate To a solution of tert-butyl (1R,5S,6r)-6-[(Z)-chloro(hydroxyimino)methyl]-3-azabicyclo[3.1.0]hexane-3-carboxylate (220 mg, 0.8400 mmol) and 1-methyl-3-(2-methyl-1-propen-1-yl)benzene (246.78 mg, 1.69 mmol) in DCM (5 mL) was added triethylamine (0.23 mL, 1.69 mmol). The reaction mixture was stirred at 10° C. for 16 hr to give a yellow solution. TLC (PE/EA=3/1 Rf=0.7) showed a new spot was detected. H₂O (15 mL) was added and it was extracted with EtOAc (15 mL×2). The combined organic layer was dried over Na₂SO₄ and concentrated in vacuum to give a yellow oil. The crude was purified by silica gel chromatography (PE/EA=1/0 to 3/1) to give the title compound (120 mg, 0.3239 mmol, 38.385% yield) as yellow oil.

¹H NMR (400 MHz, CHLOROFORM-d) δ 7.40-7.30 (m, 1H), 7.20-7.10 (m, 1H), 6.80-6.70 (m, 2H), 3.62 (s, 1H), 3.55-3.35 (m, 2H), 3.35-3.20 (m, 2H), 2.29 (s, 3H), 1.70-1.60 (m, 1H), 1.32 (s, 9H), 1.108 (s, 3H), 0.86 (s, 3H), 0.60-0.50 (m, 2H).

(1R,5S,6r)-6-[5,5-dimethyl-4-(3-methylphenyl)-4,5-dihydro-1,2-oxazol-3-yl]-3-azabicyclo[3.1.0]hexane TFA Salt A solution of tert-butyl (1R,5S,6r)-6-[5,5-dimethyl-4-(3-methylphenyl)-4,5-dihydro-1,2-oxazol-3-yl]-3-azabicyclo [3.1.0]hexane-3-carboxylate (120 mg, 0.3200 mmol) in HCl/dioxane (2 mL, 0.3200 mmol) was stirred at 10° C. for 3 hr to give a yellow solution. It was evaporated in vacuum to give the title compound (110 mg, 0.3585 mmol, 110.69% yield) as yellow oil {(1R,5S,6r)-6-[5,5-dimethyl-4-(3-methylphenyl)-4, 5-dihydro-1,2-oxazol-3-yl]-3-azabicyclo[3.1.0]hex-3-yl}(5-isopropyl-1H-pyrazol-3-yl)methanone To a solution of 5-isopropyl-1H-pyrazole-3-carboxylic acid (12 mg, 0.0800 mmol) and N-ethyl-N-isopropylpropan-2-amine (0.04 mL, 0.2300 mmol) in DMF (1 mL) was added HATU (32.73 mg, 0.0900 mmol). After stirred for 30 min, (1R,5S,6r)-6-[5,5-dimethyl-4-(3-methylphenyl)-4,5-dihydro-1,2-oxazol-3-yl]-3-azabicyclo[3.1.0]hexane TFA salt (20.3 mg, 0.0700 mmol) was added to be stirred for 16 hr to give a yellow solution. H₂O (30 mL) was added and it was extracted with EtOAc (30 mL×2). The combined organic layer was dried over Na₂SO₄ and concentrated in vacuum to give a yellow oil. The crude was purified by Prep-HPLC (FA). The afford flows were concentrated in vacuum to remove most of CH₃CN and lyophilized to give the title compound (1.25 mg, 0.0031 mmol, 3.9505% yield) as white solid.

LC-MS Method1: 407.1 [M+H⁺]

¹H NMR (400 MHz, CHLOROFORM-d) δ 7.22 (d, J=7.50 Hz, 1H), 7.11 (br d, J=7.38 Hz, 1H), 6.81-6.87 (m, 2H), 6.40 (s, 1H), 4.10-4.20 (m, 1H), 3.98-4.08 (m, 1H), 3.84 (ddd, J=4.44, 11.29, 19.54 Hz, 1H), 3.70 (d, J=3.00 Hz, 1H), 3.57 (td, J=4.60, 12.57 Hz, 1H), 2.99 (td, J=6.86, 13.91 Hz, 1H), 2.35 (s, 3H), 2.29 (td, J=3.86, 7.41 Hz, 1H), 2.13 (td, J=3.77, 7.35 Hz, 1H), 2.01 (td, J=3.81, 7.13 Hz, 1H), 1.89 (td, J=3.85, 7.32 Hz, 1H), 1.39 (s, 3H), 1.27 (d, J=7.00 Hz, 6H), 0.94 (s, 3H)

Example 95 (5-isopropyl-1H-pyrazol-3-yl)[(1R,5S, 6r)-6-(4-oxa-5-azaspiro[2.4]hept-5-en-6-yl)-3-azabicyclo[3.1.0]hex-3-yl]methanone (5-isopropyl-1H-pyrazol-3-yl)[(1R,5S,6r)-6-(4-oxa-5-azaspiro[2.4]hept-5-en-6-yl)-3-azabicyclo[3.1.0] hex-3-yl]methanone A 100 ml round-bottom flask was charged with 5-isopropyl-1H-pyrazole-3-carboxylic acid (125 mg, 0.8100 mmol), HATU (371.96 mg, 0.9700 mmol), DMF (4 mL), N-ethyl-N-isopropylpropan-2-amine (0.42 mL, 2.43 mmol) and DMF (4 mL). After stirred for 30 min, 6-[(1R,5S,6r)-3-azabicyclo[3.1.0]hex-6-yl]-4-oxa-5-azaspiro[2.4]hept-5-ene hydrochloride (236.95 mg, 0.8100 mmol) was added. The reaction mixture was stirred at 10° C. for 16 hr to give a yellow solution. H₂O (20 mL) was added and it was extracted with EtOAc (30 mL×2). The combined organic layer was dried over Na₂SO₄ and concentrated in vacuum to give a yellow oil. The crude was purified by Prep-HPLC (FA). The afford flows were concentrated in vacuum to remove most of CH₃CN and lyophilized to give the title compound (36.35 mg, 0.1156 mmol, 14.261% yield) as white solid.

LC-MS Method1: 315.1 [M+H⁺]

¹H NMR (400 MHz, CHLOROFORM-d) δ 6.48 (s, 1H), 4.29-4.34 (m, 1H), 4.21 (d, J=12.55 Hz, 1H), 3.93 (dd, J=4.52, 11.54 Hz, 1H), 3.66 (dd, J=4.39, 12.67 Hz, 1H), 3.00-3.06 (m, 1H), 2.98 (s, 2H), 2.19 (td, J=3.58, 7.40 Hz,

1H), 2.08 (td, J=3.89, 7.28 Hz, 1H), 1.50 (t, J=3.39 Hz, 1H), 1.30 (d, J=7.03 Hz, 6H), 1.09-1.14 (m, 2H), 0.65-0.74 (m, 2H)

Example 96 (5-isopropyl-1H-pyrazol-3-yl){(1R,5S,6r)-6-[(1S,5S)-2-oxa-3-azabicyclo[3.1.0]hex-3-en-4-yl]-3-azabicyclo[3.1.0]hex-3-yl}methanone (5-isopropyl-1H-pyrazol-3-yl) {(1R,5S,6r)-6-[(1S,5S)-2-oxa-3-azabicyclo[3.1.0]hex-3-en-4-yl]-3-azabicyclo[3.1.0]hex-3-yl}methanone 12 mg of (5-isopropyl-1H-pyrazol-3-yl)[(1R,5S,6r)-6-(2-oxa-3-azabicyclo[3.1.0]hex-3-en-4-yl)-3-azabicyclo[3.1.0]hex-3-yl]methanone (Example 97) was sent for SFC chiral separation to afford the title compound (4.95 mg)

LC-MS Method1: 301.2 [M+H$^+$]

$^1$H NMR (400 MHz, CHLOROFORM-d) δ ppm 10.27 (1H, br s), 6.41 (1H, s), 4.79 (1H, td, J=5.33, 2.13 Hz), 4.27 (1H, br d, J=11.04 Hz), 4.16 (1H, dd, J=12.67, 1.38 Hz), 3.82-3.93 (1H, m), 3.60 (1H, br dd, J=12.55, 5.02 Hz), 2.95 (1H, spt, J=6.94 Hz), 2.25-2.36 (1H, m), 2.13-2.21 (1H, m), 2.08 (1H, br s), 1.96-2.21 (1H, m), 1.96-2.03 (1H, m), 1.57 (1H, t, J=3.39 Hz), 1.23 (6H, d, J=7.03 Hz), 0.81 (1H, dt, J=9.29, 5.52 Hz), 0.24 (1H, br d, J=2.51 Hz)

Example 97 (5-isopropyl-1H-pyrazol-3-yl)[(1R,5S,6r)-6-(2-oxa-3-azabicyclo[3.1.0]hex-3-en-4-yl)-3-azabicyclo[3.1.0]hex-3-yl]methanone (5-isopropyl-1H-pyrazol-3-yl)[(1R,5S,6r)-6-(2-oxa-3-azabicyclo[3.1.0]hex-3-en-4-yl)-3-azabicyclo[3.1.0]hex-3-yl]methanone To a solution of 5-isopropyl-1H-pyrazole-3-carboxylic acid (25.82 mg, 0.1700 mmol) in DMF (2.0833 mL) were added HATU (75.67 mg, 0.2000 mmol) and DIPEA (0.08 mL, 0.4600 mmol). The mixture was stirred at 25° C. for 30 min. Then 4-[(1R,5S,6r)-3-azabicyclo[3.1.0]hex-6-yl]-2-oxa-3-azabicyclo[3.1.0]hex-3-ene (25 mg, 0.1500 mmol) was added to the mixture. The mixture was stirred at 25° C. for 3 h to give brown solution. The reaction mixture was concentrated directly. The residue was purified by prep-HPLC (NH$_3$) to give the title compound (21.39 mg, 0.0712 mmol, 46.774% yield) as white solid.

LC-MS Method1: 301.2 [M+H$^+$]

$^1$H NMR (400 MHz, CHLOROFORM-d) δ ppm 10.27 (1H, br s), 6.41 (1H, s), 4.79 (1H, td, J=5.33, 2.13 Hz), 4.27 (1H, br d, J=11.04 Hz), 4.16 (1H, dd, J=12.67, 1.38 Hz), 3.82-3.93 (1H, m), 3.60 (1H, br dd, J=12.55, 5.02 Hz), 2.95 (1H, spt, J=6.94 Hz), 2.25-2.36 (1H, m), 2.13-2.21 (1H, m), 2.08 (1H, br s), 1.96-2.21 (1H, m), 1.96-2.03 (1H, m), 1.57 (1H, t, J=3.39 Hz), 1.23 (6H, d, J=7.03 Hz), 0.81 (1H, dt, J=9.29, 5.52 Hz), 0.24 (1H, br d, J=2.51 Hz)

Example 98 [(1R,5S,6r)-6-(4-isobutyl-5,5-dimethyl-4,5-dihydro-1,2-oxazol-3-yl)-3-azabicyclo[3.1.0]hex-3-yl](5-isopropyl-1H-pyrazol-3-yl)methanone

[(1R,5S,6r)-6-(4-isobutyl-5,5-dimethyl-4,5-dihydro-1,2-oxazol-3-yl)-3-azabicyclo[3.1.0]hex-3-yl](5-isopropyl-1H-pyrazol-3-yl)methanone To a solution of (1R,5S,6r)-6-(4-isobutyl-5,5-dimethyl-4,5-dihydro-1,2-oxazol-3-yl)-3-azabicyclo[3.1.0]hexane hydrochloride (300 mg, 1.27 mmol) and DIPEA (1.05 mL, 6.35 mmol) in DMF (8.5 mL) were added HATU (578 mg, 1.52 mmol) and 5-isopropyl-1H-pyrazole-3-carboxylic acid (195 mg, 1.27 mmol), and the mixture was stirred at 20° C. for 12 hr. LCMS showed the desired mass was detected. The reaction mixture was poured into H$_2$O (30 mL) and extracted by EtOAc (20 mL×3). The organic phase was washed by brine (50 mL), dried over anhydrous Na$_2$SO$_4$ and concentrated to give a residue. The residue was purified by Prep-HPLC (NH$_3$) to afford the title compound (12 mg, 0.03 mmol, 2.53% yield) as a white solid.

LC-MS Method1: 373.2 [M+H$^+$]

$^1$H NMR (400 MHz, METHANOL-d$_4$) δ ppm 0.93-1.01 (m, 6H) 1.19 (d, J=1.6 Hz, 3H) 1.30 (d, J=6.9 Hz, 9H) 1.35 (d, J=2.1 Hz, 3H) 1.41-1.49 (m, 2H) 1.69-1.79 (m, 1H) 1.98-2.25 (m, 3H) 2.95 (br t, J=7.2 Hz, 1H) 2.99-3.08 (m, 1H) 3.57-3.69 (m, 1H) 3.93 (br d, J=12.0 Hz, 1H) 4.01-4.15 (m, 1H) 4.37 (br dd, J=11.9, 5.4 Hz, 1H) 6.45 (s, 1H)

Example 99 (5-isopropyl-1H-pyrazol-3-yl)[(1R,5S,6r)-6-(4,5,5-trimethyl-4,5-dihydro-1,2-oxazol-3-yl)-3-azabicyclo[3.1.0]hex-3-yl]methanone (5-isopropyl-1H-pyrazol-3-yl)[(1R,5S,6r)-6-(4,5,5-trimethyl-4,5-dihydro-1,2-oxazol-3-yl)-3-azabicyclo[3.1.0]hex-3-yl]methanone To a mixture of 5-isopropyl-1H-pyrazole-3-carboxylic acid (39.68 mg, 0.2600 mmol) in DMF (0.4639 mL) were added HATU (127.91 mg, 0.3300 mmol) and DIPEA (0.21 mL, 1.29 mmol). The mixture was heated at 50° C. for 30 min. (1R,5S,6r)-6-(4,5,5-trimethyl-4,5-dihydro-1,2-oxazol-3-yl)-3-azabicyclo[3.1.0]hexane TFA salt (50 mg, 0.2600 mmol) was added. The resulting mixture was stirred at 20° C. for 4 hr. The reaction mixture was diluted with H$_2$O (10 mL), extracted with EtOAc (10 mL×2), and then washed with brine (10 mL). The combined organic layers were separated, then dried over Na$_2$SO$_4$ and concentrated in vacuum to give crude oil. The crude oil was purified by prep-HPLC (NH$_3$) and lyophilized to give the title compound (4.91 mg, 0.0149 mmol, 5.7737% yield) as white solid.

$^1$H NMR (400 MHz, MeOD) δ=6.47 (s, 1H), 4.39 (br d, J=12.0 Hz, 1H), 4.12 (dd, J=5.4, 12.7 Hz, 1H), 3.95 (br d, J=12.5 Hz, 1H), 3.64 (br d, J=12.8 Hz, 1H), 3.16-3.01 (m, 1H), 2.92 (q, J=7.2 Hz, 1H), 2.25-2.00 (m, 2H), 1.37 (br s, 1H), 1.36-1.27 (m, 12H), 1.22 (s, 3H)

Example 100 [(1R,5S,6r)-6-(5-ethyl-5-methyl-4,5-dihydro-1,2-oxazol-3-yl)-3-azabicyclo[3.1.0]hex-3-yl](5-isopropyl-1H-pyrazol-3-yl)methanone

[(1R,5S,6r)-6-(5-ethyl-5-methyl-4,5-dihydro-1,2-oxazol-3-yl)-3-azabicyclo[3.1.0]hex-3-yl](5-isopropyl-1H-pyrazol-3-yl)methanone To a mixture of 5-isopropyl-1H-pyrazole-3-carboxylic acid (23.81 mg, 0.1500 mmol) in DMF (0.2783 mL) were added HATU (76.75 mg, 0.2000 mmol), DIPEA (0.13 mL, 0.7700 mmol) and (1R,5S,6r)-6-(5-ethyl-5-methyl-4,5-dihydro-1,2-oxazol-3-yl)-3-azabicyclo[3.1.0]hexane TFA salt (30 mg, 0.1500 mmol). The resulting mixture was stirred at 20° C. for 4 hr. The reaction mixture was diluted with H$_2$O (5 mL), extracted with EtOAc (5 mL×2), and then washed with brine (8 mL). The combined organic layers were separated, then dried over Na$_2$SO$_4$ and concentrated in vacuum to give crude oil. The crude oil was purified by prep-HPLC (NH₃) and lyophilized to give the title compound (1.82 mg, 0.0055 mmol, 3.5669% yield) as white solid.

¹H NMR (400 MHz, MeOD) δ=6.47 (br s, 1H), 4.37 (br s, 1H), 4.12 (d, J=12.8 Hz, 1H), 3.95 (dd, J=3.8, 12.3 Hz, 1H), 3.64 (dd, J=4.4, 12.4 Hz, 1H), 3.08-3.01 (m, 1H), 2.87-2.74 (m, 1H), 2.73-2.59 (m, 1H), 2.19-2.04 (m, 2H), 1.68-1.60 (m, 2H), 1.52-1.48 (m, 1H), 1.32-1.30 (m, 9H), 0.94 (t, J=7.5 Hz, 3H)

Example 101 (5-isopropyl-1H-pyrazol-3-yl)[(1R,5S, 6r)-6-(4-methoxy-5,5-dimethyl-4,5-dihydro-1,2-oxazol-3-yl)-3-azabicyclo[3.1.0]hex-3-yl]methanone (5-isopropyl-1H-pyrazol-3-yl)[(1R,5S,6r)-6-(4-methoxy-5,5-dimethyl-4,5-dihydro-1,2-oxazol-3-yl)-3-azabicyclo[3.1.0]hex-3-yl]methanone To a solution of 5-isopropyl-1H-pyrazole-3-carboxylic acid (49.12 mg, 0.3200 mmol) in DMF (2.393 mL) were added HATU (91.62 mg, 0.4800 mmol) and DIPEA (0.16 mL, 0.9600 mmol). The reaction mixture was stirred at 15° C. for 30 min. Then (1R,5S,6r)-6-(4-methoxy-5,5-dimethyl-4,5-dihydro-1,2-oxazol-3-yl)-3-azabicyclo[3.1.0]hexane TFA salt (67 mg, 0.3200 mmol) was added to the reaction. The reaction mixture was stirred at 15° C. for 0.5 hr to give a yellow mixture. LCMS showed the desired MS. The reaction mixture was purified by prep-HPLC (NH₃) to give the title compound (43.85 mg, 0.1266 mmol, 39.725% yield) as white powder.

LC-MS Method1: 347.2 [M+H⁺]

¹H NMR (400 MHz, CHLOROFORM-d) δ=6.48 (s, 1H), 4.31 (br d, J=11.0 Hz, 1H), 4.22 (m, 1H), 4.03 (d, J=16.1 Hz, 1H), 3.93 (m, 1H), 3.66 (m, 1H), 3.45 (s, 3H), 3.02 (m, 1H), 2.30-2.19 (m, 1H), 2.11 (m, 1H), 1.47-1.42 (m, 1H), 1.35 (s, 3H), 1.30 (d, J=7.0 Hz, 9H)

Example 102 (5-isopropyl-1H-pyrazol-3-yl){(1R, 5S,6r)-6-[6a-methyl-4,5,6,6a-tetrahydro-3aH-cyclopenta[d][1,2]oxazol-3-yl]-3-azabicyclo[3.1.0]hex-3-yl}methanone tert-butyl (1R,5S,6r)-6-[6a-methyl-4.5.6.6a-tetrahydro-3aH-cyclopenta[d][1.2]oxazol-3-yl]-3-azabicyclo[3.1.0]hexane-3-carboxylate To a mixture of tert-butyl (1R,5S,6r)-6-[(Z)-chloro(hydroxyimino)methyl]-3-azabicyclo[3.1.0]hexane-3-carboxylate (100 mg, 0.3800 mmol) and 1-methylcyclopent-1-ene (0.61 mL, 5.75 mmol) in tert-Butyl methyl ether (4 mL) was added Et₃N (0.07 mL, 0.3800 mmol) in tert-Butyl methyl ether (1 mL) dropwise over 1 h. The mixture was stirred at 20° C. for 5 hr. TLC (PE/EA=3/1) showed a major new spot (Rf=0.4) and the reaction was completed. The mixture was washed with H₂O (10 mL) and then extracted with EtOAc (10 mL×2). The combined organic layer was dried over Na₂SO₄ and concentrated to give crude oil. The crude oil was purified by prep-TLC (PE/EA=3/1) to give the title compound (40 mg, 0.1305 mmol, 34.037% yield) as pale yellow solid.

LC-MS Method1 1.077 min, MS (m/z) 307.1 (M+H⁺).

3-[(1R,5S,6r)-3-azabicyclo[3.1.0]hex-6-yl]-6a-methyl-4,5,6,6a-tetrahydro-3aH-cyclopenta[d][1,2]oxazole hydrochloride A mixture of tert-butyl (1R,5S,6r)-6-[6a-methyl-4,5,6,6a-tetrahydro-3aH-cyclopenta[d][1,2]oxazol-3-yl]-3-azabicyclo[3.1.0]hexane-3-carboxylate (40 mg, 0.1300 mmol) in HCl/dioxane (5 mL, 4 M) was stirred at 20° C. for 2 hr. The mixture was concentrated to dryness with EA (15 mL) directly to give the title compound (26.9 mg, crude product) as pale yellow solid.

LC-MS Method1 0.535 min, MS (m/z) 207.0 (M+H⁺).

(5-isopropyl-1H-pyrazol-3-yl) {(1R,5S,6r)-6-[6a-methyl-4,5,6,6a-tetrahydro-3aH-cyclopenta[d][1,2]oxazol-3-yl]-3-azabicyclo[3.1.0]hex-3-yl}methanone To a mixture of (3aR,6aR)-3-[(1R,5S,6r)-3-azabicyclo[3.1.0]hex-6-yl]-6a-methyl-4,5,6,6a-tetrahydro-3aH-cyclopenta[d][1,2]oxazole hydrochloride (26.9 mg, 0.1300 mmol) in DMF (1.5 mL) were added 5-isopropyl-1H-pyrazole-3-carboxylic acid (20.1 mg, 0.1300 mmol), DIPEA (0.06 mL, 0.3900 mmol) and HATU (64.42 mg, 0.1700 mmol), and the mixture was stirred at 20° C. for 16 hr. TLC (PE/EA=0/1) showed a major new spot (Rf=0.6) and the reaction was completed. The mixture was diluted with H₂O (10 mL) and EA (10 mL×2). The combined organic layer was separated, then dried over Na₂SO₄ and concentrated in vacuum to give crude oil. The crude oil was purified by prep-TLC (PE/EA=0/1) to give the title compound (28 mg, 0.0818 mmol, 62.702% yield) as pale yellow solid.

¹H NMR (400 MHz, DMSO-d₆) δ=13.05-12.79 (m, 1H), 6.37 (s, 1H), 4.35 (br dd, J=4.0, 12.0 Hz, 1H), 4.01-3.91 (m, 1H), 3.82 (br d, J=11.8 Hz, 1H), 3.55-3.53 (m, 1H), 3.48 (br d, J=12.8 Hz, 1H), 3.12 (br d, J=3.3 Hz, 1H), 2.97 (td, J=7.1, 13.7 Hz, 1H), 2.09-1.94 (m, 1H), 2.07-1.90 (m, 1H), 1.90-1.73 (m, 4H), 1.68-1.49 (m, 3H), 1.42-1.30 (m, 4H), 1.22 (d, J=7.0 Hz, 8H).

Example 103 (5-isopropyl-1H-pyrazol-3-yl)[(1R,5S, 6r)-6-(5-methyl-1,2-oxazol-3-yl)-3-azabicyclo[3.1.0] hex-3-yl]methanone (5-isopropyl-1H-pyrazol-3-yl)[(1R,5S,6r)-6-(5-methyl-1,2-oxazol-3-yl)-3-azabicyclo[3.1.0]hex-3-yl]methanone A 100 mL round-bottom flask was charged with 5-isopropyl-1H-pyrazole-3-carboxylic acid (70 mg, 0.4500 mmol), N-ethyl-N-isopropylpropan-2-amine (0.24 mL, 1.41 mmol), HATU (190.94 mg, 0.5000 mmol) and DMF (3 mL). After stirring for 30 min, (1R,5S,6r)-6-(5-methyl-1,2-oxazol-3-yl)-3-azabicyclo[3.1.0]hexane TFA salt (126.33 mg, 0.4500 mmol) was added. The reaction mixture was stirred at 20° C. for 16 hr to give a yellow solution. LCMS showed a new peak gives the desired ms. H₂O (30 mL) was added and it was extracted with EtOAc (30 mL×2). The combined organic layer was dried over Na₂SO₄ and concentrated in vacuum to give a yellow oil. The crude was purified by Prep-HPLC (FA). The afforded flows were concentrated in vacuum to remove most of CH₃CN and lyophilized to give the title compound (13.52 mg, 0.0448 mmol, 9.8741% yield) as white solid.

LC-MS Method1: 301.1 [M+H⁺]

¹H NMR (400 MHz, CHLOROFORM-d) δ 6.48 (br s, 1H), 5.75 (s, 1H), 4.21-4.33 (m, 2H), 3.96 (br dd, J=3.81, 10.94 Hz, 1H), 3.69 (br dd, J=3.69, 12.44 Hz, 1H), 3.04 (td, J=6.83, 13.73 Hz, 1H), 2.36 (s, 3H), 2.15 (br d, J=3.38 Hz, 1H), 2.04-2.09 (m, 1H), 1.75 (t, J=3.06 Hz, 1H), 1.30 (d, J=6.88 Hz, 6H)

Example 104 {(1R,5S,6r)-6-[5-(difluoromethyl)-4-methyl-1,2-oxazol-3-yl]-3-azabicyclo[3.1.0]hex-3-yl}(5-isopropyl-1H-pyrazol-3-yl)methanone tert-butyl (1R,5S,6r)-6-[1-hydroxypropyl]-3-azabicyclo[3.1.0]hexane-3-carboxylate To a solution of tert-butyl (1R,5S,6r)-6-formyl-3-azabicyclo[3.1.0]hexane-3-carboxylate (500 mg, 2.37 mmol) in THF (10 mL) was added bromo(ethyl)magnesium (1.6 mL, 4.73 mmol, 3M in Et$_2$O) drop-wise at −78° C. The reaction was allowed to warm to 0° C. and stirred for further 20 min to give pale yellow mixture. The reaction was quenched with H$_2$O (15 mL), diluted with EA (30 mL) and acidified with 2N HCl to pH=5. The aqueous layer was extracted with EA (20 mL×2). The combined EA layer was dried over Na$_2$SO$_4$ and concentrated in vacuum to give the title compound (590 mg, 2.4448 mmol, crude) as pale yellow oil.

tert-butyl (1R,5S,6r)-6-propionyl-3-azabicyclo[3.1.0]hexane-3-carboxylate

To a mixture of tert-butyl (1R,5S,6r)-6-[1-hydroxypropyl]-3-azabicyclo[3.1.0]hexane-3-carboxylate (590 mg, 2.44 mmol) and NaHCO$_3$ (410.77 mg, 4.89 mmol) in DCM (25 mL) was added Dess-Martin's reagent (1555.4 mg, 3.67 mmol) at 0° C. The mixture was stirred at 20° C. for 12 h to give white mixture. The mixture was diluted with DCM (30 mL) and H$_2$O (20 mL) and basified with saturated NaHCO$_3$ to pH=8. The aqueous layer was extracted with DCM (20 mL). The combined DCM layer was dried over Na$_2$SO$_4$ and concentrated in vacuum to give crude product which was purified by flash column (PE/EA=1/0 to 3/1) to give the title compound (500 mg, 2.0893 mmol, 85.461% yield) as pale yellow oil.

tert-butyl (1R,5S,6r)-6-(4-ethoxy-2-methyl-3,4-dioxobutanoyl)-3-azabicyclo[3.1.0]hexane-3-carboxylate To a solution of tert-butyl (1R,5S,6r)-6-propionyl-3-azabicyclo[3.1.0]hexane-3-carboxylate (500 mg, 2.09 mmol) in THF (10 mL) was added LHMDS (2.5 mL, 2.51 mmol, 1 M in THF) at −78° C. The reaction was stirred at −78° C. for 1 h. Then, a solution of diethyl oxalate (0.34 mL, 2.51 mmol) in THF (2 mL) was added at −78° C. The reaction was allowed to warm to 20° C. and stirred for further 12 h to give pale yellow solution. The reaction was cooled to 0° C., diluted with EA (30 mL), quenched with H$_2$O (15 mL) and acidified with 2M HCl to pH=6. The aqueous layer was extracted with EA (20 mL×2). The combined organic layer was dried over Na$_2$SO$_4$ and concentrated in vacuum to give pale yellow oil. The crude oil was purified by flash column (PE/EA=1/0 to 4/1) to give the title compound (300 mg, 0.8840 mmol, 42.308% yield) as pale yellow oil. Meanwhile, about 160 mg of B76-2a was recovered.

tert-butyl (1R,5S,6r)-6-[(1E)-4-ethoxy-N-hydroxy-2-methyl-3,4-dioxobutanimidoyl]-3-azabicyclo[3.1.0]hexane-3-carboxylate To a solution of NaOH (42.43 mg, 1.06 mmol) in H$_2$O (2 mL) was added hydroxylamine hydrochloride (0.04 mL, 1.06 mmol) at 0° C. After stirred for 5 min, the reaction was added to a solution of tert-butyl (1R,5S,6r)-6-(4-ethoxy-2-methyl-3,4-dioxobutanoyl)-3-azabicyclo[3.1.0]hexane-3-carboxylate (300 mg, 0.8800 mmol) in THF (2 mL) drop-wise at 0° C. The reaction was stirred at 20° C. for 12 h to give pale yellow suspension. The suspension was diluted with EA (20 mL) and H$_2$O (10 mL) and adjusted with 2M HCl to pH=7. The aqueous layer was extracted with EA (15 mL×2). The combined organic layer was dried over Na$_2$SO$_4$ and concentrated in vacuum to give the title compound (300 mg, 0.8465 mmol, 95.762% yield) as pale yellow oil.

tert-butyl (1R,5S,6r)-6-[5-(ethoxycarbonyl)-4-methyl-1,2-oxazol-3-yl]-3-azabicyclo[3.1.0]hexane-3-carboxylate To a solution of tert-butyl (1R,5S,6r)-6-[(1E)-4-ethoxy-N-hydroxy-2-methyl-3,4-dioxobutanimidoyl]-3-azabicyclo[3.1.0]hexane-3-carboxylate (300 mg, 0.8500 mmol) and Et$_3$N (0.15 mL, 1.1 mmol) in DCM (8 mL) was added methanesulfonyl chloride (126.06 mg, 1.1 mmol) at 0° C. The reaction was stirred at 20° C. for 4 h to give pale yellow solution. The reaction was cooled to 0° C. and treated with additional MsCl (60 uL) and Et$_3$N (0.8 mL). The reaction was stirred at 20° C. for further 1 h to give pale yellow solution. The reaction was concentrated in vacuum. The residue was purified by prep-TLC (PE/EA=3/1) to give the title compound (75 mg, 0.2230 mmol, 26.339% yield) as pale yellow gum.

$^1$H NMR (400 MHz, CHLOROFORM-d) δ=4.36 (q, J=6.8 Hz, 2H), 3.80-3.55 (m, 2H), 3.50-3.40 (m, 2H), 2.23 (s, 3H), 2.15-2.10 (m, 1H), 2.10-2.00 (m, 1H), 1.60-1.50 (m, 1H), 1.40 (s, 9H), 1.02 (t, J=6.8 Hz, 3H).

tert-butyl (1R,5S,6r)-6-[5-(hydroxymethyl)-4-methyl-1,2-oxazol-3-yl]-3-azabicyclo[3.1.0]hexane-3-carboxylate To a solution of tert-butyl (1R,5S,6r)-6-[5-(ethoxycarbonyl)-4-methyl-1,2-oxazol-3-yl]-3-azabicyclo[3.1.0]hexane-3-carboxylate (100 mg, 0.3000 mmol) in THF (4 mL) was added LiAlH$_4$ (20.33 mg, 0.5400 mmol) at 0° C. The reaction was stirred at 0° C. for 20 min to give white mixture. The mixture was quenched with H$_2$O (3 drops), diluted with EA (20 mL) and stirred with Na$_2$SO$_4$ (10 g) for 10 min. The solid was filtered off. The filtrate was concentrated in vacuum to give the title compound (80 mg, 0.2718 mmol, 91.423% yield) as pale yellow oil.

tert-butyl (1R,5S,6r)-6-(5-formyl-4-methyl-1,2-oxazol-3-yl)-3-azabicyclo[3.1.0]hexane-3-carboxylate To a mixture of tert-butyl (1R,5S,6r)-6-[5-(hydroxymethyl)-4-methyl-1,2-oxazol-3-yl]-3-azabicyclo[3.1.0]hexane-3-carboxylate (80 mg, 0.2700 mmol) and NaHCO$_3$ (57.08 mg, 0.6800 mmol) in DCM (4 mL) was added Dess-Martin reagent (172.91 mg, 0.4100 mmol) at 0° C. The mixture was stirred at 20° C. for 12 h to give white mixture. The mixture was diluted with DCM (15 mL) and H$_2$O (10 mL) and basified with saturated NaHCO$_3$ to pH=8. The organic layer was collected, concentrated and purified by prep-TLC (PE/EA=3/1, rf=0.5) to give the title compound (45 mg, 0.1539 mmol, 56.639% yield) as colorless oil.

tert-butyl (1R,5S,6r)-6-[5-(difluoromethyl)-4-methyl-1,2-oxazol-3-yl]-3-azabicyclo[3.1.0]hexane-3-carboxylate To a solution of tert-butyl (1R,5S,6r)-6-(5-formyl-4-methyl-1,2-oxazol-3-yl)-3-azabicyclo[3.1.0]hexane-3-carboxylate (45 mg, 0.1500 mmol) in DCM (3 mL) was added DAST (74.35 mg, 0.4600 mmol) drop-wise at −78° C. The reaction was allowed to warm to 20° C. and stirred for further 12 h to give pale yellow solution. The reaction was diluted with DCM (10 mL), cooled to 0° C., treated with $H_2O$ (5 mL) and saturated $NaHCO_3$ (3 mL). The aqueous layer was extracted with EA (10 mL×2). The combined organic layers were dried over $Na_2SO_4$ and concentrated in vacuum to give the title compound (55 mg, 0.1750 mmol) as pale yellow oil.

(1R,5S,6r)-6-[5-(difluoromethyl)-4-methyl-1,2-oxazol-3-yl]-3-azabicyclo[3.1.0]hexane TFA Salt A solution of tert-butyl (1R,5S,6r)-6-[5-(difluoromethyl)-4-methyl-1,2-oxazol-3-yl]-3-azabicyclo[3.1.0]hexane-3-carboxylate (55 mg, 0.1700 mmol) in DCM (2 mL) was treated with TFA (0.2 mL, 0.1700 mmol) and stirred at 20° C. for 10 min to give pale brown solution. The reaction was concentrated in vacuum to give the title compound (60 mg, 0.2801 mmol, TFA salt) as pale brown oil.

{(1R,5S,6r)-6-[5-(difluoromethyl)-4-methyl-1,2-oxazol-3-yl]-3-azabicyclo[3.1.0]hex-3-yl}(5-isopropyl-1H-pyrazol-3-yl)methanone To a solution of (1R,5S,6r)-6-[5-(difluoromethyl)-4-methyl-1,2-oxazol-3-yl]-3-azabicyclo[3.1.0]hexane TFA salt (60 mg, 0.1800 mmol) and 5-isopropyl-1H-pyrazole-3-carboxylic acid (28.2 mg, 0.1800 mmol) in DMF (1 mL) were added HATU (69.93 mg, 0.1800 mmol) and $Et_3N$ (0.05 mL, 0.3700 mmol) at 0° C. The reaction was stirred at 20° C. for 12 h to give pale yellow solution. The reaction was concentrated in vacuum to give pale yellow oil, which was purified by prep-TLC (PE/EA=1/2) twice to give desired product. The product was lyophilized to give the title compound (21.2 mg, 0.0605 mmol, 33.078% yield) as a white solid.

LC-MS Method1: 350.9 [M+H$^+$]
$^1$H NMR (400 MHz, CHLOROFORM-d) δ=10.05 (s, 1H), 6.78-6.48 (m, 1H), 6.45 (s, 1H), 4.31 (br d, J=10.3 Hz, 1H), 4.21 (d, J=12.5 Hz, 1H), 3.92 (dd, J=4.4, 11.4 Hz, 1H), 3.64 (dd, J=4.3, 12.8 Hz, 1H), 2.96 (td, J=6.9, 13.8 Hz, 1H), 2.29 (td, J=3.8, 7.4 Hz, 1H), 2.13 (td, J=3.7, 7.3 Hz, 1H), 2.06 (t, J=2.0 Hz, 3H), 1.26-1.21 (m, 6H)

Example 105 {(1R,5S,6r)-6-[4-(dimethylamino)-5-methyl-1,2-oxazol-3-yl]-3-azabicyclo[3.1.0]hex-3-yl}(5-isopropyl-1H-pyrazol-3-yl)methanone tert-butyl (1R,5S,6r)-6-[4-(ethoxycarbonyl)-5-methyl-1,2-oxazol-3-yl]-3-azabicyclo[3.1.0]hexane-3-carboxylate A round-bottom flask was charged with tert-butyl (1R,5S,6r)-6-[(E)-(hydroxyimino)methyl]-3-azabicyclo[3.1.0]hexane-3-carboxylate (600 mg, 2.3 mmol), methyl 3-oxobutanoate (0.5 mL, 4.6 mmol) and triethylamine (0.96 mL, 6.9 mmol) and DMF (12 mL). The reaction mixture was stirred at 20° C. for 16 hr to give a yellow solution. LCMS showed a major peak gives the desired ms. $H_2O$ (30 mL) was added and it was extracted with EtOAc (30 mL×2). The combined organic layer was dried over $Na_2SO_4$ and concentrated in vacuum to give the title compound (950 mg, 2.947 mmol, 128.06% yield) as yellow oil. It was directly used in the next step.

LC-MS Method1 0.925, MS (m/z) 308.0 (M−$CH_2CH_3$+ H$^+$).

5-methyl-3-[(1R,5S,6r)-3-{[(tert-butyl)oxy]carbonyl}-3-azabicyclo[3.1.0]hex-6-yl]-1,2-oxazole-4-carboxylic acid A 100 mL round-bottom flask was charged with tert-butyl (1R,5S,6r)-6-[4-(ethoxycarbonyl)-5-methyl-1,2-oxazol-3-yl]-3-azabicyclo[3.1.0]hexane-3-carboxylate (380 mg, 1.18 mmol), hydroxylithium hydrate (148.39 mg, 3.54 mmol) and THF (6 mL). The reaction mixture was stirred at 20° C. for 16 hr to give a yellow solution. The reaction was diluted with $H_2O$ (15 mL). pH was adjusted to 3 with 1M HCl aq. and the reaction mixture was extracted with EtOAc (30 mL×2). The combined organic layer was dried over $Na_2SO_4$ and concentrated in vacuum to give the title compound (330 mg, 1.0703 mmol, 90.794% yield) as yellow oil.

tert-butyl (1R,5S,6r)-6-(4-{[(benzyloxy)carbonyl]amino}-5-methyl-1,2-oxazol-3-yl)-3-azabicyclo[3.1.0]hexane-3-carboxylate A round-bottom flask was charged with 5-methyl-3-[(1R,5S,6r)-3-{[(tert-butyl)oxy]carbonyl}-3-azabicyclo[3.1.0]hex-6-yl]-1,2-oxazole-4-carboxylic acid (300 mg, 0.9700 mmol), DPPA (401.65 mg, 1.46 mmol), $Et_3N$ (0.41 mL, 2.92 mmol) and Toluene (2.7273 mL). The reaction mixture was stirred at 110° C. for 2 hr, and then phenylmethanol (0.4 mL, 3.89 mmol) was added. The reaction mixture was stirred at 110° C. for 10 min to give a yellow solution. $H_2O$ (30 mL) was added and it was extracted with EtOAc (30 mL×2). The combined organic layer was dried over $Na_2SO_4$ and concentrated in vacuum to give a yellow oil. The crude was purified by silica gel chromatography (PE/EA=10/1 to 3/1) to give the title compound (160 mg, 0.3870 mmol, 39.771% yield) as yellow oil.

$^1$H NMR (400 MHz, CHLOROFORM-d) δ ppm 7.45-7.20 (m, 5H), 5.12 (brs, 2H), 3.80-3.25 (m, 4H), 2.25 (brs, 3H), 2.00-1.90 (m, 1H), 1.50-1.40 (m, 1H), 1.39 (s, 9H).

tert-butyl (1R,5S,6r)-6-(4-amino-5-methyl-1,2-oxazol-3-yl)-3-azabicyclo[3.1.0]hexane-3-carboxylate A round-bottom flask was charged with tert-butyl (1R,5S,6r)-6-(4-{[(benzyloxy)carbonyl]amino}-5-methyl-1,2-oxazol-3-yl)-3-azabicyclo[3.1.0]hexane-3-carboxylate (1200 mg, 2.9 mmol), Pd/C (120 mg, 2.9 mmol) and MeOH (10 mL). The reaction mixture was stirred under molecular hydrogen (15 psi) atmosphere to give a black suspension. The suspension was filtrated through a pad of celite and the filtrate was concentrated in vacuum to give the title compound as yellow solid.

LC-MS Method1 0.765 min, MS (m/z) 280.1 (M+H$^+$).

tert-butyl (1R,5S,6r)-6-[4-(dimethylamino)-5-methyl-1,2-oxazol-3-yl]-3-azabicyclo[3.1.0]hexane-3-carboxylate To a solution of tert-butyl (1R,5S,6r)-6-(4-amino-5-methyl-1,2-oxazol-3-yl)-3-azabicyclo[3.1.0]hexane-3-carboxylate (100 mg, 0.3600 mmol) in MeOH (2.8571 mL) was added formaldehyde (1 mL, 2.15 mmol). After stirring for 15 min, $NaBH_3CN$ (134.98 mg, 2.15 mmol) was added to give a yellow solution. $H_2O$ (30 mL) was added and it was extracted with EtOAc (30 mL×2). The combined organic layer dried over $Na_2SO_4$ and concentrated in vacuum to give the title compound (150 mg, crude) as yellow oil. It was directly used in the next step.

3-[(1R,5S,6r)-3-azabicyclo[3.1.0]hex-6-yl]-N,N,5-trimethyl-1,2-oxazol-4-amine TFA Salt A round-bottom flask was charged with tert-butyl (1R,5S,6r)-6-[4-(dimethylamino)-5-methyl-1,2-oxazol-3-yl]-3-azabicyclo[3.1.0]hexane-3-carboxylate (150 mg, 0.4900 mmol), 2,2,2-trifluoroacetic acid (0.04 mL, 0.4900 mmol), DCM (6 mL) and 2,2,2-trifluoroacetic acid (0.04 mL, 0.4900 mmol). The reaction mixture was stirred at 30° C. under N$_2$ protection to give a yellow solution. The reaction mixture was evaporated in vacuum to give the title compound (220 mg, 0.5054 mmol, 103.56% yield) as yellow oil. It was directly used in the next step.
LC-MS Method1 0.443 min, MS (m/z) 207.9 (M+H$^+$).

{(1R,5S,6r)-6-[4-(dimethylamino)-5-methyl-1,2-oxazol-3-yl]-3-azabicyclo[3.1.0]hex-3-yl}(5-isopropyl-1H-pyrazol-3-yl)methanone To a solution of 5-isopropyl-1H-pyrazole-3-carboxylic acid (80 mg, 0.5200 mmol) and HATU (238.05 mg, 0.6200 mmol) in DMF (2 mL) was added N-ethyl-N-isopropylpropan-2-amine (0.36 mL, 2.08 mmol). After stirring for 15 min, 3-[(1R,5S,6r)-3-azabicyclo[3.1.0]hex-6-yl]-N,N,5-trimethyl-1,2-oxazol-4-amine TFA salt (225.89 mg, 0.5200 mmol) was added and the reaction mixture was stirred for 16 hr to give a yellow solution. H$_2$O (30 mL) was added and it was extracted with EtOAc (30 mL×2). The combined organic layer was dried over Na$_2$SO$_4$ and concentrated in vacuum to give a yellow oil. The crude was purified by Prep-HPLC (NH$_3$). The afforded flows were concentrated in vacuum to remove most of CH$_3$CN and lyophilized to give the title compound (38.86 mg, 0.1132 mmol, 21.807% yield) as white solid.
LC-MS Method1: 344.2 [M+H$^+$]
$^1$H NMR (400 MHz, CHLOROFORM-d) δ 6.49 (s, 1H), 4.19-4.37 (m, 2H), 3.99 (dd, J=4.39, 11.17 Hz, 1H), 3.71 (dd, J=4.52, 12.55 Hz, 1H), 3.03 (td, J=7.00, 13.87 Hz, 1H), 2.71 (s, 6H), 2.32-2.40 (m, 4H), 2.14 (td, J=3.83, 7.40 Hz, 1H), 1.68 (t, J=3.51 Hz, 1H), 1.30 (d, J=7.03 Hz, 6H)

Example 106 (5-isopropyl-1H-pyrazol-3-yl){(1R,5S,6r)-6-[5-methyl-4-(2-pyridinyl)-1,2-oxazol-3-yl]-3-azabicyclo[3.1.0]hex-3-yl}methanone tert-butyl (1R,5S,6r)-6-[5-methyl-4-(2-pyridinyl)-1,2-oxazol-3-yl]-3-azabicyclo[3.1.0]hexane-3-carboxylate To a solution of tert-butyl (1R,5S,6r)-6-(4-bromo-5-methyl-1,2-oxazol-3-yl)-3-azabicyclo[3.1.0]hexane-3-carboxylate (100 mg, 0.29 mmol) in 1,4-Dioxane (2 mL) were added tributyl(2-pyridyl)stannane (214.52 mg, 0.58 mmol), X-Phos (27.78 mg, 0.0600 mmol) and X-Phos-Pd-G2 (22.92 mg, 0.0300 mmol) under N$_2$. The resulting mixture was stirred at 110° C. for 16 hours to give a black brown solution. LCMS showed the reaction was completed. The reaction was diluted with EA (15 mL) and filtered through a pad of Celite. The filtrate was concentrated and the residue was purified by prep-TLC (EA/PE=1/1, Rf=0.5) to afford the title compound (71 mg, 71.379% yield) as a light yellow solid.

(1R,5S,6r)-6-[5-methyl-4-(2-pyridinyl)-1,2-oxazol-3-yl]-3-azabicyclo[3.1.0]hexane hydrochloride A solution of tert-butyl (1R,5S,6r)-6-[5-methyl-4-(2-pyridinyl)-1,2-oxazol-3-yl]-3-azabicyclo[3.1.0]hexane-3-carboxylate (71 mg, 0.2100 mmol) in 4M HCl in MeOH (1 mL, 0.2100 mmol) was stirred at 15° C. for 10 min to give a light yellow solution. TLC showed the starting material was consumed up and a new spot was detected. The reaction was concentrated to afford the title compound (62 mg, 123.55% yield) as a light yellow gum.

(5-isopropyl-1H-pyrazol-3-yl){(1R,5S,6r)-6-[5-methyl-4-(2-pyridinyl)-1,2-oxazol-3-yl]-3-azabicyclo[3.1.0]hex-3-yl}methanone To a solution of (1R,5S,6r)-6-[5-methyl-4-(2-pyridinyl)-1,2-oxazol-3-yl]-3-azabicyclo[3.1.0]hexane hydrochloride (62 mg, 0.26 mmol) in DMF (1 mL) were added 5-isopropyl-1H-pyrazole-3-carboxylic acid (39.61 mg, 0.26 mmol), DIPEA (0.13 mL, 0.77 mmol) and HATU (146.46 mg, 0.39 mmol) at 0 to 5° C. The resulting mixture was stirred at 15° C. for 16 hours to give a light brown solution. The reaction was diluted with H$_2$O (15 mL) and extracted with EA (5 mL×3). The combined organic layers were washed with NH$_4$Cl aq. (5 mL×2) and brine (5 mL), dried over Na$_2$SO$_4$, filtered and concentrated to dryness. The residue was purified by prep-TLC (EA/MeOH=12/1, Rf=0.6) and lyophilized to afford the title compound (34 mg, 35.057% yield) as a white solid.
LC-MS Method1: 378.1 [M+H$^+$]
$^1$H NMR (400 MHz, CHLOROFORM-d) δ ppm 1.29 (d, J=6.88 Hz, 6H) 1.92 (t, J=3.44 Hz, 1H) 2.18 (dt, J=7.41, 3.86 Hz, 1H) 2.46 (dt, J=7.44, 3.91 Hz, 1H) 2.55 (s, 3H) 2.97-3.08 (m, 1H) 3.73 (dd, J=12.69, 4.44 Hz, 1H) 3.99 (dd, J=11.13, 4.38 Hz, 1H) 4.20 (d, J=12.76 Hz, 1H) 4.28 (br d, J=11.13 Hz, 1H) 6.44 (s, 1H) 7.23 (dd, J=7.32, 5.19 Hz, 1H) 7.38 (d, J=7.88 Hz, 1H) 7.75 (td, J=7.75, 1.75 Hz, 1H) 8.66 (d, J=4.63 Hz, 1H)

Example 107 [(1R,5S,6r)-6-{4-[1-(cyclopropylmethyl)-1H-pyrazol-3-yl]-5-methyl-1,2-oxazol-3-yl}-3-azabicyclo[3.1.0]hex-3-yl](5-isopropyl-1H-pyrazol-3-yl)methanone 3-bromo-1-(cyclopropylmethyl)-1H-pyrazole To a solution of 3-bromopyrazole (1. g, 6.8 mmol) in DMF (10 mL) were added K$_2$CO$_3$ (1.88 g, 13.61 mmol) and (bromomethyl)cyclopropane (0.66 mL, 6.8 mmol). The reaction was stirred at 15° C. for 3 hours to give a white suspension. LCMS showed about half of the starting material was remained and the reaction was stirred for 16 hours to give a white suspension. TLC (PE/EA=5/1, Rf=0.7, I$_2$) showed most of the starting material was consumed and a new spot was detected. The reaction was diluted with H$_2$O (90 mL) and extracted with EA (10 mL×3). The combined organic layers were washed with NH$_4$Cl aq. (10 mL) and brine (10 mL), dried over Na$_2$SO$_4$, filtered and concentrated to afford a mixture of the title compounds and its isomer as colorless oil (1.36 g, 99.413% yield).
Isomer a: $^1$H NMR (400 MHz, CHLOROFORM-d) δ ppm 7.49 (d, J=1.2 Hz, 1H), 6.28 (d, J=1.2 Hz, 1H), 4.03 (d, J=6.8 Hz, 2H), 1.40-1.20 (m, 2H), 0.60-0.50 (m, 1H), 0.45-0.40 (m, 1H).
Isomer b; $^1$H NMR (400 MHz, CHLOROFORM-d) δ ppm 7.39 (d, J=1.2 Hz, 1H), 6.26 (d, J=1.2 Hz, 1H), 3.92 (d, J=6.8 Hz, 2H), 1.40-1.20 (m, 2H), 0.70-0.60 (m, 1H), 0.40-0.35 (m, 1H).

1-(cyclopropylmethyl)-3-(tributylstannyl)-1H-pyrazole

To a solution of the mixture of 3-bromo-1-(cyclopropylmethyl)-1H-pyrazole and its isomer (1.39 g, 6.91 mmol) in THF (15 mL) was added n-BuLi (3.04 mL, 7.6 mmol) dropwise at −75 to −70° C. After stirring for 1 hour at −75 to −70° C., tributyl(chloro)stannane (2.48 g, 7.6 mmol) in THF (5 mL) was added to the reaction at −75 to −70° C. The resulting mixture was stirred at 15° C. for 16 hours to give a light yellow solution. The reaction was quenched with NH$_4$Cl aq (5 mL). The mixture was diluted with H$_2$O (50 mL) and extracted with EA (15 mL×3). The combined organic layers were washed with brine (15 mL), dried over Na$_2$SO$_4$, filtered and concentrated to dryness. The residue was purified by flash column (eluted with 5% EA in PE, EA/PE=1/9) to afford the title compound (525 mg, Rf=0.45) as colorless oil.

LC-MS Method1 1.060 min, MS (m/z) 413.0 (M+H$^+$).

tert-butyl (1R,5S,6r)-6-{4-[1-(cyclopropylmethyl)-1H-pyrazol-3-yl]-5-methyl-1,2-oxazol-3-yl}-3-azabicyclo[3.1.0]hexane-3-carboxylate To a solution of tert-butyl (1R,5S,6r)-6-(4-bromo-5-methyl-1,2-oxazol-3-yl)-3-azabicyclo[3.1.0]hexane-3-carboxylate (300 mg, 0.87 mmol) in 1,4-Dioxane (3 mL) were added 1-(cyclopropylmethyl)-3-(tributylstannyl)-1H-pyrazole (431.31 mg, 1.05 mmol), X-Phos (83.34 mg, 0.17 mmol) and X-Phos-Pd-G2 (68.77 mg, 0.09 mmol) under N$_2$. The resulting mixture was stirred at 100° C. for 16 hours to give a black brown solution. The reaction was diluted with EA (30 mL) and filtered through a pad of celite. The filtrate was concentrated and purified by flash column (8% EA in PE, PE/EA=3/1, Rf=0.5) to afford the title compound (205 mg, 16.47% yield) as a light yellow solid.

$^1$H NMR (400 MHz, CHLOROFORM-d) δ ppm 7.50 (d, J=2.0 Hz, 1H), 6.40 (d, J=2.0 Hz, 1H), 4.00 (d, J=3.2 Hz, 2H), 3.79 (d, J=11.2 Hz, 1H), 3.70 (d, J=11.2 Hz, 1H), 3.50-3.40 (m, 2H), 2.38 (s, 3H), 2.11 (m, 2H), 1.70-1.65 (m, 1H), 1.47 (s, 9H), 70-0.60 (m, 1H), 0.55-0.50 (m, 2H), 0.45-0.35 (m, 2H).

(1R,5S,6r)-6-{4-[1-(cyclopropylmethyl)-1H-pyrazol-3-yl]-5-methyl-1,2-oxazol-3-yl}-3-azabicyclo[3.1.0]hexane hydrochloride A solution of tert-butyl (1R,5S,6r)-6-{4-[1-(cyclopropylmethyl)-1H-pyrazol-3-yl]-5-methyl-1,2-oxazol-3-yl}-3-azabicyclo[3.1.0]hexane-3-carboxylate (205 mg, 0.5300 mmol) in 4M HCl in MeOH (3 mL, 0.5300 mmol) was stirred at 15° C. for 15 min to give a colorless solution. LCMS showed the starting material was consumed up and one new peak with desired mass was detected. The reaction was concentrated to afford the title compound (77.8 mg, 51.312% yield) as an off-white solid.

LC-MS Method1 0.652 min, MS (m/z) 284.9 (M+H$^+$).

[(1R,5S,6r)-6-{4-[1-(cyclopropylmethyl)-1H-pyrazol-3-yl]-5-methyl-1,2-oxazol-3-yl}-3-azabicyclo[3.1.0]hex-3-yl](5-isopropyl-1H-pyrazol-3-yl)methanone To a solution of (1R,5S,6r)-6-{4-[1-(cyclopropylmethyl)-1H-pyrazol-3-yl]-5-methyl-1,2-oxazol-3-yl}-3-azabicyclo[3.1.0]hexane hydrochloride (77.8 mg, 0.27 mmol) in DMF (1 mL) were added 5-isopropyl-1H-pyrazole-3-carboxylic acid (42.18 mg, 0.27 mmol), DIPEA (0.23 mL, 1.37 mmol) and HATU (155.95 mg, 0.41 mmol). The resulting mixture was stirred at 15° C. for 16 hours to give a brown solution. The reaction was diluted with H$_2$O (20 mL) and extracted with EA (5 mL×3). The combined organic layers were washed with NH$_4$Cl aq. (8 mL) and brine (8 mL), dried over Na$_2$SO$_4$, filtered and concentrated to dryness. The residue was purified by prep-TLC (EA/MeOH=10/1) and lyophilized to afford the title compound (21.33 mg, 18.54% yield) as a white solid.

$^1$H NMR (400 MHz, CHLOROFORM-d) δ ppm 0.35 (q, J=5.02 Hz, 2H) 0.57-0.66 (m, 2H) 1.21-1.27 (m, 1H) 1.30 (d, J=7.03 Hz, 7H) 2.00 (t, J=3.51 Hz, 1H) 2.18 (dt, J=7.40, 3.83 Hz, 1H) 2.41 (dt, J=7.40, 3.83 Hz, 1H) 2.52 (s, 3H) 3.02 (dt, J=13.74, 6.81 Hz, 1H) 3.71 (dd, J=12.67, 4.39 Hz, 1H) 3.97 (d, J=7.03 Hz, 2H) 4.21-4.34 (m, 2H) 6.31 (d, J=2.26 Hz, 1H) 6.46 (s, 1H) 7.53 (d, J=2.26 Hz, 1H)

Example 108 [(1R,5S,6r)-6-(1,2-benzoxazol-3-yl)-3-azabicyclo[3.1.0]hex-3-yl](5-isopropyl-1H-pyrazol-3-yl)methanone

[(1R,5S,6r)-6-(1,2-benzoxazol-3-yl)-3-azabicyclo[3.1.0]hex-3-yl](5-isopropyl-1H-pyrazol-3-yl)methanone To a solution of 5-isopropyl-1H-pyrazole-3-carboxylic acid (10.75 mg, 0.0700 mmol) in DMF (1 mL) were added HATU (33.71 mg, 0.0900 mmol), DIPEA (0.03 mL, 0.1900 mmol) and 3-[(1R,5S,6r)-3-azabicyclo[3.1.0]hex-6-yl]-1,2-benzoxazole (15 mg, 0.0600 mmol). The mixture was stirred at 20° C. for 12 h to give yellow solution. LCMS showed the desired MS. The reaction mixture was poured into H$_2$O (15 mL) and extracted with EtOAc (20 mL×4). The combined organic layers were washed with brine (50 mL), dried over Na$_2$SO$_4$, filtered and concentrated under reduced pressure. The residue was purified by prep-TLC (PE:EtOAc=1:1) and lyophilized to give the title compound (5.1 mg, 0.0152 mmol, 23.924% yield) as white solid.

$^1$H NMR (400 MHz, DMSO-d6) δ ppm 12.96 (br s, 1H), 7.99 (br d, J=7.78 Hz, 1H), 7.56-7.75 (m, 2H), 7.36 (br t, J=7.78 Hz, 1H), 6.42 (s, 1H), 4.50 (br d, J=12.05 Hz, 1H), 4.10 (br d, J=12.30 Hz, 1H), 3.96 (br d, J=11.80 Hz, 1H), 3.61 (br d, J=8.03 Hz, 1H), 2.93-3.04 (m, 1H), 2.42 (br s, 1H), 2.22 (br s, 1H), 1.23 (br d, J=6.53 Hz, 6H)

Example 109 (5-isopropyl-1H-pyrazol-3-yl)[(1R,5S,6r)-6-(4,5,5-trimethyl-4,5-dihydro-1,2,4-oxadiazol-3-yl)-3-azabicyclo[3.1.0]hex-3-yl]methanone (5-isopropyl-1H-pyrazol-3-yl)[(1R,5S,6r)-6-(4,5,5-trimethyl-4,5-dihydro-1,2,4-oxadiazol-3-yl)-3-azabicyclo[3.1.0]hex-3-yl]methanone To a solution of 5-isopropyl-1H-pyrazole-3-carboxylic acid (72.64 mg, 0.4700 mmol) in DMF (3.5385 mL) was added HATU (135.48 mg, 0.7100 mmol). The reaction mixture was stirred at 15° C. for 30 min. Then (1R,5S,6r)-6-(4,5,5-trimethyl-4,5-dihydro-1,2,4-oxadiazol-3-yl)-3-azabicyclo[3.1.0]hexane (92 mg, 0.4700 mmol) was added. The reaction mixture was stirred at 15° C. for 0.5 hr to give a yellow mixture. LCMS showed the desired MS. The reaction mixture was purified by prep-HPLC (NH$_3$) to give the title compound (14.45 mg, 0.0436 mmol, 9.254% yield) as white powder.

LC-MS Method1: 332.0 [M+H$^+$]

$^1$H NMR (400 MHz, CHLOROFORM-d) δ=10.62 (br s, 1H), 6.49 (s, 1H), 4.35 (br d, J=10.4 Hz, 1H), 4.22 (d, J=12.8 Hz, 1H), 3.99-3.89 (m, 1H), 3.65 (dd, J=4.0, 12.8 Hz, 1H), 3.02 (m, 1H), 2.78 (s, 3H), 2.33 (m, 1H), 2.04 (m, 1H), 1.41 (d, J=7.3 Hz, 6H), 1.30 (d, J=7.0 Hz, 6H), 1.14 (t, J=3.5 Hz, 1H)

Example 110 [(1R,5S,6r)-6-(4-ethyl-5,5-dimethyl-4,5-dihydro-1,2,4-oxadiazol-3-yl)-3-azabicyclo[3.1.0]hex-3-yl](5-isopropyl-1H-pyrazol-3-yl)methanone

[(1R,5S,6r)-6-(4-ethyl-5,5-dimethyl-4,5-dihydro-1,2,4-oxadiazol-3-yl)-3-azabicyclo[3.1.0]hex-3-yl](5-isopropyl-1H-pyrazol-3-yl)methanone To a solution of 5-isopropyl-1H-pyrazole-3-carboxylic acid (69.24 mg, 0.4500 mmol) in DMF (3.373 mL) were added HATU (129.15 mg, 0.6700 mmol) and DIPEA (171.4 mg, 1.35 mmol). The reaction mixture was stirred at 15° C. for 30 min. Then (1R,5S,6r)-6-(4-ethyl-5,5-dimethyl-4,5-dihydro-1,2,4-oxadiazol-3-yl)-3-azabicyclo[3.1.0]hexane TFA salt (94 mg, 0.4500 mmol) was added. The reaction mixture was stirred at 15° C. for 0.5 hr to give a yellow mixture. LCMS showed the desired MS. The reaction mixture was purified by prep-HPLC ($NH_3$) to give the title compound (41.23 mg, 0.1194 mmol, 26.574% yield) as white powder.
LC-MS Method1: 346.0 [M+H$^+$]
$^1$H NMR (400 MHz, CHLOROFORM-d) δ=10.80 (br s, 1H), 6.50 (s, 1H), 4.35 (br s, 1H), 4.21 (d, J=12.8 Hz, 1H), 3.97 (dd, J=4.3, 11.6 Hz, 1H), 3.67 (dd, J=4.4, 12.8 Hz, 1H), 3.18 (q, J=7.3 Hz, 2H), 3.02 (td, J=6.9, 13.8 Hz, 1H), 2.41 (td, J=3.9, 7.4 Hz, 1H), 2.05 (td, J=3.6, 7.2 Hz, 1H), 1.43 (d, J=12.8 Hz, 6H), 1.30 (d, J=6.8 Hz, 6H), 1.20 (t, J=7.2 Hz, 3H), 1.14 (t, J=3.4 Hz, 1H)

Example 111 [(1R,5S,6r)-6-(4-cyclopropyl-5,5-dimethyl-4,5-dihydro-1,2,4-oxadiazol-3-yl)-3-azabicyclo[3.1.0]hex-3-yl](5-isopropyl-1H-pyrazol-3-yl)methanone

[(1R,5S,6r)-6-(4-cyclopropyl-5,5-dimethyl-4,5-dihydro-1,2,4-oxadiazol-3-yl)-3-azabicyclo[3.1.0]hex-3-yl](5-isopropyl-1H-pyrazol-3-yl)methanone To a solution of (1R,5S,6r)-6-(4-cyclopropyl-5,5-dimethyl-4,5-dihydro-1,2,4-oxadiazol-3-yl)-3-azabicyclo[3.1.0]hexane TFA salt (90 mg, 0.41 mmol), 5-isopropyl-1H-pyrazole-3-carboxylic acid (68.9 mg, 0.45 mmol) and DIPEA (0.34 mL, 2.03 mmol) in DMF (4 mL) was added HATU (171 mg, 0.45 mmol). The mixture was stirred at 20° C. for 16 h.
The reaction mixture was diluted with $H_2O$ (50 mL) and extracted by EA (25 mL×3). The organic phase was washed with brine (50 mL×3), dried over anhydrous $Na_2SO_4$ and concentrated to give a residue. The residue was purified by Prep-HPLC ($NH_3$) to afford the title compound (20 mg, 0.056 mmol, 13.7% yield) as a white solid.
LC-MS Method1: 358.1 [M+H$^+$]
$^1$H NMR (400 MHz, CHLOROFORM-d) δ ppm 10.39 (br s, 1H) 6.51 (s, 1H) 4.14-4.39 (m, 2H) 3.96 (dd, J=11.4, 4.4 Hz, 1H) 3.69 (dd, J=12.6, 4.4 Hz, 1H) 3.03 (spt, J=6.9 Hz, 1H) 2.28-2.37 (m, 2H) 2.06 (dt, J=7.2, 3.8 Hz, 1H) 1.48 (d, J=8.9 Hz, 6H) 1.43 (t, J=3.5 Hz, 1H) 1.31 (d, J=6.9 Hz, 6H) 0.67-0.77 (m, 4H)

Example 112 [(1R,5S,6r)-6-(5,5-dimethyl-4-phenyl-4,5-dihydro-1,2,4-oxadiazol-3-yl)-3-azabicyclo[3.1.0]hex-3-yl](5-isopropyl-1H-pyrazol-3-yl)methanone N-phenyl-2-propanimine To a solution of aniline (0.2 mL, 2.15 mmol) in Toluene (4.6 mL) was added acetone (374.19 mg, 6.44 mmol), followed by 4A MS (200 mg). Then the mixture was stirred at 110° C. for 3 h. The mixture was filtered and the filtrate was concentrated to dryness to give the title compound (300 mg, crude) as yellow oil, which was used to next step without purification.

tert-butyl (1R,5S,6r)-6-(5,5-dimethyl-4-phenyl-4,5-dihydro-1,2,4-oxadiazol-3-yl)-3-azabicyclo[3.1.0]hexane-3-carboxylate To a solution of tert-butyl (1R,5S,6r)-6-[(Z)-chloro(hydroxyimino)methyl]-3-azabicyclo[3.1.0]hexane-3-carboxylate (115.23 mg, crude) in DMF (3 mL) was added $Et_3N$ (0.3 mL, 2.34 mmol), followed by N-phenyl-2-propanimine (186.64 mg, crude) at 20° C. and then the mixture was stirred at 25° C. for 1 h. The mixture was poured into $H_2O$ (5 mL) and extracted with EtOAc (5 mL×5). The combined organic layer was washed with brine (5 mL), dried over $Na_2SO_4$ and concentrated to dryness. The residue was purified by silica gel column (EA in PE from 0% to 50%) to give the title compound (140 mg, 0.3917 mmol, 83.849% yield) as white solid.
$^1$H NMR (400 MHz, CHLOROFORM-d) δ ppm 7.40-7.20 (m, 3H), 7.20-7.10 (m, 2H), 3.50-3.25 (m, 4H), 2.25-2.00 (m, 2H), 1.40 (brs, 3H), 1.37 (brs, 3H), 1.30 (s, 9H), 0.89 (s, 1H).

(1R,5S,6r)-6-(5,5-dimethyl-4-phenyl-4,5-dihydro-1,2,4-oxadiazol-3-yl)-3-azabicyclo[3.1.0]hexane TFA Salt A solution of tert-butyl (1R,5S,6r)-6-(5,5-dimethyl-4-phenyl-4,5-dihydro-1,2,4-oxadiazol-3-yl)-3-azabicyclo[3.1.0]hexane-3-carboxylate (70 mg, 0.20 mmol) in TFA (0.5 mL)/DCM (2.5 mL) was stirred at 20° C. for 0.5 h. The mixture was concentrated to give the title compound (73 mg, crude as TFA salt) which was used to next step without purification.

[(1R,5S,6r)-6-(5,5-dimethyl-4-phenyl-4,5-dihydro-1,2,4-oxadiazol-3-yl)-3-azabicyclo[3.1.0]hex-3-yl](5-isopropyl-1H-pyrazol-3-yl)methanone To a solution of 3-isopropyl-1H-pyrazole-5-carboxylic acid (39.4 mg, 0.26 mmol) and $Et_3N$ (0.17 mL, 0.98 mmol) in DMF (2 mL) was added HATU (89.64 mg, 0.24 mmol) at 15° C. and then the mixture was stirred at 15° C. for 20 min. To the mixture was added (1R,5S,6r)-6-(5,5-dimethyl-4-phenyl-4,5-dihydro-1,2,4-oxadiazol-3-yl)-3-azabicyclo[3.1.0]hexane TFA salt (73 mg, crude as TFA salt) at 15° C. and then the resulting mixture was stirred at 15° C. for 16 h. The mixture was concentrated to remove $Et_3N$ and the residue was purified by prep-HPLC ($NH_3$) and then lyophilized for 16 h to give the title compound (40.08 mg, 0.1019 mmol, 51.816% yield) as white solid.
LC-MS Method1: 394.0 [M+H$^+$]
$^1$H NMR (400 MHz, CHLOROFORM-d) δ=10.32 (brs, 1H), 7.44-7.32 (m, 3H), 7.19 (d, J=7.6 Hz, 2H), 6.43 (s, 1H), 4.30-4.00 (m, 1H), 3.97-3.90 (m, 2H), 3.65 (dd, J=4.4, 12.8 Hz, 1H), 3.05-2.96 (m, 1H), 2.48-2.40 (m, 1H), 2.22-2.15 (m, 1H), 1.51 (s, 3H), 1.45 (s, 3H), 1.29 (d, J=6.8 Hz, 6H), 0.99 (t, J=3.2 Hz, 1H).

Example 113 {(1R,5S,6r)-6-[5,5-dimethyl-4-(3-methylphenyl)-4,5-dihydro-1,2,4-oxadiazol-3-yl]-3-azabicyclo[3.1.0]hex-3-yl}(5-isopropyl-1H-pyrazol-3-yl)methanone {(1R,5S,6r)-6-[5,5-dimethyl-4-(3-methylphenyl)-4,5-dihydro-1,2,4-oxadiazol-3-yl]-3-azabicyclo[3.1.0]hex-3-yl}(5-isopropyl-1H-pyrazol-3-yl)methanone To a solution of 5-isopropyl-1H-pyrazole-3-carboxylic acid (57.61 mg, 0.3700 mmol) in DMF (2 mL) were added HATU (166.66 mg, 0.4400 mmol), DIPEA (0.18 mL, 1.09 mmol) and (1R,5S,6r)-6-[5,5-dimethyl-4-(3-methylphenyl)-4,5-dihydro-1,2,4-oxadiazol-3-yl]-3-azabicyclo[3.1.0]hexane TFA salt (120 mg, 0.3100 mmol, TFA salt). The mixture was stirred at 20° C. for 12 h to give yellow solution. The mixture was poured into $H_2O$ (15 mL) and extracted with EtOAc (15 mL×5). The combined organic layer was washed with brine (50 mL), dried over $Na_2SO_4$ and concentrated to dryness. The residue was purified by prep-TLC (EtOAc) and lyophilized to give the title compound (65.74 mg, 0.1613 mmol, 51.808% yield) as white solid.

LC-MS Method1: 408.1 [M+H$^+$]

$^1$H NMR (400 MHz, CHLOROFORM-d) δ ppm 9.97-10.66 (1H, m), 7.24-7.27 (1H, m), 7.13 (1H, d, J=7.75 Hz), 6.92-7.00 (2H, m), 6.40 (1H, s), 4.11 (1H, br d, J=10.88 Hz), 3.87-3.97 (2H, m), 3.64 (1H, dd, J=12.69, 4.44 Hz), 2.94-3.06 (1H, m), 2.38-2.47 (1H, m), 2.37 (3H, s), 2.18 (1H, dt, J=7.35, 3.77 Hz), 1.49 (3H, s), 1.43 (3H, s), 1.28 (6H, d, J=6.88 Hz), 0.97 (1H, t, J=3.50 Hz)

Example 114 {(1R,5S,6r)-6-[5,5-dimethyl-4-(4-methylphenyl)-4,5-dihydro-1,2,4-oxadiazol-3-yl]-3-azabicyclo[3.1.0]hex-3-yl}(5-isopropyl-1H-pyrazol-3-yl)methanone N-(4-methylphenyl)-2-propanimine To a solution of 4-amino toluene (0.18 mL, 1.87 mmol) in Toluene (4 mL) was added acetone (325.23 mg, 5.6 mmol), followed by 4A MS (200 mg). Then the mixture was stirred at 110° C. for 5 h. Without monitoring. The mixture was filtered and the filtrate was concentrated to dryness to give the title compound (300 mg, crude) as yellow oil, which was used to next step without purification.

$^1$H NMR (400 MHz, CHLOROFORM-d) δ ppm 7.25 (d, J=8.0 Hz, 2H), 7.09 (d, J=8.0 Hz, 2H), 3.53 (brs, 6H), 2.35 (s, 3H).

tert-butyl (1R,5S,6r)-6-[5,5-dimethyl-4-(4-methylphenyl)-4,5-dihydro-1,2,4-oxadiazol-3-yl]-3-azabicyclo[3.1.0]hexane-3-carboxylate To a solution of tert-butyl (1R,5S,6r)-6-[(Z)-chloro(hydroxyimino)methyl]-3-azabicyclo[3.1.0]hexane-3-carboxylate (115.23 mg, crude reaction from above) in DMF (3 mL) was added Et$_3$N (0.3 mL, 2.34 mmol), followed by N-(4-methylphenyl)-2-propanimine (206.3 mg, crude) at 20° C. and then the mixture was stirred at 25° C. for 1 h. The mixture was poured into $H_2O$ (5 mL) and extracted with EtOAc (5 mL×5). The combined organic layer was washed with brine (5 mL), dried over $Na_2SO_4$ and concentrated to dryness. The residue was purified by silica gel column (EA in PE from 0% to 50%) to give the title compound (150 mg, 0.4038 mmol, 86.448% yield) as white solid.

$^1$H NMR (400 MHz, CHLOROFORM-d) δ ppm 7.21 (d, J=8.0 Hz, 2H), 7.06 (d, J=8.0 Hz, 2H), 3.50-3.30 (m, 4H), 2.39 (s, 3H), 2.20-2.10 (m, 1H), 2.10-2.00 (m, 1H), 1.47 (s, 6H), 1.38 (s, 9H), 0.95-0.90 (m, 1H).

(1R,5S,6r)-6-[5,5-dimethyl-4-(4-methylphenyl)-4,5-dihydro-1,2,4-oxadiazol-3-yl]-3-azabicyclo[3.1.0]hexane TFA Salt A solution of tert-butyl (1R,5S,6r)-6-[5,5-dimethyl-4-(4-methylphenyl)-4,5-dihydro-1,2,4-oxadiazol-3-yl]-3-azabicyclo[3.1.0]hexane-3-carboxylate (120 mg, 0.3200 mmol) in TFA (1 mL)/DCM (5 mL) was stirred at 20° C. for 0.5 h. The mixture was concentrated to give the title compound (124.49 mg, crude), it was used to next step without purification.

{(1R,5S,6r)-6-[5,5-dimethyl-4-(4-methylphenyl)-4,5-dihydro-1,2,4-oxadiazol-3-yl]-3-azabicyclo[3.1.0]hex-3-yl}(5-isopropyl-1H-pyrazol-3-yl)methanone To a solution of 3-isopropyl-1H-pyrazole-5-carboxylic acid (64.49 mg, 0.420 mmol) and Et$_3$N (0.28 mL, 1.61 mmol) in DMF (2 mL) was added HATU (158.95 mg, 0.420 mmol) at 15° C. and then the mixture was stirred at 15° C. for 20 min. To the mixture was added (1R,5S,6r)-6-[5,5-dimethyl-4-(4-methylphenyl)-4,5-dihydro-1,2,4-oxadiazol-3-yl]-3-azabicyclo[3.1.0]hexane TFA salt (124 mg, 0.320 mmol, TFA salt) at 15° C. and then the resulting mixture was stirred at 15° C. for 2 h. The mixture was concentrated to remove Et$_3$N (about 3 mL of DMF remained). Precipitate solids were collected by filtration and the cake was washed with MeCN (0.5 mL×2) to give the title compound (18.1 mg, 0.0444 mmol, 13.804% yield) as white solid. The filtrate was purified by prep-HPLC (NH$_3$) and then lyophilized to give the title compound (34.44 mg, 0.0845 mmol, 26.266% yield) as white solid.

LC-MS Method1: 408.0 [M+H$^+$]

$^1$H NMR (400 MHz, CHLOROFORM-d) δ=10.75-9.95 (m, 1H), 7.20 (br d, J=8.0 Hz, 1H), 7.07 (d, J=8.0 Hz, 2H), 6.62-6.17 (m, 1H), 4.40-3.55 (m, 4H), 3.11-2.93 (m, 1H), 2.49-2.05 (m, 5H), 1.45 (d, J=27.6 Hz, 6H), 1.29 (d, J=7.2 Hz, 6H), 0.96 (t, J=3.2 Hz, 1H).

Example 115 (5-isopropyl-1H-pyrazol-3-yl){(1R,5S,6r)-6-[4-(4-methoxyphenyl)-5,5-dimethyl-4,5-dihydro-1,2,4-oxadiazol-3-yl]-3-azabicyclo[3.1.0]hex-3-yl}methanone N-(4-methoxyphenyl)propan-2-imine To a solution of 4-methoxyaniline (0.83 mL, 8.12 mmol) in toluene (10 mL) was added acetone (1.41 g, 24.36 mmol), followed by 4A MS (1. g, 8.12 mmol). Then the mixture was stirred at 110° C. for 5 h to give brown suspension. The mixture was filtered and the filtrate was concentrated to dryness to give the title compound (1.5 g, 9.1901 mmol, 113.18% yield) as brown oil, which was used to next step without purification.

$^1$H NMR (400 MHz, CHLOROFORM-d) δ ppm 6.75 (d, J=8.0 Hz, 2H), 6.65 (d, J=8.0 Hz, 2H), 3.77 (s, 3H), 2.15 (s, 6H).

tert-butyl (1R,5S,6r)-6-[4-(4-methoxyphenyl)-5,5-dimethyl-4,5-dihydro-1,2,4-oxadiazol-3-yl]-3-azabicyclo[3.1.0]hexane-3-carboxylate To a solution of tert-butyl (1R,5S,6r)-6-[(Z)-chloro(hydroxyimino)methyl]-3-azabicyclo[3.1.0]hexane-3-carboxylate in DMF (2 mL) was added Et₃N (0.48 mL, 2.88 mmol), followed by N-(4-methoxyphenyl)propan-2-imine (375.62 mg, 2.3 mmol) at 20° C. and then the mixture was stirred at 25° C. for 1 h to give brown solution. The mixture was poured into H₂O (15 mL) and extracted with EtOAc (15 mL×5). The combined organic layer was washed with brine (50 mL), dried over Na₂SO₄ and concentrated to dryness. The residue was purified by silica gel column (EA in PE from 0% to 50%) to give the title compound (140 mg, 0.3613 mmol, 62.802% yield) as brown oil.

¹H NMR (400 MHz, CHLOROFORM-d) δ ppm 7.11 (d, J=8.0 Hz, 2H), 6.93 (d, J=8.0 Hz, 2H), 3.83 (s, 3H), 3.50-3.30 (m, 4H), 2.20-2.10 (m, 1H), 2.10-2.00 (m, 1H), 1.45 (s, 3H), 1.42 (s, 3H), 1.40 (s, 9H), 0.95-0.90 (m, 1H).

(1R,5S,6r)-6-[4-(4-methoxyphenyl)-5,5-dimethyl-4,5-dihydro-1,2,4-oxadiazol-3-yl]-3-azabicyclo[3.1.0]hexane TFA Salt To a solution of tert-butyl (1R,5S,6r)-6-[4-(4-methoxyphenyl)-5,5-dimethyl-4,5-dihydro-1,2,4-oxadiazol-3-yl]-3-azabicyclo[3.1.0]hexane-3-carboxylate (140 mg, 0.3600 mmol) in DCM (5 mL) was added TFA (1 mL, 13.46 mmol). The mixture was stirred at 20° C. for 0.5 h to give black solution. TLC (PE:EtOAc=1:1) showed the reaction was completed. The reaction mixture was concentrated directly to give the title compound (140 mg, 0.3488 mmol, 96.534% yield, TFA, salt) as brown gum.

(5-isopropyl-1H-pyrazol-3-yl){(1R,5S,6r)-6-[4-(4-methoxyphenyl)-5,5-dimethyl-4,5-dihydro-1,2,4-oxadiazol-3-yl]-3-azabicyclo[3.1.0]hex-3-yl}methanone To a solution of 5-isopropyl-1H-pyrazole-3-carboxylic acid (64.53 mg, 0.4200 mmol) in DMF (2 mL) were added HATU (186.68 mg, 0.4900 mmol), DIPEA (0.2 mL, 1.22 mmol) and (1R,5S,6r)-6-[4-(4-methoxyphenyl)-5,5-dimethyl-4,5-dihydro-1,2,4-oxadiazol-3-yl]-3-azabicyclo[3.1.0]hexane TFA salt (140 mg, TFA, salt 0.3500 mmol). The mixture was stirred at 20° C. for 12 h to give brown solution. The mixture was poured into H₂O (15 mL) and extracted with EtOAc (15 mL×5). The combined organic layer was washed with brine (50 mL), dried over Na₂SO₄ and concentrated to dryness. The residue was purified by prep-HPLC (FA). The afforded flows were combined, concentrated to remove most of CH₃CN and lyophilized to give the title compound (59.06 mg, 0.1395 mmol, 39.981% yield) as brown solid.

LC-MS Method1: 404.3 [M+H⁺]

¹H NMR (400 MHz, CHLOROFORM-d) δ ppm 7.11 (2H, d, J=8.76 Hz), 6.91 (2H, d, J=8.75 Hz), 6.39 (1H, s), 4.92 (2H, br s), 3.96-4.06 (1H, m), 3.84-3.95 (2H, m), 3.83 (3H, s), 3.62 (1H, br dd, J=12.63, 4.25 Hz), 3.06 (1H, dt, J=13.88, 6.94 Hz), 2.35-2.45 (1H, m), 2.12-2.23 (1H, m), 1.44 (6H, d, J=15.01 Hz), 1.30 (6H, d, J=6.88 Hz), 0.97 (1H, t, J=3.13 Hz)

Example 116 (5-isopropyl-1H-pyrazol-3-yl){(1R,5S,6r)-6-[4-(3-methoxyphenyl)-5,5-dimethyl-4,5-dihydro-1,2,4-oxadiazol-3-yl]-3-azabicyclo[3.1.0]hex-3-yl}methanone (5-isopropyl-1H-pyrazol-3-yl){(1R,5S,6r)-6-[4-(3-methoxyphenyl)-5,5-dimethyl-4,5-dihydro-1,2,4-oxadiazol-3-yl]-3-azabicyclo[3.1.0]hex-3-yl}methanone To a solution of 5-isopropyl-1H-pyrazole-3-carboxylic acid (64.53 mg, 0.4200 mmol) in DMF (2 mL) were added HATU (186.68 mg, 0.4900 mmol), DIPEA (0.2 mL, 1.22 mmol) and (1R,5S,6r)-6-[4-(3-methoxyphenyl)-5,5-dimethyl-4,5-dihydro-1,2,4-oxadiazol-3-yl]-3-azabicyclo[3.1.0]hexane TFA salt (140 mg, 0.3500 mmol, TFA salt). The mixture was stirred at 20° C. for 12 h to give brown solution. The mixture was poured into H₂O (15 mL) and extracted with EtOAc (15 mL×5). The combined organic layer was washed with brine (50 mL), dried over Na₂SO₄ and concentrated to dryness. The residue was purified by prep-HPLC (NH₃). The afforded flows were combined, concentrated to remove most of CH₃CN and lyophilized to give the title compound (62.38 mg, 0.1473 mmol, 42.229% yield) to give white solid.

LC-MS Method1: 424.0 [M+H⁺]

¹H NMR (400 MHz, CHLOROFORM-d) δ ppm 10.34 (1H, br s), 7.28-7.33 (1H, m), 6.86 (1H, dd, J=8.41, 1.88 Hz), 6.75 (1H, dd, J=7.91, 1.13 Hz), 6.70 (1H, t, J=2.13 Hz), 6.45-6.45 (1H, m), 6.42 (1H, br s), 4.14 (1H, br s), 3.88-3.99 (2H, m), 3.82 (3H, s), 3.65 (1H, dd, J=12.80, 4.27 Hz), 3.00 (1H, dt, J=13.80, 6.90 Hz), 2.42 (1H, dt, J=7.47, 3.92 Hz), 2.14-2.21 (1H, m), 1.42-1.53 (6H, m), 1.28 (6H, d, J=6.78 Hz), 1.02 (1H, t, J=3.39 Hz)

Example 117 [(1R,5S,6r)-6-(4-benzyl-5,5-dimethyl-4,5-dihydro-1,2,4-oxadiazol-3-yl)-3-azabicyclo[3.1.0]hex-3-yl](5-isopropyl-1H-pyrazol-3-yl)methanone N-benzyl-2-propanimine To a solution of benzylamine (0.5 mL, 4.67 mmol) and acetone (1 mL, 14 mmol) in Toluene (5 mL) was added 4AMS (3 g), and the mixture was stirred at 110° C. for 4 h without monitor. The mixture was filtered and the filtrate was concentrated to give the title compound (330 mg, 2.24 mmol) as a colorless oil. The product was used directly for next step.

tert-butyl (1R,5S,6r)-6-(4-benzyl-5,5-dimethyl-4,5-dihydro-1,2,4-oxadiazol-3-yl)-3-azabicyclo[3.1.0]hexane-3-carboxylate To a solution of tert-butyl (1R,5S,6r)-6-[(Z)-chloro(hydroxyimino)methyl]-3-azabicyclo[3.1.0]hexane-3-carboxylate (150 mg, 0.58 mmol) and Et₃N (0.29 mL, 1.73 mmol) in DMF (2 mL) was added N-benzyl-2-propanimine (330 mg, 2.24 mmol). The mixture was stirred at 20° C. for 2 h. The reaction was diluted with H₂O (50 mL) and extracted by EtOAc (20 mL×3). The organic phase was washed three times with brine, dried over anhydrous Na₂SO₄ and concentrated to give a residue. The residue was purified by flash column (PE:EA=1:0-1:1) to give the title compound (50 mg, 0.1346 mmol, 23.3% yield) (PE:EA=3:1, Rf=0.5) as a pale yellow solid.

(1R,5S,6r)-6-(4-benzyl-5,5-dimethyl-4,5-dihydro-1,2,4-oxadiazol-3-yl)-3-azabicyclo[3.1.0]hexane TFA Salt To a solution of tert-butyl (1R,5S,6r)-6-(4-benzyl-5,5-dimethyl-4,5-dihydro-1,2,4-oxadiazol-3-yl)-3-azabicyclo[3.1.0]hexane-3-carboxylate (50 mg, 0.13 mmol) in DCM (3 mL) was added TFA (0.3 mL, 4.04 mmol), and the mixture was stirred at 20° C. for 1 h. The reaction mixture was concentrated to give the title compound (50 mg, 0.18 mmol) as a yellow oil.

[(1R,5S,6r)-6-(4-benzyl-5,5-dimethyl-4,5-dihydro-1, 2,4-oxadiazol-3-yl)-3-azabicyclo[3.1.0]hex-3-yl](5-isopropyl-1H-pyrazol-3-yl)methanone To a solution of (1R,5S,6r)-6-(4-benzyl-5,5-dimethyl-4,5-dihydro-1,2,4-oxadiazol-3-yl)-3-azabicyclo[3.1.0]hexane TFA salt (50 mg, 0.1800 mmol), HATU (84.5 mg, 0.22 mmol) and DIPEA (0.15 mL, 0.92 mmol) in DMF (3 mL) was added 5-isopropyl-1H-pyrazole-3-carboxylic acid (34.0 mg, 0.22 mmol), and the mixture was stirred at 20° C. for 16 hr. The mixture was diluted with $H_2O$ (30 mL) and extracted by EA (20 mL×2), and the organic phase was washed by brine (30 mL×3), dried over anhydrous $Na_2SO_4$ and concentrated to give a residue. The residue was purified by Prep-HPLC (FA) to afford the title compound (2.5 mg) as a white solid.

LC-MS Method1: 357.1 [M+H$^+$]

$^1$H NMR (400 MHz, CDCl$_3$) δ ppm 7.28-7.32 (m, 5H) 6.38 (br s, 1H) 4.29 (s, 2H) 3.88 (br d, J=12.8 Hz, 1H) 3.78-3.83 (m, 1H) 3.69-3.76 (m, 1H) 3.49 (br dd, J=12.6, 4.1 Hz, 1H) 3.04 (dt, J=13.7, 6.8 Hz, 1H) 2.10-2.16 (m, 1H) 2.03 (dt, J=7.2, 3.7 Hz, 1H) 1.44 (d, J=6.3 Hz, 6H) 1.31 (dd, J=6.8, 2.3 Hz, 6H) 0.97 (t, J=3.3 Hz, 1H)

Example 118 (5-isopropyl-1H-pyrazol-3-yl)[(1R,5S,6r)-6-(7a-methyl-5,6,7,7a-tetrahydropyrrolo[1,2-d][1,2,4]oxadiazol-3-yl)-3-azabicyclo[3.1.0]hex-3-yl]methanone 5-methyl-3,4-dihydro-2H-pyrrole To a solution of 4-chlorobutanenitrile (1.83 mL, 19.31 mmol) in 2-methoxy-2-methylpropane (20 mL, 23.18 mmol) was added bromo(methyl)magnesium (2763.65 mg, 23.18 mmol) drop-wise at 0° C. It was allowed to reach room temperature. After 15 min, THF (10 mL) was added drop-wise over 5 min. $H_2O$ (30 mL) was added and it was extracted with MTBE (30 mL×2). The combined organic layer was dried over $Na_2SO_4$ and concentrated in vacuum to give the title compound (800 mg, 9.6235 mmol, 49.826% yield) as yellow oil. It was directly used in the next step.

tert-butyl (1R,5S,6r)-6-(7a-methyl-5,6,7,7a-tetrahydropyrrolo[1,2-d][1,2,4]oxadiazol-3-yl)-3-azabicyclo[3.1.0]hexane-3-carboxylate A 100 mL round-bottom flask was charge with tert-butyl (1R,5S,6r)-6-[(Z)-chloro(hydroxyimino)methyl]-3-azabicyclo[3.1.0]hexane-3-carboxylate (250 mg, 0.9600 mmol), 5-methyl-3,4-dihydro-2H-pyrrole (500 mg, 6.01 mmol), triethylamine (0.4 mL, 2.88 mmol) and DMF (12.5 mL). The reaction was stirred at 20° C. for 16 hr to give a yellow solution. $H_2O$ (30 mL) was added and it was extracted with EtOAc (30 mL×2). The combined organic layer was dried over $Na_2SO_4$ and concentrated in vacuum to give the title compound (300 mg, 0.9760 mmol, 101.78% yield) as yellow oil. It was directly used in the next step.

LC-MS Method1 0.810 min, MS (m/z) 307.9 (M+H$^+$).

3-[(1R,5S,6r)-3-azabicyclo[3.1.0]hex-6-yl]-7a-methyl-5,6,7,7a-tetrahydropyrrolo[1,2-d][1,2,4]oxadiazole TFA Salt A 100 mL round-bottom flask was charged with tert-butyl (1R,5S,6r)-6-(7a-methyl-5,6,7,7a-tetrahydropyrrolo[1,2-d][1,2,4]oxadiazol-3-yl)-3-azabicyclo[3.1.0]hexane-3-carboxylate (250 mg, 0.8100 mmol), 2,2,2-trifluoroacetic acid (1 mL, 13.06 mmol) and DCM (10 mL). The reaction was stirred at 20° C. for 3 hr to give a yellow solution. The reaction mixture was evaporated in vacuum to give the title compound (260 mg, 0.8092 mmol, 99.498% yield) as red oil. It was directly use in the next step.

(5-isopropyl-1H-pyrazol-3-yl)[(1R,5S,6r)-6-(7a-methyl-5,6,7,7a-tetrahydropyrrolo[1,2-d][1,2,4]oxadiazol-3-yl)-3-azabicyclo[3.1.0]hex-3-yl]methanone A 100 mL round-bottom flask was charged with 5-isopropyl-1H-pyrazole-3-carboxylic acid (130 mg, 0.8400 mmol), HATU (354.6 mg, 0.9300 mmol), N-ethyl-N-isopropylpropan-2-amine (0.58 mL, 3.37 mmol) and DMF (6.5 mL). After stirred for 30 min, 3-[(1R,5S,6r)-3-azabicyclo[3.1.0]hex-6-yl]-7a-methyl-5,6,7,7a-tetrahydropyrrolo[1,2-d][1,2,4]oxadiazole TFA salt (270.93 mg, 0.8400 mmol) was added. The reaction mixture was stirred at 20° C. for 16 hr to give a yellow solution. $H_2O$ (30 mL) was added and it was extracted with EtOAc (30 mL×2). The combined organic layer was dried over $Na_2SO_4$ and concentrated in vacuum to give a yellow oil. The crude was purified by Prep-HPLC (NH$_3$). The afforded flows were concentrated in vacuum to remove most of CH$_3$CN and lyophilized to give the title compound (32.74 mg, 0.0950 mmol, 11.269% yield) as white solid.

LC-MS Method1: 344.1 [M+H$^+$]

$^1$H NMR (400 MHz, DMSO-d$_6$) δ 6.36 (br s, 1H), 4.20-4.44 (m, 1H), 3.95 (br s, 1H), 3.80 (br s, 1H), 3.45-3.57 (m, 2H), 2.97 (ddd, J=6.32, 9.01, 11.44 Hz, 2H), 2.03-2.15 (m, 1H), 1.95 (br s, 1H), 1.85-1.91 (m, 1H), 1.80-1.85 (m, 1H), 1.69-1.76 (m, 1H), 1.57-1.66 (m, 1H), 1.35 (s, 3H), 1.22 (d, J=6.88 Hz, 6H)

Example 119 (5-isopropyl-1H-pyrazol-3-yl)[(1R,5S,6r)-6-(5-methyl-1,3,4-oxadiazol-2-yl)-3-azabicyclo[3.1.0]hex-3-yl]methanone ethyl (1R,5S,6r)-3-[(5-isopropyl-1H-pyrazol-3-yl)carbonyl]-3-azabicyclo[3.1.0]hexane-6-carboxylate To a solution of 5-isopropyl-1H-pyrazole-3-carboxylic acid (1.69 g, 10.96 mmol) in DMF (20 mL) were added HATU (5.41 g, 14.24 mmol), DIPEA (5.43 mL, 32.87 mmol) and ethyl (1R,5S,6r)-3-azabicyclo[3.1.0]hexane-6-carboxylate (2.1 g, 10.96 mmol). The mixture was stirred at 15° C. for 4 h to give brown solution. The reaction mixture was poured into $H_2O$ (100 mL) and extracted with EtOAc (100 mL×3). The combined organic layers were washed with brine (250 mL), dried over $Na_2SO_4$, filtered and concentrated under reduced pressure. The crude product was purified by flash column (PE to 40% EtOAc in PE) to give brown solid. The afforded solid was triturated with EtOAc/PE (10 mL/20 mL) and dried in air to give the title compound (1.45 g, 4.9768 mmol, 45.422% yield) as white solid.

$^1$H NMR (400 MHz, CHLOROFORM-d) δ ppm=10.58 (brs, 1H), 6.47 (s, 1H), 4.35 (d, J=11.2 Hz, 1H), 4.20 (d, J=11.2 Hz, 1H), 4.20 (q, J=6.8 Hz, 2H), 3.95 (d, J=11.6, 4.0 Hz, 1H), 3.68 (d, J=11.6, 4.0 Hz, 1H), 3.02 (qn, J=3.6 Hz, 1H), 2.30-2.15 (m, 2H), 1.50-1.45 (m, 1H), 1.31 (d, J=6.8 Hz, 6H), 1.26 (t, J=6.8 Hz, 3H).

(1R,5S,6r)-3-[(5-isopropyl-1H-pyrazol-3-yl)carbonyl]-3-azabicyclo[3.1.0]hexane-6-carbohydrazide To a solution of ethyl (1R,5S,6r)-3-[(5-isopropyl-1H-pyrazol-3-yl)carbonyl]-3-azabicyclo[3.1.0]hexane-6-carboxylate (450 mg, 1.54 mmol) in EtOH (4 mL) was added hydrazine hydrate (236.69 mg, 4.63 mmol). The mixture was stirred at 80° C. for 13 h under $N_2$ to give white suspension. LCMS showed the desire MS and a part of the starting material was remained. Then hydrazine hydrate (236.69 mg, 4.63 mmol) was added to the mixture. The mixture was stirred at 80° C. for 13 h under $N_2$ to give white suspension. LCMS showed the desire MS and a part of the starting material was remained. Then hydrazine hydrate (236.69 mg, 4.63 mmol) was added to the mixture. The mixture was stirred at 80° C. for 13 h under $N_2$ to give white suspension. LCMS showed desire MS and a part of the starting material was remained. The reaction mixture was concentrated directly. The afforded solid was triturated with PE (15 mL) and dried in air to give the title compound (390 mg, 1.4063 mmol, 91.0510% yield) as white solid.

$^1$H NMR (400 MHz, DMSO-$d_6$) δ ppm 12.96 (brs, 1H), 9.06 (s, 1H), 6.37 (brs, 1H), 4.50-3.80 (m, 6H), 3.50-3.40 (m, 1H), 3.00-2.90 (m, 1H), 2.05-1.95 (m, 1H), 1.95-1.85 (m, 1H), 1.25 (d, J=7.2 Hz, 6H), 0.90-0.80 (m, 1H).

(1R,5S,6r)-N'-acetyl-3-[(5-isopropyl-1H-pyrazol-3-yl)carbonyl]-3-azabicyclo[3.1.0]hexane-6-carbohydrazide To a mixture of (1R,5S,6r)-3-[(5-isopropyl-1H-pyrazol-3-yl)carbonyl]-3-azabicyclo[3.1.0]hexane-6-carbohydrazide (270 mg, 0.9700 mmol) in DCM (10 mL) were added acetic anhydride (119.27 mg, 1.17 mmol) and $Et_3N$ (0.34 mL, 1.95 mmol). The reaction mixture was stirred at 15° C. for 12 h to give white suspension. The suspension was filtered. The filter cake was washed with DCM (5 mL×3) and dried in vacuo to afford the title compound (250 mg, 0.7828 mmol, 80.404% yield) as white solid.

(5-isopropyl-1H-pyrazol-3-yl)[(1R,5S,6r)-6-(5-methyl-1,3,4-oxadiazol-2-yl)-3-azabicyclo[3.1.0] hex-3-yl]methanone A solution of (1R,5S,6r)-N'-acetyl-3-[(5-isopropyl-1H-pyrazol-3-yl)carbonyl]-3-azabicyclo[3.1.0]hexane-6-carbohydrazide (250 mg, 0.7800 mmol) in $POCl_3$ (5 mL, 69.14 mmol) was stirred at 90° C. for 4 h to give brown mixture. TLC showed one new spot (Rf=0.3) was detected. The reaction mixture was concentrated in vacuo to give a residue. The residue was dissolved with DCM (15 mL). The resulting mixture was washed with $NaHCO_3$ (eq., 15 mL×2). The aqueous phase was extracted with DCM (10 mL×3). The combined organic phase was dried with anhydrous $Na_2SO_4$, filtered and concentrated in vacuum to give a residue. The residue was purified by prep-TLC ($SiO_2$, DCM:MeOH=10:1) and lyophilized to afford the title compound (120 mg, 0.3799 mmol, 48.535% yield) as yellow powder.

LC-MS Method1: 301.9 [M+H$^+$]

$^1$H NMR (400 MHz, CHLOROFORM-d) δ ppm 9.99-10.47 (m, 1H), 6.53 (s, 1H), 4.45 (br d, J=10.6 Hz, 1H), 4.29 (d, J=12.8 Hz, 1H), 3.99 (dd, J=11.6, 4.0 Hz, 1H), 3.72 (dd, J=12.7, 4.1 Hz, 1H), 2.99-3.09 (m, 1H), 2.49 (s, 3H), 2.35-2.43 (m, 1H), 2.26-2.34 (m, 1H), 1.96 (t, J=3.4 Hz, 1H), 1.31 (d, J=6.9 Hz, 6H)

Example 120 (5-isopropyl-1H-pyrazol-3-yl)[(1R,5S,6r)-6-(4-methyl-4H-1,2,4-triazol-3-yl)-3-azabicyclo[3.1.0]hex-3-yl]methanone N'-({(1R,5S,6r)-3-[(5-isopropyl-1H-pyrazol-3-yl)carbonyl]-3-azabicyclo[3.1.0]hex-6-yl}carbonyl)-N,N-dimethylhydrazonoformamide To a solution of (1R,5S,6r)-3-[(5-isopropyl-1H-pyrazol-3-yl)carbonyl]-3-azabicyclo[3.1.0]hexane-6-carbohydrazide (390 mg, 1.41 mmol) in DMF (4 mL) was added 1,1-dimethoxy-N,N-dimethylmethanamine (0.2 mL, 1.48 mmol). The mixture was stirred at 100° C. for 15 h to give yellow solution. The reaction mixture was concentrated directly to give the title compound (450 mg, 1.3538 mmol, 96.265% yield) as white solid.

$^1$H NMR (400 MHz, DMSO-$d_6$) δ ppm 12.94 (brs, 1H), 10.10 (s, 1H), 7.66 (s, 1H), 6.36 (brs, 1H), 4.40-4.30 (m, 1H), 4.00-3.70 (m, 2H), 3.50-3.40 (m, 1H), 3.00-2.90 (m, 1H), 2.80-2.75 (m, 1H), 2.76 (s, 6H), 2.00-1.80 (m, 2H), 1.21 (d, J=7.2 Hz, 6H), 1.25-1.20 (m, 1H).

(5-isopropyl-1H-pyrazol-3-yl)[(1R,5S,6r)-6-(4-methyl-4H-1,2,4-triazol-3-yl)-3-azabicyclo[3.1.0] hex-3-yl]methanone To a solution of N'-({(1R,5S,6r)-3-[(5-isopropyl-1H-pyrazol-3-yl)carbonyl]-3-azabicyclo[3.1.0]hex-6-yl}carbonyl)-N,N-dimethylhydrazonoformamide (200 mg, 0.6000 mmol) in THF (4 mL) was added methanamine (0.49 mL, 12.03 mmol). Then HOAc (2 mL, 0.6000 mmol) was added to the mixture at 0° C. The mixture was stirred at 100° C. to give colorless solution. The reaction mixture was concentrated directly. The residue was purified by prep-HPLC (HCl) to give the title compound (37.05 mg, 0.1234 mmol, 20.501% yield) as white solid.

$^1$H NMR (400 MHz, DMSO-d6) δ ppm 9.39 (br s, 1H), 6.42 (s, 1H), 4.46 (br d, J=11.88 Hz, 1H), 4.10 (br d, J=12.51 Hz, 1H), 3.95 (br dd, J=12.01, 3.88 Hz, 1H), 3.85 (s, 3H), 3.60 (br dd, J=12.44, 4.06 Hz, 1H), 2.97 (spt, J=6.90 Hz, 1H), 2.47 (br s, 2H), 2.16 (t, J=3.25 Hz, 1H), 1.22 (d, J=6.75 Hz, 6H)

Example 121 (5-isopropyl-1H-pyrazol-3-yl)[(1R,5S,6r)-6-(4-phenyl-4H-1,2,4-triazol-3-yl)-3-azabicyclo[3.1.0]hex-3-yl]methanone (5-isopropyl-1H-pyrazol-3-yl)[(1R,5S,6r)-6-(4-phenyl-4H-1,2,4-triazol-3-yl)-3-azabicyclo[3.1.0]hex-3-yl]methanone To a solution of (1R,5S,6r)-3-[(5-isopropyl-1H-pyrazol-3-yl)carbonyl]-3-azabicyclo[3.1.0]hexane-6-carbohydrazide in MeCN (2 mL) was added 1,1-dimethoxy-N,N-dimethylmethanamine (21.52 mg, 0.1800 mmol). The mixture was stirred at 50° C. for 30 min. Then aniline (0.03 mL, 0.3600 mmol) was added to the mixture, followed by AcOH (2 mL). The mixture was stirred at 120° C. for 5 h to give colorless solution. The residue was purified by prep-HPLC (HCl). The afforded flows were combined, concentrated to remove most of $CH_3CN$ and lyophilized to give the title compound (24.12 mg, 0.0666 mmol, 36.912% yield) as white solid.

LC-MS Method1: 362.9 [M+H$^+$]

$^1$H NMR (400 MHz, DMSO-$d_6$) δ ppm 9.28-9.55 (1H, m), 7.58-7.70 (5H, m), 6.34 (1H, s), 4.26 (1H, br d, J=12.01 Hz), 3.81-3.92 (2H, m), 3.54 (1H, dd, J=12.44, 4.19 Hz), 2.93 (1H, dt, J=13.85, 6.89 Hz), 2.54-2.58 (1H, m), 2.39 (1H, dt, J=7.19, 3.66 Hz), 1.68 (1H, t, J=3.31 Hz), 1.19 (6H, d, J=7.00 Hz)

Example 122 {(1R,5S,6r)-6-[4-(4-fluorophenyl)-4H-1,2,4-triazol-3-yl]-3-azabicyclo[3.1.0]hex-3-yl}(5-isopropyl-1H-pyrazol-3-yl)methanone {(1R,5S,6r)-6-[4-(4-fluorophenyl)-4H-1,2,4-triazol-3-yl]-3-azabicyclo[3.1.0]hex-3-yl}(5-isopropyl-1H-pyrazol-3-yl)methanone To a solution of (1R,5S,6r)-3-[(5-isopropyl-1H-pyrazol-3-yl)carbonyl]-3-azabicyclo[3.1.0]hexane-6-carbohydrazide in MeCN (2 mL) was added 1,1-dimethoxy-N,N-dimethylmethanamine (47.96 mg, 0.3600 mmol). The mixture was stirred at 80° C. for 30 min. Then 4-fluoroaniline (0.07 mL, 0.7200 mmol) and AcOH (216.36 mg, 3.61 mmol) were added. The mixture was stirred at 90° C. for 5 h to give colorless solution. The reaction mixture was concentrated directly. The residue was purified by prep-HPLC (HCl) to give the title compound (5.67 mg, 0.0149 mmol, 4.1333% yield) as gray solid.

LC-MS Method1: 381.0 [M+H$^+$]

$^1$H NMR (400 MHz, DMSO-d$_6$) δ ppm 12.92 (1H, br s), 8.67 (1H, s), 7.62 (2H, br dd, J=8.91, 4.89 Hz), 7.35-7.51 (2H, m), 6.33 (1H, s), 4.28 (1H, br d, J=12.05 Hz), 3.80-3.94 (2H, m), 3.52 (1H, br d, J=8.03 Hz), 2.85-3.01 (1H, m), 2.19 (1H, br s), 1.92-2.04 (1H, m), 1.51 (1H, br s), 1.13-1.27 (6H, m)

Example 123 [(1R,5S,6r)-6-(4,5-dimethyl-4H-1,2,4-triazol-3-yl)-3-azabicyclo[3.1.0]hex-3-yl](5-isopropyl-1H-pyrazol-3-yl)methanone

[(1R,5S,6r)-6-(4,5-dimethyl-4H-1,2,4-triazol-3-yl)-3-azabicyclo[3.1.0]hex-3-yl](5-isopropyl-1H-pyrazol-3-yl)methanone To a solution of (5-isopropyl-1H-pyrazol-3-yl)[(1R,5S,6r)-6-(5-methyl-1,3,4-oxadiazol-2-yl)-3-azabicyclo[3.1.0]hex-3-yl]methanone (30 mg, 0.1000 mmol) in xylene (2 mL, 0.1000 mmol) were added methylamine (0.74 mL, 1.99 mmol) and TsOH (1.71 mg, 0.0100 mmol). The mixture was stirred at 140° C. for 12 h to give brown solution. The reaction mixture was concentrated directly. The residue was purified by prep-HPLC (HCl). The afforded flows were combined, concentrated to remove most of CH$_3$CN and lyophilized to give the title compound (11.82 mg, 0.0376 mmol, 37.765% yield) as light yellow solid.

LC-MS Method1: 314.9 [M+H$^+$]

$^1$H NMR (400 MHz, DMSO-d$_6$) δ ppm 6.41 (1H, s), 4.44 (1H, br d, J=11.80 Hz), 4.09 (1H, d, J=12.30 Hz), 3.94 (1H, br dd, J=11.92, 4.14 Hz), 3.71 (3H, s), 3.59 (1H, br dd, J=12.55, 4.27 Hz), 2.96 (1H, dt, J=13.80, 6.90 Hz), 2.56 (3H, s), 2.38 (1H, br d, J=3.76 Hz), 2.29-2.35 (1H, m), 2.28 (1H, s), 2.14 (1H, t, J=3.39 Hz), 1.21 (6H, dd, J=7.03, 1.00 Hz)

Example 124 [(1R,5S,6r)-6-(4-cyclobutyl-5-methyl-4H-1,2,4-triazol-3-yl)-3-azabicyclo[3.1.0]hex-3-yl](5-isopropyl-1H-pyrazol-3-yl)methanone

[(1R,5S,6r)-6-(4-cyclobutyl-5-methyl-4H-1,2,4-triazol-3-yl)-3-azabicyclo[3.1.0]hex-3-yl](5-isopropyl-1H-pyrazol-3-yl)methanone To a mixture of (5-isopropyl-1H-pyrazol-3-yl)[(1R,5S,6r)-6-(5-methyl-1,3,4-oxadiazol-2-yl)-3-azabicyclo[3.1.0]hex-3-yl]methanone (30 mg, 0.1000 mmol) in o-Xylene (1 mL) were added TsOH (0.17 mg, 0 mmol) and cyclobutanamine (0.02 mL, 0.2000 mmol). The reaction mixture was stirred at 140° C. for 16 h to give brown mixture. The reaction mixture was concentrated in vacuo to give a residue. The residue was purified by prep-HPLC (HCl). The afforded flows were combined, concentrated to remove most of CH$_3$CN and lyophilized to afford the title compound (10.71 mg, 0.0302 mmol, 30.351% yield) as yellow solid.

LC-MS Method1: 355.0 [M+H$^+$]

$^1$H NMR (400 MHz, DMSO-d6) δ ppm 6.42 (s, 1H), 4.85-4.98 (m, 1H), 4.45 (br d, J=12.0 Hz, 1H), 4.05 (d, J=12.3 Hz, 1H), 3.93 (br dd, J=11.9, 4.1 Hz, 2H), 3.61 (br s, 1H), 3.58 (br s, 1H), 2.91-3.01 (m, 1H), 2.63-2.69 (m, 2H), 2.60 (s, 3H), 2.42-2.45 (m, 1H), 2.36 (br d, J=3.8 Hz, 1H), 2.04 (t, J=3.4 Hz, 1H), 1.84 (td, J=10.2, 5.0 Hz, 2H), 1.22 (d, J=7.0 Hz, 6H)

Example 125 [(1R,5S,6r)-6-(4-cyclohexyl-5-methyl-4H-1,2,4-triazol-3-yl)-3-azabicyclo[3.1.0]hex-3-yl](5-isopropyl-1H-pyrazol-3-yl)methanone tert-butyl (1R,5S,6r)-6-(cyclohexylcarbamoyl)-3-azabicyclo[3.1.0]hexane-3-carboxylate To a solution of (1R,5S,6r)-3-{[(tert-butyl)oxy]carbonyl}-3-azabicyclo[3.1.0]hexane-6-carboxylic acid (500 mg, 2.2 mmol) in DMF (6 mL) were added HATU (1086.86 mg, 2.86 mmol), cyclohexanamine (0.28 mL, 2.42 mmol) and Et$_3$N (0.91 mL, 5.5 mmol). The mixture was stirred at 20° C. for 12 h to give gray suspension. TLC (PE:EtOAc=1:1) showed the reaction was completed. The reaction mixture was poured into H$_2$O (15 mL) and filtered. The filter cake was washed with H$_2$O (15 mL×2) and dried in air to give the title compound (650 mg, 2.1075 mmol, 95.791% yield) as white solid.

$^1$H NMR (400 MHz, CHLOROFORM-d) δ ppm 5.48 (d, J=8.0 Hz, 1H), 3.85-3.70 (m, 1H), 3.67 (d, J=11.2 Hz, 1H), 3.59 (d, J=11.2 Hz, 1H), 3.45-3.35 (m, 2H), 2.04 (brs, 2H), 1.91 (brd, J=9.6 Hz, 2H), 1.80-1.70 (m, 2H), 1.65-1.55 (m, 1H), 1.44 (s, 9H), 1.50-1.20 (m, 2H), 1.25-1.05 (m, 4H).

tert-butyl (1R,5S,6r)-6-(cyclohexylcarbamothioyl)-3-azabicyclo[3.1.0]hexane-3-carboxylate To a solution of tert-butyl (1R,5S,6r)-6-(cyclohexylcarbamoyl)-3-azabicyclo[3.1.0]hexane-3-carboxylate (600 mg, 1.95 mmol) in THF (6 mL) was added 2,4-bis(4-methoxyphenyl)-1,3,2,4-dithiadiphosphetane 2,4-disulfide (802.59 mg, 1.98 mmol). The mixture was stirred at 20° C. for 12 h to give brown solution. TLC (PE:EtOAc=5:1) showed a new spot. The reaction mixture was poured into H$_2$O (20 mL) and extracted with EtOAc (20 mL×4). The combined organic layers were washed with brine (50 mL×2), dried over Na$_2$SO$_4$, filtered and concentrated under reduced pressure. The crude product was purified by flash column (PE to 10% EtOAc in PE) to give the title compound (350 mg, 1.0786 mmol, 55.446% yield) as gray solid.

$^1$H NMR (400 MHz, CHLOROFORM-d) δ ppm 7.58 (brd, J=7.2 Hz, 1H), 4.50-4.35 (m, 1H), 3.65 (d, J=11.2 Hz, 1H), 3.57 (d, J=11.2 Hz, 1H), 3.50-3.40 (m, 2H), 2.45-2.35 (m, 2H), 2.15-2.05 (m, 2H), 1.80-1.50 (m, 4H), 1.45 (s, 9H), 1.50-1.40 (m, 2H), 1.30-1.10 (m, 4H).

tert-butyl (1R,5S,6r)-6-[(Z)-(cyclohexylimino)(methylthio)methyl]-3-azabicyclo[3.1.0]hexane-3-carboxylate To a solution of tert-butyl (1R,5S,6r)-6-(cyclohexylcarbamothioyl)-3-azabicyclo[3.1.0]hexane-3-carboxylate (300 mg, 0.9200 mmol), 1-methyl-4-(methylsulfonyl)benzene (0.12 mL, 0.9300 mmol) in DMF (6 mL) was added tert-butoxypotassium (124.49 mg, 1.11 mmol). The mixture was stirred at 20° C. for 9 h to give yellow solution. The reaction mixture was poured into H$_2$O (20 mL) and extracted with EtOAc (20 mL×4). The combined organic layers were washed with brine (50 mL×2), dried over Na$_2$SO$_4$, filtered and concentrated under reduced pressure to give the title compound (300 mg, 0.8862 mmol, 95.855% yield) as a light yellow solid.

LC-MS Method1 0.693 min, MS (m/z) 339.0 (M+H$^+$).

tert-butyl (1R,5S,6r)-6-(4-cyclohexyl-5-methyl-4H-1,2,4-triazol-3-yl)-3-azabicyclo[3.1.0]hexane-3-carboxylate To a solution of tert-butyl (1R,5S,6r)-6-[(Z)-(cyclohexylimino)(methylthio)methyl]-3-azabicyclo[3.1.0]hexane-3-carboxylate (300 mg, 0.8900 mmol) and acetohydrazide (98.48 mg, 1.33 mmol) in THF (5 mL) was added 2,2,2-trifluoroacetic acid (0.03 mL, 0.4400 mmol). The mixture was stirred at 75° C. for 16 h to give colorless solution. The reaction mixture was poured into H$_2$O (20 mL) and extracted with EtOAc (20 mL×4). The combined organic layers were washed with brine (50 mL), dried over Na$_2$SO$_4$, filtered and concentrated under reduced pressure. The crude product was purified by flash column (EtOAc/MeOH=1/0 to 5/1) to give the title compound (280 mg, 0.8082 mmol, 91.189% yield) as colorless gum.

LC-MS Method1 0.718 min, MS (m/z) 347.1 (M+H$^+$).

(1R,5S,6r)-6-(4-cyclohexyl-5-methyl-4H-1,2,4-triazol-3-yl)-3-azabicyclo[3.1.0]hexane hydrochloride A solution of tert-butyl (1R,5S,6r)-6-(4-cyclohexyl-5-methyl-4H-1,2,4-triazol-3-yl)-3-azabicyclo[3.1.0]hexane-3-carboxylate (130 mg, 0.3800 mmol) in HCl/dioxane (0.09 mL, 0.3800 mmol) was stirred at 20° C. for 30 min to give colorless solution. LCMS showed the desire MS and the starting material was consumed up. The reaction mixture was concentrated directly to give the title compound (100 mg, 0.3536 mmol, 94.238% yield) as yellow gum.

[(1R,5S,6r)-6-(4-cyclohexyl-5-methyl-4H-1,2,4-triazol-3-yl)-3-azabicyclo[3.1.0]hex-3-yl](5-isopropyl-1H-pyrazol-3-yl)methanone To a solution of 5-isopropyl-1H-pyrazole-3-carboxylic acid (65.42 mg, 0.4200 mmol) in DMF (1.7422 mL) were added HATU (188.11 mg, 0.5000 mmol), Et$_3$N (0.18 mL, 1.06 mmol) and (1R,5S,6r)-6-(4-cyclohexyl-5-methyl-4H-1,2,4-triazol-3-yl)-3-azabicyclo[3.1.0]hexane hydrochloride (100 mg, 0.3500 mmol). The mixture was stirred at 20° C. for 12 h to give yellow solution. LCMS showed the desire MS and the starting material was consumed up. The reaction mixture was poured into H$_2$O (20 mL) and extracted with EtOAc (20 mL×4). The combined organic layers were washed with brine (50 mL), dried over Na$_2$SO$_4$, filtered and concentrated under reduced pressure. The residue was purified by prep-HPLC (HCl). The afforded flows were combined, concentrated to remove most of CH$_3$CN and lyophilized to give yellow solid(crude). The residue was purified by prep-TLC (EtOAc) and lyophilized to give the title compound as a white solid.

$^1$H NMR (400 MHz, CHLOROFORM-d) δ ppm 10.84-11.67 (1H, m), 6.53 (1H, s), 4.46 (1H, br d, J=10.76 Hz), 4.26 (1H, br d, J=12.76 Hz), 3.96-4.12 (2H, m), 3.76 (1H, br dd, J=12.88, 4.25 Hz), 3.02-3.18 (1H, m), 2.74 (1H, br s), 2.51 (3H, br s), 2.11 (1H, br s), 1.89-2.00 (5H, m), 1.79 (1H, br d, J=13.76 Hz), 1.67-1.75 (2H, m), 1.38-1.50 (2H, m), 1.33 (6H, dd, J=6.88, 1.63 Hz), 1.25 (1H, br d, J=6.38 Hz)

Example 126 (5-isopropyl-1H-pyrazol-3-yl)[(1R,5S,6r)-6-(5-methyl-4-phenyl-4H-1,2,4-triazol-3-yl)-3-azabicyclo[3.1.0]hex-3-yl]methanone (5-isopropyl-1H-pyrazol-3-yl)[(1R,5S,6r)-6-(5-methyl-4-phenyl-4H-1,2,4-triazol-3-yl)-3-azabicyclo[3.1.0]hex-3-yl]methanone To a mixture of (5-isopropyl-1H-pyrazol-3-yl)[(1R,5S,6r)-6-(5-methyl-1,3,4-oxadiazol-2-yl)-3-azabicyclo[3.1.0]hex-3-yl]methanone (30 mg, 0.1000 mmol) in o-Xylene (1 mL) were added aniline (0.02 mL, 0.2000 mmol) and TsOH (0.17 mg, 0 mmol). The reaction mixture was stirred at 140° C. for 16 h to give brown mixture. The reaction mixture was concentrated in vacuo to give a residue. The residue was purified by prep-HPLC (HCl). The afforded flows were combined, concentrated to remove most of CH$_3$CN and lyophilized to afford the title compound (18.55 mg, 0.0493 mmol, 49.496% yield) as white powder.

LC-MS Method1: 377.0 [M+H$^+$]

$^1$H NMR (400 MHz, DMSO-d6) δ ppm 7.54-7.79 (m, 5H), 6.32 (s, 1H), 4.17 (br d, J=12.0 Hz, 1H), 3.85 (br dd, J=11.8, 4.1 Hz, 2H), 3.74 (br d, J=12.4 Hz, 2H), 2.93 (dt, J=13.9, 7.1 Hz, 1H), 2.68 (br d, J=1.8 Hz, 1H), 2.35 (s, 3H), 2.28 (dt, J=7.5, 3.6 Hz, 1H), 1.45 (t, J=3.3 Hz, 1H), 1.19 (d, J=6.9 Hz, 6H)

Example 127 {(1R,5S,6r)-6-[4-(4-fluorophenyl)-5-methyl-4H-1,2,4-triazol-3-yl]-3-azabicyclo[3.1.0]hex-3-yl}(5-isopropyl-1H-pyrazol-3-yl)methanone {(1R,5S,6r)-6-[4-(4-fluorophenyl)-5-methyl-4H-1,2,4-triazol-3-yl]-3-azabicyclo[3.1.0]hex-3-yl}(5-isopropyl-1H-pyrazol-3-yl)methanone To a solution of (5-isopropyl-1H-pyrazol-3-yl)[(1R,5S,6r)-6-(5-methyl-1,3,4-oxadiazol-2-yl)-3-azabicyclo[3.1.0]hex-3-yl]methanone (25 mg, 0.0800 mmol) in p-Xylene (0.50 mL) were added 4-fluoroaniline (0.02 mL, 0.1700 mmol) and TsOH (0.14 mg, 0 mmol). The mixture was stirred at 140° C. for 12 h to give brown solution. The reaction mixture was concentrated directly. The residue was purified by prep-HPLC (HCl). The afforded flows were combined, concentrated to remove most of CH$_3$CN and lyophilized to give the title compound (13.91 mg, 0.0353 mmol, 42.506% yield) as white solid.

LC-MS Method1: 395.0 [M+H$^+$]

$^1$H NMR (400 MHz, DMSO-d$_6$) δ ppm 7.76 (1H, dd, J=8.69, 4.82 Hz), 7.73-7.80 (1H, m), 7.55 (2H, t, J=8.63 Hz), 6.30-6.37 (1H, m), 4.18 (1H, br d, J=12.01 Hz), 3.86 (1H, br dd, J=11.94, 4.06 Hz), 3.75 (1H, br d, J=12.51 Hz), 3.51 (1H, br dd, J=12.44, 4.06 Hz), 2.88-2.99 (1H, m), 2.39 (3H, s), 2.31-2.37 (1H, m), 1.53 (1H, t, J=3.25 Hz), 1.19 (6H, d, J=7.00 Hz)

Example 128 (5-isopropyl-1H-pyrazol-3-yl){(1R,5S,6r)-6-[5-methyl-4-(4-methylphenyl)-4H-1,2,4-triazol-3-yl]-3-azabicyclo[3.1.0]hex-3-yl}methanone (5-isopropyl-1H-pyrazol-3-yl){(1R,5S,6r)-6-[5-methyl-4-(4-methylphenyl)-4H-1,2,4-triazol-3-yl]-3-azabicyclo[3.1.0]hex-3-yl}methanone To a mixture of (5-isopropyl-1H-pyrazol-3-yl)[(1R,5S,6r)-6-(5-methyl-1,3,4-oxadiazol-2-yl)-3-azabicyclo[3.1.0]hex-3-yl]methanone (20 mg, 0.0700 mmol) in o-Xylene (1 mL) were added p-toluidine (0.01 mL, 0.1300 mmol) and TsOH (0.11 mg). The reaction mixture was stirred at 140° C. for 12 h to give brown mixture. The reaction mixture was concentrated in vacuo to give a residue. The residue was purified by prep-HPLC (HCl). The afforded flows were combined, concentrated to remove most of $CH_3CN$ and lyophilized to afford the title compound (11.42 mg, 0.0278 mmol, 41.954% yield) as yellow solid.

LC-MS Method1: 391.0 [M+H$^+$]

$^1$H NMR (400 MHz, DMSO-d6) δ ppm 7.49-7.53 (m, 2H), 7.45-7.49 (m, 2H), 6.33 (s, 1H), 4.20 (br d, J=12.1 Hz, 1H), 3.86 (br dd, J=12.0, 4.3 Hz, 2H), 3.75 (br d, J=12.4 Hz, 1H), 2.93 (dt, J=13.9, 6.9 Hz, 1H), 2.46 (br d, J=3.1 Hz, 1H), 2.41 (s, 3H), 2.34 (s, 3H), 2.29 (dt, J=7.4, 3.8 Hz, 1H), 1.46 (t, J=3.4 Hz, 1H), 1.19 (d, J=6.9 Hz, 6H)

Example 129 {(1R,5S,6r)-6-[4-(4-ethylphenyl)-5-methyl-4H-1,2,4-triazol-3-yl]-3-azabicyclo[3.1.0]hex-3-yl}(5-isopropyl-1H-pyrazol-3-yl)methanone {(1R,5S,6r)-6-[4-(4-ethylphenyl)-5-methyl-4H-1,2,4-triazol-3-yl]-3-azabicyclo[3.1.0]hex-3-yl}(5-isopropyl-1H-pyrazol-3-yl)methanone To a mixture of (5-isopropyl-1H-pyrazol-3-yl)[(1R,5S,6r)-6-(5-methyl-1,3,4-oxadiazol-2-yl)-3-azabicyclo[3.1.0]hex-3-yl]methanone (20 mg, 0.0700 mmol) in o-Xylene (0.9535 mL) were added 4-ethylaniline (0.02 mL, 0.1300 mmol) and TsOH (0.11 mg). The reaction mixture was stirred at 140° C. for 12 h to give brown mixture. LCMS showed the starting material was consumed completely. The reaction mixture was concentrated in vacuo to give a residue. The residue was purified by prep-HPLC (HCl). The afforded flows were combined, concentrated to remove most of $CH_3CN$ and lyophilized to afford the title compound (9.41 mg, 0.0229 mmol, 34.521% yield) as white powder.

LC-MS Method1: 405.0 [M+H$^+$]

$^1$H NMR (400 MHz, DMSO-d6) δ ppm 7.47-7.57 (m, 4H), 6.25-6.40 (m, 1H), 4.18 (br d, J=11.9 Hz, 1H), 3.86 (br dd, J=11.9, 4.1 Hz, 2H), 3.75 (br d, J=12.5 Hz, 1H), 3.49 (br s, 2H), 2.87-2.97 (m, 1H), 2.66-2.76 (m, 2H), 2.36 (s, 3H), 2.28-2.33 (m, 2H), 1.46 (t, J=3.3 Hz, 1H), 1.16-1.25 (m, 9H)

Example 130 (5-isopropyl-1H-pyrazol-3-yl)[(1R,5S,6r)-6-(6-methyl[1,2,4]triazolo[4,3-a]pyridin-3-yl)-3-azabicyclo[3.1.0]hex-3-yl]methanone tert-butyl (1R,5S,6r)-6-{[2-(5-methyl-2-pyridinyl)hydrazino]carbonyl}-3-azabicyclo[3.1.0]hexane-3-carboxylate To a mixture of (1R,5S,6r)-3-{[(tert-butyl)oxy]carbonyl}-3-azabicyclo[3.1.0]hexane-6-carboxylic acid (300 mg, 1.32 mmol) in DMF (5 mL) were added 2-hydrazino-5-methylpyridine (162.58 mg, 1.32 mmol), Et$_3$N (0.24 mL, 1.45 mmol) and HATU (551.79 mg, 1.45 mmol). The reaction mixture was stirred at 15° C. for 16 h to give brown mixture. The reaction mixture was concentrated in vacuo to give a residue. The residue was purified by column chromatography (SiO$_2$, PE/EA=6/1) to give the title compound (330 mg, 0.9928 mmol, 75.206% yield) as yellow solid.

LC-MS Method1 0.639 min, MS (m/z) 332.9 (M+H$^+$).

tert-butyl (1R,5S,6r)-6-(6-methyl[1,2,4]triazolo[4,3-a]pyridin-3-yl)-3-azabicyclo[3.1.0]hexane-3-carboxylate To a mixture of tert-butyl (1R,5S,6r)-6-{[2-(5-methyl-2-pyridinyl)hydrazino]carbonyl}-3-azabicyclo[3.1.0]hexane-3-carboxylate (270 mg, 0.8100 mmol) in MeCN (5 mL) was added Burgess reagent (387.13 mg, 1.62 mmol). The reaction mixture was stirred at 90° C. for 12 h. TLC showed the starting material was consumed completely, and one new spot was detected. The reaction mixture was concentrated in vacuo to give a residue. The residue was purified by prep-TLC (SiO$_2$, DCM:MeOH=10:1) to afford the title compound (130 mg, 0.4135 mmol, 50.908% yield) as yellow solid.

LC-MS Method1 0.693 min, MS (m/z) 314.9 (M+H$^+$).

3-[(1R,5S,6r)-3-azabicyclo[3.1.0]hex-6-yl]-6-methyl[1,2,4]triazolo[4,3-a]pyridine TFA Salt To a solution of tert-butyl (1R,5S,6r)-6-(6-methyl[1,2,4]triazolo[4,3-a]pyridin-3-yl)-3-azabicyclo[3.1.0]hexane-3-carboxylate (130 mg, 0.4100 mmol) in DCM (4 mL) was added TFA (1 mL, 13.46 mmol). The reaction mixture was stirred at 15° C. for 2 h to give yellow mixture. TLC (DCM:MeOH=10:1) showed the starting material was consumed completely. The reaction mixture was concentrated in vacuo to give the title compound (135 mg, 0.4112 mmol, 99.446% yield) as yellow oil.

(5-isopropyl-1H-pyrazol-3-yl)[(1R,5S,6r)-6-(6-methyl[1,2,4]triazolo[4,3-a]pyridin-3-yl)-3-azabicyclo[3.1.0]hex-3-yl]methanone To a mixture of 3-[(1R,5S,6r)-3-azabicyclo[3.1.0]hex-6-yl]-6-methyl[1,2,4]triazolo[4,3-a]pyridine TFA salt (130 mg, 0.4000 mmol) in DMF (3.0297 mL) were added 5-isopropyl-1H-pyrazole-3-carboxylic acid (61.05 mg, 0.4000 mmol), DIPEA (0.2 mL, 1.19 mmol) and HATU (180.57 mg, 0.4800 mmol). The reaction mixture was stirred at 15° C. for 12 h to give brown mixture. LCMS showed the starting material was consumed completely. The reaction mixture was purified by prep-HPLC (HCl). The afforded flows were combined, concentrated to remove most of $CH_3CN$ and lyophilized to afford the title compound (25.34 mg, 0.0698 mmol, 17.624% yield) as white solid.

LC-MS Method1: 350.9 [M+H$^+$]

$^1$H NMR (400 MHz, DMSO-d6) δ ppm 1.23 (dd, J=6.9, 1.2 Hz, 6H), 2.37 (d, J=3.6 Hz, 1H), 2.40 (s, 3H), 2.44 (br d, J=1.9 Hz, 1H), 2.47 (dd, J=3.4, 1.6 Hz, 1H), 2.93-3.03 (m, 1H), 3.62 (br s, 1H), 3.66 (br d, J=3.5 Hz, 1H), 4.00 (br dd, J=11.9, 4.2 Hz, 1H), 4.21 (d, J=12.4 Hz, 1H), 4.53 (br d, J=11.8 Hz, 1H), 6.45 (s, 1H), 7.78 (d, J=9.5 Hz, 1H), 7.91 (d, J=9.3 Hz, 1H), 8.86 (s, 1H).

Example 131 (5-isopropyl-1H-pyrazol-3-yl)[(1R,5S,6r)-6-(6-methoxy[1,2,4]triazolo[4,3-a]pyridin-3-yl)-3-azabicyclo[3.1.0]hex-3-yl]methanone 2-hydrazino-5-methoxypyridine 2-chloro-5-methoxypyridine (1.5. g, 7.98 mmol) and hydrazine hydrate (20. g, 379.54 mmol) was combined and heated slowly to 140° C. The reaction mixture was stirred at 140° C. for 16 hours. LCMS showed the desired peak was found. The mixture was concentrated under reduced pressure to afford a residue. The residue was purified by Combi Flash with silica gel (MeOH/DCM=1/10) to give the title compound (650 mg, 4.6709 mmol, 58.548% yield) as yellow oil.

LC-MS Method1 0.192 min, MS (m/z) 140.0 (M+H$^+$).

tert-butyl (1R,5S,6r)-6-{[2-(5-methoxy-2-pyridinyl)hydrazino]carbonyl}-3-azabicyclo[3.1.0]hexane-3-carboxylate To a mixture of (1R,5S,6r)-3-{[(tert-butyl)oxy]carbonyl}-3-azabicyclo[3.1.0]hexane-6-carboxylic acid (979.85 mg, 4.31 mmol) and HATU (2.46 g, 6.47 mmol) in DCM (20 mL) was added Et$_3$N (1.43 mL, 8.62 mmol), and the resulting mixture was stirred at 20° C. for 10 min. Then 2-hydrazino-5-methoxypyridine (600 mg, 4.31 mmol) was added. The resulting mixture was stirred at 20° C. under N$_2$ for 16 hours to give brown mixture. The reaction mixture was diluted with H$_2$O (20 mL) and extracted with EtOAc (30 mL×3). The organic layer was washed with brine (20 mL), dried over Na$_2$SO$_4$ and concentrated in vacuum to give brown oil. The crude oil was purified by prep-TLC (PE/EA=1/1) to give the title compound (400 mg, 1.1481 mmol, 26.628% yield) as yellow solid.

LC-MS Method1: 349.1 [M+H$^+$].

tert-butyl (1R,5S,6r)-6-(6-methoxy[1,2,4]triazolo[4,3-a]pyridin-3-yl)-3-azabicyclo[3.1.0]hexane-3-carboxylate To a solution of tert-butyl (1R,5S,6r)-6-{[2-(5-methoxy-2-pyridinyl)hydrazino]carbonyl}-3-azabicyclo[3.1.0]hexane-3-carboxylate (380 mg, 1.09 mmol) in MeCN (20 mL) was added Burgess reagent (649.78 mg, 2.73 mmol). The mixture was stirred at 95° C. under N$_2$ for 16 hours. The reaction mixture was diluted with H$_2$O (20 mL) and extracted with EtOAc (30 mL×3). The combined organic layers were dried over Na$_2$SO$_4$, filtered and concentrated under reduced pressure to give a residue. The residue was purified by Combi Flash with silica gel (EtOAc/PE=1/1) to give the title compound (120 mg, 0.3133 mmol, 28.723% yield) as yellow solid.

LC-MS Method1: 331.0 [M+H$^+$].

3-[(1R,5S,6r)-3-azabicyclo[3.1.0]hex-6-yl]-6-methoxy[1,2,4]triazolo[4,3-a]pyridine TFA Salt To a solution of tert-butyl (1R,5S,6r)-6-(6-methoxy[1,2,4]triazolo[4,3-a]pyridin-3-yl)-3-azabicyclo[3.1.0]hexane-3-carboxylate (100 mg, 0.30 mmol) in DCM (3 mL) was added TFA (0.13 mL, 1.82 mmol) at 20° C. The mixture was stirred at 20° C. for 16 hours. The reaction mixture was concentrated to give the title compound (100 mg, 0.4343 mmol, 143.48% yield) as yellow oil.

LC-MS Method1: 230.95 [M+H$^+$].

(5-isopropyl-1H-pyrazol-3-yl)[(1R,5S,6r)-6-(6-methoxy[1,2,4]triazolo[4,3-a]pyridin-3-yl)-3-azabicyclo[3.1.0]hex-3-yl]methanone To a mixture of 5-isopropyl-1H-pyrazole-3-carboxylic acid (65 mg, 0.42 mmol) in DCM (3 mL) were added HATU (241.77 mg, 0.6300 mmol) and Et$_3$N (0.14 mL, 0.8400 mmol), and the mixture was stirred at 20° C. for 10 min under N$_2$. Then, 3-[(1R,5S,6r)-3-azabicyclo[3.1.0]hex-6-yl]-6-methoxy[1,2,4]triazolo[4,3-a]pyridine TFA salt (97.08 mg, 0.4200 mmol) in DCM (2 mL) was added. The resulting mixture was stirred at 20° C. for 16 hr to give brown mixture. The reaction was diluted with H$_2$O (20 mL) and extracted with DCM (20 mL). The combined organic layers were separated, then dried over Na$_2$SO$_4$ and concentrated in vacuum to give brown oil. The brown oil was purified by prep-HPLC (FA) and the afforded flows were lyophilized to afford the title compound (40.47 mg, 0.1054 mmol, 24.997% yield) as pale yellow solid.

LC-MS Method1: 367.0 [M+H$^+$].

$^1$H NMR (400 MHz, CHLOROFORM-d) δ=8.11 (s, 1H), 7.65 (d, J=10.0 Hz, 1H), 7.39 (s, 1H), 7.06 (dd, J=2.0, 10.0 Hz, 1H), 6.57 (s, 1H), 4.55 (d, J=11.5 Hz, 1H), 4.44 (d, J=12.5 Hz, 1H), 4.10 (dd, J=3.8, 11.8 Hz, 1H), 3.89 (s, 3H), 3.84-3.73 (m, 1H), 3.07 (td, J=7.2, 13.8 Hz, 1H), 2.82-2.74 (m, 1H), 2.31-2.29 (m, 1H), 1.89 (br s, 1H), 1.33 (d, J=6.8 Hz, 6H)

Example 132 (5-isopropyl-1H-pyrazol-3-yl)[(1R,5S,6r)-6-([1,2,3]triazolo[1,5-a]pyridin-3-yl)-3-azabicyclo[3.1.0]hex-3-yl]methanone

(5-isopropyl-1H-pyrazol-3-yl)[(1R,5S,6r)-6-([1,2,3]triazolo[1,5-a]pyridin-3-yl)-3-azabicyclo[3.1.0]hex-3-yl]methanone To a solution of 5-isopropyl-1H-pyrazole-3-carboxylic acid (25.64 mg, 0.1700 mmol) in DMF (1.2489 mL) were added HATU (47.82 mg, 0.2500 mmol) and DIPEA (64.5 mg, 0.50 mmol). The reaction mixture was stirred at 15° C. for 30 min. Then 3-[(1R,5S,6r)-3-azabicyclo[3.1.0]hex-6-yl]-1[1,2,3]triazolo[1,5-a]pyridine TFA salt (33.3 mg, 0.1700 mmol) was added. The reaction mixture was stirred at 15° C. for 0.5 hr to give a yellow mixture. LCMS showed the desired MS. The reaction mixture was purified by prep-HPLC (NH$_3$) to give the title compound (18.6 mg, 0.0553 mmol, 33.249% yield) as white powder.

LC-MS Method1: 336.9 [M+H$^+$]

$^1$H NMR (400 MHz, CHLOROFORM-d) δ=8.64 (d, J=7.2 Hz, 1H), 7.67 (d, J=8.8 Hz, 1H), 7.19 (dd, J=6.8, 8.3 Hz, 1H), 6.94 (dt, J=1.0, 6.9 Hz, 1H), 6.52 (s, 1H), 4.42 (br d, J=11.3 Hz, 1H), 4.35 (d, J=12.8 Hz, 1H), 4.05 (dd, J=4.4, 11.1 Hz, 1H), 3.77 (dd, J=4.4, 12.6 Hz, 1H), 3.09-2.98 (m, 1H), 2.49 (td, J=3.8, 7.4 Hz, 1H), 2.30 (td, J=3.8, 7.4 Hz, 1H), 1.96 (t, J=3.4 Hz, 1H), 1.31 (d, J=6.8 Hz, 6H).

Example 133 (5-isopropyl-1H-pyrazol-3-yl)[(1R,5S,6r)-6-(5-methyl[1,2,3]triazolo[1,5-a]pyridin-3-yl)-3-azabicyclo[3.1.0]hex-3-yl]methanone bromo(4-methyl-2-pyridinyl)magnesium

To a solution of 2-bromo-4-methylpyridine (0.67 mL, 6.33 mmol) in THF (10 mL) was added chloro(isopropyl)magnesium (3.2 mL, 6.33 mmol) at 15° C. The reaction mixture was stirred at 0° C. for 4 hr to give the title compound as a mixture. The reaction mixture was used for the next step without further purification.

tert-butyl (1R,5S,6r)-6-[hydroxy(4-methyl-2-pyridinyl)methyl]-3-azabicyclo[3.1.0]hexane-3-carboxylate To a solution of tert-butyl (1R,5S,6r)-6-formyl-3-azabicyclo[3.1.0]hexane-3-carboxylate (300 mg, 1.42 mmol) in THF (3 mL) was added bromo(4-methyl-2-pyridinyl)magnesium (418.2 mg, 2.13 mmol) at 0° C. The reaction mixture was stirred at 0° C. for 2 hr to give a light yellow mixture. TLC (EA) showed a new spot. The reaction mixture was quenched with H$_2$O (30 mL) and extracted with EtAOc (30 mL×2). The organic layer was washed with brine (30 mL×2), dried over anhydrous Na$_2$SO$_4$, filtered and concentrated under reduced pressure to give a residue. The residue was purified by silica gel column (PE/EA=1:0 to 1:2) to give the title compound (400 mg, 1.3141 mmol, 92.542% yield) as light yellow gum.

$^1$H NMR (400 MHz, DMSO-d$_6$) δ=8.31 (d, J=5.2 Hz, 1H), 7.30 (s, 1H), 7.08 (d, J=5.2 Hz, 1H), 5.36 (d, J=4.8 Hz, 1H), 4.50-4.40 (m, 1H), 3.45-3.35 (m, 4H), 2.32 (s, 3H), 1.65-1.50 (m, 2H), 1.34 (s, 9H), 0.85-0.80 (m, 1H).

tert-butyl (1R,5S,6r)-6-[(4-methyl-2-pyridinyl)carbonyl]-3-azabicyclo[3.1.0]hexane-3-carboxylate To a solution of tert-butyl (1R,5S,6r)-6-[hydroxy(4-methyl-2-pyridinyl)methyl]-3-azabicyclo[3.1.0]hexane-3-carboxylate (300 mg, 0.9900 mmol) in DCM (6 mL) was added DMP (418.04 mg, 0.9900 mmol) at 15° C. The reaction mixture was stirred at 15° C. for 20 min to give a white mixture. TLC (PE/EA=1:1) showed a new spot. The combined reaction mixture was quenched with NaHCO$_3$ (30 mL) and extracted with EtOAc (30 mL×2). The organic layer was washed with brine (30 mL×2), dried over anhydrous Na$_2$SO$_4$, filtered and concentrated under reduced pressure to give a crude product as light yellow solid. The crude product was purified by silica column (PE/EA=1:1) to give the title compound (300 mg, 0.9922 mmol, 100.66% yield) as white solid.

$^1$H NMR (400 MHz, DMSO-d$_6$) δ=8.60 (d, J=4.8 Hz, 1H), 7.76 (s, 1H), 7.51 (d, J=4.8 Hz, 1H), 4.50-4.40 (m, 1H), 3.57 (d, J=11.2 Hz, 2H), 3.45-3.35 (m, 2H), 3.25-3.20 (m, 1H), 2.40 (s, 3H), 2.20 (brs, 2H), 1.40 (s, 9H).

tert-butyl (1R,5S,6r)-6-(5-methyl[1,2,3]triazolo[1,5-a]pyridin-3-yl)-3-azabicyclo[3.1.0]hexane-3-carboxylate To a solution of tert-butyl (1R,5S,6r)-6-[(4-methyl-2-pyridinyl)carbonyl]-3-azabicyclo[3.1.0]hexane-3-carboxylate (150 mg, 0.5000 mmol) in EtOH (3 mL) was added hydrazine hydrate (37.25 mg, 0.7400 mmol). The reaction mixture was stirred at 60° C. for 6 hr to give a colorless mixture. Then copper acetate (4.94 mg, 0.0200 mmol) and ethyl acetate (14.304 mL) were added. Then the reaction mixture was stirred at 20° C. for 1 hr to give a colorless mixture. The reaction mixture was concentrated to give a residue. The residue was purified by prep-TLC (PE/EA=1:1) to give the title compound (50 mg, 0.1590 mmol, 32.06% yield) as colorless oil.

$^1$H NMR (400 MHz, CHLOROFORM-d) δ=8.51 (d, J=7.2 Hz, 1H), 7.43 (s, 1H), 6.75 (dd, J=7.2, 1.6 Hz, 1H), 3.84 (d, J=11.2 Hz, 1H), 3.75 (d, J=11.2 Hz, 1H), 3.45-3.35 (m, 2H), 2.43 (s, 3H), 2.35-2.35 (m, 1H), 2.20-2.10 (m, 1H), 1.95-1.90 (m, 1H), 1.48 (s, 9H).

3-[(1R,5S,6r)-3-azabicyclo[3.1.0]hex-6-yl]-5-methyl[1,2,3]triazolo[1,5-a]pyridine TFA Salt To a solution of tert-butyl (1R,5S,6r)-6-(5-methyl[1,2,3]triazolo[1,5-a]pyridin-3-yl)-3-azabicyclo[3.1.0]hexane-3-carboxylate in DCM (5 mL) was added TFA (0.01 mL, 0.1600 mmol). The reaction mixture was stirred at 20° C. for 16 hr to give a colorless mixture. LCMS showed the desired MS. The solvent was removed from the reaction mixture to give the title compound. The product was used for the next step directly.

LC-MS Method1 0.398 min, MS (m/z) 214.9 (M+H$^+$).

(5-isopropyl-1H-pyrazol-3-yl)[(1R,5S,6r)-6-(5-methyl[1,2,3]triazolo[1,5-a]pyridin-3-yl)-3-azabicyclo[3.1.0]hex-3-yl]methanone To a solution of 5-isopropyl-1H-pyrazole-3-carboxylic acid (24.46 mg, 0.1600 mmol) in DMF (1.1917 mL) was added HATU (45.63 mg, 0.2400 mmol). The reaction mixture was stirred at 15° C. for 30 min. Then 3-[(1R,5S,6r)-3-azabicyclo[3.1.0]hex-6-yl]-5-methyl[1,2,3]triazolo[1,5-a]pyridine TFA salt (34 mg, 0.1600 mmol) and DIPEA (61.52 mg, 0.476 mmol) were added. The reaction mixture was stirred at 15° C. for 0.5 hr to give a yellow mixture. LCMS showed the desired MS. The reaction mixture was purified by prep-HPLC (NH$_3$) to give the title compound (22.4 mg, 0.0639 mmol, 40.285% yield) as white powder.

LC-MS Method1: 350.9 [M+H$^+$]

$^1$H NMR (400 MHz, CHLOROFORM-d) δ=8.52 (d, J=7.2 Hz, 1H), 7.41 (s, 1H), 6.76 (dd, J=1.6, 7.2 Hz, 1H), 6.51 (s, 1H), 4.40 (br d, J=10.8 Hz, 1H), 4.34 (d, J=12.4 Hz, 1H), 4.03 (dd, J=4.4, 11.2 Hz, 1H), 3.76 (dd, J=4.4, 12.4 Hz, 1H), 3.04 (spt, J=6.9 Hz, 1H), 2.47-2.44 (m, 1H), 2.42 (s, 3H), 2.26 (td, J=3.8, 7.4 Hz, 1H), 1.91 (t, J=3.4 Hz, 1H), 1.31 (d, J=7.2 Hz, 6H)

Example 134 (5-isopropyl-1H-pyrazol-3-yl)[(1R,5S,6r)-6-(1H-tetrazol-5-yl)-3-azabicyclo[3.1.0]hex-3-yl]methanone (5-isopropyl-1H-pyrazol-3-yl)[(1R,5S,6r)-6-(1H-tetrazol-5-yl)-3-azabicyclo[3.1.0]hex-3-yl]methanone To a solution of 5-isopropyl-1H-pyrazole-3-carboxylic acid (90 mg, 0.5800 mmol) in DMF (6 mL) were added N-ethyl-N-isopropylpropan-2-amine (0.4 mL, 2.34 mmol) and HATU (266.2 mg, 0.7000 mmol). After stirred for 30 min, (1R,5S,6r)-6-(1H-tetrazol-5-yl)-3-azabicyclo[3.1.0]hexane TFA salt (79.42 mg, 0.5300 mmol) was added and the reaction mixture was stirred at 15° C. for 16 hr to give a red solution. H$_2$O (30 mL) was added and it was extracted with EtOAc (30 mL×2). The combined organic layer was dried over Na$_2$SO$_4$ and concentrated in vacuum to give yellow oil. The crude was purified by prep-HPLC (FA) to give the title compound (13.3 mg, 0.0463 mmol, 7.9295% yield) as white solid.

LC-MS Method1: 288.0 [M+H$^+$]

$^1$H NMR (400 MHz, DMSO-d$_6$) δ 6.41 (s, 1H), 4.42 (br d, J=12.05 Hz, 1H), 4.05 (d, J=12.30 Hz, 1H), 3.90 (dd, J=3.89, 11.92 Hz, 1H), 3.57 (br dd, J=4.02, 12.30 Hz, 1H), 2.96 (td, J=6.96, 13.68 Hz, 1H), 2.26-2.35 (m, 1H), 2.21 (m, 1H), 1.97 (t, J=3.26 Hz, 1H), 1.22 (d, J=7.03 Hz, 7H)

Example 135 (5-isopropyl-1H-pyrazol-3-yl)[(1R,5S,6r)-6-(1-phenyl-1H-tetrazol-5-yl)-3-azabicyclo[3.1.0]hex-3-yl]methanone tert-butyl (1R,5S,6r)-6-(phenylcarbamoyl)-3-azabicyclo[3.1.0]hexane-3-carboxylate A solution of (1R,5S,6r)-3-{[(tert-butyl)oxy]carbonyl}-3-azabicyclo[3.1.0]hexane-6-carboxylic acid (500 mg, 2.2 mmol), HOBt (356.74 mg, 2.64 mmol), aniline (0.45 mL, 2.64 mmol) and EDCI (506.12 mg, 2.64 mmol) in DCM (5 mL) was stirred at 10° C. for 30 min. Then it was cooled to 0° C. and aniline (0.3 mL, 3.3 mmol) was added drop-wise to be stirred for 16 hr to give a white suspension. TLC (DCM/MeOH=10/1 Rf=0.1) showed a new spot was detected. H₂O (10 mL) was added and it was extracted with EtOAc (10 mL×2). The combined organic layer was dried over Na₂SO₄ and concentrated in vacuum to give a white solid. The crude was purified by silica gel chromatography (PE/EA=10/1 to 3/1) to give the title compound (590 mg, 1.9513 mmol, 88.688% yield) as white solid.

LC-MS Method1 0.858 min, MS (m/z) 303.0 (M+H⁺).

(1R,5S,6r)-N-phenyl-3-azabicyclo[3.1.0]hexane-6-carboxamide hydrochloride

A solution of tert-butyl (1R,5S,6r)-6-(phenylcarbamoyl)-3-azabicyclo[3.1.0]hexane-3-carboxylate (640 mg, 2.12 mmol) in HCl/dionane (6 mL, 2.12 mmol) was stirred at 10° C. for 3 hr to give a yellow solution. The reaction mixture was evaporated in vacuum to give the title compound (500 mg, 2.0946 mmol, 98.96% yield) as white solid.

LC-MS Method1 0.285 min, MS (m/z) 203.0 (M+H⁺).

(1R,5S,6r)-3-benzyl-N-phenyl-3-azabicyclo[3.1.0]hexane-6-carboxamide

To a solution of (1R,5S,6r)-N-phenyl-3-azabicyclo[3.1.0]hexane-6-carboxamide hydrochloride (500 mg, 2.09 mmol) and benzaldehyde (0.25 mL, 2.51 mmol) in DCM (15 mL) and MeOH (5 mL) was added triethylamine (0.29 mL, 2.09 mmol). After stirring for 5 min, sodium triacetoxyhydroborate (887.86 mg, 4.19 mmol) was added. The reaction mixture was stirred at 10° C. for 16 hr to give a yellow solution. TLC (DCM/MeOH=10/1 Rf=0.6) showed a new spot was detected. H₂O (30 mL) was added and it was extracted with EtOAc (30 mL×2). The combined organic layer was dried over Na₂SO₄ and concentrated in vacuo to give a yellow oil. The crude was purified by silica gel chromatography (DCM/MeOH=10/1 to 3/1) to give the title compound (600 mg, 2.0522 mmol, 97.976% yield) as white solid.

LC-MS Method1 0.692 min, MS (m/z) 293.2 (M+H⁺).

(1R,5S,6r)-3-benzyl-6-(1-phenyl-1H-tetrazol-5-yl)-3-azabicyclo[3.1.0]hexane

To a solution of (1R,5S,6r)-3-benzyl-N-phenyl-3-azabicyclo[3.1.0]hexane-6-carboxamide (330 mg, 1.13 mmol) in DCM (10 mL) was added Tf₂O (0.39 mL, 2.26 mmol). After stirred for 5 min, TMSN₃ (0.59 mL, 4.51 mmol) was added and the reaction was stirred for 16 hr to give a yellow solution. H₂O (30 mL) was added and it was extracted with EtOAc (30 mL×2). The combined organic layer was dried over Na₂SO₄ and concentrated in vacuum to give the title compound (298 mg, 0.9389 mmol, 83.184% yield) as yellow solid.

LC-MS Method1 0.712 min, MS (m/z) 318.1 (M+H⁺).

(1R,5S,6r)-6-(1-phenyl-1H-tetrazol-5-yl)-3-azabicyclo[3.1.0]hexane

To a solution of (1R,5S,6r)-3-benzyl-6-(1-phenyl-1H-tetrazol-5-yl)-3-azabicyclo[3.1.0]hexane (500 mg, 1.58 mmol) in MeOH (15 mL) was added Pd/C (50.0 mg). It was stirred at 10° C. for under H₂ atmosphere for 3 hr to give a yellow solid. It was filtered through a pad of celite and the filtrate was concentrated in vacuum to give the title compound (400 mg, 1.76 mmol, 111.72% yield) as white solid.

LC-MS Method1 0.538 min, MS (m/z) 228.0 (M+H⁺).

(5-isopropyl-1H-pyrazol-3-yl)[(1R,5S,6r)-6-(1-phenyl-1H-tetrazol-5-yl)-3-azabicyclo[3.1.0]hex-3-yl]methanone A solution of 5-isopropyl-1H-pyrazole-3-carboxylic acid (50 mg, 0.3200 mmol), N-ethyl-N-isopropylpropan-2-amine (0.17 mL, 0.9700 mmol) and HATU (74.61 mg, 0.3900 mmol) in DMF (2 mL) was stirred at 10° C. for 30 min. Then (1R,5S,6r)-6-(1-phenyl-1H-tetrazol-5-yl)-3-azabicyclo[3.1.0]hexane (66.34 mg, 0.2900 mmol) was added and the reaction mixture was stirred for 16 hr to give a yellow solution. H₂O (10 mL) was added and it was extracted with EtOAc (10 mL×2). The combined organic layer was dried over Na₂SO₄ and concentrated in vacuum to give a yellow oil. The crude was purified by silica gel chromatography (DCM/EA=3/1 to 1/2) to give the title compound (21.25 mg, 0.0584 mmol, 3.5987% yield) as a white solid.

LC-MS Method1: 364.1 [M+H⁺]

¹H NMR (400 MHz, DMSO-d₆) δ 12.94 (br s, 1H), 7.64-7.72 (m, 5H), 6.35 (s, 1H), 4.38 (br d, J=12.30 Hz, 1H), 3.90-3.98 (m, 2H), 3.58 (br dd, J=4.27, 12.55 Hz, 1H), 2.91-2.97 (m, 1H), 2.35 (br dd, J=3.76, 7.78 Hz, 1H), 1.79 (br s, 1H), 1.20 (d, J=6.78 Hz, 6H)

Example 136 (1R,5S,6r)-N-(propan-2-yl)-3-[5-(propan-2-yl)-1H-pyrazole-3-carbonyl]-3-azabicyclo[3.1.0]hexane-6-carboxamide

(1R,5S,6r)-3-[(5-isopropyl-1H-pyrazol-3-yl)carbonyl]-3-azabicyclo[3.1.0]hexane-6-carboxylic acid To a solution of ethyl (1R,5S,6r)-3-[(5-isopropyl-1H-pyrazol-3-yl)carbonyl]-3-azabicyclo[3.1.0]hexane-6-carboxylate (400 mg, 1.37 mmol) in THF (5 mL) and H₂O (1 mL, 1.37 mmol) was added LiOH·H₂O (172.82 mg, 4.12 mmol). The mixture was stirred at 25° C. for 3 h to give brown suspension. The reaction was poured into H₂O (20 mL) and acidified with 1 N HCl to pH=3 to 4 and extracted with EtOAc (100 mL×3). The combined organic layers was dried over Na₂SO₄, filtered and concentrated under reduced pressure to give as the title compound (310 mg, 1.1774 mmol, 85.76% yield) white solid.

(1R,5S,6r)-N-(propan-2-yl)-3-[5-(propan-2-yl)-1H-pyrazole-3-carbonyl]-3-azabicyclo[3.1.0]hexane-6-carboxamide To a mixture of (1R,5S,6r)-3-[(5-isopropyl-1H-pyrazol-3-yl)carbonyl]-3-azabicyclo[3.1.0]hexane-6-carboxylic acid (50 mg, 0.19 mmol) in DMF (1.5 mL) were added isopropyl amine (16.55 mg, 0.1900 mmol), HATU (86.6 mg, 0.2300 mmol) and DIPEA (0.06 mL, 0.3800 mmol). The mixture was stirred at 100° C. for 16 h to give brown mixture. LCMS showed the starting material was consumed completely. The reaction mixture was filtered and the filtrate was purified by prep-HPLC (FA). The afforded flows were combined, concentrated to remove most of CH₃CN and lyophilized to afford the title compound (6.83 mg, 0.0205 mmol, 10.819% yield) as white powder.

¹H NMR (400 MHz, CHLOROFORM-d) δ ppm 6.45 (s, 1H), 4.09-4.19 (m, 2H), 3.95 (br dd, J=11.1, 4.3 Hz, 1H), 3.69 (br dd, J=12.5, 4.3 Hz, 2H), 3.10 (dt, J=13.9, 7.1 Hz, 1H), 3.03 (s, 3H), 2.23-2.31 (m, 1H), 2.09-2.17 (m, 1H), 1.60 (br s, 1H), 1.40 (s, 9H), 1.33 (d, J=6.9 Hz, 6H)

Example 137 (1R,5S,6r)-N-tert-butyl-N-methyl-3-[5-(propan-2-yl)-1H-pyrazole-3-carbonyl]-3-azabicyclo[3.1.0]hexane-6-carboxamide (1R,5S,6r)-N-tert-butyl-N-methyl-3-[5-(propan-2-yl)-1H-pyrazole-3-carbonyl]-3-azabicyclo[3.1.0]hexane-6-carboxamide To a mixture of (1R,5S,6r)-3-[(5-isopropyl-1H-pyrazol-3-yl)carbonyl]-3-azabicyclo[3.1.0]hexane-6-carboxylic acid (100 mg, 0.3800 mmol) in DMF (2 mL) were added tert-butyl methylamine (22.45 mg, 0.3800 mmol), HATU (173.19 mg, 0.4600 mmol) and DIPEA (0.13 mL, 0.7600 mmol). The mixture was stirred at 30° C. for 16 h to give yellow suspension. LCMS showed the starting material was consumed completely. The suspension was filtered and the filter cake was washed with EtOAc (3 mL). The filter cake was dried in vacuo to afford the title compound (72.08 mg, 0.2368 mmol, 62.347% yield) as white solid.

$^1$H NMR (400 MHz, DMSO-d6) δ ppm 13.07 (s, 1H), 12.94 (s, 1H), 7.87 (d, J=7.5 Hz, 1H), 6.45-6.52 (m, 1H), 6.50 (d, J=1.6 Hz, 1H), 6.35 (d, J=1.9 Hz, 1H), 4.29 (d, J=12.0 Hz, 1H), 3.86-3.97 (m, 1H), 3.72-3.84 (m, 2H), 3.39-3.49 (m, 1H), 2.89-3.05 (m, 1H), 1.90-1.96 (m, 1H), 1.85 (dt, J=7.4, 3.6 Hz, 1H), 1.30 (t, J=3.1 Hz, 1H), 1.18-1.23 (m, 6H), 1.02 (dd, J=6.5, 4.6 Hz, 6H)

Example 138 (1R,5S,6r)-N-methyl-N-(1-methylcyclopropyl)-3-[5-(propan-2-yl)-1H-pyrazole-3-carbonyl]-3-azabicyclo[3.1.0]hexane-6-carboxamide (1R,5S,6r)-N-methyl-N-(1-methylcyclopropyl)-3-[5-(propan-2-yl)-1H-pyrazole-3-carbonyl]-3-azabicyclo[3.1.0]hexane-6-carboxamide To a solution of (1R,5S,6r)-N-methyl-N-(1-methylcyclopropyl)-3-azabicyclo[3.1.0]hexane-6-carboxamide hydrochloride (80 mg, 0.4100 mmol) in DMF (3.2 mL) were added 5-isopropyl-1H-pyrazole-3-carboxylic acid (63.49 mg, 0.4100 mmol), HATU (203.43 mg, 0.5400 mmol) and Et$_3$N (0.2 mL, 1.24 mmol). The mixture was stirred at 20° C. for 16 hr. TLC (PE/EA=0/1) showed a new spot (rf=0.5) and the reaction was completed. The mixture was diluted with H$_2$O (10 mL) and extracted with EA (10 mL×2). The combined organic layers were washed with H$_2$O (5 mL) and NH$_4$Cl (5 mL), dried over Na$_2$SO$_4$ and concentrated in vacuum to give crude oil. The crude oil was purified by prep-TLC (PE/EA=0/1) to give crude product. The crude product was purified by prep-HPLC (FA) to give the title compound (20.8 mg, 0.0630 mmol, 15.287% yield) as white powder.

LC-MS Method1: 341.0 [M+H$^+$]

$^1$H NMR (400 MHz, CHLOROFORM-d) δ=6.44 (br s, 1H), 4.13 (br s, 1H), 4.04 (d, J=12.8 Hz, 1H), 3.94 (dd, J=4.0, 11.3 Hz, 1H), 3.68 (dd, J=4.1, 12.8 Hz, 1H), 3.01-2.92 (m, 1H), 2.84 (s, 3H), 2.03-1.87 (m, 1H), 1.28 (s, 3H), 1.24 (d, J=6.9 Hz, 6H), 1.21-1.14 (m, 1H), 0.98-0.66 (m, 3H), 0.58 (br s, 1H)

Example 139 [(1R,5S,6r)-6-(2,2-dimethyl-2,3-dihydro-1H-indole-1-carbonyl)-3-azabicyclo[3.1.0]hexan-3-yl][5-(propan-2-yl)-1H-pyrazol-3-yl]methanone

[(1R,5S,6r)-6-(2,2-dimethyl-2,3-dihydro-1H-indole-1-carbonyl)-3-azabicyclo[3.1.0]hexan-3-yl][5-(propan-2-yl)-1H-pyrazol-3-yl]methanone To a solution of 5-isopropyl-1H-pyrazole-3-carboxylic acid and EDCI (55.95 mg, 0.2900 mmol) in Pyridine (3 mL) was added (1R,5S,6r)-3-azabicyclo[3.1.0]hex-6-yl(2,2-dimethyl-2,3,3a,7a-tetrahydro-1H-indol-1-yl)methanone TFA salt (49.88 mg, 0.1900 mmol), and the reaction mixture was stirred at 20° C. under N$_2$ for 16 hours. LCMS showed the desired peak was found. The reaction was diluted with H$_2$O (30 mL) and extracted with EtOAc (20 mL×3). The combined organic layers were separated, then dried over Na$_2$SO$_4$ and concentrated in vacuum to give brown oil. The brown oil was purified by prep-HPLC (NH$_3$) and the afforded flows were combined, concentrated to remove most of CH$_3$CN and lyophilized to afford the title compound (36.39 mg, 0.0927 mmol, 47.647% yield) as white solid.

LC-MS Method1: 393.1 [M+H$^+$].

$^1$H NMR (400 MHz, CHLOROFORM-d) δ=7.23-6.89 (m, 4H), 6.50 (s, 1H), 4.34 (br d, J=11.5 Hz, 1H), 4.29-4.20 (m, 1H), 4.05 (dd, J=4.3, 11.6 Hz, 1H), 3.81 (dd, J=4.4, 12.9 Hz, 1H), 3.13-2.87 (m, 3H), 2.54 (td, J=3.7, 7.3 Hz, 1H), 2.32 (td, J=3.7, 7.2 Hz, 1H), 1.93 (br s, 1H), 1.61 (s, 3H), 1.53 (br s, 3H), 1.30 (d, J=7.0 Hz, 6H)

Example 140 (5-isopropyl-1H-pyrazol-3-yl){(1R,5S,6r)-6-[(4-methyl-2-thienyl)carbonyl]-3-azabicyclo[3.1.0]hex-3-yl}methanone (5-isopropyl-1H-pyrazol-3-yl){(1R,5S,6r)-6-[(4-methyl-2-thienyl)carbonyl]-3-azabicyclo[3.1.0]hex-3-yl}methanone To a solution of (1R,5S,6r)-3-azabicyclo[3.1.0]hex-6-yl (4-methyl-2-thienyl)methanone TFA salt (60 mg, 0.2900 mmol) in DMF (2 mL) were added HATU (165.98 mg, 0.4300 mmol) and Et$_3$N (0.07 mL, 0.5800 mmol), and the mixture was stirred at 20° C. for 10 min under N$_2$. Then, 5-isopropyl-1H-pyrazole-3-carboxylic acid (44.62 mg, 0.2900 mmol) in DMF (1 mL) was added, and the resulting mixture was stirred at 20° C. for 16 hours to give a yellow mixture. The reaction mixture was poured into H$_2$O (5 mL) and extracted with EA (5 mL×3). The combined organic layers were washed with brine (10 mL), dried over Na$_2$SO$_4$, filtered and concentrated under reduced pressure. The crude product was purified by Prep-HPLC (NH$_3$) and lyophilized to give the title compound (90 mg, 0.2621 mmol, 90.535% yield) as a white solid.

LC-MS Method1: 344.2 [M+H$^+$]

$^1$H NMR (400 MHz, CHLOROFORM-d) δ=10.33 (br s, 1H), 7.60 (d, J=0.8 Hz, 1H), 7.26 (s, 1H), 6.53 (s, 1H), 4.37 (br d, J=11.5 Hz, 1H), 4.26 (d, J=13.1 Hz, 1H), 4.02 (dd, J=4.1, 11.7 Hz, 1H), 3.74 (dd, J=4.1, 12.9 Hz, 1H), 3.04 (td, J=6.8, 13.7 Hz, 1H), 2.49 (td, J=3.5, 7.2 Hz, 1H), 2.38 (td, J=3.6, 7.3 Hz, 1H), 2.34-2.31 (m, 1H), 2.30 (s, 3H), 1.32 (d, J=6.8 Hz, 6H)

Example 141 [(1R,5S,6r)-6-(5,5-dimethyl-4,5-dihydro-1,2-oxazol-3-yl)-6-methyl-3-azabicyclo[3.1.0]hex-3-yl](5-isopropyl-1H-pyrazol-3-yl)methanone

[(1R,5S,6r)-6-(5,5-dimethyl-4,5-dihydro-1,2-oxazol-3-yl)-6-methyl-3-azabicyclo[3.1.0]hex-3-yl](5-isopropyl-1H-pyrazol-3-yl)methanone To a solution of 5-isopropyl-1H-pyrazole-3-carboxylic acid (38.5 mg, 0.2500 mmol) in DMF (1.5 mL) were added HATU (112.84 mg, 0.3000 mmol), DIPEA (0.13 mL, 0.7900 mmol) and (1R,5S,6r)-6-(5,5-dimethyl-4,5-dihydro-1,2-oxazol-3-yl)-6-methyl-3-azabicyclo[3.1.0]hexane TFA salt (70 mg, 0.2300 mmol). The mixture was stirred at 20° C. for 12 h to give brown solution. The mixture was poured into H₂O (15 mL) and extracted with EtOAc (15 mL×5). The combined organic layer was washed with brine (50 mL), dried over Na₂SO₄ and concentrated to dryness. The residue was purified by prep-TLC (PE:EtOAc=1:1) to give white solid. The residue was purified by prep-HPLC (NH₃). The afforded flows were combined, concentrated to remove most of CH₃CN and lyophilized to give the title compound (3.63 mg, 0.0110 mmol, 4.8386% yield) as a white solid.

LC-MS Method1: 331.0 [M+H⁺]

¹H NMR (400 MHz, CHLOROFORM-d) δ ppm 6.50 (1H, s), 4.09-4.18 (1H, m), 4.01 (1H, br d, J=11.54 Hz), 3.81-3.95 (2H, m), 3.03 (1H, dt, J=13.93, 7.09 Hz), 2.68 (2H, s), 2.22 (1H, dd, J=8.16, 5.40 Hz), 2.06 (1H, dd, J=7.91, 4.14 Hz), 1.38 (6H, d, J=2.26 Hz), 1.31 (6H, d, J=7.03 Hz), 1.17 (3H, s)

Example 142 [5-(1-cyclopropylethyl)-1H-pyrazol-3-yl][(1R,5S,6r)-6-(5,5-dimethyl-4,5-dihydro-1,2-oxazol-3-yl)-6-methyl-3-azabicyclo[3.1.0]hex-3-yl]methanone

[5-(1-cyclopropylethyl)-1H-pyrazol-3-yl][(1R,5S,6r)-6-(5,5-dimethyl-4,5-dihydro-1,2-oxazol-3-yl)-6-methyl-3-azabicyclo[3.1.0]hex-3-yl]methanone To a stirred solution of (1R,5S,6r)-6-(5,5-dimethyl-4,5-dihydro-1,2-oxazol-3-yl)-6-methyl-3-azabicyclo[3.1.0]hexane TFA salt (40 mg, 0.2200 mmol) and HATU (110.32 mg, 0.2900 mmol) in DMF (1 mL) was added DIPEA (0.23 mL, 1.33 mmol). After stirred for 30 min, 5-(1-cyclopropylethyl)-1H-pyrazole-3-carboxylic acid (68.44 mg, 0.2200 mmol) was added. The reaction mixture was stirred at 20° C. for 16 h to give a yellow solution. LCMS showed a new peak gives the desired ms. H₂O (30 mL) was added and it was extracted with EtOAc (30 mL×2). The combined organic layer dried over Na₂SO₄ and concentrated in vacuum to give a yellow oil. The crude was purified by prep-HPLC (NH₃). The afforded flows were concentrated in vacuum to remove most of CH₃CN and lyophilized to give the title compound (16.69 mg, 0.0468 mmol, 21.093% yield) as white solid.

LC-MS Method1: 357.2 [M+H⁺]

¹H NMR (400 MHz, CHLOROFORM-d) δ 6.58 (s, 1H), 4.11-4.17 (m, 1H), 4.00-4.08 (m, 1H), 3.82-3.92 (m, 2H), 2.67 (s, 2H), 2.21 (dd, J=5.40, 7.91 Hz, 1H), 2.13 (dd, J=7.03, 9.03 Hz, 1H), 2.04 (dd, J=5.02, 7.03 Hz, 1H), 1.36-1.40 (m, 9H), 1.17 (d, J=0.75 Hz, 3H), 0.88-0.97 (m, 1H), 0.58 (br d, J=7.28 Hz, 2H), 0.20-0.31 (m, 2H)

Example 143 (5-isopropyl-1H-pyrazol-3-yl)[(1R,5S,6r)-6-methyl-6-(4-oxa-5-azaspiro[2.4]hept-5-en-6-yl)-3-azabicyclo[3.1.0]hex-3-yl]methanone (5-isopropyl-1H-pyrazol-3-yl)[(1R,5S,6r)-6-methyl-6-(4-oxa-5-azaspiro[2.4]hept-5-en-6-yl)-3-azabicyclo[3.1.0]hex-3-yl]methanone A 100 mL round-bottom flask was charged with 5-isopropyl-1H-pyrazole-3-carboxylic acid (50.34 mg, 0.3300 mmol), HATU (149.78 mg, 0.3900 mmol), N-ethyl-N-isopropylpropan-2-amine (0.17 mL, 0.9800 mmol) and DMF (1.6108 mL). After stirred for 30 min, 6-[(1R,5S,6r)-6-methyl-3-azabicyclo[3.1.0]hex-6-yl]-4-oxa-5-azaspiro[2.4]hept-5-ene TFA salt (100 mg, 0.3300 mmol) was added. The reaction mixture was stirred at 10° C. for 1 hr to give a yellow solution. The reaction mixture was diluted with H₂O (20 mL) and extracted with EtOAc (30 mL×2). The combined organic layer was dried over Na₂SO₄ and concentrated in vacuum to give a residue as yellow oil. The crude was purified by Prep-HPLC (NH₃). The afford flows was concentrated in vacuum to remove most of CH₃CN and lyophilized to give the title compound (48.63 mg, 0.1481 mmol, 45.353% yield) as white solid.

LC-MS Method1: 329.2 [M+H⁺]

¹H NMR (400 MHz, CHLOROFORM-d) δ=6.50 (s, 1H), 4.19-4.10 (m, 1H), 4.03 (br d, J=11.9 Hz, 1H), 3.94-3.84 (m, 2H), 3.06-2.98 (m, 3H), 2.26 (m, 1H), 2.16-2.07 (m, 1H), 1.30 (d, J=7.2 Hz, 6H), 1.20 (s, 3H), 1.15-1.10 (m, 2H), 0.74-0.69 (m, 2H)

Example 144 (5-cyclopropyl-1H-pyrazol-3-yl)[(1R,5S,6r)-6-methyl-6-(4-oxa-5-azaspiro[2.4]hept-5-en-6-yl)-3-azabicyclo[3.1.0]hex-3-yl]methanone (5-cyclopropyl-1H-pyrazol-3-yl)[(1R,5S,6r)-6-methyl-6-(4-oxa-5-azaspiro[2.4]hept-5-en-6-yl)-3-azabicyclo[3.1.0]hex-3-yl]methanone To a solution of 5-cyclopropyl-1H-pyrazole-3-carboxylic acid (21.86 mg, 0.1400 mmol) in Pyridine (1.5 mL) were added EDCI (62.59 mg, 0.3300 mmol) and 6-[(1R,5S,6r)-6-methyl-3-azabicyclo[3.1.0]hex-6-yl]-4-oxa-5-azaspiro[2.4]hept-5-ene TFA salt (40 mg, 0.1300 mmol). The mixture was stirred at 25° C. for 2 h to give a yellow solution. LCMS showed the desire MS as a major peak. The reaction mixture was concentrated directly. The residue was purified by prep-HPLC (NH₃) to give the title compound (11.2 mg, 0.0343 mmol, 26.275% yield) as yellow solid.

LC-MS Method1: 327.1 [M+H⁺]

¹H NMR (400 MHz, CHLOROFORM-d) δ ppm 6.35 (1H, s), 4.07-4.16 (1H, m), 3.95-4.02 (1H, m), 3.83-3.95 (2H, m), 3.01 (2H, s), 2.27 (1H, dd, J=8.16, 5.40 Hz), 2.12 (1H, dd, J=7.40, 4.64 Hz), 1.88-1.95 (1H, m), 1.18-1.22 (3H, m), 1.11-1.17 (2H, m), 0.95-1.02 (2H, m), 0.71-0.79 (4H, m)

Example 145 (1R,5S,6r)-N-tert-butyl-6-methyl-3-[5-(propan-2-yl)-1H-pyrazole-3-carbonyl]-3-azabicyclo[3.1.0]hexane-6-carboxamide (1R,5S,6r)-N-tert-butyl-6-methyl-3-[5-(propan-2-yl)-1H-pyrazole-3-carbonyl]-3-azabicyclo[3.1.0]hexane-6-carboxamide To a solution of 5-isopropyl-1H-pyrazole-3-carboxylic acid (15.71 mg, 0.10 mmol) in DMF (0.50 mL) were added HATU (50.64 mg, 0.13 mmol) and Et₃N (0.04 mL, 0.31 mmol). The mixture was stirred at 20 to 25° C. for 0.5 h. Then (1R,5S,6r)-6-methyl-N-(tert-butyl)-3-azabicyclo[3.1.0]hexane-6-carboxamide TFA salt (20 mg, 0.10 mmol) was added to the mixture. The resulting mixture was stirred at 20 to 25° C. for 2 h. LCMS showed the desired MS (as a major peak). The residue was purified by prep-HPLC (NH₃). The afforded flows were combined, concentrated to remove most of CH₃CN and lyophilized to afford the title compound (6.94 mg, 0.0209 mmol, 20.489% yield) as a white solid.

LC-MS Method1: 333.3 [M+H⁺]

¹H NMR (400 MHz, CHLOROFORM-d) δ=6.49 (s, 1H), 5.59 (s, 1H), 4.13 (dd, J=5.7, 11.9 Hz, 1H), 3.95-3.86 (m, 2H), 3.79-3.71 (m, 1H), 3.03 (td, J=6.9, 13.8 Hz, 1H), 2.33 (dd, J=5.4, 8.1 Hz, 1H), 2.18 (dd, J=5.4, 8.0 Hz, 1H), 1.36 (s, 9H), 1.31 (d, J=6.9 Hz, 6H), 1.14 (s, 3H)

Biological Example 1

Biochemical KDM5A Inhibition Assay

Using 384-well white Greiner784075 (Greiner), representative compounds were characterized for their inhibition of KDM5A using HTRF® technology (Cisbio Bioassays). Briefly, the test compounds, reference compounds, and DMSO control (typical compound concentration range 1 pM-10 µM, final assay concentration (FAC*) of DMSO 0.5%) were added to 384-well plate by the Echo® acoustic dispensing platform (Labcyte). Five (5) µl of KDM5A protein (produced by the method described in Nat Chem Biol 12, 531-538 (2016)). (5-20 nM FAC*) in assay buffer (50 mM MES, 50 mM NaCl, 1 mM TCEP, 0.01% v/v Tween 20, 0.03% BSA, pH 6.5) was added to wells and plates were incubated for 10-20 minutes at 25 degrees celsius. Then, 5 µl of alpha-ketoglutaric acid (100 µM FAC*), biotin-labelled H3K4-Me3 substrate (Anaspec Cat #AS-64357-1; 200 nM FAC*), Fe(II)SO$_4$ (100 µM FAC*) and ascorbic acid (2 mM FAC*) in assay buffer was added to wells and plates were incubated for 20 minutes at room temperature. The reaction was stopped with the addition of 10 µl of anti-H3K4-Me2-Eu(K) (Cisbio Bioassays Cat #61KA2KAH; 0.75 nM FAC)+Streptavidin XL665 (Cisbio Bioassays Cat #610SAXLB; 25 nM FAC) in HTRF detection buffer (Cisbio Bioassays Cat #62SDBRDF). The mixture was incubated for 30 minutes at room temperature before 340 nm excitation and measurement of dual emission at 620 nm and 665 nm.

*FAC: final assay concentration calculated based on 10 µl of the assay buffer
 **FAC: final assay concentration calculated based on 20 µl of the detection buffer The raw data (a 665 nm and a 620 nm reading from each well) for individual assay plates were analyzed. The ratio of emissions was calculated using the following calculation:

Ratio=(665 nm emission/620 nm emission)×10000.

Using DMSO control (maximum response or 0% inhibition) and 1 µM reference control compound (minimum response or 100% inhibition), percentage inhibition values for each well were calculated using the median values of the minimum and maximum control wells and the following calculation:

% Inhibition=(Well ratio−max control ratio)/(min control ratio−max control ratio)×100.

Compound IC$_{50}$ values were calculated from graphs of % inhibition plotted against compound concentration, using a four parameter curve fit.

[Results]

The present compounds exhibited a strong KDM5 inhibitory activity. IC$_{50}$ values (µM) of representative present compounds are shown in the table below. IC$_{50}$ values (µM) of comparative compound, (R)—N-(1-(3-isopropyl-1H-pyrazole-5-carbonyl)pyrrolidin-3-yl)cyclopropane carboxamide (the compound of Examples 29 described in PTL 1 (the pamphlet of International Publication No. WO2016057924)) was 0.02 µM.

| EXAMPLE No. | IC$_{50}$ value (µM) |
| --- | --- |
| Example 1 | 0.02 |
| Example 9 | 0.4 |
| Example 12 | 0.06 |
| Example 22 | 0.4 |
| Example 24 | 0.2 |
| Example 27 | 1.0 |
| Example 33 | 0.03 |
| Example 40 | 0.2 |
| Example 51 | 0.02 |
| Example 55 | 0.02 |
| Example 56 | 0.2 |
| Example 59 | 0.02 |
| Example 60 | 0.2 |
| Example 62 | 0.01 |
| Example 63 | 0.01 |
| Example 65 | 0.02 |
| Example 66 | 0.03 |
| Example 69 | 0.2 |
| Example 75 | 0.4 |
| Example 76 | 0.06 |
| Example 77 | 0.02 |
| Example 81 | 0.06 |
| Example 82 | 0.03 |
| Example 84 | 0.03 |
| Example 85 | 0.02 |
| Example 87 | 0.04 |
| Example 88 | 0.07 |
| Example 90 | 0.05 |
| Example 93 | 0.2 |
| Example 96 | 0.03 |
| Example 103 | 0.2 |
| Example 104 | 0.04 |
| Example 106 | 0.04 |
| Example 110 | 0.05 |
| Example 119 | 0.3 |
| Example 121 | 0.04 |
| Example 124 | 0.04 |
| Example 131 | 0.01 |
| Example 132 | 0.04 |
| Example 134 | 0.004 |
| Example 136 | 0.05 |
| Example 138 | 0.8 |
| Example 144 | 0.02 |
| Example 145 | 0.09 |

Biological Example 2

Metabolic Stability in Human Liver Microsomes

Human liver microsome (BD Gentest Corporation, Cat No. #452161) incubations were conducted in duplicate in 96-well plates. Each well contains 40 µL of 0.1 M potassium phosphate buffer (pH 7.4), 4.125 mM MgCl$_2$, 0.625 mg/mL liver microsomes, and test compound (1.25 µM). After 5-min preincubation at 37° C., 10 uL of 5.0 mM NADPH in 0.1M potassium phosphate buffer was added to initiate the enzymatic reaction. The final component concentrations are 0.1M potassium phosphate buffer (pH 7.4), 1.0 mM NADPH, 3.3 mM MgCl$_2$, 0.5 mg/mL liver microsomes, and test compound (1.0 µM). Reactions were terminated at 0 and 60 min by adding 200 µL of ice-cold acetonitrile containing internal standard.

LC-MS/MS analysis was conducted as specified below.

| LC | System | ACQUITY UPLC H-Class PLUS System (Waters) |
| --- | --- | --- |
| | Column | ACQUITY UPLC BEH C18 Column 2.1 mm ID × 50 mm (Waters) |
| | Elution conditions | Column temperature: 25° C.<br>Mobile phase:<br>A: water (0.1% formic acid)<br>B: acetonitrile (0.1% formic acid)<br>Gradient program:<br>Time (min)  0  1.20  1.40  1.41  1.50<br>Mobile phase B (%)  10  90  90  10  10<br>Flow rate: 0.6 mL/min |

| | |
|---|---|
| MS System | API4000 (AB Sciex) |
| Condition | Electrospray ionization, positive ion mode, multiple reaction monitoring mode |

The remaining at 60 min (%) of test compound was calculated from the peak area ratio (test compound/internal standard) of samples collected 0 and 60 min after the start of the reaction according to the formula described below.

Remaining at 60 min (%)=peak area ratio of sample collected at 60 min/peak area ratio of sample collected at 0 min×100

[Results]

The present compounds were stable against hepatic metabolism. The metabolic stability in human liver microsomes of representative present compounds are shown in the table below.

| EXAMPLE No. | Metabolic stability in human liver microsomes (% remaining at 60 min) |
|---|---|
| Example 1 | 95 |
| Example 9 | 93 |
| Example12 | 100 |
| Example 24 | 101 |
| Example 27 | 97 |
| Example 33 | 103 |
| Example 40 | 103 |
| Example 51 | 95 |
| Example 59 | 100 |
| Example 60 | 102 |
| Example 62 | 83 |
| Example 65 | 93 |
| Example 66 | 89 |
| Example 69 | 89 |
| Example 75 | 102 |
| Example 81 | 100 |
| Example 82 | 104 |
| Example 84 | 92 |
| Example 85 | 98 |
| Example 87 | 99 |
| Example 88 | 95 |
| Example 90 | 100 |
| Example 93 | 86 |
| Example 96 | 83 |
| Example 110 | 85 |
| Example 119 | 102 |
| Example 121 | 114 |
| Example 124 | 97 |
| Example 131 | 84 |
| Example 136 | 97 |
| Example 144 | 101 |
| Example 145 | 99 |

Biological Example 3

Brain Concentration in Mice

Test compounds were orally administered to mice (C57BL/6) at 1 or 3 mg/kg. Brain samples were collected 2 h after the administration and homogenized with 3-fold volumes of distilled water.

LC-MS/MS analysis was conducted as specified below. Standard calibration samples were prepared using the same matrix and analyzed in the same manner.

| | | |
|---|---|---|
| Extraction procedure | | Mix 40 μL of sample with 40 μL of acetonitrile and 160 μL of acetonitrile/ethanol (7:3) containing internal standard, and stir the mixture. Transfer all to a deproteinization filter plate for suction filtration and inject the filtrate to a LC system. |
| LC | System | Prominence UFLC$_{XR}$ (Shimadzu Corporation) |
| | Column | Shim-pack XR-ODSII 2.0 mm ID × 75 mm (Shimadzu Corporation) |
| | Elution conditions | Column temperature: 40° C. Mobile phase: A: 0.2% formic acid 5 mM ammonium acetate aqueous solution B: acetonitrile Gradient program: Time (min)    0    1.5    3.0    3.1    4 Mobile phase B (%)   10   90   90   10   10 Flow rate: 0.5 mL/min |
| MS | System | API4000 (AB Sciex) |
| | Condition | Electrospray ionization, positive ion mode, multiple reaction monitoring mode |

Standard calibration samples were analyzed to calculate a regression equation from the peak area ratio (test compound/internal standard). The peak area ratio was determined for a measurement sample and assigned to the regression equation to calculate an assay value.

[Results]

The Unbound-Brain Concentration of the present compounds was high. The Unbound-Brain Concentration at 2 h at 1 mg/kg of representative present compounds are shown in the table below. Values with * are obtained by proportional calculation from the 3 mg/kg data. Unbound-Brain Concentration at 2 h of comparative compound, (R)—N-(1-(3-isopropyl-1H-pyrazole-5-carbonyl)pyrrolidin-3-yl)cyclopropane carboxamide (the compound of Examples 29 described in PTL 1 (the pamphlet of International Publication No. WO2016057924)) was 2.5 ng/g.

| EXAMPLE No. | Unbound-Brain Concentration at 2 h at 1 mg/kg (ng/g) |
|---|---|
| Example 1 | 93.7* |
| Example 12 | 10.8 |
| Example 33 | 62.1 |
| Example 51 | 55.3 |
| Example 81 | 21.9 |
| Example 82 | 57.4 |
| Example 85 | 76.7 |
| Example 88 | 39.5* |

Formulation Example 1

Tablets containing 5 mg of [(1R,5S,6r)-6-(5,5-dimethyl-4,5-dihydro-1,2-oxazol-3-yl)-3-azabicyclo[3.1.0]hex-3-yl](5-isopropyl-1H-pyrazol-3-yl)methanone The following components can be mixed and compressed to tablets according to standard methods to obtain 10,000 tablets each containing 5 mg of the active component.

[(1R,5S,6r)-6-(5,5-dimethyl-4,5-dihydro-1,2-oxazol-3-yl)-3-azabicyclo[3.1.0]hex-3-yl](5-isopropyl-1H-pyrazol-3-yl)methanone: 50 g Carboxymethylcellulose calcium (disintegrating agent): 20 g Magnesium stearate (lubricant): 10 g Microcrystalline cellulose: 920 g

Formulation Example 2

Tablets containing 5 mg of [(1R,5S,6r)-6-(5,5-dimethyl-4,5-dihydro-1,2-oxazol-3-yl)-3-azabicyclo[3.1.0]hex-3-yl](1-isopropyl-1H-imidazol-4-yl)methanone The following components can be mixed and compressed to tablets according to standard methods to obtain 10,000 tablets each containing 5 mg of the active component.

[(1R,5S,6r)-6-(5,5-dimethyl-4,5-dihydro-1,2-oxazol-3-yl)-3-azabicyclo[3.1.0]hex-3-yl](1-isopropyl-1H-imidazol-4-yl)methanone: 50 g
Carboxymethylcellulose calcium (disintegrating agent): 20 g
Magnesium stearate (lubricant): 10 g
Microcrystalline cellulose: 920 g

Formulation Example 3

Injections containing 20 mg of [(1R,5S,6r)-6-(5,5-dimethyl-4,5-dihydro-1,2-oxazol-3-yl)-3-azabicyclo[3.1.0]hex-3-yl](5-isopropyl-1H-pyrazol-3-yl)methanone The following components can be mixed according to the standard method, and the solution can be then sterilised according to the standard method, divided into ampoules at 5-mL aliquot and lyophilised according to the standard method to obtain 10,000 ampoules each containing 20 mg of the active component.

[(1R,5S,6r)-6-(5,5-dimethyl-4,5-dihydro-1,2-oxazol-3-yl)-3-azabicyclo[3.1.0]hex-3-yl](5-isopropyl-1H-pyrazol-3-yl)methanone: 200 g
Mannitol: 20 g
Distilled water: 50 L

INDUSTRIAL APPLICABILITY

The present compound has KDM5 inhibitory activity, and thus is useful as a prophylactic and/or therapeutic agent for cancer, Huntington's disease, Alzheimer's disease and the like.

The invention claimed is:

1. A pharmaceutical composition comprising [(1R,5S,6r)-6-(5,5-dimethyl-4,5-dihydro-1,2-oxazol-3-yl)-3-azabicyclo[3.1.0] hex-3-yl] [1-(1-methylcyclopropyl)-1H-imidazol-4-yl] methanone or a salt thereof, and a pharmaceutically acceptable carrier.

2. A pharmaceutical composition comprising a compound of the formula:

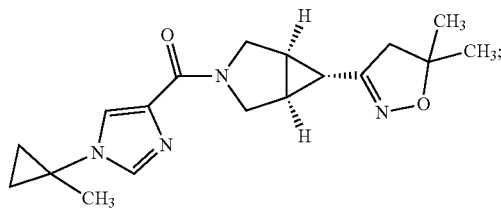 [SMILES: CC1(C)CC([C@H]2[C@@H]3CN(C(=O)c4cn(C5(C)CC5)cn4)C[C@@H]32)=NO1]

and a pharmaceutically acceptable carrier.

3. A pharmaceutical composition comprising a salt of a compound of the formula:

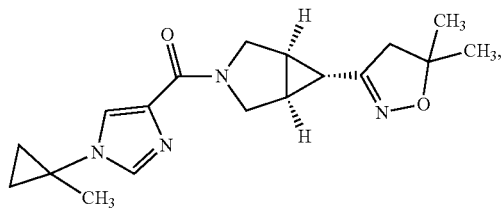 [SMILES: CC1(C)CC([C@H]2[C@@H]3CN(C(=O)c4cn(C5(C)CC5)cn4)C[C@@H]32)=NO1]

and a pharmaceutically acceptable carrier.

* * * * *